(12) United States Patent
Cherkasov et al.

(10) Patent No.: US 10,612,082 B2
(45) Date of Patent: Apr. 7, 2020

(54) PROCESS FOR THE ENZYMATIC SYNTHESIS AND AMPLIFICATION OF NUCLEIC ACIDS

(71) Applicant: AGCT GmbH, Luebeck (DE)

(72) Inventors: Dmitry Cherkasov, Marburg (DE);
Norbert Basler, Gross Hansdorf (DE);
Claus Becker, Oetigheim (DE);
Hans-Joerg Hess, Berlin (DE);
Andreas Mueller-Hermann, Munich (DE)

(73) Assignee: AGCT GmbH, Luebeck (DE)

( * ) Notice: Subject to any disclaimer, the term of this patent is extended or adjusted under 35 U.S.C. 154(b) by 0 days.

(21) Appl. No.: 16/328,141

(22) PCT Filed: Aug. 21, 2017

(86) PCT No.: PCT/EP2017/071011
§ 371 (c)(1),
(2) Date: Feb. 25, 2019

(87) PCT Pub. No.: WO2018/036955
PCT Pub. Date: Mar. 1, 2018

(65) Prior Publication Data
US 2019/0185914 A1    Jun. 20, 2019

(30) Foreign Application Priority Data
Aug. 25, 2016    (EP) .................................... 16185624

(51) Int. Cl.
*C12P 19/34* (2006.01)
*C12Q 1/686* (2018.01)
(Continued)

(52) U.S. Cl.
CPC ............ *C12Q 1/686* (2013.01); *C12Q 1/6806* (2013.01); *C12Q 1/6848* (2013.01); *C12Q 1/6853* (2013.01); *C12Q 1/6876* (2013.01)

(58) Field of Classification Search
None
See application file for complete search history.

(56) References Cited

U.S. PATENT DOCUMENTS 8,110,353 B2 * 2/2012 Zhang .................... C12Q 1/682
                                                                435/6.1
9,284,602 B2 * 3/2016 Zhang .................. C12Q 1/6832
(Continued)

FOREIGN PATENT DOCUMENTS

CN    104 164 487 A    11/2014
EP    2 746 395 A1     6/2014
(Continued)

OTHER PUBLICATIONS

PCT/EP2017/071011—International Search Report, dated Nov. 3, 2017.
(Continued)

*Primary Examiner* — Kenneth R Horlick
(74) *Attorney, Agent, or Firm* — Curatolo Sidoti Co., LPA; Salvatore A. Sidoti; Floyd Trillis, III

(57) ABSTRACT

A method for amplification of nucleic acids in which substantially use is made of the fact that a pre-defined nucleic acid chain (target sequence) can be multiplied/amplified in the presence of a target sequence-specific activator oligonucleotide. The target sequence-specific activator oligonucleotide causes the separation of re-synthesized complementary primer extension products by strand displacement, so that a new primer oligonucleotide can attach to the respective template strand. The thus formed complex of a primer oligonucleotide and a template strand can initiate a new primer extension reaction. The thus formed primer
(Continued)

Strand displacement by the activator oligonucleotide extension products in turn function as templates, so that an exponential amplification reaction results.

9 Claims, 43 Drawing Sheets
(38 of 43 Drawing Sheet(s) Filed in Color)

Specification includes a Sequence Listing.

(51) Int. Cl.
    *C12Q 1/6853*    (2018.01)
    *C12Q 1/6848*    (2018.01)
    *C12Q 1/6806*    (2018.01)
    *C12Q 1/6876*    (2018.01)

(56) References Cited

U.S. PATENT DOCUMENTS

| | | | |
|---|---|---|---|
| 10,273,534 B2* | 4/2019 | Higuchi | C12Q 1/686 |
| 2015/0203905 A1* | 7/2015 | Takahashi | C12Q 1/6834 |
| | | | 435/6.11 |

FOREIGN PATENT DOCUMENTS

| | | |
|---|---|---|
| WO | WO 2008/097929 A2 | 8/2008 |
| WO | WO 2012/058488 A1 | 5/2012 |
| WO | WO 2016/077291 A1 | 5/2016 |
| WO | WO 2016/100388 A1 | 6/2016 |

OTHER PUBLICATIONS

PCT/EP2017/071011—International Written Opinion, dated Nov. 3, 2017.
N. Srinivas, et al., "On the biophysics and kinetics of toehold-mediated DNA strand displacement", Nucleic Acids Research, vol. 41, No. 22, Sep. 9, 2013, pp. 10641-10658.
David Yu Zhang, et al., "Control of DNA Strand Displacement Kinetics Using Toehold Exchange", Journal of the American Chemical Society, vol. 131, No. 47, Dec. 2, 2009, pp. 17303-17314.
International Preliminary Report on Patentability in PCT/EP2017/071011, dated Feb. 26, 2019.

* cited by examiner

Fig. 1
PCR
A)
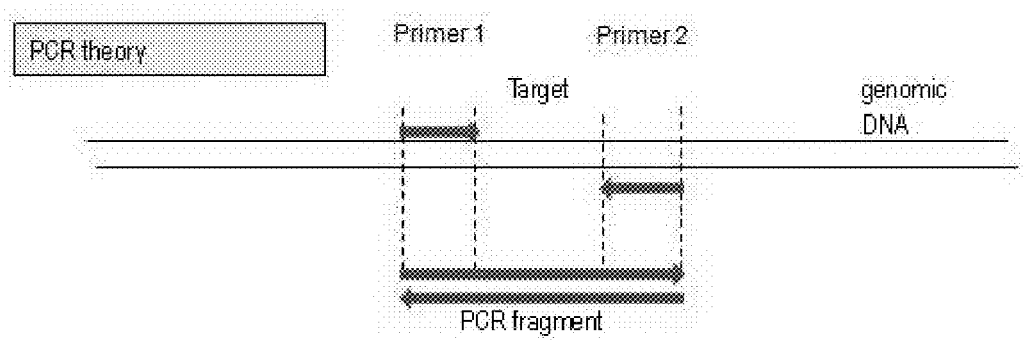
B)
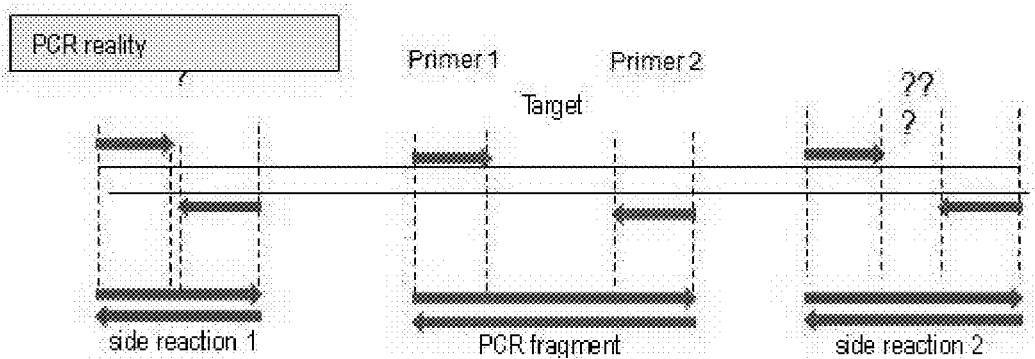

Principle of the exponential amplification of both strands

Fig. 3
A) Primer Oligonucleotides
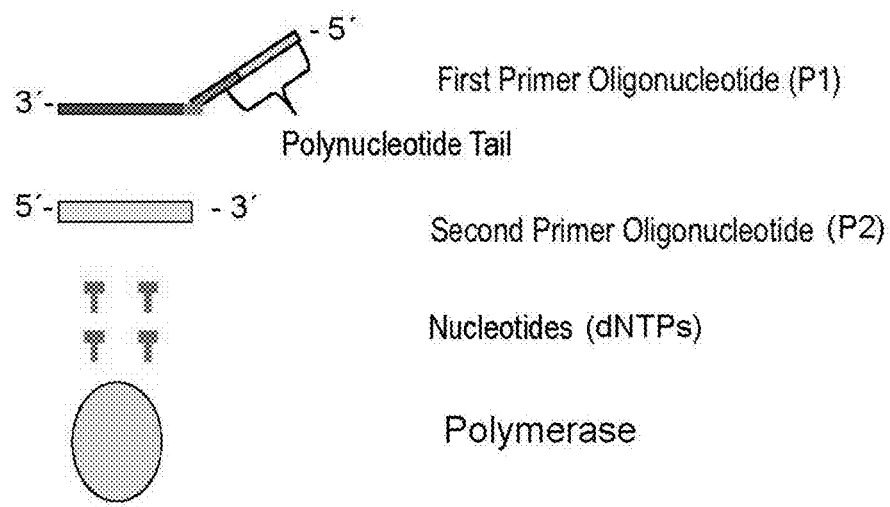
First Primer Oligonucleotide (P1)
Polynucleotide Tail
Second Primer Oligonucleotide (P2)
Nucleotides (dNTPs)
Polymerase
B) Nucleic acid to be amplified
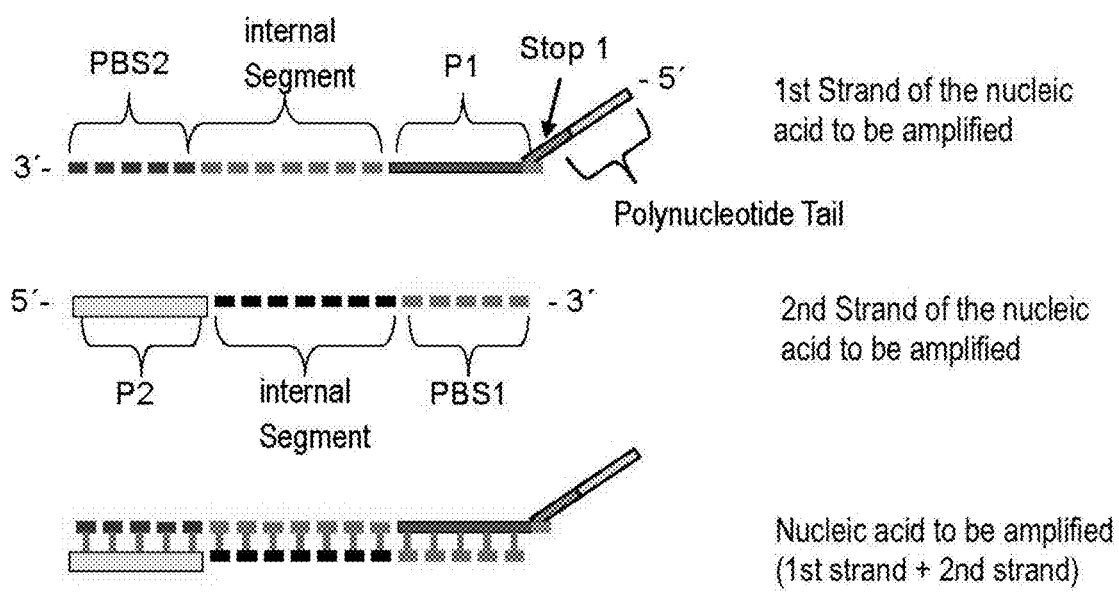
1st Strand of the nucleic acid to be amplified
Polynucleotide Tail
2nd Strand of the nucleic acid to be amplified
Nucleic acid to be amplified (1st strand + 2nd strand)

Strand displacement by the activator oligonucleotide

First Primer Oligonucleotide

Complementary Binding of the first Primer to the nucleic acid to be amplified

Fig. 8

First Primer Oligonucleotide and First Primer Extension Product

Complementary Binding of the first Primer to the nucleic acid to be amplified

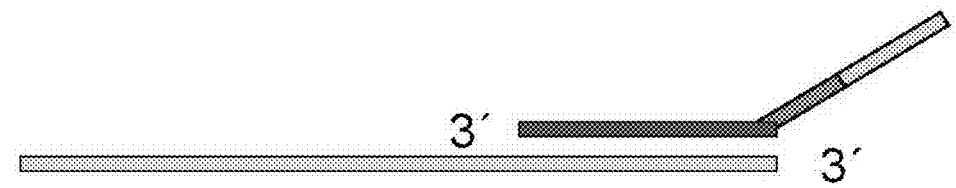

The first primer oligonucleotide specifically bound to the complementary position in the template strand

complementary extended first primer oligonucleotide bound to the complementary position in the template strand after primer extension

First Primer Extension Product

Complementary Binding of Primer to the nucleic acid to be amplified

3' Extension Product     First Primer Oligonucleotide extended first Primer Oligonucleotide = First Primer Extension Product Fig. 10
Activator Oligonucleotide
A)
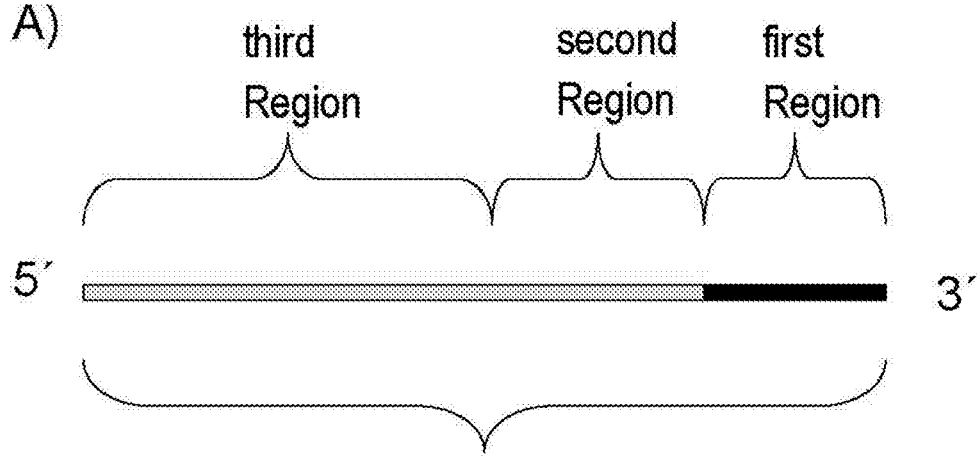
Activator Oligonucleotide
B)
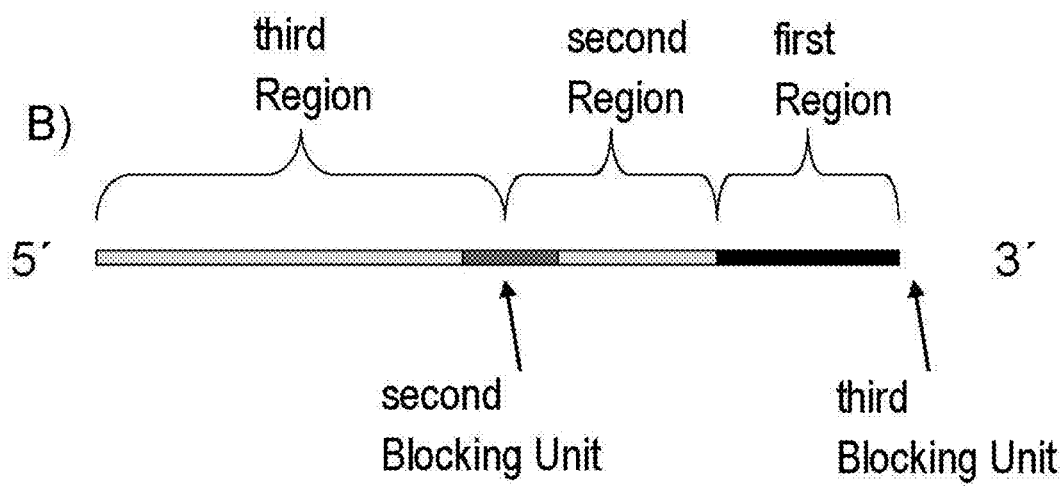

1st Strand Synthesis

Relations between individual components after the synthesis of the first primer extension product 1 = nucleic acid to be amplified
2 = activator oligonucleotide
3 = the first primer oligonucleotide
4 = the extension product of the first primer oligonucleotide

2nd Strand Synthesis

Relations between individual components
before the synthesis of the second primer extension product 1 = nucleic acid to be amplified
2 = activator oligonucleotide
3 = the first primer oligonucleotide
4 = the extension product of the first primer oligonucleotide
5 = the second primer oligonucleotide

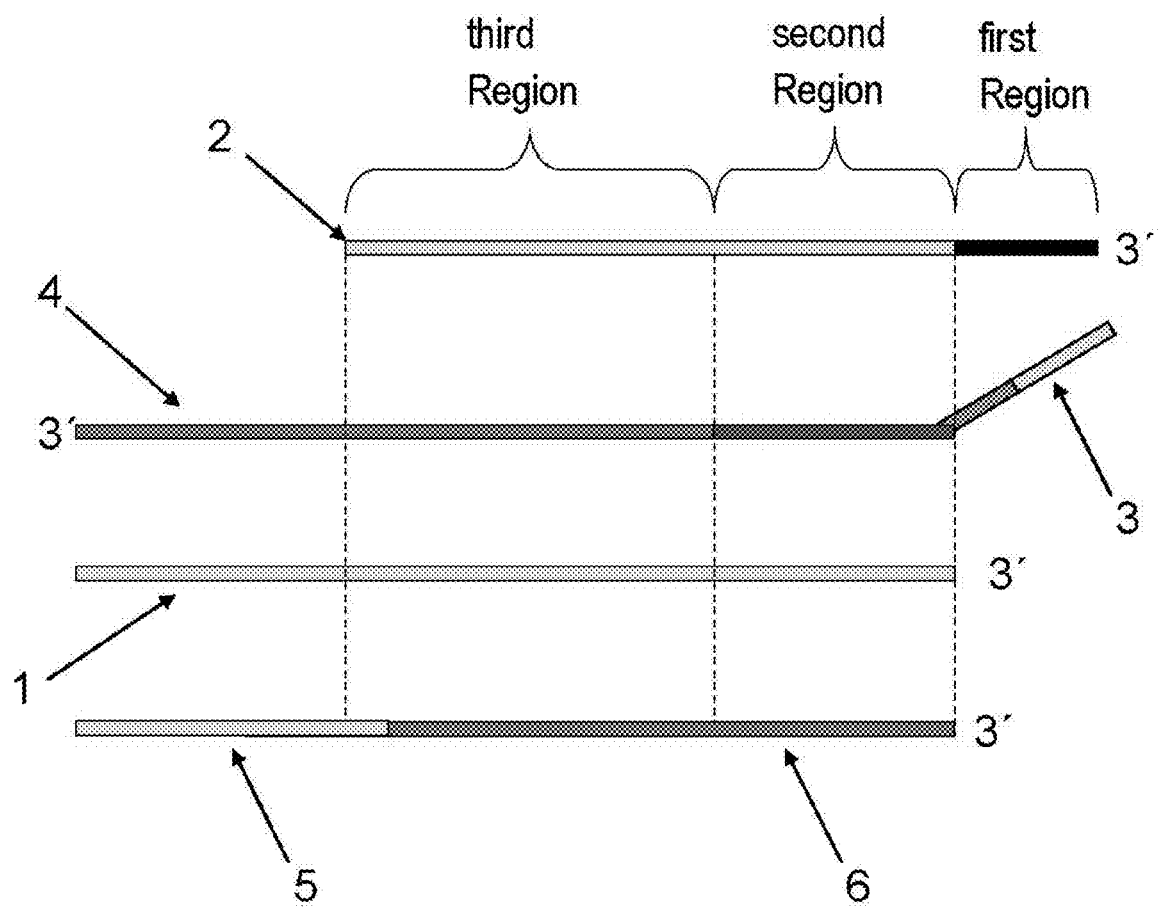

Fig. 14A

2nd Strand Synthesis

Relations between individual components after the synthesis of the second primer extension product 1 = nucleic acid to be amplified
2 = activator oligonucleotide
3 = the first primer oligonucleotide
4 = the extension product of the first primer oligonucleotide
5 = the second primer oligonucleotide
6 = the extension product of the second primer oligonucleotide

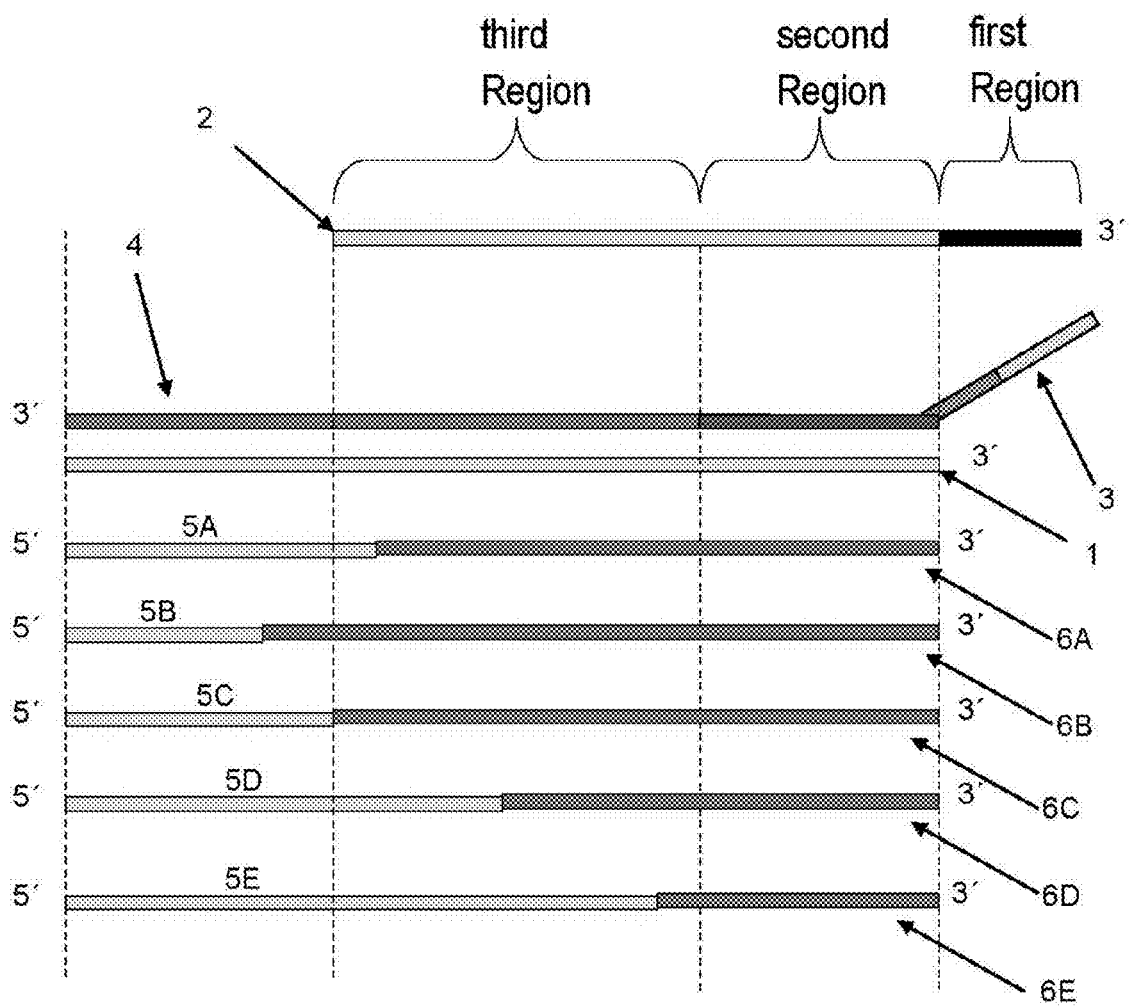

Fig. 14C

2nd Strand Synthesis

Examples of extension products after the synthesis of the second primer extension product 1 = nucleic acid to be amplified
2 = activator oligonucleotide
3 = the first primer oligonucleotide
4 = the extension product of the first primer oligonucleotide
5 = the second primer oligonucleotide (5A - 5E, different lengths)
6 = the extension product (6A - 6E) starting from the second primers 5A - 5E

Interactions between Components

Interactions between complementary regions of individual components after the synthesis of the first primer extension product 1 = nucleic acid to be amplified
2 = activator oligonucleotide
3 = the first primer oligonucleotide
4 = the extension product of the first primer oligonucleotide

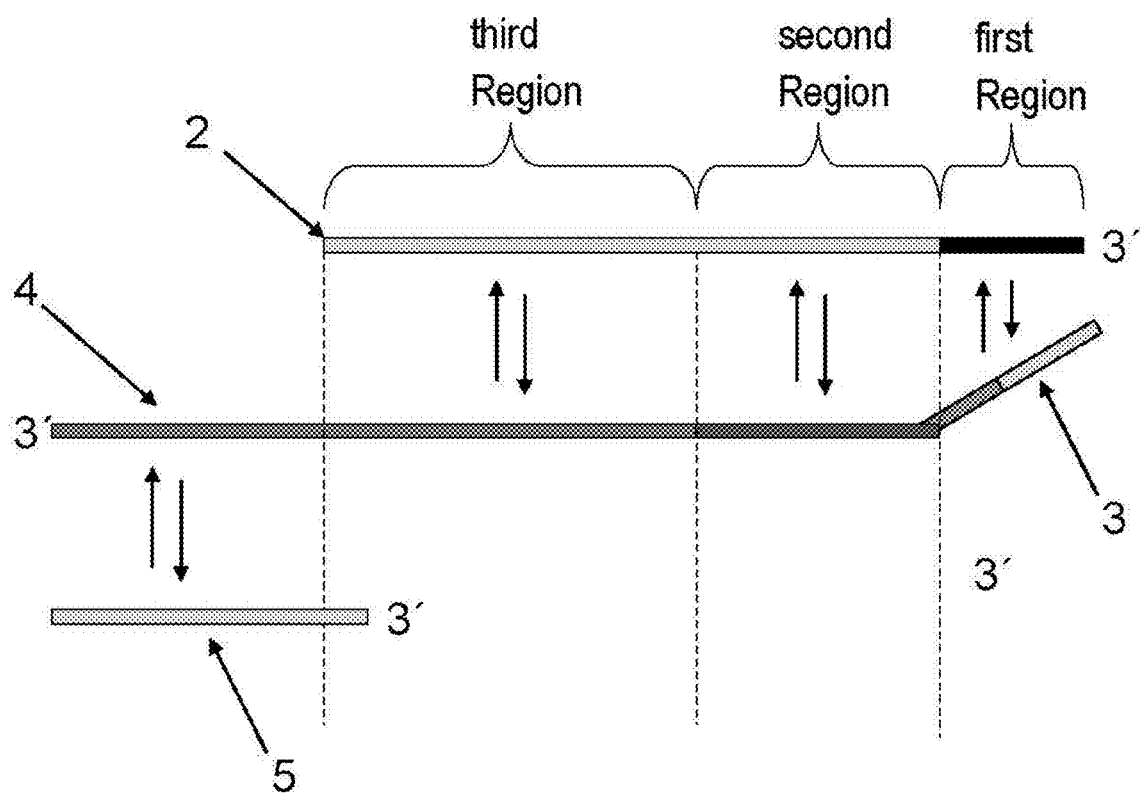

Fig. 17

Interactions between Components

Interactions between complementary regions of individual components before the synthesis of the second primer extension product 1 = nucleic acid to be amplified
2 = activator oligonucleotide
3 = the first primer oligonucleotide
4 = the extension product of the first primer oligonucleotide
5 = the second primer oligonucleotide

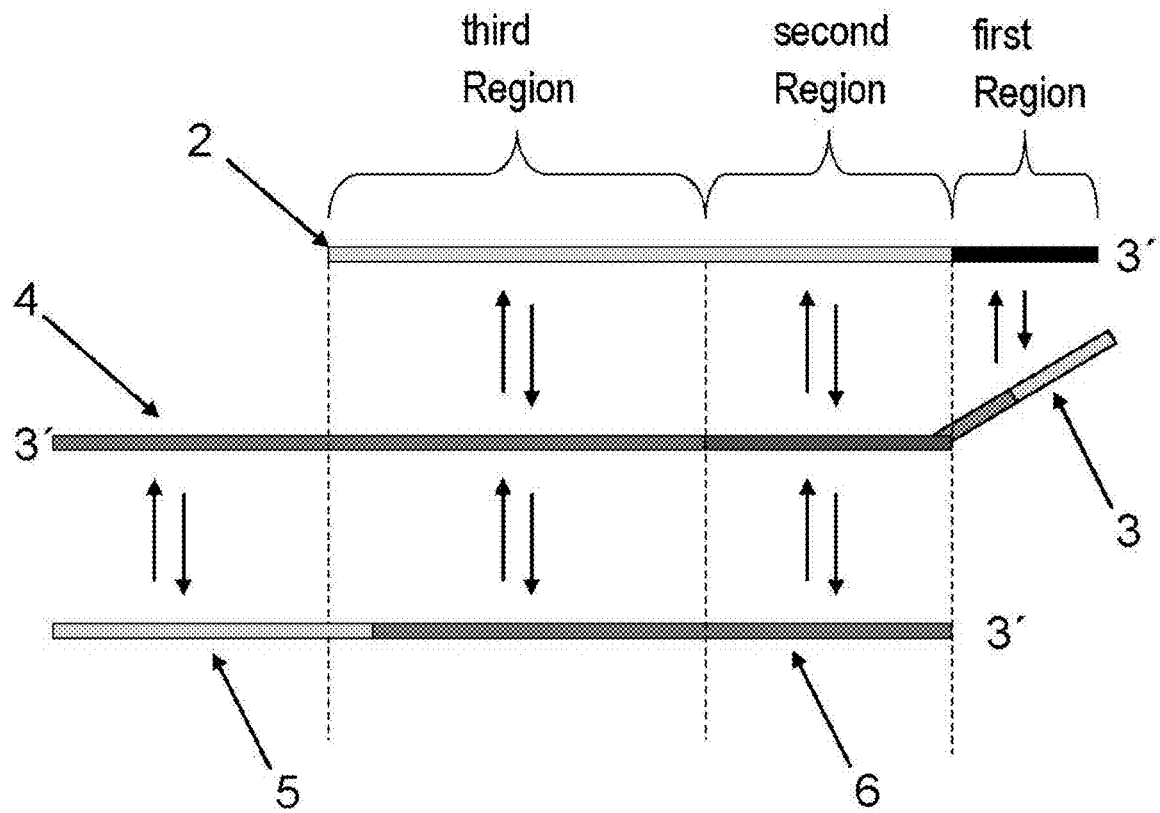

Fig. 18

Interactions between Components

Interactions between complementary regions of individual components after the synthesis of the second primer extension product 1 = nucleic acid to be amplified
2 = activator oligonucleotide
3 = the first primer oligonucleotide
4 = the extension product of the first primer oligonucleotide
5 = the second primer oligonucleotide
6 = the extension product of the second primer oligonucleotide

Sequence Products of the Reaction

First and Second Primer Extension Products

3 = the first primer oligonucleotide
4 = the extension product of the first primer oligonucleotide
5 = the second primer oligonucleotide
6 = the extension product of the second primer oligonucleotide

Interactions between Components in the Reaction

Change of States:
double-stranded Sections vs. single-stranded Sections

Intermediate Step:
separation of the second
primer extension product from the complex
with the double strand consisting of
the first primer extension product and the
activator oligonucleotide

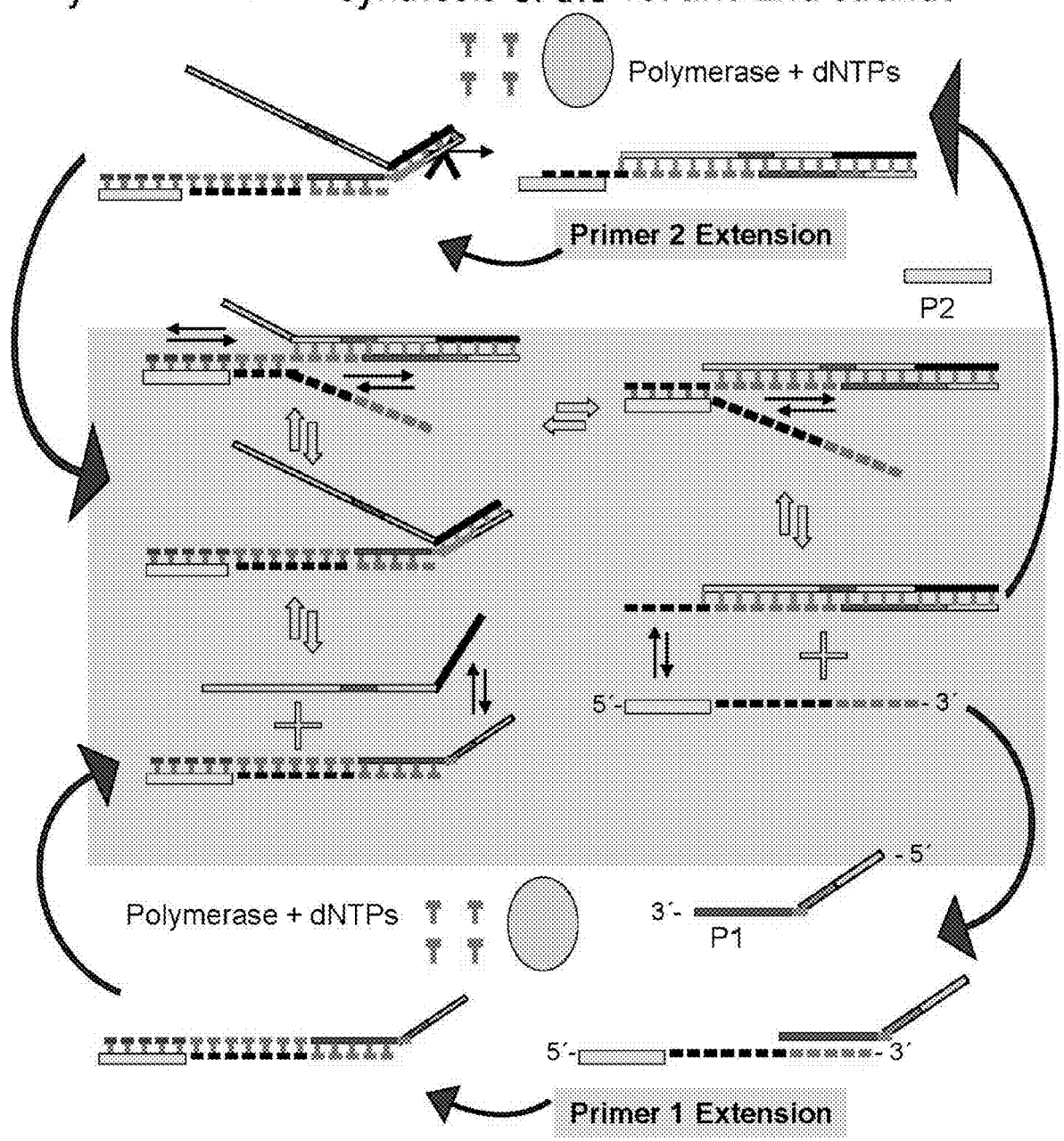

Fig. 23B
Start of the Reaction
A) 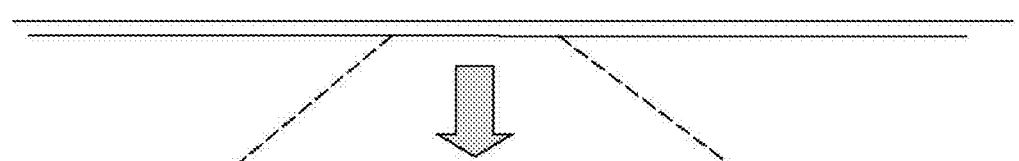
B) 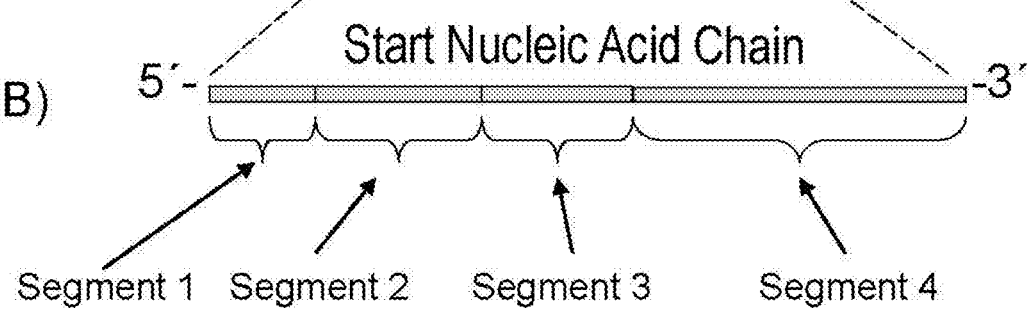
Start Nucleic Acid Chain
Segment 1   Segment 2   Segment 3   Segment 4
C) 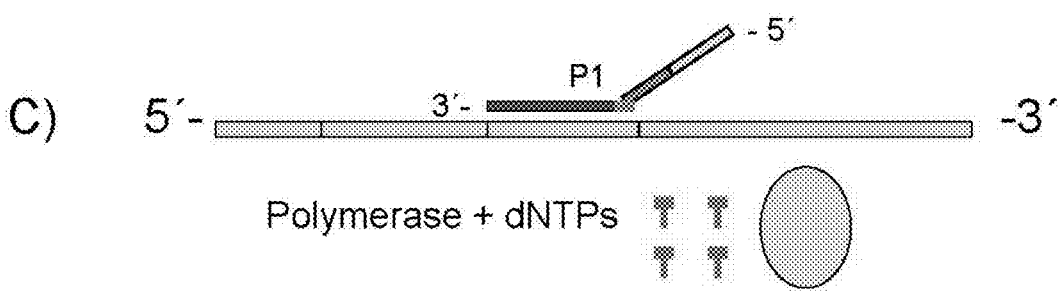
Polymerase + dNTPs
D) 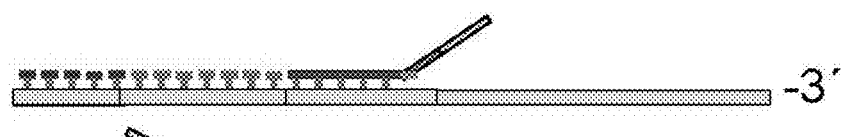
E) 
F) 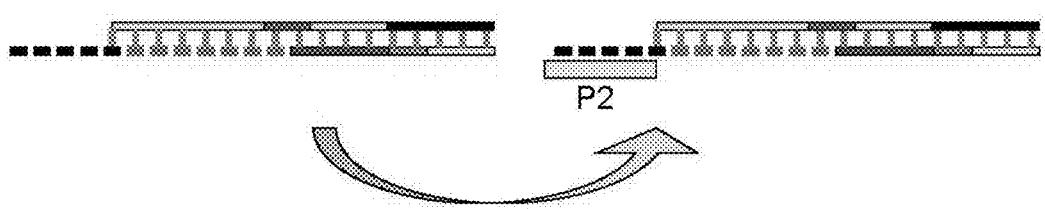
P2

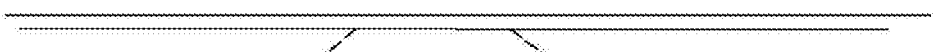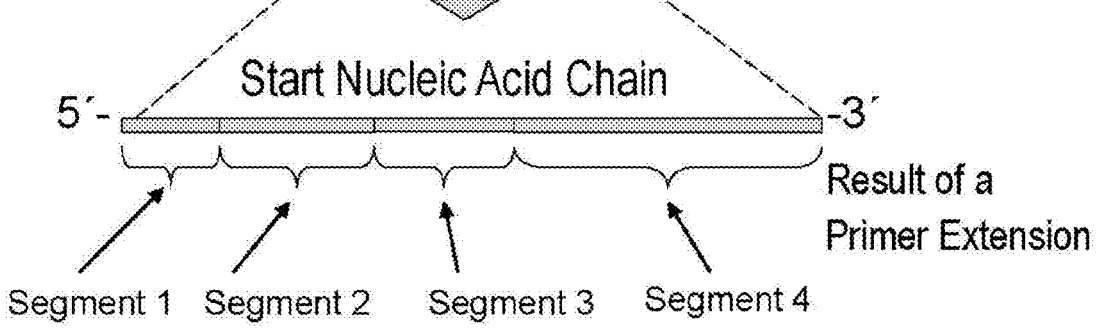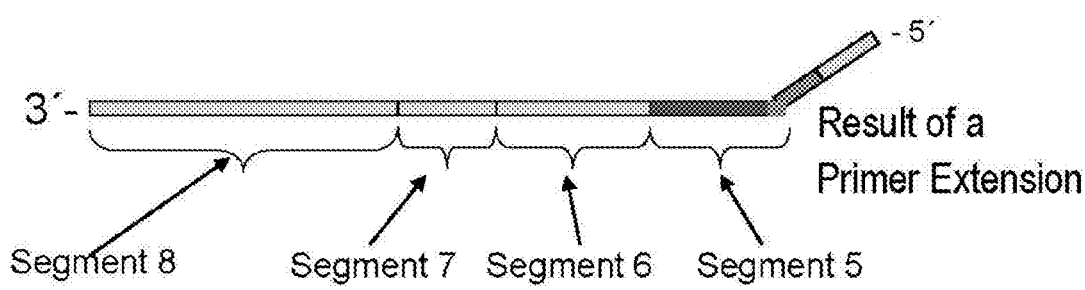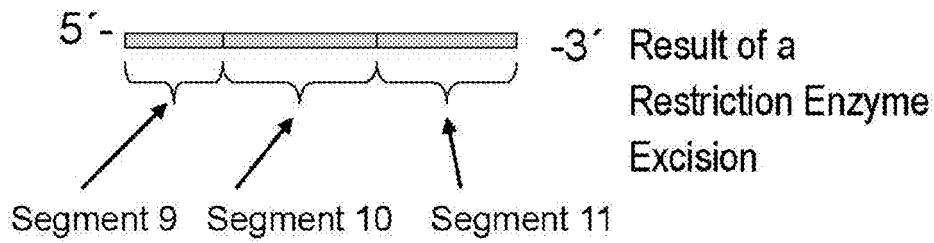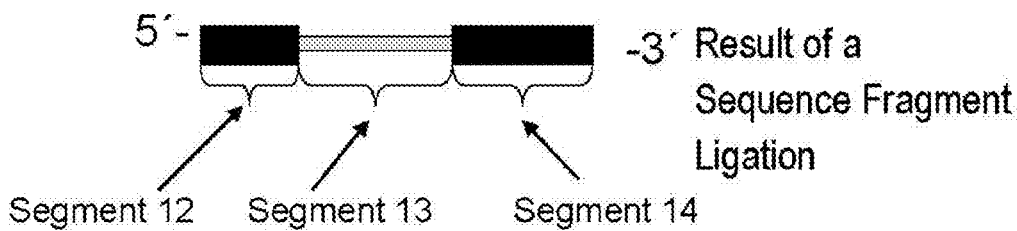
Fig. 23D

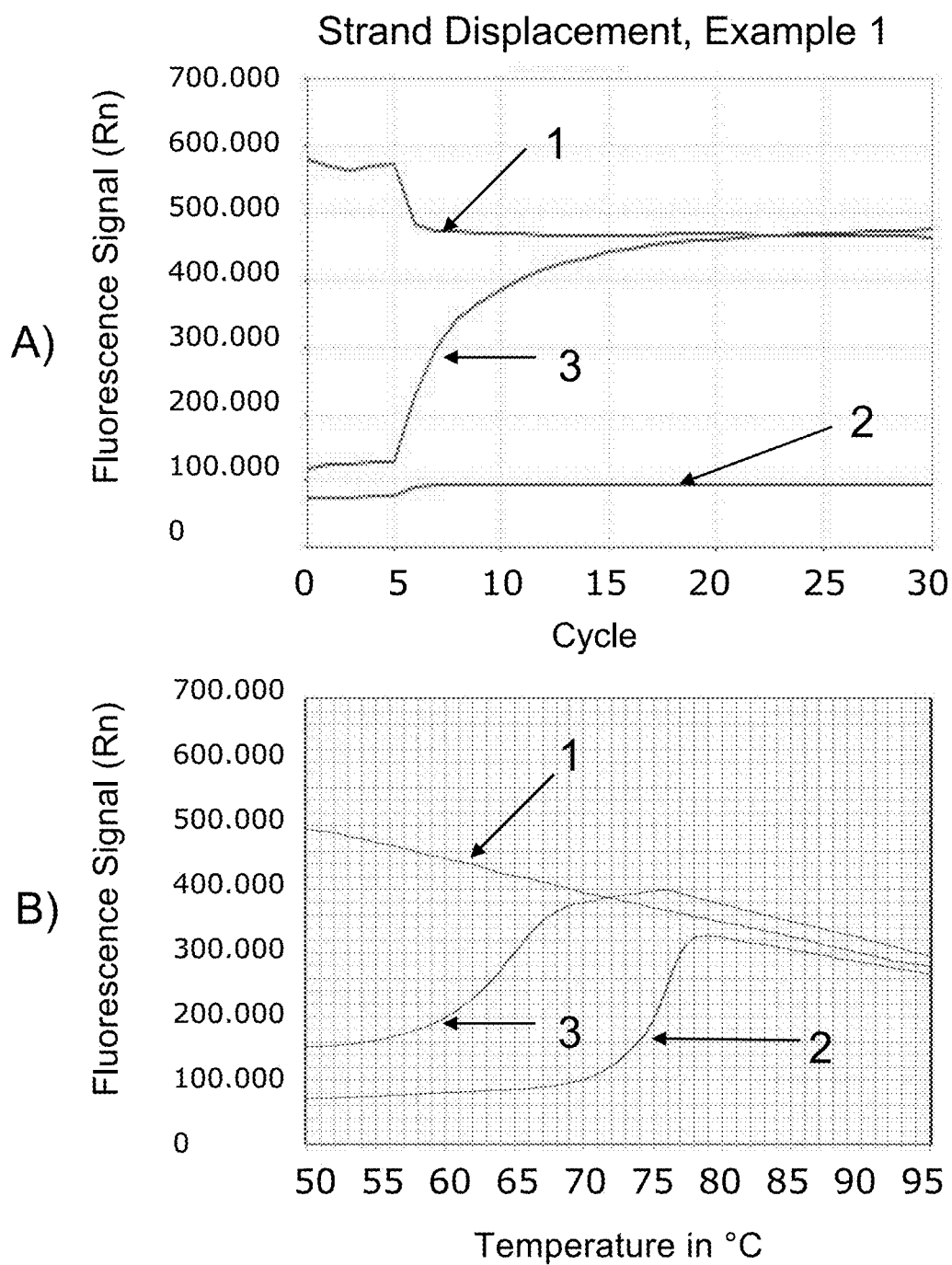

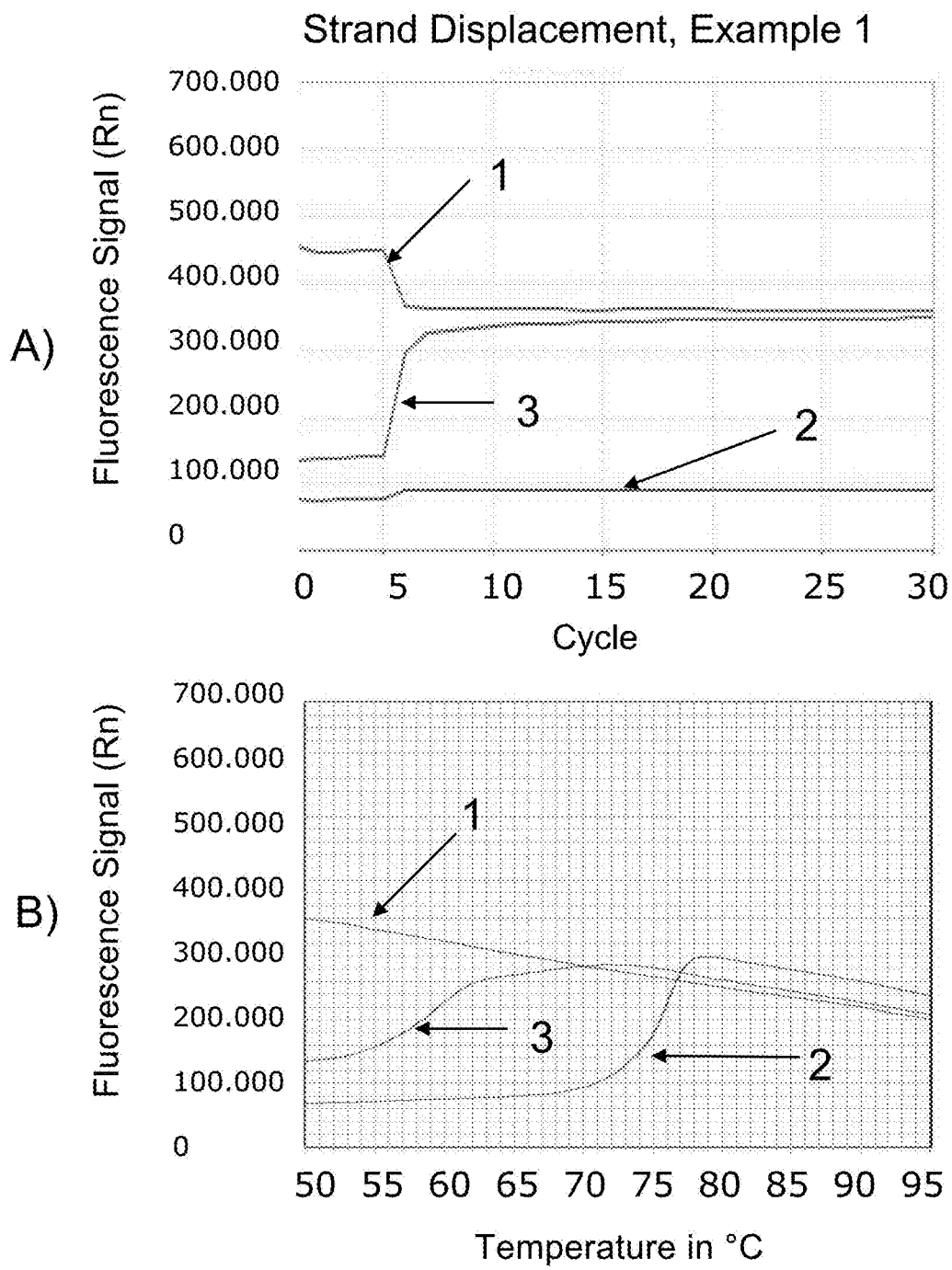

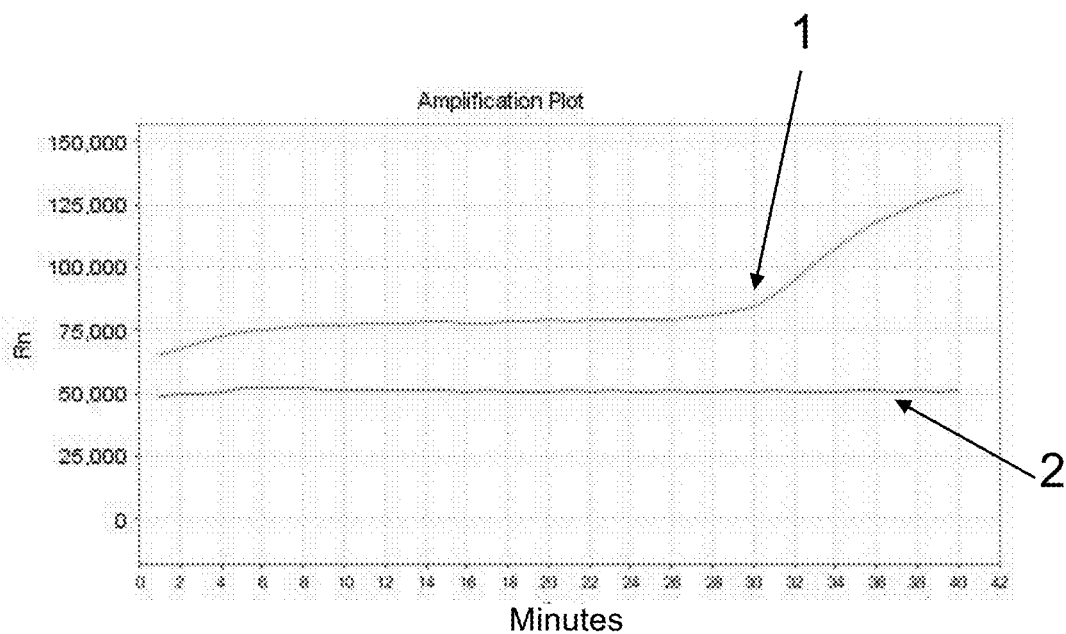
Signal intensity during an exponential amplification in example 2

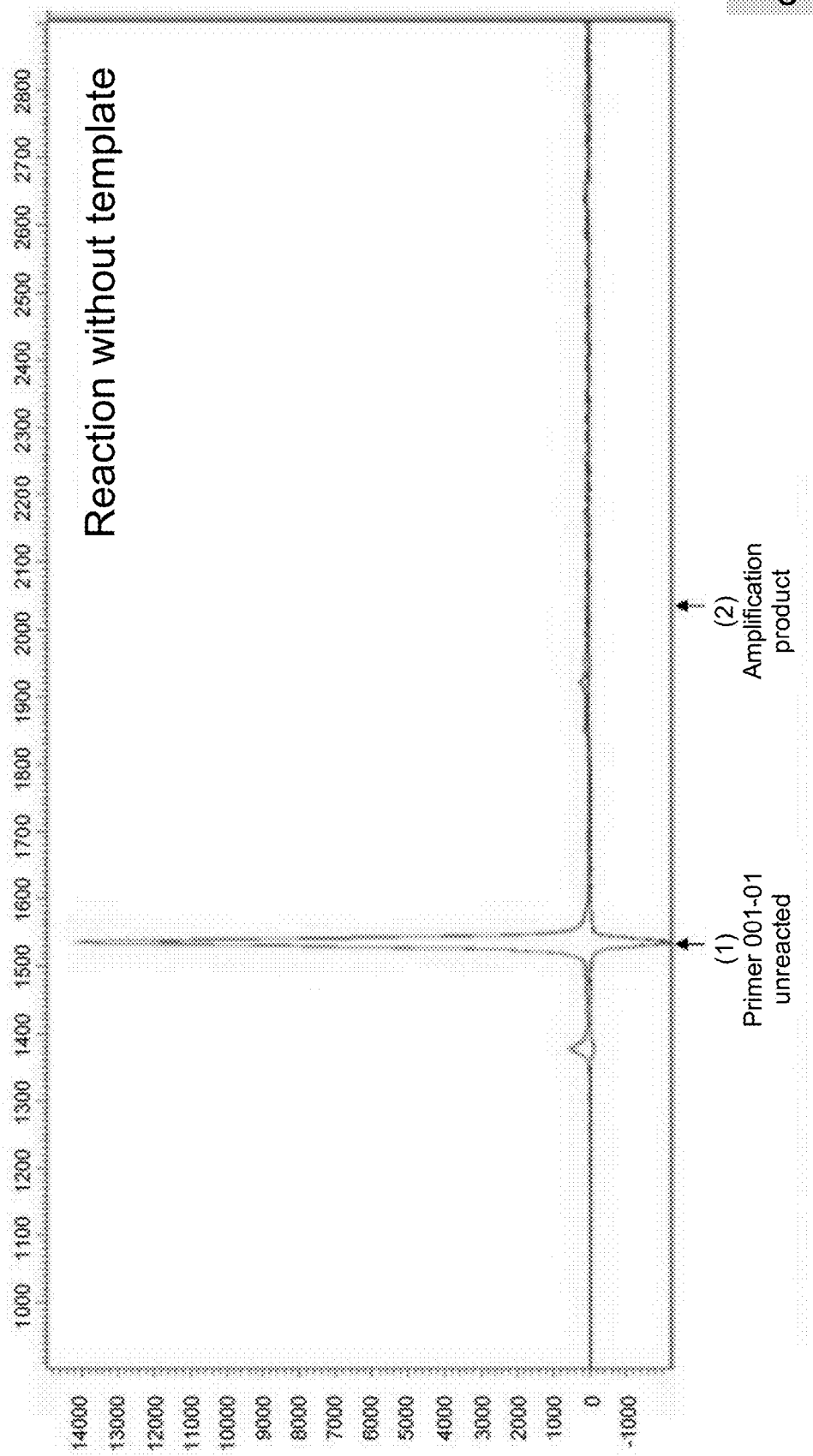

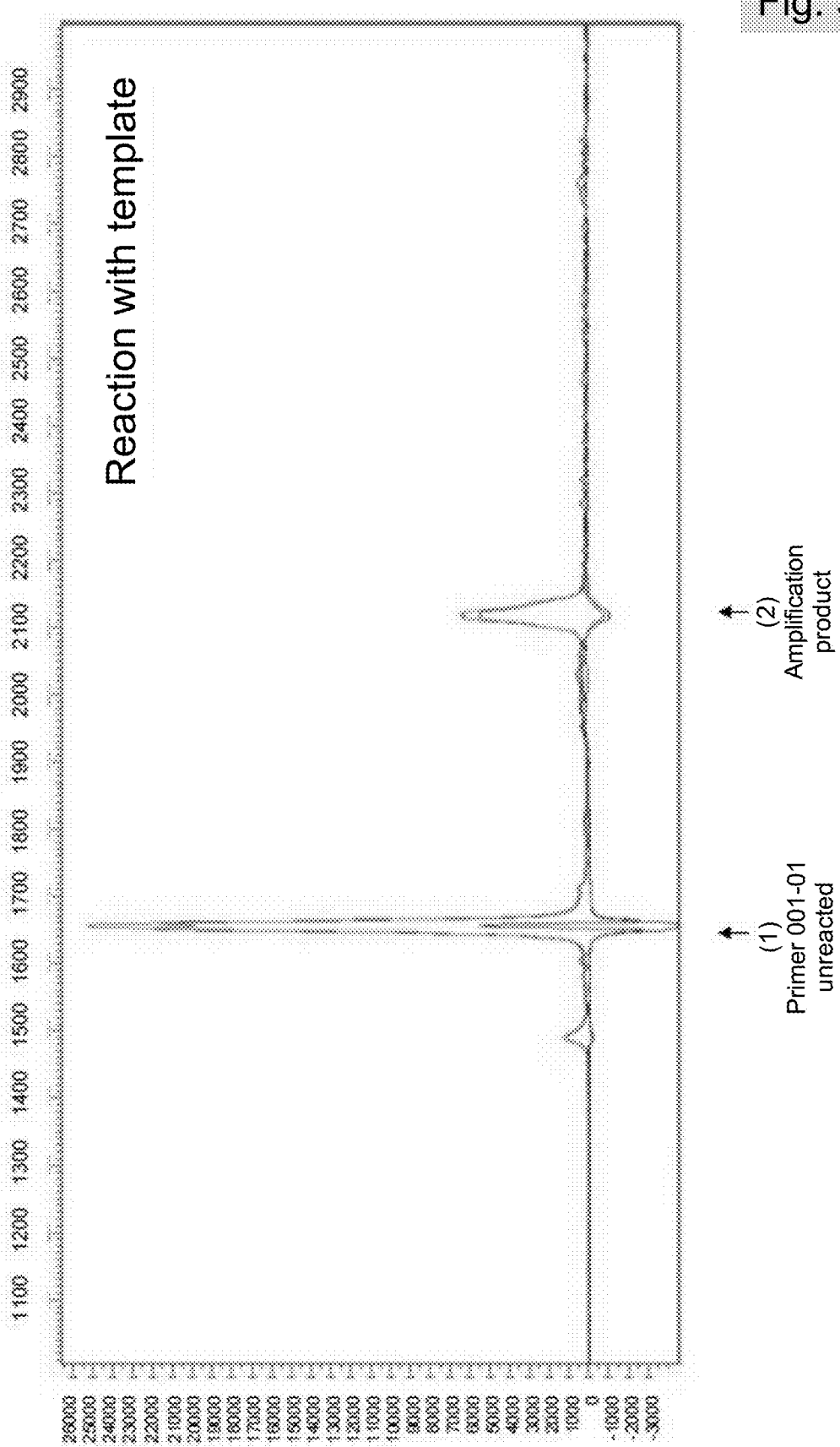

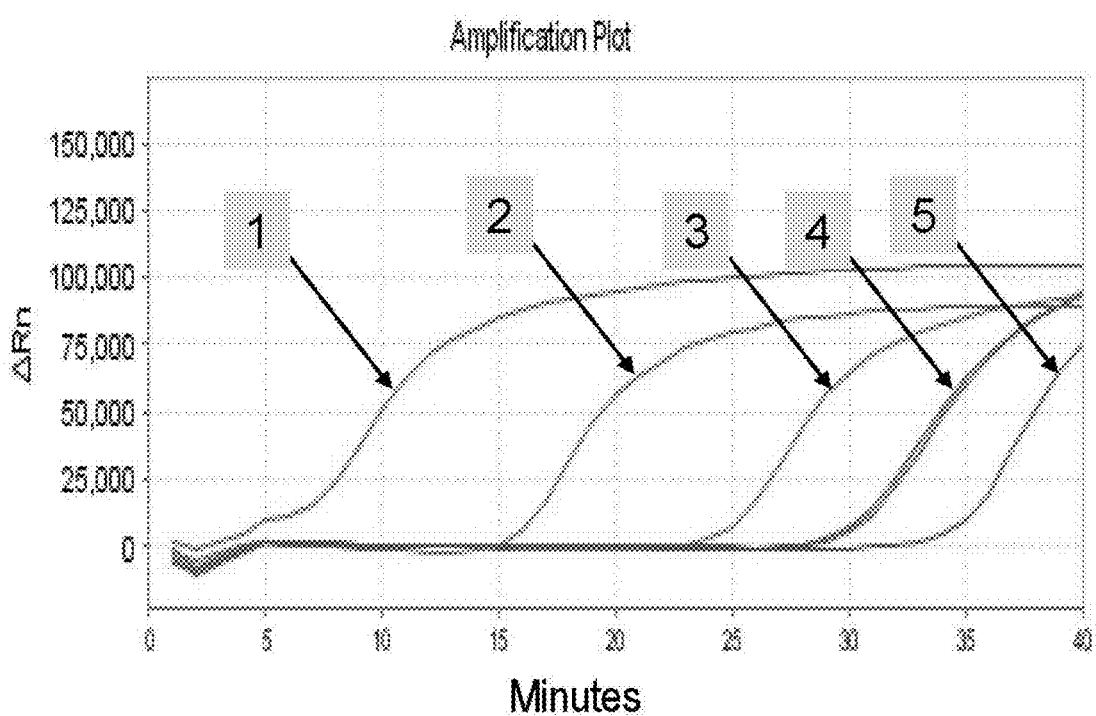
Signal intensity during an exponential amplification in Example 3

Signal intensity during an exponential amplification in example 4

Reaction with perfect match template (Seq ID No 26) 10 pmol/l concentration (arrow 1)
Reaction with mismatch template (Seq ID No 27) 10 pmol/l concentration (arrow 2)
Negative Control: no template in the reaction (arrow 3)

Reaction with Primer 1 (C3 linker), 60 min

Signal Intensity during an exponential amplification in example 5

Arrow 1: reaction with template
Arrow 2: reaction without template

Reaction with Primer 1 (C18 linker), 30 min

Signal Intensity during an exponential amplification in example 5

Arrow 1: reaction with template
Arrow 2: reaction without template

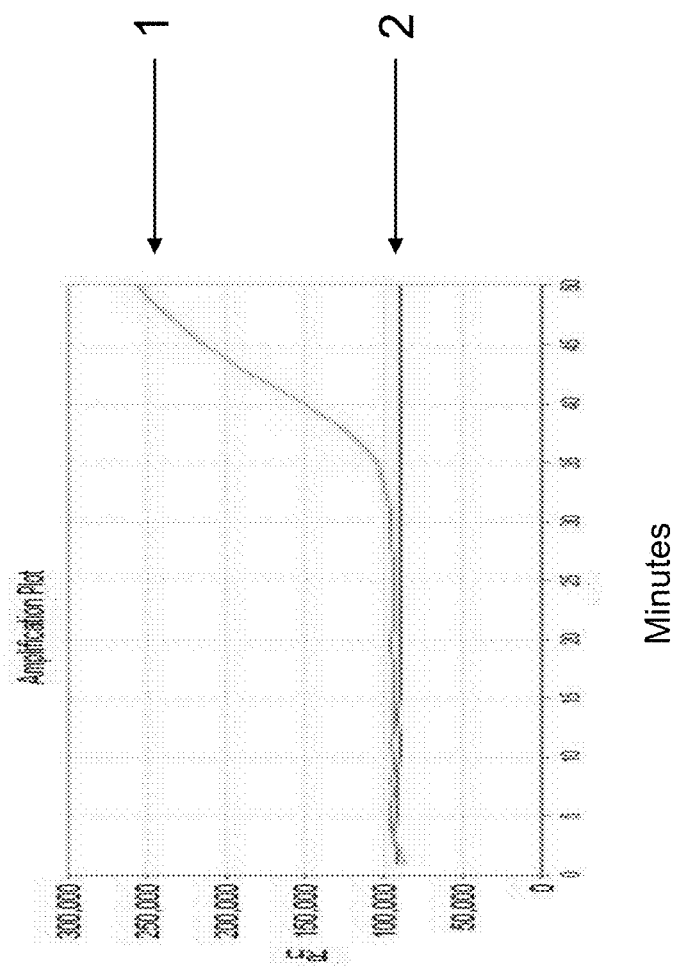

A)
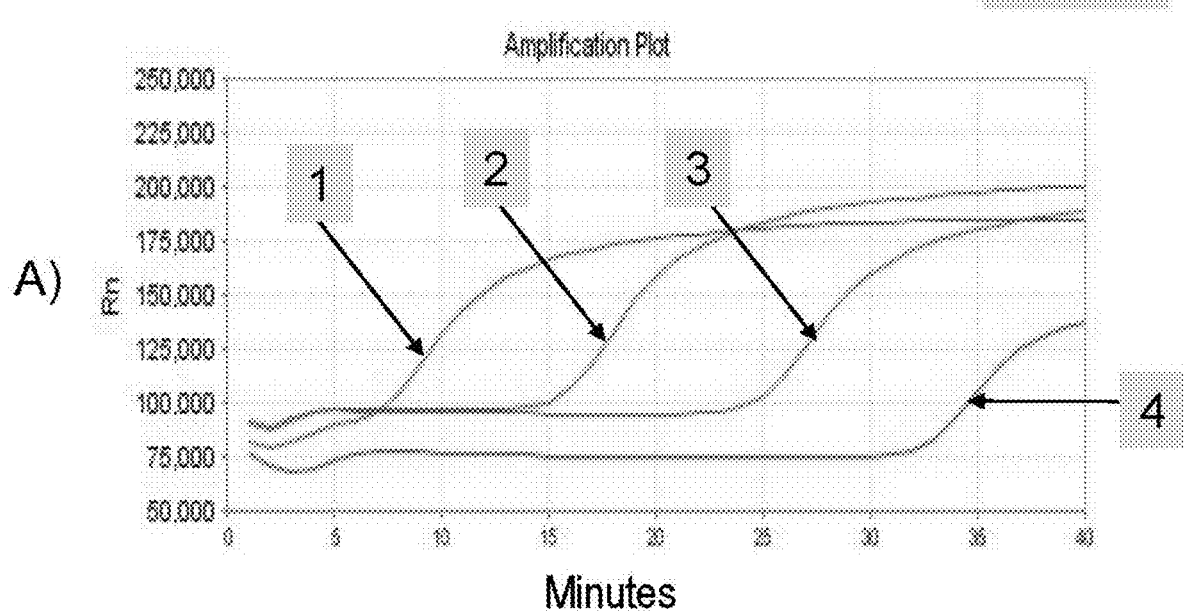
Signal intensity during an exponential amplification in example 6
B)
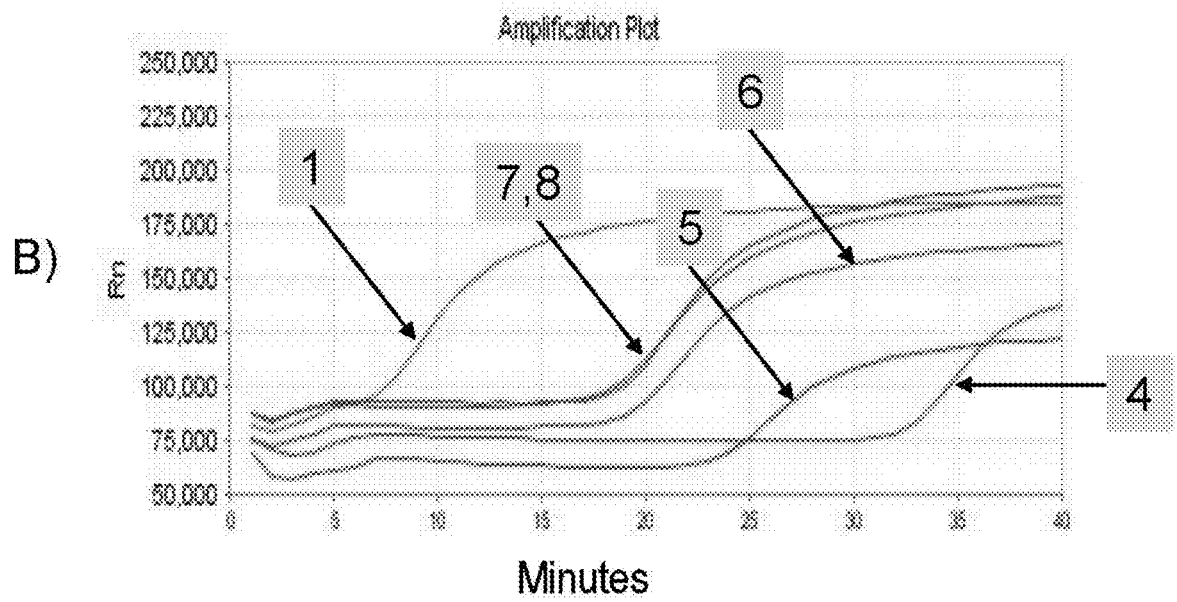
Fig. 35

PROCESS FOR THE ENZYMATIC SYNTHESIS AND AMPLIFICATION OF NUCLEIC ACIDS

CROSS REFERENCE TO RELATED APPLICATIONS

This application is a national stage application under 35 U.S.C. § 371 of International Application No. PCT/EP2017/071011, filed 21 Aug. 2017, which claims priority from European Patent Application No. 16185624.0, filed 25 Aug. 2016, which applications are hereby incorporated herein by reference.

Today, synthesis of nucleic acid chains plays a central role in biotechnology. Methods like PCR have significantly developed both the research landscape and industrial fields of application such as diagnostics in medicine and food industry. The combination of PCR with other technologies such as sequencing, real-time detection, microarray technology, microfluidic management etc. has contributed to the technological development of the basic technology and was able to partly overcome some barriers of the PCR basic technology. Also, further amplification methods such as isothermal amplification techniques (LAMP, HDA, RPA, TMA, SDA etc.) have been developed. They have especially been intended for use in the field of POCT.

Despite enormous progress in this field PCR plays the central role and thus, defines the individual technological barriers of the applications.

One of the properties of common amplification methods such as PCR is that during the amplification operation of the nucleic acid the amplified sequence parts between both primers are not controlled. Substantially, primer binding is in focus of optimizations of PCR amplification reactions. At the beginning of the PCR amplification and its course continuously more or less specific primer binding and initiation of the synthesis of main products and by-products occur. For example, the by-products may be generated as a result of a non-specific primer extension event in a synthesis cycle. In case of a backward synthesis reaction that optionally takes place the non-specifically extended primer is read as a template what generally results in the formation of a complete primer binding site. Thus, an incorrect sequence information is transferred from one synthesis cycle to the next synthesis cycle what in the sum of synthesis cycles not only results in the initial generation, but above all in the exponential increase of by-products.

Such side reactions may possibly result in the initial generation and exponential increase of fragments that interfere with the main reaction (amplification of a target sequence) and result in interferences in following steps of analysis, respectively. Such by-products typically comprise primer sequences and corresponding primer sequences so that their amplification can be in parallel to the main reaction (FIG. 1). Instead of a target sequence, however, such by-products comprise another nucleic acid sequence. In order to optimize the synthesis of the main products and to minimize the generation of by-products, typically primer sequences are optimized and there are chosen such reaction conditions that support the specificity of primer bonds. If the initiation of by-products has nevertheless taken place, these can usually be duplicated in parallel with the main products, since all the newly formed strands are denaturized during the amplification method independent of their composition. During this step primer binding sites are regenerated what represents the prerequisite for a new synthesis round. In methods such as PCR or HDA or SDA there are used means that do not cause a sequence-dependent strand separation (in PCR temperature raising is employed, in HDA a helicase and ATP, in SDA a polymerase capable of strand displacement). Accordingly, both in main products and by-products primer binding sites for new bonds and subsequent synthesis reaction are regenerated. After a single initiation both main products and by-products may be duplicated in parallel if the primers used find corresponding primer binding sites. Particularly susceptible for such side reactions are amplification methods that have to run under reaction conditions that are in some cases difficult to control (e.g. point-of-care testing) or have a strong presence of factors favoring side reactions (e.g. amplification of sequence fragments with minor sequence divergences such as for example mutations or SNV, in the presence of large amounts of wild-type sequences, such analyses may be important for example in forensic science, prenatal diagnosis, or for example in ctDNA detection as part of a liquid biopsy investigation).

As a matter of priority, specificity of PCR amplification is achieved by optimizing the primer binding to target sequences. Here, for example additional oligonucleotides can be used that are capable of partially binding to primers and thus, competitively take part in the primer binding to other nucleic acid chains. Such probes generally bind to a sequence part of the primer and on the primer leave a single-stranded sequence part unoccupied, so that the primer with this part can bind to the target nucleic acid and initiate a synthesis reaction. Here, specificity of a primer binding is to be improved by the fact that primer template mismatches can competitively be displaced by such oligonucleotides. As a result, it is generally possible to improve the specificity of the initiation of PCR reactions. The effect of such oligonucleotides is limited to the interaction with primer sequences. Such additional oligonucleotides do not interact with the nucleic acid chain to be amplified in sections between both primers. However, due to a molar excess of primers, non-specific interactions of primers with templates can occur during amplification. If such a non-specific event of primer extension takes place (initiation of an exponential side reaction) a fully functional primer binding site is formed as a result or as part of backward synthesis of a complementary strand of the by-product. The presence of such a complete primer binding site in the by-product results in a loss of the competitive effect of such additional oligonucleotides on primer binding. Thus, controlling the specificity of the binding of a primer to the template by such oligonucleotides makes only initiation of a side reaction less likely, but can hardly affect its exponential amplification after a by-product has been generated.

Further, usually labeled oligonucleotide probes are employed as part of a detection method for improving the specificity of the analysis for a specific proof of certain sequences. These probes do not affect exponential amplification substantially. Generally, probes need a sufficiently high concentration of nucleic acid chains and therefore, develop their effect on terminal stages of an amplification if there is enough product (e.g. TaqMan probes or LightCycler probes).

Generally, the specificity of the synthesis of an amplification method can be improved with the reduced generation and co-amplification of by-products that differ from the target sequence, for example contribute to an improvement of diagnostic methods.

It is an object of the present invention to provide a method and components that enable enzymatic synthesis and amplification of nucleic acid chains. It is intended to provide a new enzymatic method and components for the synthesis of nucleic acid chains as well as the amplification of nucleic acid chains.

A further object of the invention is to provide a method with improved specificity of the synthesis of target nucleic acid chains in an exponential amplification.

A further object of the invention is to provide means for implementing an exponential amplification method with improved specificity of the synthesis.

A further object of the invention is to provide means and methods that verify synthesized sequence parts between primers and are able to affect the efficacy of an amplification reaction or the duration of an amplification reaction of sequences, respectively depending on their matching with a sequence target.

A further object of the invention is to provide means and methods that enable the verification of the synthesized sequences in real-time and perform a control about the applicability of the synthesized sequences in further amplification cycles (real-time controlling/on-line quality control).

A further object of the invention is to provide means and methods that provide an exponential amplification method for a nucleic acid chain with a feedback function of verifying the contents of nucleic acid chains. Here, the feedback function of verifying is to be in parallel to the exponential amplification. Here, the individual amplification elements form a control system.

With the method according to the invention nucleic acid chains of a defined sequence composition are to be synthesized and amplified, respectively.

The problem of the invention is solved by the provision of amplification methods and corresponding means for performing the same.

Preferably, the amplification is an exponential amplification in which re-synthesized products of both primers (primer extension products) occur as templates for further synthesis steps. Here, primer sequences are at least partially copied, so that complementary primer binding sites are generated that are present as sequence segments of a double strand immediately after having been synthesized. In the amplification method synthesis steps of both strands and double strand opening steps of the re-synthesized sequence parts take place in mutual alternation. A sufficient double strand separation after a synthesis represents an important prerequisite for a further synthesis. Altogether, such an alternation of synthesis and double strand separation steps can result in an exponential amplification.

In the amplification method according to the invention the double strand opening of main products of the amplification (amplification of a target sequence-comprising nucleic acid chains) inter alia is by means of an oligonucleotide, referred to as activator oligonucleotide. The activator oligonucleotide preferably comprises sequence segments that correspond to the target sequence.

Disclosed is a method for amplification of nucleic acids in which substantially use is made of the fact that a pre-defined nucleic acid chain (target sequence) can be multiplied/amplified in the presence of a target sequence-specific activator oligonucleotide. The target sequence-specific activator oligonucleotide causes the separation of re-synthesized complementary primer extension products by means of strand displacement, so that a new primer oligonucleotide can attach to the respective template strand. The thus formed complex of a primer oligonucleotide and a template strand can initiate a new primer extension reaction. The thus formed primer extension products in turn function as templates, so that an exponential amplification reaction results.

Here, the activator oligonucleotide itself does not function as a template and preferably is inert over a primer extension reaction. The activator oligonucleotide functions as a co-factor in the reaction that regenerates the single-stranded state of the relevant strand segments of the templates needed for the reaction.

By the use of a set of components comprising at least one primer oligonucleotide, at least one polymerase, a set of substrates for polymerase (e.g., dNTPs), and at least one specific activator oligonucleotide a nucleic acid to be amplified can be amplified linearly.

By the use of such a set and a second primer oligonucleotide a nucleic acid to be amplified can be amplified exponentially, wherein the resulting specific primer extension products are used for further primer extension reactions as templates.

In detail, according to the invention strand separation is achieved by employing activator oligonucleotides having pre-defined sequences that preferably separate a re-synthesized double strand consisting of both specific primer extension products by means of a sequence-dependent nucleic acid mediated strand displacement. The resulting single-stranded segments of primer extension products comprise the target sequence as well as corresponding primer binding sites that can serve as binding sites for further primer oligonucleotides, so that an exponential amplification of nucleic acid chains to be amplified is achieved. Basically, the primer extension reactions and strand displacement reactions preferably take place at the same time. Amplification preferably takes place under reaction conditions that do not allow a spontaneous separation of both specific synthesized primer extension products.

Specific exponential amplification of a target sequence-comprising nucleic acid chain comprises a repetition of synthesis steps and double strand opening steps (activation steps for primer binding sites) as a mandatory prerequisite for the multiplication of the nucleic acid chain.

Opening of synthesized double strands is implemented as a reaction step that is to be sequence-specifically affected by the activator oligonucleotide. Said opening can be done completely, up to the dissociation of both complementary primer extension products, or may also be done partial.

According to the invention the activator oligonucleotide comprises sequence parts that can interact with the target sequence and further sequence parts that cause, permit or favor, respectively said interaction. In the course of the interaction with the activator oligonucleotide double-stranded sections of the synthesized primer extension products are converted into a single-stranded form via sequence-specific strand displacement. This process is sequence-dependent: only if the sequence of the synthesized double strand has a certain amount of complementarity with the corresponding sequence of the activator oligonucleotide a sufficient double strand opening occurs, so that the sequence parts essential for continuing the synthesis such as e.g. primer binding sites are converted into the single-stranded form, which corresponds to an "active state". Thus, the activator oligonucleotide specifically "activates" the re-synthesized primer extension products comprising the target sequence for further synthesis steps.

In contrast, sequence parts that do not comprise a target sequence are not converted into the single-stranded state and remain as double strand, which corresponds to an "inactive" state. The potential primer binding sites in such a double strand are disadvantaged or completely prevented from interaction with new primers, so that further synthesis steps on such "non-activated" strands generally do not take place. This lacking or reduced activation (i.e. conversion into a single-stranded state) of synthesized nucleic acid strands after a synthesis step results in the fact that in the subsequent synthesis step only a reduced amount of primers can successfully take part in a primer extension reaction.

Due to an exponential amplification of main products (a nucleic acid chain to be amplified that comprises target sequences) to be aimed several synthesis steps and activation steps (double strand opening steps) are combined in one amplification method and performed or repeated, respectively until the desired amount of the specific nucleic acid chain is provided.

Here, the reaction conditions (e.g., temperature) are designed such that a spontaneous separation of complementary primer extension products in the absence of an activator oligonucleotide is unlikely or significantly decelerated.

Thus, the increase in the specificity of an amplification to be aimed results from the sequence-dependency of the separation of complementary primer extension products comprising a target sequence: the activator oligonucleotide enables or favors this double strand separation as a result of the matching of its sequence parts with given sequence parts of the primer extension products. This matching is verified after each synthesis cycle by the activator oligonucleotide. The exponential amplification results as a consequence from successful repetitions from synthesis processes and sequence-specific strand displacements by the activator oligonucleotide, i.e. "activations" (double strand openings/double strand separations/strand displacement processes resulting in a single-stranded form of corresponding primer binding sites) of re-synthesized primer extension products.

Designing the activator oligonucleotide and the reaction conditions results in the fact that the interaction of the activator oligonucleotide with non-specific primer extension products is different. Due to an insufficient complementarity between the activator oligonucleotide and a non-specific primer extension product there is no sufficient double strand separation/strand displacement of such a non-specific primer extension product from its template strand. Thus, the non-specific product mainly remains in an "inactive", double-stranded state.

Thus, using a pre-defined activator oligonucleotide enables a sequence-dependent verification of the contents of primer extension products between individual synthesis steps during the exponential amplification and obtaining a selection or choice of sequences for subsequent synthesis steps. Here, distinction can be made between "active", single-stranded states of re-synthesized specific primer extension products as a result of a successful interaction with an activator oligonucleotide, and "inactive", double-stranded states of re-synthesized non-specific primer extension products as a result of a deficient and/or insufficient and/or reduced and/or decelerated interaction with an activator oligonucleotide.

The following effects result for an exponential amplification:

Under non-denaturant conditions separation of specifically synthesized strands takes place with cooperation of an activator oligonucleotide.

Exponential amplification of target sequence-comprising nucleic acid chains is sequence-controlled (main reaction). Said sequence control takes place after each synthesis step and includes sequence segments lying between primers and comprising a target sequence. The successful verification of the results of the synthesis after each synthesis step results in the separation of both specific primer extension products, which is the prerequisite for further specific synthesis steps.

During the amplification an initial generation of non-specific primer extension products basically cannot be excluded (by-products). Due to a template dependency such non-specific primer extension products immediately after their synthesis are generally present in the double-stranded form. However, the interaction with the activator oligonucleotide either completely fails to come or is limited, so that there is no strand separation or the strand separation is decelerated over the main reaction. Thus, there is no transfer of incorrect sequence information from one synthesis cycle to the next.

By the choice of the reaction conditions and the design of an activator oligonucleotide it is thus possible to specifically affect the efficacy of the regeneration of correct nucleic acid chain templates between single synthesis steps during an amplification method. Generally, the higher the degree of matching of the synthesized sequence with the given sequence of the activator oligonucleotide, the more successful the separation of the synthesized products and in turn the more successful the regeneration of correct templates from one synthesis step to the next. On the other hand, a sequence divergence in by-products results in an insufficient regeneration of template strands and thus, in a deceleration of the synthesis initiation and a reduction of the yield in each subsequent cycle. The whole exponential amplification of by-products either proceeds more slowly or does not takes place at all and/or remains at an undetectable level.

Reduction of the kinetics of the multiplication of by-products or even a prevention of the formation of certain types of by-products can result in an increase of the specificity of the amplification and thus, have influence on the specificity of the whole amplification-based tests.

Thus, the method enables a verification of the synthesized sequences in real-time, i.e. without stopping the reactions and thus, represents potential for the development of homogeneous assays in which all components of the assay are already present in the reaction mixture at the beginning of a reaction.

The method according to the invention represents an exponential amplification method for nucleic acid chains having a feedback function (regulation function). Simplified, the function of single structures can be summarized as follows (following an block diagram in accordance with DIN EN 60027-6):

The activator oligonucleotide together with both primers due to their pre-selected sequences defines a "set point" of the sequence that has to be synthesized during the amplification (the nucleic acid chain to be amplified that comprises the target sequence). The new primer extension products generated in each synthesis cycle form the "controlled value" (actual value). The activator oligonucleotide forms a part of a regulatory system (comprising "sensor", "regulator", and "control element") that can affect both the adjustment of the complementarity between newly synthesized strands and the strand of the activator oligonucleotide and the "adjustable variable" (as a result of said adjustment). Here, "adjustable variable" is meant to be the conversion of the synthesized strands into the single-stranded form ("activation of primer binding sites" or "regeneration of the template strands") in case of a sufficient matching between "actual value" and "set point" or the maintenance of the double-stranded form of the synthesized strands in case of insufficient matching ("failure of activation", primer binding sites remain in the double-stranded state and thus, inaccessible to new primer binding).

Since the content of the synthesized sequences is continuously controlled within/during the amplification the activator oligonucleotide can also be regarded as a "control oligonucleotide".

Control of the synthesized sequences by the activator oligonucleotide goes much further than primer regions or primer binding sites and comprises internal sequence regions of synthesized nucleic acid chains lying between both primers. In one embodiment the total sequence of the target sequence or of the nucleic acid chain to be amplified can be controlled.

Said control (verification of the sequence) already takes place in the stage of the exponential synthesis and has an effect on the result/yields of the synthesis reaction, and not only following the exponential amplification.

Altogether, by the use of pre-defined sequences in the activator oligonucleotide in combination with reaction conditions an influence can be exerted to the exponential amplification that goes beyond the primer regions. Said influence can result in a tolerance for certain sequence divergences in the target sequence or a suppression of the reaction rate of the amplification reaction up to a complete blockade of the exponential amplification.

TERMS AND DEFINITIONS

In the context of the present invention the terms used have the following meaning:

The term "oligonucleotide", as used here with respect to primers, activator oligonucleotide, probes, nucleic acid chain to be amplified, is defined as a molecule comprising two or more, preferably more than three deoxyribonucleotides and/or ribonucleotides and/or nucleotide modifications and/or non-nucleotide modifications. Its length comprises for example regions between 3 to 300 nucleotide units or analogues thereof, preferably between 5 to 200 nucleotide units or analogues thereof. Its exact size depends on a number of factors that in turn depend on the final function or use of the oligonucleotides.

The term "primer", as used herein, relates to an oligonucleotide, regardless of whether it is naturally occurring, e.g. in a purified restriction cleavage, or was synthetically produced. A primer is capable of acting as an initiation point of the synthesis if it is used under conditions in which the synthesis of a primer extension product that is complementary to a nucleic acid strand is induced, i.e. in the presence of nucleotides and an inducing agent such as e.g., DNA polymerase at a suitable temperature and a suitable pH value. Preferably, the primer for a maximum efficacy in the amplification is single-stranded. The primer has to be sufficiently long in order to initiate synthesis of the extension product in the presence of the inducing agent. The exact length of the primer depends on a number of factors, including the reaction temperature and the primer source and the application of the method. For example, the length of the oligonucleotide primer in diagnostic applications, according to the complexity of the target sequence, is between 5 to 100 nucleotides, preferably 6 to 40, and especially preferred 7 to 30 nucleotides. Short primer molecules generally require lower reaction temperatures to carry out their primer function in order to form sufficiently stable complexes with the template, or higher concentrations of other reaction components, for example DNA polymerases, so that primer template complexes formed can sufficiently be lengthened.

The primers used here are selected such that they are "substantially" complementary to the various strands of each specific sequence to be amplified. This means, that the primers have to be sufficiently complementary to hybridize with their respective strands and to initiate a primer extension reaction. Thus, for example the primer sequence does not have to reflect the exact sequence of the target sequence. For example, a non-complementary nucleotide fragment can be attached to the 5' end of the primer, wherein the remaining primer sequence is complementary to the strand. In another embodiment single non-complementary bases or longer non-complementary sequences can be inserted into a primer, provided that the primer sequence has a sufficiently large complementarity with the sequence of the strand to be amplified, in order to hybridize therewith and thus, generate a primer template complex capable for the synthesis of the extension product.

In the course of the enzymatic synthesis of a strand complementary to the template a primer extension product is generated that is completely complementary to the template strand.

Tm—Melting Temperature

The melting temperature of a complementary or partially complementary double strand is generally understood to be a measured value of a reaction temperature at which ca. half of the strands is present as a double strand and the other half is present as a single strand. The system (association and dissociation of strands) is in equilibrium.

Due to a number of factors that can affect the Tm of a double strand (e.g., sequence length, CG content of the sequence, buffer conditions, concentration of divalent metal cations, etc.) the Tm of a nucleic acid to be amplified is to be determined under the same conditions as the intended amplification reaction.

Because the measurable melting temperature depends on multiple reaction parameters, e.g., the respective buffer conditions and respective concentrations of the reaction partners, the melting temperature is meant to be a value that was measured in the same reaction buffer as the exponential amplification, at concentrations of both complementary components of a double strand of about 0.1 µmol/l to about 10 µmol/l, preferably in a concentration of about 0.3 µmol/l to ca. 3 µmol/l, preferably at ca. 1 µmol/l. The respective value of the melting temperature is a guide value that correlates with the stability of a corresponding double strand.

The deoxyribonucleoside triphosphates (dNTPs) dATP, dCTP, dGTP, and TTP (or dUTP, or dUTP/TTP mixture) are added to the synthesis mixture in adequate amounts. In one embodiment at least one further type of dNTP analogues can be added to the synthesis mixture in addition to the dNTPs. In one embodiment, these dNTP analogues comprise for example a characteristic mark (e.g., biotin or fluorescent dye), so that when built into a nucleic acid strand also this mark is integrated in the nucleic acid strand. In another embodiment, these dNTP analogues comprise at least one modification of the sugar phosphate proportion of the nucleotide, e.g., alpha-phosphorothioate-2'-deoxyribonucleoside triphosphates (or other modifications imparting a nuclease resistance to a nucleic acid strand), 2',3'-dideoxyribonucleoside triphosphates, acyclo-nucleoside triphosphates (or other modifications resulting in the termination of a synthesis). In a further embodiment, these dNTP analogues comprise at least one modification of a nucleobase, e.g., iso-cytosines, iso-guanosines (or also other modifications of the nucleobases of the extended genetic alphabet), 2-amino-adenosines, 2-thiouridines, inosines, 7-deaza-adenosines, 7-deaza-guanosines, 5-me-cytosines, 5-propyl-uridines, 5-propyl-cytosines (or also other modifications of nucleobases that can be built in by a polymerase compared to natural nucleobases and result in the change of the strand stability). In a further embodiment, a dNTP analogue comprises both a modification of the nucleobase and a modification of the sugar phosphate proportion. In a further embodiment, at least one further type of dNTP analogues is added to the synthesis mixture instead of the at least one natural dNTP substrate.

The agent inducing the nucleic acid synthesis can be an enzyme-entrapping compound or a system that acts such that as a result the synthesis of the primer extension product is caused. Suitable enzymes for this purpose comprise e.g., DNA polymerases such as Bst polymerase and its modifications, Vent polymerase and other—preferably thermostable DNA polymerases that enable the incorporation of the nucleotides in the correct manner, whereby the primer extension products are formed that are complementary to each synthesized nucleic acid strand. Generally, the synthesis is initiated on the 3' end of each primer and then progresses toward the 5' direction along the template strand until the synthesis is completed or interrupted.

Preferably, there are used polymerases that are capable of strand displacement. These include for example the large fragment of the Bst polymerase or its modifications (e.g., Bst 2.0 DNA polymerase), the Klenow fragment, Vent exo minus polymerase, Deepvent exo minus DNA polymerase, a large fragment of the Bsu DNA polymerase, a large fragment of the Bsm DNA polymerase.

In one embodiment, there are preferably employed polymerases that have no 5'-3'-exonuclease activity or no 5'-3'-FEN activity, respectively.

In one embodiment, at least two different polymerases are employed, for example polymerases capable of strand displacement and such that have a 3'-5'-proof reading activity.

In preferred embodiments, there are employed polymerases with a hot start function that only exert their function after having reached a certain temperature.

Reaction Conditions

The reaction conditions comprise among others buffer conditions, temperature conditions, duration of the reaction, and concentrations of respective reaction components.

During the reaction the amount of the specifically produced nucleic acid to be amplified accumulates in an exponential manner. The reaction comprising the synthesis of the extension products can be carried out for the production of the desired amount of the specific nucleic acid sequence as long as needed. The method according to the invention is preferably carried out continuously. In a preferable embodiment, the amplification reaction proceeds at the same reaction temperature, wherein the temperature is preferably between 50° C. and 70° C. In another embodiment, the reaction temperature can also be controlled variably, so that single steps of the amplification each proceed at different temperatures.

The reagents needed for the exponential amplification are preferably present already at the beginning of a reaction in the same batch. In another embodiment, reagents can also be added in later stages of the method.

Preferably, no helicases or recombinases are used in the reaction mixture for the separation of the newly synthesized double strands of the nucleic acid to be amplified.

In a preferred embodiment, the reaction mixture does not contain biochemical energizing compounds such as ATP.

The amount of the nucleic acid to be amplified that is present at the beginning of the reaction can be present in one batch between a few copies and several billions of copies. In case of diagnostic use the amount of the nucleic acid chain to be amplified can be unknown.

In the reaction also further nucleic acids not to be amplified can be present. These nucleic acids can be derived from natural DNA or RNA or their equivalents. In one embodiment, control sequences are present in the same batch that have to be amplified in parallel to the nucleic acid to be amplified.

Preferably, a molar excess of approximately $10^3$:1 to approximately $10^{15}$:1 (ratio of primer:template) of the primers used and of the activator oligonucleotide is added to the reaction mixture that comprises template strands for the synthesis of the nucleic acid chain to be amplified.

The amount of the target nucleic acids may not be known if the method according to the invention is used in diagnostic applications, so that the relative amount of the primer and of the activator oligonucleotide with respect to the complementary strand cannot certainly be determined. The amount of the primer added will generally be present in the molar excess with respect to the amount of the complementary strand (template) if the sequence to be amplified is contained in a mixture of complex long-chain nucleic acid strands. A large molar excess is preferred in order to improve efficacy of the method.

The concentrations of primer 1, primer 2 and activator oligonucleotide used are for example in ranges between 0.01 µmol/l and 100 µmol/l, preferably between 0.1 µmol/l and 100 µmol/l, preferably between 0.1 µmol/l and 50 µmol/l, better between 0.1 µmol/l and 20 µmol/l. The high concentration of components can increase the rate of the amplification. The respective concentrations of individual components can independently be varied in order to achieve the desired reaction result.

The concentration of polymerase is in the range between 0.001 µmol/l and 50 µmol/l, preferably between 0.01 µmol/l and 20 µmol/l, better between 0.1 µmol/l and 10 µmol/l.

The concentration of individual dNTP substrates is in ranges between 10 µmol/l and 10 mmol/l, preferably between 50 µmol/l and 2 mmol/l, better between 100 µmol/l and 1 mmol/l. The concentration of dNTP can affect the concentration of divalent metal cations. Optionally, this is correspondingly adjusted.

As divalent metal cations there are for example used Mg2+. As the corresponding anion Cl, acetate, sulphate, glutamate, etc. can be used, for example.

The concentration of divalent metal cations is adapted for example to the region that is optimal for the corresponding polymerase and comprises regions between 0.1 mmol/l and 50 mmol/l, better between 0.5 mmol/l and 20 mmol/l, preferably between 1 mmol/l and 15 mmol/l.

In general, enzymatic synthesis takes place in a buffered aqueous solution. As buffer solutions dissolved conventional buffer substances such as Tris HCl, Tris acetate, potassium glutamate, HEPES buffer, sodium glutamate in common concentrations can be used. The pH value of said solutions is usually between 7 and 9.5, preferably about 8 to 8.5.

The buffer conditions may be adapted for example in accordance with the recommendations of the manufacturer of the polymerase used.

Further substances such as so-called Tm depressors (e.g., DMSO, betaines, TPAC), etc. can be added to the buffer. Such substances decrease the melting temperature ("Tm depressors") of double strands and thus, can have a positive influence on the opening of double strands. Also, polymerase-stabilizing components such as Tween 20 or Triton 100 can be added to the buffer in the usual amounts. EDTA or EGTA can be added in conventional amounts for complexation of heavy metals. Also, polymerase-stabilizing substances such as trehalose or PEG 6000 can be added to the reaction mixture.

Preferably, the reaction mixture does not contain any inhibitors of the strand displacement reaction and no inhibitors of a polymerase-depending primer extension.

In one embodiment, the reaction mixture contains DNA-binding dyes, preferably intercalating dyes such as e.g., EvaGreen or SybrGreen. Such dyes can optionally enable the detection of the reproduction of nucleic acid chains.

The reaction mixture can further contain proteins or other substances that for example originate from an original material and that preferably do not affect the amplification.

Temperature Conditions

The temperature has a substantial influence on the stability of the double strands.

In a preferred embodiment, during the amplification reaction no temperature conditions are used that substantially result in a separation of double strands of the nucleic acid to be amplified in the absence of an activator oligonucleotide. In this way, it is to be ensured that the double strand separation of nucleic acid chains to be amplified depends on the presence of the activator oligonucleotide throughout the amplification.

At a temperature approximately equal to the measured melting temperature (Tm) of the nucleic acid to be amplified a spontaneous separation of both strands of the nucleic acid to be amplified occurs, so that the influence of the activator oligonucleotide on the separation of synthesized strands and thus, on the sequence specificity of the amplification is minimally limited.

In an exponential amplification that has to proceed less sequence-specifically (i.e. little activator oligonucleotide-dependent) the reaction temperature can be for example around the melting temperature (i.e. Tm plus/minus 3° C. to 5° C.) of the nucleic acid to be amplified. At such a temperature sequence differences between activator oligonucleotide and the synthesized primer extension product generally can be well tolerated during a strand displacement reaction.

Also in the temperature range of ca. (Tm minus 3° C.) to ca. (Tm minus 10° C.) there can still be a spontaneous strand separation of synthesized primer extension products, although with less efficacy. The influence of the activator oligonucleotide on the sequence specificity of the nucleic acid to be amplified is higher than at temperature conditions around the melting temperature (Tm) of the nucleic acid chain to be amplified.

Certainly, with a decreasing reaction temperature strand separation substantially takes place owing to the interaction of the re-synthesized double strand with the activator oligonucleotide, but duplexes of primers can spontaneously decompose at an extension temperature under the mentioned conditions, i.e. without sequence-dependent strand displacement by the activator oligonucleotide. For example, the reaction temperature in a less sequence-specific amplification is in ranges between ca. (Tm minus 3° C.) and ca. (Tm minus 10° C.), preferably between ca. (Tm minus 5° C.) and ca. (Tm minus 10° C.). At such a temperature sequence differences between the activator oligonucleotide and the synthesized primer extension product are tolerated less well during a strand displacement reaction.

A high sequence specificity of the amplification of the method is achieved above all when the re-synthesized strands of the nucleic acid to be amplified under reaction conditions cannot spontaneously dissociate into single strands. In such a case, sequence-specific strand displacement by the activator oligonucleotide plays a decisive role for a sequence-specific strand separation and is mainly responsible for the sequence specificity of the amplification reaction. This can generally be achieved when the reaction temperature is significantly below the melting temperature of both strands of the nucleic acid to be amplified and no further components are used for a strand separation, for example no helicases or recombinases. For example, the reaction temperature in a sequence-specific amplification is in ranges between ca. (Tm minus 10° C.) and ca. (Tm minus 50° C.), preferably between ca. (Tm minus 15° C.) and ca. (Tm minus 40° C.), better between ca. (Tm minus 15° C.) and ca. (Tm minus 30° C.).

In a preferred embodiment of the amplification the maximum reaction temperature during the whole amplification reaction will not be increased above the melting temperature of the nucleic acid chain to be amplified.

In a further embodiment of the amplification the reaction temperature can be increased above the melting temperature of the nucleic acid chains to be amplified at least once. The increase in temperature may be for example at the beginning of the amplification reaction and result in a denaturation of double strands of a genomic DNA. Here, it has to be noted that during such a step the dependency of double strand separation on the effect of the activator oligonucleotide is canceled or at least significantly reduced.

The reaction temperatures of the individual steps of the amplification reaction can be in the range of ca. 15° C. to ca. 85° C., better in the range of ca. 15° C. to ca. 75° C., preferably in the range of ca. 25° C. to ca. 70° C.

In examples 2 and 3 described below a reaction temperature of the amplification reaction of 65° C. was used, wherein the Tm of the nucleic acids to be amplified was between ca. 75° C. and ca. 80° C. Thus, the double strand of the nucleic acid to be amplified was stable under the reaction conditions and the amplification reaction was sequence-specific (see, example 3).

Generally, the reaction temperature can optimally be adjusted for each individual reaction step, so that for each reaction step such a temperature is brought about. Thus, the amplification reaction comprises a repeating change in temperatures that is repeated cyclically. In an advantageous embodiment of the method reaction conditions for several reaction steps are unified, so that the number of temperature steps is lower than the number of reaction steps. In such a preferred embodiment of the invention at least one of the steps of the amplification takes place at a reaction temperature that differs from the reaction temperature of other steps of the amplification. Thus, the reaction does not proceed isothermal, but the reaction temperature is cyclically changed.

For example, during amplification at least two temperature ranges are used that are mutually brought about (cyclic change in temperatures between individual temperature ranges). In one embodiment, for example the lower temperature range comprises temperatures between 25° C. and 60° C., better between 35° C. and 60° C., preferably between 50° C. and 60° C., and the upper temperature range comprises temperatures between 60° C. and 75° C., better between 60° C. and 70° C., for example.

In a further embodiment, for example the lower temperature range comprises temperatures between 15° C. and 50° C., better between 25° C. and 50° C., preferably between 30° C. and 50° C., and the upper temperature range comprises temperatures between 50° C. and 75° C., better between 50° C. and 65° C., for example.

In a further embodiment, for example the lower temperature range comprises temperatures between 15° C. and 40° C., better between 25° C. and 40° C., preferably between 30° C. and 40° C., and the upper temperature range comprises temperatures between 40° C. and 75° C., better between 40° C. and 65° C., for example.

The temperature can be maintained constant in the respective range or changed as a temperature gradient (falling or rising).

Further explanations on the temperature adjustments are given in detail in the following sections in the embodiments.

Each temperature brought about can be maintained for a certain period of time, so that in this way an incubation step results. Thus, the reaction mixture can be incubated during an amplification at a selected temperature for a certain period of time. This time can be different for the respective incubation step and can depend on the progress of the respective reaction at a given temperature (e.g., primer extension or strand displacement etc.). The time of an incubation step can comprise the following ranges: between 0.1 sec and 10.000 sec, better between 0.1 sec and 1000 sec, preferably between 1 sec and 300 sec, more preferably between 1 sec and 100 sec.

By such a temperature change individual reaction steps can preferably be carried out at a selected temperature. In this way, yields of a respective reaction step can be improved. Temperature change or temperature alteration between individual temperature ranges can optionally be brought about several times within one synthesis cycle. Thus, a synthesis cycle can comprise at least one temperature alteration. Such a temperature alteration can for example be carried out in a PCR instrument/thermocycler as a matter of routine as a time program.

In one embodiment, an amplification method is preferred in which at least one of the steps comprising strand displacement and at least one of the steps comprising primer extension reactions take place at the same time or in parallel and under the same reaction conditions. In such an embodiment, for example a primer extension reaction of at least one primer oligonucleotide (e.g., of the first primer oligonucleotide) can preferably take place at temperature conditions in the lower temperature range. In contrast, strand displacement takes place with cooperation of an activator oligonucleotide and the one further primer extension reaction (e.g., of the second primer oligonucleotide) preferably in the reaction step in the upper temperature range.

In a further embodiment, an amplification method is preferred in which at least one of the steps comprising strand displacement by the activator oligonucleotide and at least one of the steps comprising primer extension reactions are carried out at different temperatures. In such an embodiment, for example primer extension reactions of at least one primer oligonucleotide (e.g., of the first primer oligonucleotide and/or of the second primer oligonucleotide) can preferably take place at temperature conditions in the lower temperature range. In contrast, strand displacement takes place with cooperation of an activator oligonucleotide preferably in the reaction step in the upper temperature range.

In a further preferred embodiment, all the steps of an amplification reaction proceed under the same reaction conditions.

In such an embodiment, the amplification method can be carried out under isothermal conditions, i.e. no temperature changes are required to carry out the method. In such a preferred embodiment of the invention the whole amplification reaction takes place under a constant temperature, i.e. the reaction is isothermal. The duration of such a reaction comprises for example the following ranges: between 100 sec and 30.000 sec, better between 100 sec and 10.000 sec, still better between 100 sec and 1000 sec. In section "Examples" it is shown that it is possible to adapt structures of individual reaction components and the corresponding reaction steps to each other to such an extent that an isothermal reaction is possible.

The sum of all method steps resulting in a doubling of the amount of a nucleic acid chain to be amplified can be referred to as synthesis cycle. Such a cycle can correspondingly proceed isothermal or be characterized in its course by changes of the temperature. The temperature changes can be repeated from cycle to cycle and made identical.

Of particular advantage are amplification methods in which the maximum achievable temperature only substantially allows a strand separation with the cooperation of an activator oligonucleotide if more than 5 nucleotides of the third region of the activator oligonucleotide are able to complementary bind to the first primer extension product, it is more preferred if more than 10, still more preferred if more than 20 nucleotides of the activator oligonucleotide bind to the first primer extension product. Generally, the longer the required binding between activator oligonucleotide and the complementary strand of the first primer extension product, before the synthesized strands dissociate under reaction conditions, the more specific the amplification reaction. In detail, by extending or shortening the third section of the activator oligonucleotide the desired degree of specificity can be determined.

A method step when repeated can take place at a constant temperature over the total duration of the method or also at different temperatures.

Individual method steps each can be carried out consecutively by adding individual components. In an advantageous embodiment all the reaction components required to carry out an amplification are present at the beginning of an amplification in one reaction mixture.

The start of an amplification reaction can be by adding one component, e.g., by adding a nucleic acid chain comprising a target sequence (e.g., a start nucleic acid chain), or a polymerase or divalent metal ions, or also by bringing about reaction conditions needed for amplification, e.g., adjusting a required reaction temperature for one or more method steps.

Amplification can be carried out until the desired amount of nucleic acid to be amplified has been achieved. In another embodiment, the amplification reaction is carried out for a period of time that would have been sufficient, in the presence of a nucleic acid to be amplified, to get a sufficient amount. In another embodiment, the amplification reaction is carried out over a sufficient number of synthesis cycles (duplication times) that would have been sufficient, in the presence of a nucleic acid to be amplified, to get a sufficient amount.

The reaction can be stopped by various interventions. For example, by changing the temperature (e.g., cooling or heating, wherein for example polymerase is interfered in its function) or by adding a substance that stops a polymerase reaction, e.g., EDTA or formamide.

Following the amplification the amplified nucleic acid chain can be used for further analyses. Here, synthesized nucleic acid chains can be analyzed by various detection methods. For example, fluorescence-labeled oligonucleotide probes can be used or sequencing methods (Sanger sequencing or next generation sequencing), solid phase analyses such as microarray or bead array analyses etc. The synthesized nucleic acid chain can be used as a substrate/template in further primer extension reactions.

In an advantageous embodiment, the progress of the synthesis reaction during the reaction is monitored. This can be done for example by employing intercalating dyes, e.g., SYBRgreen or Evagreen, or by employing labeled primers (e.g., Lux primers or Scorpion primers) or by employing fluorescence-labeled oligonucleotide probes.

The amplification method can be applied to verify the presence of a target nucleic acid chain in a biological material or a diagnostic material during a diagnostic method.

First Primer Oligonucleotide:

The first primer oligonucleotide (FIGS. 5 and 6) comprises a first primer region and a second region. The first primer region is able to bind to a substantially complementary sequence within the nucleic acid to be amplified or equivalents thereof and to initiate a primer extension reaction. The second region comprises a polynucleotide tail that is able to bind to an activator oligonucleotide and thus, to cause a spatial proximity between the activator oligonucleotide and other parts of the first primer extension product that is sufficient to initiate a strand displacement by the activator oligonucleotide. The second region of the first primer oligonucleotide further comprises at least one modification (a nucleotide modification or non-nucleotide modification) that prevents the polymerase from copying the polynucleotide tail by inhibiting the continuation of the polymerase-dependent synthesis. Said modification is located for example at the transition between the first and the second regions of the first primer oligonucleotide. Accordingly, the first primer region of the first primer oligonucleotide can be copied by a polymerase, so that a sequence complementary to this region can be generated by the polymerase during the synthesis of the second primer extension product. The polynucleotide tail of the second region of the first primer oligonucleotide is preferably not copied by the polymerase. In one embodiment, this is achieved by the modification in the second region that stops the polymerase before the polynucleotide tail. In a further embodiment, this is achieved by nucleotide modifications in the second region, wherein the entire polynucleotide tail substantially consists of such nucleotide modifications and thus, cannot be copied by polymerase.

In one embodiment, each first primer oligonucleotide is specific for one nucleic acid to be amplified each.

In one embodiment, each first primer oligonucleotide is specific for at least two of the nucleic acids to be amplified that each comprise substantially different sequences.

In one embodiment, the first primer oligonucleotide is labeled with a characteristic marker, e.g., a fluorescent dye (e.g., TAMRA, fluorescein, Cy3, Cy5) or an affinity marker (e.g., biotin, digoxigenin) or an additional sequence fragment, e.g., for binding a specific oligonucleotide probe for detection or immobilization or barcode labeling.

Second Primer Oligonucleotide:

Oligonucleotide that with its 3' segment is able to bind to a substantially complementary sequence within the nucleic acid to be amplified or equivalents thereof and to initiate a specific second primer extension reaction. Thus, this second primer oligonucleotide is able to bind to the 3' segment of a first specific primer extension product of the first primer oligonucleotide and to initiate a polymerase-dependent synthesis of a second primer extension product.

The length of the second primer oligonucleotide can be between 15 and 100 nucleotides, preferably between 20 and 60 nucleotides, particularly preferred between 30 and 50 nucleotides.

In one embodiment, each of the second primer oligonucleotides is specific for one nucleic acid to be amplified each.

In one embodiment, each of the second primer oligonucleotides is specific for at least two of the nucleic acids to be amplified that each comprise substantially different sequences.

In one embodiment, the second primer oligonucleotide is labeled with a characteristic marker, e.g., a fluorescent dye (e.g., TAMRA, fluorescein, Cy3, Cy5) or an affinity marker (e.g., biotin, digoxigenin) or an additional sequence fragment, e.g., for binding a specific oligonucleotide probe for detection or immobilization or barcode labeling.

Primer Extension Product:

A primer extension product (also referred to as primer elongation product) is generated by enzymatic (polymerase-dependent) extension of a primer oligonucleotide as a result of a template-dependent synthesis that is catalyzed by a polymerase.

A primer extension product comprises the sequence of the primer oligonucleotide in its 5' segment and the sequence of the extension product (also referred to as elongation product) that was synthesized by a polymerase in a template-dependent manner. The extension product synthesized by the polymerase is complementary to the template strand to which it was synthesized.

A specific primer extension product (FIGS. 12 to 14) (main product) comprises sequences of the nucleic acid chain to be amplified. It is the result of a specific synthesis or a proper performance of an intended primer extension reaction in which the nucleic acid chain specifically to be amplified serves as a template. In a preferred embodiment, the sequence of the synthesized primer extension products completely corresponds to the expected sequence of a nucleic acid to be amplified. In another embodiment, divergences in the obtained sequence from the theoretically expected sequence can be tolerated. In one embodiment, the degree of matching of the sequence obtained as a result of an amplification with the sequence of the theoretically expected nucleic acid to be amplified is for example between 90% and 100%, preferably the matching is above 95%, ideally the matching is above 98% (based on the proportion of the synthesized bases).

The length of the extension product of a specific primer extension product can be between 10 and 300 nucleotides, better between 10 and 180 nucleotides, preferably between 20 and 120 nucleotides, particularly preferably between 30 and 80 nucleotides.

A non-specific primer extension product (by-product) comprises for example sequences that have been generated as a result of a non-specific or incorrect or unintended primer extension reaction. These include for example primer extension products that have been generated as a result of a false initiation result (false priming) or as a result of other side reactions, including polymerase-dependent sequence changes such as base substitution, deletion etc. The degree of sequence divergences of non-specific primer extension products generally exceeds the ability of activator oligonucleotides to successfully displace such double-stranded by-products from their templates, so that amplification of such by-products proceeds slower or is completely absent. The degree of acceptance or the limit of tolerance for divergences for example depends on reaction temperatures and the type of sequence divergence. Examples of non-specific primer extension products are primer dimers or sequence variants that do not correspond to the nucleic acid to be amplified, e.g., sequences that do not comprise a target sequence.

Assessment as to a sufficient specificity of the amplification is often linked to the problem formulation. In many amplification methods a certain degree of non-specificity of the amplification reaction can be tolerated as long as the desired result can be obtained. In a preferred embodiment, the proportion of nucleic acid chains to be amplified in the total result of the reaction is more than 1%, better more than 10%, more preferably more than 30%, based on the total amount of re-synthesized strands.

Nucleic Acid to be Amplified

The nucleic acid to be amplified is a nucleic acid chain that is to be sequence-specifically or at least mainly sequence-specifically amplified by the polymerase by means of the exponential amplification by employing primers and activator oligonucleotides.

The length of the nucleic acid to be amplified can be between 20 and 300 nucleotides, better between 30 and 200 nucleotides, preferably between 40 and 150 nucleotides, particularly preferred between 50 and 100 nucleotides.

The nucleic acid chain to be amplified can comprise one or more target sequences or equivalents thereof. Furthermore, a nucleic acid to be amplified can comprise the sequences that are substantially complementary to a target sequence and that are multiplied with a similar efficacy such as a target sequence in an amplification reaction and comprises a target sequence or sections thereof. In addition to a target sequence the nucleic acid to be amplified can further include sequence segments, for example primer sequences, sequences with primer binding sites and/or sequence segments for binding detection probes, and/or sequence segments for sequence coding of strands by barcode sequences and/or sequence segments for binding to a solid phase. The primer sequences or sequence portions thereof as well as primer binding sites or sequence portions thereof may for example belong to sequence parts of a target sequence.

In one embodiment, the nucleic acid to be amplified corresponds to a target sequence.

In another embodiment, the target sequence forms a part of the sequence of the nucleic acid chain to be amplified. Such a target sequence can be flanked by the 3' side and/or 5' side of further sequences. These further sequences can for example comprise binding sites for primers or portions thereof, and/or primer sequences or portions thereof, and/or binding sites for detection probes, and/or adaptor sequences for complementary binding to a solid phase (e.g., in the context of microarrays, or bead-based analyses) and/or barcoding sequences for a digital signature of sequences.

To start the amplification a nucleic acid chain has to be added to the reaction mixture at the beginning of the reaction that acts as the initial template for the synthesis of the nucleic acid chain to be amplified. Said nucleic acid chain is referred to as the start nucleic acid chain. Said start nucleic acid chain prescribes the arrangement of individual sequence elements that are relevant for the formation/synthesis/exponential amplification of a nucleic acid chain to be amplified.

In a preferred embodiment, the initial template (start nucleic acid chain), that is added to an amplification reaction at the beginning or is added to the reaction mixture, corresponds to the sequence composition of the nucleic acid chain to be amplified.

In initial stages of the amplification reaction and in its further course the respective primers bind to the corresponding binding sites in the start nucleic acid chain and initiate the synthesis of specific primer extension products. Such specific primer extension products during the amplification exponentially accumulate and increasingly take the role of templates for the synthesis of complementary primer extension products in an exponential amplification.

By the repeated template-dependent synthesis processes during an exponential amplification there is formed thus the nucleic acid chain to be amplified.

Toward the end of an amplification reaction the main product of the reaction (the nucleic acid to be amplified) can mainly be single-stranded or mainly form a complementary double strand. This can for example be determined by the relative concentrations of both primers and the appropriate reaction conditions.

Equivalents of the nucleic acid to be amplified comprise nucleic acids of substantially identical information content. For example, complementary strands of a nucleic acid to be amplified have an identical information content and may be referred to as being equivalent.

Target Sequence

In one embodiment, a target sequence is a segment of a nucleic acid chain to be amplified that can serve as the characteristic sequence of the nucleic acid to be amplified. Said target sequence can serve as a marker for the presence or absence of another nucleic acid. Thus, said other nucleic acid serves as a source of the target sequence and for example can comprise a genomic DNA or RNA or parts of the genomic DNA or RNA (e.g., mRNA), or equivalents of the genomic DNA or RNA of an organism (e.g., cDNA, modified RNA such as rRNA, tRNA, microRNA etc.), or defined changes of the genomic DNA or RNA of an organism, for example mutations (e.g., deletions, insertions, substitutions, additions, sequence multiplication, e.g., repeat multiplication in context of microsatellite instability), splice variants, rearrangement variants (e.g., T cell receptor variants) etc. The individual target sequences may stand for a phenotypic feature, for example for antibiotic resistance or have prognostic information and thus, be of interest for diagnostic assays/tests. As the source/origin for a target sequence such a nucleic acid can for example comprise the target sequence as a sequence element of its strand. Thus, a target sequence can serve as a characteristic marker for a certain sequence content of another nucleic acid.

The target sequence can be single-stranded or double-stranded. It can be substantially identical to the nucleic acid to be amplified or only represent a part of the nucleic acid to be amplified.

Equivalents of the target sequence comprise nucleic acids of substantially identical information content. For example, complementary strands of a target sequence have an identical information content and can be referred to as being equivalent. Also, RNA and DNA variants of a sequence are examples of an equivalent information content.

In context of the material preparation for an amplification reaction such a target sequence can be isolated from its original sequence environment and prepared for the amplification reaction.

In a preferred embodiment, a nucleic acid to be amplified comprises a target sequence. In one embodiment, the target sequence corresponds to the nucleic acid to be amplified. In a further preferred embodiment, a start nucleic acid chain comprises a target sequence. In one embodiment, the target sequence corresponds to a start nucleic acid chain.

Start Nucleic Acid Chain

To start the amplification a nucleic acid chain has to be added to the reaction mixture at the beginning of the reaction that acts as the initial template for the synthesis of the nucleic acid chain to be amplified (FIG. 23B). Said nucleic acid chain is referred to as the start nucleic acid chain. Said start nucleic acid chain prescribes the arrangement of individual sequence elements that are relevant for the formation/synthesis/exponential amplification of a nucleic acid chain to be amplified.

Such a start nucleic acid chain can be single-stranded or double-stranded at the beginning of the reaction. If the complementary strands of the start nucleic acid chain are separated from each other the strands, regardless of whether the nucleic acid originally was double- or single-stranded, can serve as a template for the synthesis of specific complementary primer extension products.

Activator Oligonucleotide:

The activator oligonucleotide (FIG. 10) is a preferably single-stranded nucleic acid chain that includes a pre-defined substantially complementary sequence in a part of the first primer extension product that is specifically generated during the amplification of the nucleic acid to be amplified. In this way, the activator oligonucleotide can substantially complementary bind to the first primer oligonucleotide and at least to the 5' segment of the specific extension product of the first primer oligonucleotide. In one embodiment, the activator oligonucleotide in its inner sequence segment comprises nucleotide modifications that prevent polymerase from synthesizing a complementary strand using the activator oligonucleotide as a template if the first primer oligonucleotide is complementary bound to the activator oligonucleotide. The activator oligonucleotide under the chosen reaction conditions is further able to completely or partially displace the second specific primer extension product from the binding with the first specific primer extension product via strand displacement. Here, the activator oligonucleotide with its complementary regions is attached to the first specific primer extension product. In case of a successful binding between the activator oligonucleotide and the first specific primer extension product this results in a restoration of a single-stranded stage of the 3'-standing segment of the second specific primer extension product that is suitable for the binding of the first primer oligonucleotide, so that a new primer extension reaction can take place. During the synthesis of the second primer extension product the activator oligonucleotide can be separated from the binding with the first primer extension product by means of strand displacement, for example by polymerase and/or by the second primer oligonucleotide.

Strand Displacement:

This refers to a process that by action of a suitable means results in a complete or partial separation of a first double strand (for example consisting of A1 and B1 strands) and in simultaneous/parallel formation of a new second double strand, wherein at least one of the strands (A1 or B1) takes part in the formation of said new second strand. Here, distinctions can be made between two types of strand displacement.

In a first type of the strand displacement formation of a new second double strand can be by using an already existing complementary strand that at the beginning of the reaction is generally present as a single-stranded form. Here, the means of the strand displacement (for example, a pre-formed single-stranded strand C1 that has a complementary sequence to strand A1, acts on the first already formed double strand (A1 and B1) and complementary binds to strand A1, whereby strand B1 is displaced from the binding with strand A1. If the displacement of B1 proceeds completely, so the result of the C1 action is a new double strand (A1:C1) and a single-stranded strand B1. If the displacement of B1 proceeds incomplete, so the result depends on several factors. For example, a complex of partially double-stranded A1:B1 and A1:C1 can be present as an intermediate product.

In a second type of the strand displacement the formation of a new second double strand can be with a simultaneously proceeding enzymatic synthesis of the complementary strand, wherein a strand of the first pre-formed double strand is present as a template for the synthesis by the polymerase. Here, the means of the strand displacement (for example, polymerase having a strand displacement ability) acts on the already pre-formed double strand (A1 and B1) and synthesizes a new strand D1 complementary to strand A1, wherein at the same time strand B1 is displaced from the binding with strand A1.

In the scientific literature many examples from nature and molecular biology/bio-nanotechnology are described including the process of the strand displacement. Examples of both protein-mediated or enzyme-mediated strand displacement and examples of nucleic acid chain-mediated strand displacement have been described. Also, examples of strand displacement processes with already pre-formed single-stranded nucleic acids have been described as well as strand displacement processes in which a new strand is only re-synthesized during the strand displacement.

In the protein or enzyme-mediated strand displacement process (e.g., mediated by polymerase or helicase) the separation of a duplex is by the aid of a protein or enzyme. Strand displacement by means of a DNA polymerase for example takes place with the simultaneous synthesis of a complementary strand during strand displacement amplification (SDA) (U.S. Pat. No. 5,455,166 and Walker et al. PNAS 89, 1992, 392-396). The polymerase used has to cause nucleic acid polymerization and displace the downstream strand, but not reduce the one 5'→3' exonuclease activity. The Klenow fragment of *E. coli* polymerase I, Bsu polymerase or the large fragment of *Bacillus stearothermophilus* (Bst polymerase and modifications thereof) as well as Vent polymerase, DeepVent polymerase and other polymerases capable of strand displacement, for example have such properties.

Another example of polymerase-associated strand displacement is the amplification method LAMP (Loop mediated isothermal amplification). Another example of protein-mediated or enzyme-mediated strand displacement is represented by recombinase reaction, e.g., with RecA. Here, an interaction between a protein nucleic acid strand complex and a double strand results in a partial strand displacement of the double strand and dissociation of the protein nucleic acid strand complex. Recombinase polymerase amplification (RPA) uses this process and is described in patent application WO 2008035205. A protein or enzyme-mediated strand displacement process is often accompanied by energy consumption, e.g., in the form of ATP in RPA.

In a nucleic acid-mediated strand displacement (FIGS. 4 and 22) a substitution of identical or similar strands is with the simultaneous/parallel formation of a new double strand. In the literature this process is synonymously referred to as strand replacement. Said phenomenon is involved/significantly participated in branch migration of homologous duplexes, overcoming of intra-molecular hairpin structures by means of single-stranded oligonucleotides, DNA cloning, DNA-based "toehold"-mediated cascade reactions, and SNP analyses. The nature of the phenomenon of the nucleic acid-based or nucleic acid-mediated strand displacement has been studied in detail since more than 40 years and is shown in many articles ("The Kinetics of Oligonucleotide Replacement", Reynaldo et al. J. Mol. Biol. 2000, 297, 511-;

"Formation of a single base mismatch impedes spontaneous DNA branch migration" Panyutin et al. J. Mol. Biol. 1993, 230, 413-; "The kinetics of spontaneous DNA branch migration" Panyutin et al. PNAS 1994, 91, 2021-; "Programmable energy landscapes for Kinetic control of DNA strand displacement" Machinek et al. Nature Commun 2014, 5, 5324-; "Remote Toehold: A mechanism for flexible control of DNA hybridization Kinetics" Genot et al. JACS, 2011, 133, 2177-; "A new class of homogeneous nucleic acid probes based on specific displacement hybridization" Li et al. NAR, 20102, v30, No. 2 e5; "On the biophysics and kinetics of toehold-mediated DNA strand displacement", Srinivas et al. NAR 2013, 10641-58; "Modelling toehold-mediated RNA strand displacement" Sulc et al. Biophysical Journal, 2015, 1238-; "Branch Migration through DNA sequence heterology" Biswas et al. J. Mol. Biol. 1998, 279, 795-; "Toehold-mediated nonenzymatic DNA strand displacement as a platform for DNA genotyping" Khodakov et al. JACS 2013, 135, 5612-; "Protected DNA Strand Displacement for enhanced single nucleotide discrimination in double stranded DNA" Khodakov et al. Nature, Scientific Reports, 2015, 5, 8721-; "Allele-Specific Holliday Junction Formation: a new mechanism of allelic discrimination for SNP Scoring" Yang et al. Genome Research 2003, 1754-; "Conditionally fluorescent molecular probes for detecting single base changes in double-stranded DNA" Chen et al. Nature Chemistry, 2013, 782-; "Optimizing the specificity of nucleic acid hybridization" Zhang et al. Nature Chemistry, 2012, 208-). In these and other sources of the prior art structural requirements of involved nucleic acid strands for a successful strand displacement process, initiation of the strand displacement, kinetics of the strand displacement, reaction conditions as well as the influence of sequence divergences in individual sections of the involved structures on strand displacement have been studied and described in detail. Here, sequence-dependency of the strand displacement process plays a particularly large role. Owing to the possibility to use pre-defined specific nucleic acid chains for a nucleic acid-mediated strand displacement the result of said process also is sequence-specific. Said sequence-dependency in the past resulted in the employment in the proof of differences in the nucleic acid chains by using branch migration (said process is related to strand displacement and described in patent application: Lishanski et al. U.S. Pat. No. 6,232,104. Use of modified nucleic acid strands in the employment in branch migration is described in Wetmur et al U.S. Pat. No. 5,958,681.)

Nucleic acid-mediated strand displacement in literature is also regarded as an example for competitor-induced dissociation of molecular complexes, see "A general mechanism for competitor-induced dissociation of molecular complexes", Paramanathan et al. Natur Commun, 2014, 5207-).

A skilled person is aware of several types of the nucleic acid-mediated strand displacement process, e.g., "Toehold-Mediated" Strand Displacement or "3-Branch-Migration".

Under the term "nucleic acid-mediated strand displacement" a sum/series of intermediate steps is brought together that can be in equilibrium with each other and as a result lead to the transient or permanent opening of a first pre-formed duplex (consisting of complementary strands A1 and B1) and formation of a new second duplex (consisting of complementary strands A1 and C1), wherein A1 and C1 are complementary. Said process is illustrated in example 1 (see below).

It is known that an en essential structural requirement for the initiation of a strand displacement is to cause a spatial proximity between a duplex end (pre-formed first duplex of A1 and B1) and a single-stranded strand (C1) that initiates the strand displacement (wherein A1 and C1 can form a complementary strand). Such a spatial proximity can preferably be caused by means of a single-stranded overhang (in the literature examples with short overhangs are known, in English referred to as "toehold", see literature above) that complementary binds the single-stranded strand (C1) transiently or permanently, and thus brings complementary segments of strands C1 and A1 sufficiently close, so that a successful strand displacement of strand B1 can be initiated. Efficacy of the initiation of the nucleic acid-mediated strand displacement generally is the higher the closer the complementary segments of strands A1 and C1 are positioned to each other.

A further essential structural requirement of the efficient continuation of a nucleic acid-mediated strand displacement in inner segments is a high complementarity between strands (e.g., between A1 and C1) that have to form a new double strand. So, for example individual nucleotide mutations (in C1) can result in the disruption of a strand displacement (e.g., described for branch migration).

The present invention uses the ability of complementary nucleic acids for sequence-dependent nucleic acid-mediated strand displacement.

The patent or application file contains at least one drawing executed in color. Copies of this patent or patent application publication with color drawings will be provided by the Office upon request and payment of the necessary fee.

Preferred embodiments of the invention are explained in detail in the figures and examples.

FIG. 1 shows the problem with the nucleic acid amplification by PCR. Theoretically, only the desired target sequence is to be amplified. However, since the primers can also bind to other irrelevant parts of the nucleic acid present in the reaction mixture by-products that can interfere with the result are generated due to (undesired) side reactions.

FIG. 2 shows the amplification of a nucleic acid to be amplified by employing the first primer oligonucleotide and the second primer oligonucleotide.

FIG. 3 describes components of the structures illustrated in FIG. 2.

FIG. 4 schematically shows the strand displacement mechanism.

FIGS. 5-6 schematically show the structure of the first primer oligonucleotide.

FIGS. 7-8 schematically show the interaction between the first primer oligonucleotide and the template as well as the synthesis of the first primer extension product.

FIG. 9 schematically shows the structure of the primer extension product of the first primer oligonucleotide.

FIG. 10 schematically shows the structure of the activator oligonucleotide.

FIGS. 11-12 schematically show the interaction between structures during the primer extension of the first primer oligonucleotide.

FIGS. 13-14 schematically show the interaction between structures during the primer extension of the second primer oligonucleotide.

FIGS. 15-21 schematically show the interaction between individual regions of components during the amplification.

FIG. 22 schematically shows the interaction of the structures in strand displacement.

FIG. 23A schematically shows the interaction of the structures during nucleic acid amplification by amplification of the first primer oligonucleotide and the second primer oligonucleotide and further the development of the activator oligonucleotide and the resulting strand displacement.

FIGS. 23B-23D schematically show some embodiments of structures of a start nucleic acid chain and its use as a template at the beginning of the reaction.

FIGS. 24-29 show the results of the strand displacement in example 1.

FIG. 30 shows the trend of the signal intensity during an exponential amplification as described in example 2.

FIG. 31 shows the course of a capillary electrophoresis after an exponential amplification as described in example 2.

FIG. 32 shows the trend of the signal intensity during an amplification according to the invention, as described in example 3.

The reaction designated with →1 corresponds to the employment of a template with perfect match (SEQ ID NO:26) in a concentration of 10 µmol/l.→2 shows the reaction with a mismatch template (SEQ ID NO:27) in an amount of 10 µmol/l, and the reaction designated with →3 represents a negative control.

Figure 34:
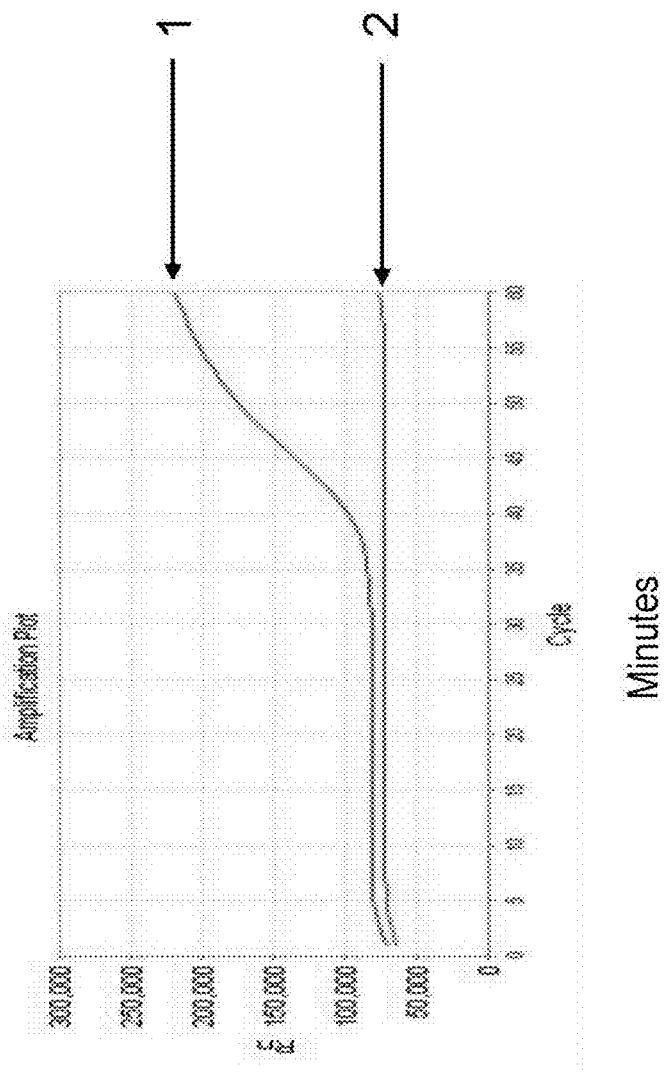
Figure 34:
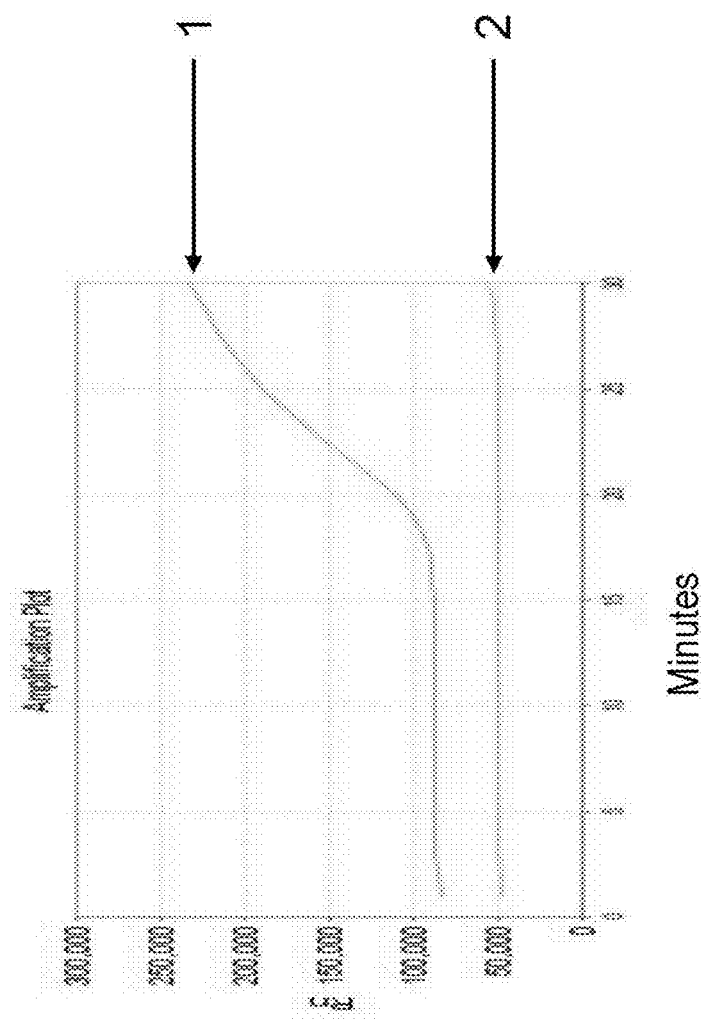

FIG. 34 shows the trend of the signal intensity during an amplification according to the invention, as described in example 5.

FIG. 35 shows the trend of the signal intensity during an amplification according to the invention, as described in example 6.

In the method (FIGS. 8 to 21) according to the invention a single-stranded nucleic acid chain or a double-stranded nucleic acid that was converted into the single-stranded form can serve as a starting material. The amplification preferably is sequence-specific, i.e. preferably the nucleic acid to be amplified is multiplied.

A nucleic acid chain to be amplified, a first specific primer oligonucleotide, a second primer, and an activator oligonucleotide that takes part in the separation of the re-synthesized strands as well as a suitable polymerase and substrates such as dNTPs serve as components of the amplification system. The amplification takes place in a buffer solution under conditions that allow a primer extension reaction of both primers as well as support a strand displacement by the activator oligonucleotide for the separation of both primer extension products.

In one embodiment, all the method steps are performed under conditions that do not allow a separation of synthesized primer extension products in the absence of a suitable activator oligonucleotide. For example, the temperature of the reaction solution is selected such that the Tm of a double strand of both primer extension products is significantly above the reaction temperature.

Under these conditions a separation of both primer extension products takes places depending on the effect of the activator oligonucleotide. Said activator oligonucleotide is able to complementary bind to the first primer extension product and thereby displace the second primer extension product from its binding with the first primer extension product. In order to initiate said strand displacement reaction the first primer oligonucleotide is provided with a polynucleotide tail in its second region that can transiently bind to the activator oligonucleotide under reaction conditions and thus, causes a spatial proximity to other regions of the first primer extension nucleotide. After the initiation of the strand displacement by the activator oligonucleotide the second primer extension product is displaced from its binding with the first primer extension product. So, its 3'-standing segment becomes free and is available for further binding of a first primer oligonucleotide.

The polynucleotide tail of the first primer oligonucleotide preferably cannot be copied by a polymerase. This can be achieved either by using appropriate modifications in this region or by inserting a first blocking unit between the first primer region and the second primer region of the first primer oligonucleotide.

The synthesis of the second primer extension product takes place after the second primer oligonucleotide has been bound to the first primer extension product in its 3'-standing segment. Said segment preferably does not bind to the activator oligonucleotide and is sufficiently long to bind the second primer oligonucleotide and support a successful primer extension reaction. The synthesis of the second primer extension product takes place by displacing the activator oligonucleotide from the binding with the first primer extension product. For example, this can be done by polymerase-dependent strand displacement or also by strand displacement by means of the second primer.

Both primer extension products include copyable regions and mutually serve as a template. The activator oligonucleotide does not serve as a template. This can preferably be achieved by the use of nucleotide modifications that certainly can complementary bind to the first primer extension product, but are not accepted as a template by the polymerase. Examples of such nucleotide modifications are nucleotide compounds having modified phosphate sugar backbone portions, e.g., 2'-O-Alkyl-RNA modifications (e.g., 2'-OMe), LNA modifications, or morpholino modifications. In general, the presence of such modifications in a strand prevents a DNA-dependent polymerase from reading such a strand. The number of such modifications can be different, generally a few modifications (between 1 and 20) may be sufficient in order to prevent a polymerase from reading such a strand. Such nucleotide modifications can for example be used at or around the site of binding of the first primer oligonucleotide to the activator oligonucleotide and/or as constituents of the second region of the first primer oligonucleotide.

Owing to the use of such modifications the polymerase function is locally hindered, so that certain segments of the structures used cannot be copied by the polymerase and mainly remain single-stranded. In this single-stranded form they can further bind reaction components and thus, exercise their function.

Under reaction conditions that do not denaturate a double strand the use of the sequence-dependent nucleic acid-mediated strand displacement results in the sequence-specific separation of both primer extension products during the amplification reaction in the described method: a sufficient complementarity between re-synthesized extension fragments of the primer oligonucleotides with the sequence of an activator oligonucleotide given at the beginning of an amplification is a prerequisite for a successful strand displacement and thus, can have influence on the efficacy of the strand separation of a double strand (consisting of the first and second primer extension products). In case of minor divergences strand displacement and thus, also strand separation are decelerated. This can cause a deceleration of the entire reaction. With an increase in the difference in the sequence of the re-synthesized extension products and the sequence of the activator oligonucleotide given at the beginning of the reaction there is an increasing disability of the strand displacement that ultimately is no longer able to bring about a sufficient separation of both primer extension products. Both re-synthesized strands can no longer sufficiently be separated from each other, so that their binding sites are no longer accessible for primer oligonucleotides. In general, this leads to the termination of an amplification of sequences having sequence divergences.

In summary, not only the specificities of the binding of both primers with their templates, but also the nature of the sequence segments between the primers can have influence on the amplification, namely in that these sections allow a sufficient strand displacement or not, in accordance with their matching in the sequence of the activator oligonucleotide given at the beginning of the reaction. Thereby, the described method possibly overall can have a higher specificity than the conventional amplification methods.

Preferably, the method according to the invention does not use specific proteins that cause a strand substitution between the activator oligonucleotide and a double strand, e.g., RecA. Rather, the method according to the invention uses the temporal coupling between a strand displacement by means of a nucleic acid chain (activator oligonucleotide) given at the beginning of the reaction and a concurrent template-dependent strand polymerization by means of polymerase. This concurrent coupling of both processes is made possible on the one hand by sequence-specific structures of components (sequence-specific activator oligonucleotides and sequence-specific primers) as well as their specific combination. On the other hand, the activity of the polymerase is sequence-specifically controlled: for example, the activator oligonucleotide does not serve as a template and the synthesis of the second primer extension product is position-specifically stopped at the first primer oligonucleotide.

The specific amplification further results by using the components at reaction conditions that preferably do not allow a spontaneous separation of re-synthesized primer extension products.

Surprisingly, we have succeeded in suitably linking these processes, namely such that both processes (sequence-specific strand displacement and primer extension) preferably can proceed in one batch. In this way, a homogeneous amplification system can be arranged that comprises sequence-specific primer oligonucleotides, a sequence-specific activator oligonucleotide, polymerase, and nucleotide substrates (dNTP). With such an amplification system a nucleic acid to be amplified can be multiplied. The sequences of both primer oligonucleotides and the sequence of the activator oligonucleotide are matched with the nucleic acid to be amplified.

The method (FIG. 23) comprises several processes that are described below. These processes can be performed in one batch or in separate batches. If the processes are to be performed in one batch, so they can be performed under the same conditions, e.g., isothermal, or under different conditions, e.g., in thermocycling. Preferably, primer oligonucleotides and the activator oligonucleotide are present at the beginning of the reaction. However, a sequential addition of individual reagents is also possible.

Also, combinations with other amplification methods are possible, e.g., with PCR, wherein the PCR for example first is performed over 1 to 10 cycles and subsequently, it is for example went on working under isothermal conditions.

In an advantageous embodiment, the method for the specific amplification of nucleic acid chains comprises the following steps:
a) hybridizing a first primer oligonucleotide to the 3' segment of a strand of a nucleic acid chain to be amplified, wherein the nucleic acid chain to be amplified comprises a target sequence, wherein the first primer oligonucleotide comprises:
   a first primer region in the 3' segment of the first primer oligonucleotide that can sequence-specifically bind to a strand of a nucleic acid chain to be amplified,
   a second region that is directly or via a linker linked to the 5' end of the first primer region of the first primer oligonucleotide and that comprises a polynucleotide tail which is suitable for binding an activator oligonucleotide and supporting strand displacement (step c) by the activator oligonucleotide, wherein the polynucleotide tail remains substantially uncopied by polymerase under the selected reaction conditions,
b) extending the first primer oligonucleotide by means of a polymerase to form a first primer extension product comprising sequence parts that are complementary to the target sequence and/or to the nucleic acid chain (a) to be amplified,
c) binding the activator oligonucleotide to the polynucleotide tail of the second region of the first extended primer oligonucleotide, wherein the activator oligonucleotide comprises:
   a first single-stranded region that can bind to the polynucleotide tail of the second region of the first primer oligonucleotide,
   a second single-stranded region that is substantially complementary and can bind to the first region of the first primer oligonucleotide,
   a third single-stranded region that is substantially complementary to at least a segment of the extension product, which has been synthesized by polymerase, of the first primer extension product,
   wherein the activator oligonucleotide does not serve as template for a primer extension of the first primer oligonucleotide,
d) binding the activator oligonucleotide to the first primer region of the first extended primer oligonucleotide by displacing the strand of the nucleic acid chain to be amplified that is complementary to said first primer region,
e) binding the activator oligonucleotide to the complementary segment of the extension product of the first extended primer oligonucleotide by displacing the strand of the nucleic acid chain to be amplified that is complementary to said extension product, wherein the 3' segment of the first primer extension product becomes single-stranded,
f) hybridizing a second oligonucleotide primer to the first primer extension product, wherein the 3' segment of the second oligonucleotide primer comprises a sequence that can hybridize to the first primer extension product; and
g) extending the second oligonucleotide primer with polymerase to form a second primer extension product, wherein the extension takes place up to and including the first primer region of the first primer oligonucleotide and said first primer region is copied by the polymerase, wherein the polynucleotide tail of the second region remains uncopied,
h) repeating steps a)-g) until the desired degree of amplification has been achieved.

In one embodiment, the method is performed under conditions that do not allow a separation of complementary strands of the nucleic acid to be amplified in the absence of activator oligonucleotide.

In one embodiment, copying the polynucleotide tail is caused in the second primer region by a stopping region for the polymerase that is arranged between the first and the second regions.

In one embodiment, the third single-stranded region of the activator oligonucleotide is substantially complementary to the segment of the extension product, which has been synthesized by the polymerase, of the first primer extension product, which immediately follows the first primer region, wherein:

In one embodiment, the third single-stranded region of the activator oligonucleotide is completely complementary to the mentioned 5' segment of the extension product of the first primer extension product, wherein the length of said complementary sequence part comprises the following ranges: of at least 3 to 70 nucleotides, better of at least 5 to 50 nucleotides, preferably of 5 to 40 nucleotides, further preferably of 5 to 30 nucleotides, particularly preferred of 5 to 20 nucleotides.

In a further embodiment, the sequences of the third single-stranded region of the activator oligonucleotide and the corresponding sequence of the mentioned 5' segment of the extension product of the first primer extension product comprise complementary sequences except for one sequence position (a pair of nucleotides/bases) having a non-complementary base pairing (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides.

In a further embodiment, the sequences of the third single-stranded region of the activator oligonucleotide and the corresponding sequence of the mentioned 5' segment of the extension product of the first primer extension product comprise complementary sequences except for two sequence positions (a pair of nucleotides/bases) having a non-complementary base pairing (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides.

In a further embodiment, the sequences of the third single-stranded region of the activator oligonucleotide and the corresponding sequence of the mentioned 5' segment of the extension product of the first primer extension product comprise complementary sequences (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides, further said segments comprise non-complementary regions in at least three sequence positions, wherein said positions are within the 5' segment of the third section of the activator oligonucleotide.

In a further embodiment, the sequences of the third single-stranded region of the activator oligonucleotide and the sequence of the mentioned 5' segment of the extension product of the first primer extension product comprise complementary sequences except for at least one and at most ten sequence positions having a non-complementary base pairing (in the meaning of Watson-Crick base pairing) over a length of at least 3 to 70 nucleotides, better of at least 5 to 60 nucleotides, preferably of 10 to 40 nucleotides, particularly preferred of 10 to 20 nucleotides, wherein in sequence positions having non-complementary base pairing (in the meaning of Watson-Crick base pairing) at least one modified nucleotide having modified nucleobases is involved. Such modified nucleobases comprise for example nucleobases with enhanced binding of natural nucleobases (e.g., 2-amino adenines), or with attenuated binding such as for example so-called universal bases such as inosines or 5-nitroindole. The modified nucleobases are preferably located in the third sequence region of the activator oligonucleotide.

In a further embodiment of the method step (e) of the method is further modified and comprises:

the binding of the activator oligonucleotide to the complementary segment of the extension product of the first extended primer oligonucleotide by displacing the strand of the nucleic acid chain to be amplified that is complementary to said extension product until said complementary strand of the nucleic acid to be amplified is detached from the first primer extension product, wherein the 3' segment of the first primer extension product becomes single-stranded.

In a further embodiment of the method step (f) of the method is further modified and comprises:

the hybridization of a second oligonucleotide primer to the first primer extension product, wherein at the same time there is at least a partial displacement of the activator oligonucleotide from the binding with the first extension product by strand displacement.

In a further embodiment of the method step (g) of the method is further modified and comprises a displacement of the activator oligonucleotide from the binding with the first primer extension product with the participation of the polymerase.

In a further embodiment of the method step (h) of the method is further modified and comprises: optionally the binding of the activator oligonucleotide to the uncopied polynucleotide tail of the first extended primer oligonucleotide and a displacement of the second primer extension product from the binding to the first primer extension product with the simultaneous formation of a complementary double strand with a segment of the first specific extension product of the first primer oligonucleotide.

In a further embodiment of the method the method is further modified and comprises: h) continuation of the reaction under conditions that allow a repletion of steps (a) to (g).

In a further embodiment of the method the method is further modified and comprises: the simultaneous amplification of the first and second primer extension products in an exponential reaction by using the first and second primer oligonucleotides and the activator oligonucleotide, wherein the formed primer extension products function as a template for the mutual synthesis.

Figure 23C:
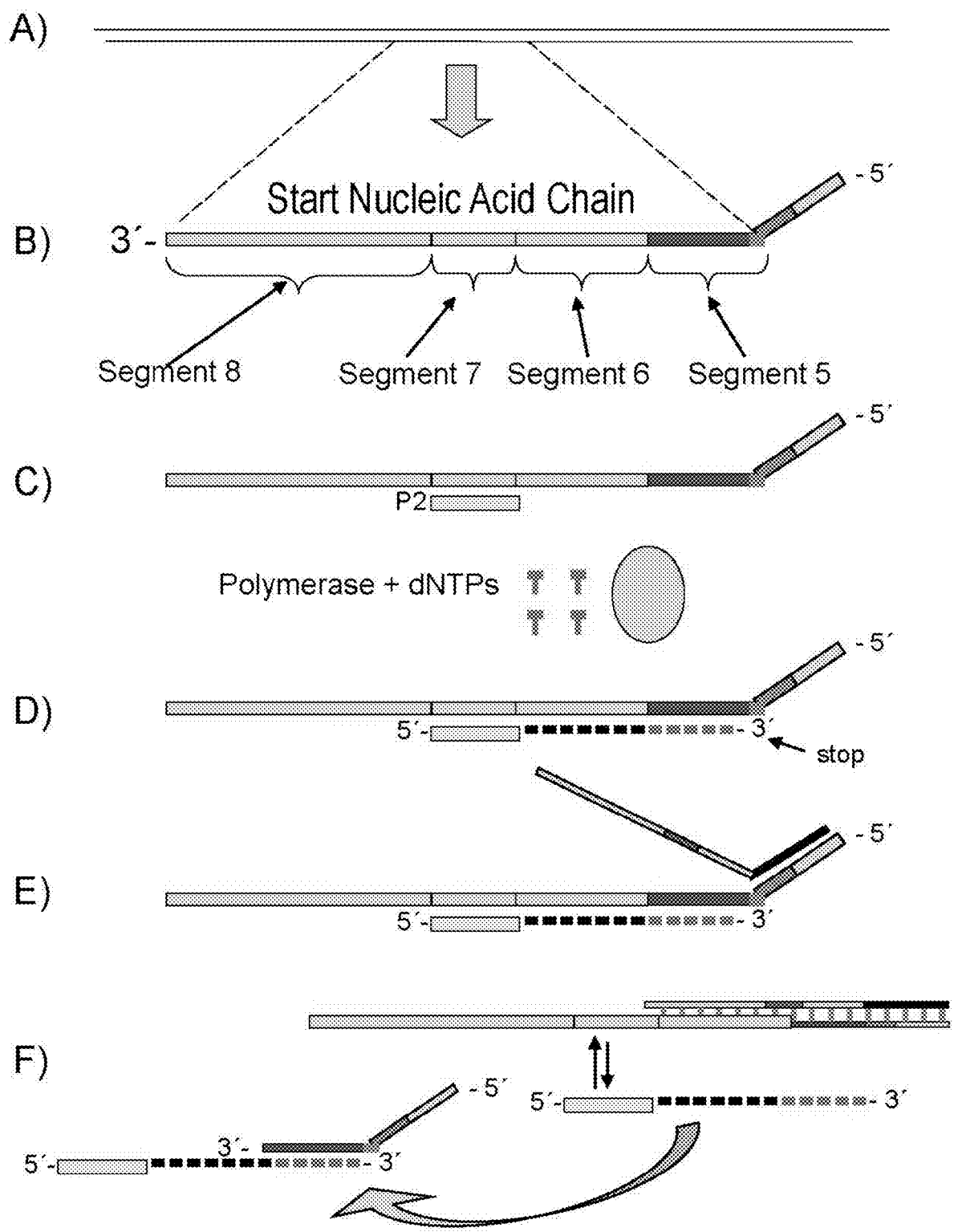

Preferred Embodiments of a Start Nucleic Acid Chain:

The nucleic acid chain employed or to be employed at the beginning of the amplification reaction can be referred to as a start nucleic acid chain (FIGS. 23B-23D).

Its function can be seen in that it represents the initial template that permits a correct positioning of primers, the synthesis sections between both primers as well as the initiation of binding and extension processes. In a preferred embodiment, a start nucleic acid chain comprises a target sequence.

By binding primers to their respective primer binding sites (PBS 1 and PBS 2) and initiating appropriate primer extension reactions first primer extension products are generated. These are synthesized as specific copies of the nucleic acid chain present at the beginning of the reaction.

In one embodiment, this nucleic acid chain (start nucleic acid chain) to be used in the reaction mixture before the beginning of the amplification reaction can be identical to the nucleic acid chain to be amplified. By the amplification reaction only the amount of such nucleic acid chain is increased.

In a further embodiment, the nucleic acid to be amplified and the start nucleic acid chain differ in that certainly the start nucleic acid chain prescribes the arrangement of individual sequence elements of the nucleic acid chain to be amplified, but the sequence composition of the start nucleic acid chain can differ from the sequence of the nucleic acid chain to be amplified. For example, in context of the primer binding and extension during an amplification new sequence contents (regarding the start nucleic acid chain) can be integrated into the nucleic acid chain to be amplified. Moreover, sequence elements of a nucleic acid chain to be amplified can differ from such sequence elements of a start nucleic acid chain in their sequence composition (e.g., primer binding sites or primer sequences). The start nucleic acid only serves as an initial template for the specific synthesis of the nucleic acid chain to be amplified. Said initial template can remain in the reaction mixture until the end of the amplification. However, by the exponential nature of the amplification the amount of the nucleic acid chain to be amplified at the end of an amplification reaction predominates the amount of a start nucleic acid chain to be added to the reaction.

In a further embodiment, the start nucleic acid chain can comprise at least one sequence part that is not amplified. Thus, such a start nucleic acid chain is identical to the sequence to be amplified. Such sections not to be amplified can represent a sequence part of a start nucleic acid chain for example as a result of sequence preparing steps or as a result of previous sequence manipulation steps, respectively.

In a preferred embodiment, the start nucleic acid chain to be added to the reaction mixture before the beginning of the reaction includes at least one target sequence.

In a further embodiment, such a start nucleic acid chain includes at least one target sequence and still further sequences that are non-target sequences. During the amplification sequence segments comprising the target sequence are exponentially multiplied and thereby, other sequence segments either are not exponentially multiplied at all or only partially.

Structure of a Start Nucleic Acid Chain

An example of such a start nucleic acid chain is a nucleic acid chain that includes a target sequence and that comprises a sequence fragment A and that comprises a sequence fragment B.

Sequence fragment A of the start nucleic acid chain comprises a sequence that has a significant homology with the sequence of one of both primers used in the amplification or is substantially identical to the copyable portion of the 3' segment of the one primer. In the synthesis of a complementary strand to this segment a complementary sequence is generated that represents a respective primer binding site.

Sequence fragment B of the start nucleic acid chain comprises a sequence suitable to complementary bind a corresponding further primer or its 3' segment to form an extendable primer template complex, wherein sequence fragment A and sequence fragment B with respect to each other mainly/preferably are non-complementary.

In a preferred embodiment, a start nucleic acid chain is added to the reaction mixture of an amplification method that has the following properties:

Preferably, sequence fragment A is in the 5' segment of the start nucleic acid chain. Preferably, said sequence fragment A forms a restriction of the nucleic acid chain strand in the 5' direction.

Preferably, sequence fragment B is downstream of sequence fragment A.

In a preferred embodiment, said sequence fragment B forms a restriction of the nucleic acid chain strand in the 3' direction. In a further embodiment, said sequence fragment B does not represent a restriction of the nucleic acid chain strand in the 3' direction, but is flanked by further sequences from the 3' side. Preferably, said sequences are no target sequences and do not participate in the exponential amplification.

In one embodiment, the target sequence comprises at least one of both sequence fragment A or sequence fragment B. In a further embodiment, the target sequence is between sequence fragment A and sequence fragment B.

In one embodiment, such a start nucleic acid chain can function as a template for the synthesis of a first primer extension product (FIG. 23B). Here, the start nucleic acid chain for example during a primer extension reaction by using the second primer oligonucleotide can be provided as a sequence segment of a longer starting nucleic acid chain (FIG. 23B, section A) during a preparatory step before the exponential amplification and converted to a single-stranded form. For example, the starting nucleic acid chain can be a genomic DNA or RNA and serves as a source of the target sequence (schematically illustrated in FIG. 23B, section A as double strand). The start nucleic acid chain in the 5' segment of the nucleic acid chain comprises a segment 1 (FIG. 23B, section B) that comprises sequence parts of the second primer oligonucleotide and represents a restriction in the 5' direction, a segment 2 that comprises a target sequence or portions thereof, a segment 3 that comprises a primer binding site for the first primer oligonucleotide, and a segment 4 that comprises a non-target sequence that is localized in the 3' segment of the start nucleic acid chain and thus, flanks segment 3 on the 3' side.

During the initiation of the amplification the first primer at least with the 3' segment of its first region can bind to such a start nucleic acid chain in segment 3 (FIG. 23B, section C) and appropriately be extended in the presence of a polymerase and nucleotides. Thereby, a first primer extension product is generated that is complementary to the template strand of the start nucleic acid chain and is restricted in its length (FIG. 23B, section D). During the amplification reaction such a primer extension product can be sequence-specifically detached from its template strand via an activator oligonucleotide (FIG. 23B, sections E-F), so that the corresponding sequence parts in the 3' segment of the now synthesized first primer extension product are available as a binding site for the second primer oligonucleotide (FIG. 23B, section F).

In a preferred embodiment, thus a start nucleic acid chain comprises the following sequence fragments (FIG. 23B):

sequence segment 1 (referred to as segment 1 in FIG. 23B) that comprises a sequence that has a significant homology with the sequence of the second primer or is substantially identical to the copyable portion of the 3' segment of the second primer. Said sequence segment 1 is in the 5' segment of the start nucleic acid chain, preferably said sequence segment 1 forms a restriction of the nucleic acid chain strand in the 5' direction.

sequence segment 3 (referred to as segment 3 in FIG. 23B) that comprises a sequence that is suitable to complementary bind the first region of the first primer or its 3' segment to form an extendable primer template complex. Preferably, sequence segment 3 is downstream of sequence segment 1.

target sequence that is partially or entirely between segment 1 and segment 3 (this portion of the target sequence is referred to as segment 2 in FIG. 23B). In a preferred embodiment, the target sequence comprises at least one of segment 1 and/or segment 3.

optionally, the start nucleic acid chain in the 3' segment comprises flanking sequence parts (referred to as segment 4 in FIG. 23B) that are not amplified.

In a further embodiment, such a start nucleic acid chain can function as a template for the synthesis of a second primer extension product (FIG. 23 C).

Here, the start nucleic acid chain for example during a primer extension reaction by using the first primer oligonucleotide can be provided as a sequence segment of a longer starting nucleic acid chain (FIG. 23C, section A) during a preparatory step before the exponential amplification and converted to a single-stranded form. For example, the starting nucleic acid chain can be a genomic DNA or RNA and serves as a source of the target sequence (schematically illustrated in FIG. 23C, section A, as double strand). The start nucleic acid chain (FIG. 23C, section B) in the 5' segment of the nucleic acid chain comprises a segment 5 that comprises sequence parts of the first primer oligonucleotide and represents a restriction in the 5' direction, a segment 6 that comprises a target sequence or portions thereof, a segment 7 that comprises a primer binding site for the second primer oligonucleotide, and a segment 8 that comprises a non-target sequence that is localized in the 3' segment of the start nucleic acid chain and thus, flanks segment 7 on the 3' side.

During the initiation of the amplification the first primer at least with the 3' segment of its first region can bind to such a start nucleic acid chain in segment 7 (FIG. 23C, section C) and appropriately be extended up to the stop section of the first primer oligonucleotide in the presence of a polymerase and nucleotides. Thereby, a second primer extension product is generated that is complementary to the template strand of the start nucleic acid chain and is restricted in its length (FIG. 23C, section D). During the amplification reaction such a primer extension product can be sequence-specifically detached from its template strand via an activator oligonucleotide (FIG. 23C, sections E-F), so that the corresponding sequence parts in the 3' segment of the now synthesized second primer extension product are available as a binding site for the first primer oligonucleotide (FIG. 23C, section F).

In this preferred embodiment, a start nucleic acid chain comprises the following sequence fragments (FIG. 23C):
  sequence segment 5 (referred to as segment 5) that comprises a sequence that has a significant homology with the sequence of the region of the first primer or is substantially identical to the copyable portion of the first region of the first primer. Said sequence segment 7 is in the 5' segment of the start nucleic acid chain and is flanked by a non-copyable oligonucleotide tail (in analogy to the first primer oligonucleotide), preferably said sequence segment 7 forms a restriction of the copyable nucleic acid chain strand in the 5' direction.
  sequence segment 7 (referred to as segment 7) that comprises a sequence that is suitable to complementary bind a second primer or its 3' segment to form an extendable primer template complex. Preferably, sequence segment 7 is downstream of sequence segment 5.
  target sequence that is partially or entirely between segment 5 and segment 7 (in FIG. 23 this portion of the target sequence is referred to as segment 6). In a preferred embodiment, the target sequence comprises at least one of segment 5 and/or segment 7.
  optionally, the start nucleic acid chain in the 3' segment comprises flanking sequence parts (referred to as segment 8 in FIG. 23C) that are not amplified.
Mode of Functioning of the Start Nucleic Acid Chain
At the beginning of the amplification reaction the start nucleic acid chain functions as a template for the initial generation of respective primer extension products. Thus, it represents the starting template for the nucleic acid chain to be amplified. The start nucleic acid chain does not necessarily have to be identical to the nucleic acid chain to be amplified. By binding and extending both primers during the amplification reaction substantially both primers prescribe which sequences on both terminal segments of the nucleic acid chain to be amplified are generated during the amplification.

In a preferred embodiment of the method reaction conditions that do not denaturize a double strand are maintained during the exponential amplification process. Hence, it is advantageous for the start nucleic acid chain to have a restriction in its 5' sequence segment that can be extended by a polymerase, which results in a stop in the enzymatic extension of a respective primer (e.g., segments 1 or 5 or 9 or 12 in FIG. 23D). Thus, the length of the primer extension fragments generated under reaction conditions is restricted. This can have a beneficial effect on the strand displacement by the activator oligonucleotide and lead to a dissociation of the respective strand, so that primer binding sites are converted to the single-stranded stage and thus, become accessible for a new binding of primers.

In a further preferred embodiment of the method reaction conditions that do not denaturize a double strand are used during initial synthesis steps (for example, initial one to ten synthesis repetitions) (e.g., temperature rising up to 90° C.), however, in subsequent repetitions of the synthesis steps non-denaturizing conditions are maintained during the exponential amplification process. For such a combination of temperature conditions it is not relevant whether or not the start nucleic acid chain has a restriction in its 5' sequence segment. By initial denaturation separation of synthesized strands is independent of their length in analogy to PCR.

Designing a Start Nucleic Acid Chain

A start nucleic acid chain can be designed before an exponential amplification in a separate reaction process. A skilled person knows many methods how to design and use a nucleic acid chain comprising a target sequence as well as further prescribed sequence parts. In designing a start nucleic acid chain methods can be applied that comprise for example template-dependent primer extension steps, restriction enzyme digestion steps, ligation steps, polyadenylation steps. These process steps can be applied alone or in combination. During such reactions start nucleic acid chains can be designed that have different structures, FIG. 23D.

In FIG. 23D a double-stranded DNA is schematically illustrated as the starting material (A), wherein a sequence part from said DNA is to function as the material or template for the preparation of a start nucleic acid chain that comprises a target sequence. Suitable start nucleic acid chains of different structures can be prepared from such a material by using the appropriate methods.

For example, a start nucleic acid chain to be prepared (FIG. 23D, section B) can comprise the following sequence segments: a segment 1 in the 5' segment of the start nucleic acid chain that comprises sequence parts of the second primer oligonucleotide and represents a restriction in the 5' direction, a segment 2 that comprises a target sequence or portions thereof, a segment 3 that comprises a primer binding site for the first primer oligonucleotide, and a segment 4 that comprises a non-target sequence located in the 3' segment of the start nucleic acid chain and thus, flanks the segment 3 on the 3' side. Such a start nucleic acid chain can be synthesized for example during a primer extension reaction or generated during restriction enzyme digestion/restriction enzyme excretion using one or more restriction enzymes.

Further, for example a start nucleic acid chain to be designed (FIG. 23D, section C) can comprise the following sequence segments: a segment 5 in the 5' segment of the start nucleic acid chain that comprises sequence parts of the first primer oligonucleotide and represents a restriction in the 5' direction, a segment 6 that comprises a target sequence or portions thereof, a segment 7 that comprises a primer binding site for the second primer oligonucleotide, and a segment 8 that comprises a non-target sequence located in the 3' segment of the start nucleic acid chain and thus, flanks segment 7 on the 3' side. Such a start nucleic acid chain can be synthesized for example during a primer extension reaction.

Moreover, a start nucleic acid chain to be designed (FIG. 23D, section D) can comprise the following sequence segments: a segment 9 in the 5' segment of the start nucleic acid chain that comprises sequence parts of the first primer oligonucleotide and represents a restriction in the 5' direction, a segment 10 that comprises a target sequence or portions thereof, a segment 11 that comprises a primer binding site for the second primer oligonucleotide. Such a start nucleic acid chain can be generated for example during restriction enzyme digestion/restriction enzyme excretion using one or more restriction enzymes.

Moreover, a start nucleic acid chain to be designed (FIG. 23D, section E) can comprise the following sequence segments: a segment 12 in the 5' segment of the start nucleic acid chain that comprises sequence parts of the first primer oligonucleotide and represents a restriction in the 5' direction, a segment 13 that comprises a target sequence or portions thereof, a segment 14 that comprises a primer binding site for the second primer oligonucleotide. Such a start nucleic acid chain can be generated for example during restriction enzyme digestion/restriction enzyme excretion using one or more restriction enzymes as well as a ligation of at least one of the segments 12 and/or 14 to segment 13 using corresponding ligase enzyme systems.

During designing the resulting start nucleic acid chain can be present in a double-stranded or single-stranded form. According to the structure of the start nucleic acid chain and the method of its design it may be necessary to convert the start nucleic acid chain to the single-stranded form before the amplification. This can be done for example in a separate step or during a clean-up procedure of the start nucleic acid chain from accompanying components.

For example, the start nucleic acid chain can be synthesized during a separate primer extension reaction using a primer used in der exponential amplification (e.g., the first primer oligonucleotide or the second primer oligonucleotide), a single-stranded DNA or RNA that comprises a target sequence as well as a polymerase and dNTPs. This results in a start nucleic acid chain that is bound to its template. For use in the exponential amplification such a start nucleic acid chain can be converted to the single-stranded form prior to exponential amplification. Thereby, a number of methods known can be applied, e.g., temperature-dependent denaturation, alkali denaturation, partial or complete strand degradation (e.g., by means of RNase H, or DNase, or 5' exonuclease). Additionally, a further primer extension reaction can be performed with an additional primer that is positioned upstream (so-called bumper primer or outer primer), so that the start nucleic acid chain is converted to the single-stranded form by polymerase-dependent strand displacement.

For the purpose of converting the start nucleic acid chain to a single-stranded form further enzymatic systems as well as their co-factors or energy source can be added to the amplification mixture that are able to convert double-stranded nucleic acid chains to a single-stranded form and thus, convert a start nucleic acid chain generated from a double-stranded stage to a single-stranded stage. Such enzymatic systems are for example helicases and recombinases (with ATP or dATP as an energy source). In a preferred embodiment, such enzymes are inactivated prior to an exponential amplification reaction so as not to cause a non-sequence-specific strand dissociation during the amplification reaction.

In an advantageous embodiment, such a start nucleic acid chain is designed prior to the exponential amplification and does not need to be treated separately.

In a further advantageous embodiment, the start nucleic acid chain is designed in the presence of components of an amplification reaction/reaction mixtures provided for amplification reactions. In this way, a start nucleic acid chain directly after having been designed can smoothly be transferred to the exponential amplification reaction. Such an embodiment permits design of a homogeneous assay format.

In an advantageous embodiment, the starting material for such a start nucleic acid chain is selected from the following group: genomic DNA or fragments thereof, plasmid DNA or fragments thereof, mRNA or fragments thereof, microRNA or fragments thereof. The nucleic acid functioning as the starting material can be derived for example from a clinically relevant material source.

In a preferred embodiment of the method the sequence of the start nucleic acid chain to be employed at the beginning of the amplification reaction is identical to the sequence of the nucleic acid chain to be amplified. Here, only one strand of the nucleic acid chain to be amplified (either as the first primer extension product or as the second primer extension product) or also both strands can be employed at the beginning of the amplification in the amplification batch.

In one embodiment of the method a start nucleic acid chain to be added to the reaction preferably at least on one side is limited in its length such that in the synthesis of the complementary strand a double-stranded fragment is generated that can dissociate to single strands with cooperation of the activator oligonucleotide at the selected temperature.

This can be achieved for example in that the start nucleic acid chain to be added to the amplification mixture includes at least one sequence fragment in its 5' segment that corresponds to an amplification primer or a part of an amplification primer and includes a further sequence fragment downstream that corresponds to a primer binding site or functions as a primer binding site to which an appropriate primer can bind in the amplification method and is able to permit a polymerase-dependent synthesis reaction of a complementary strand to the start nucleic acid chain.

Preferred Embodiments of the First Primer Oligonucleotide (Primer 1)

Figure 2:
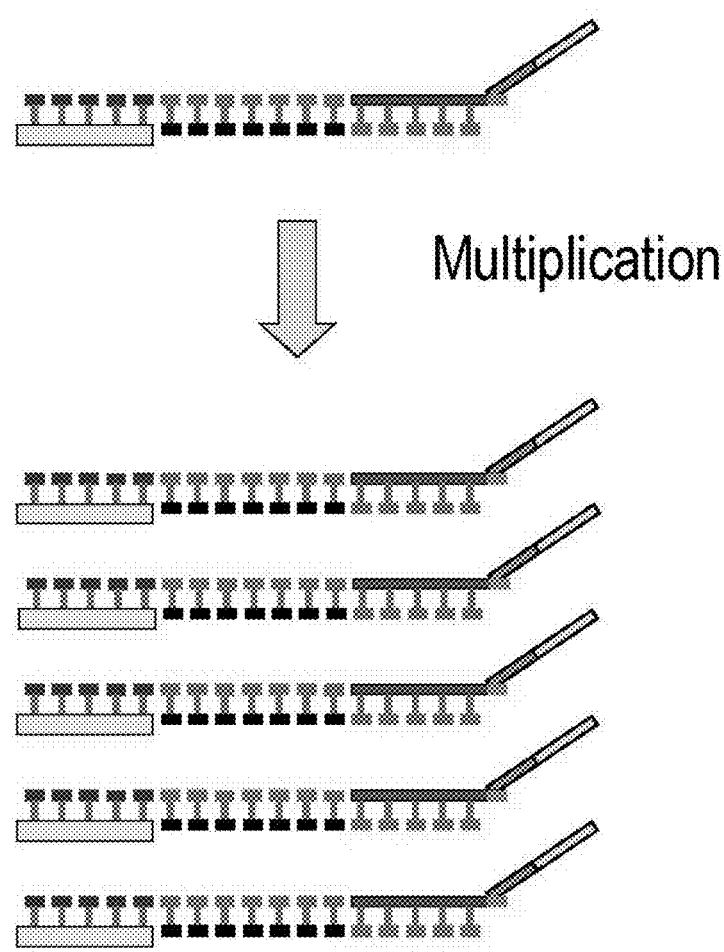
Figure 4:
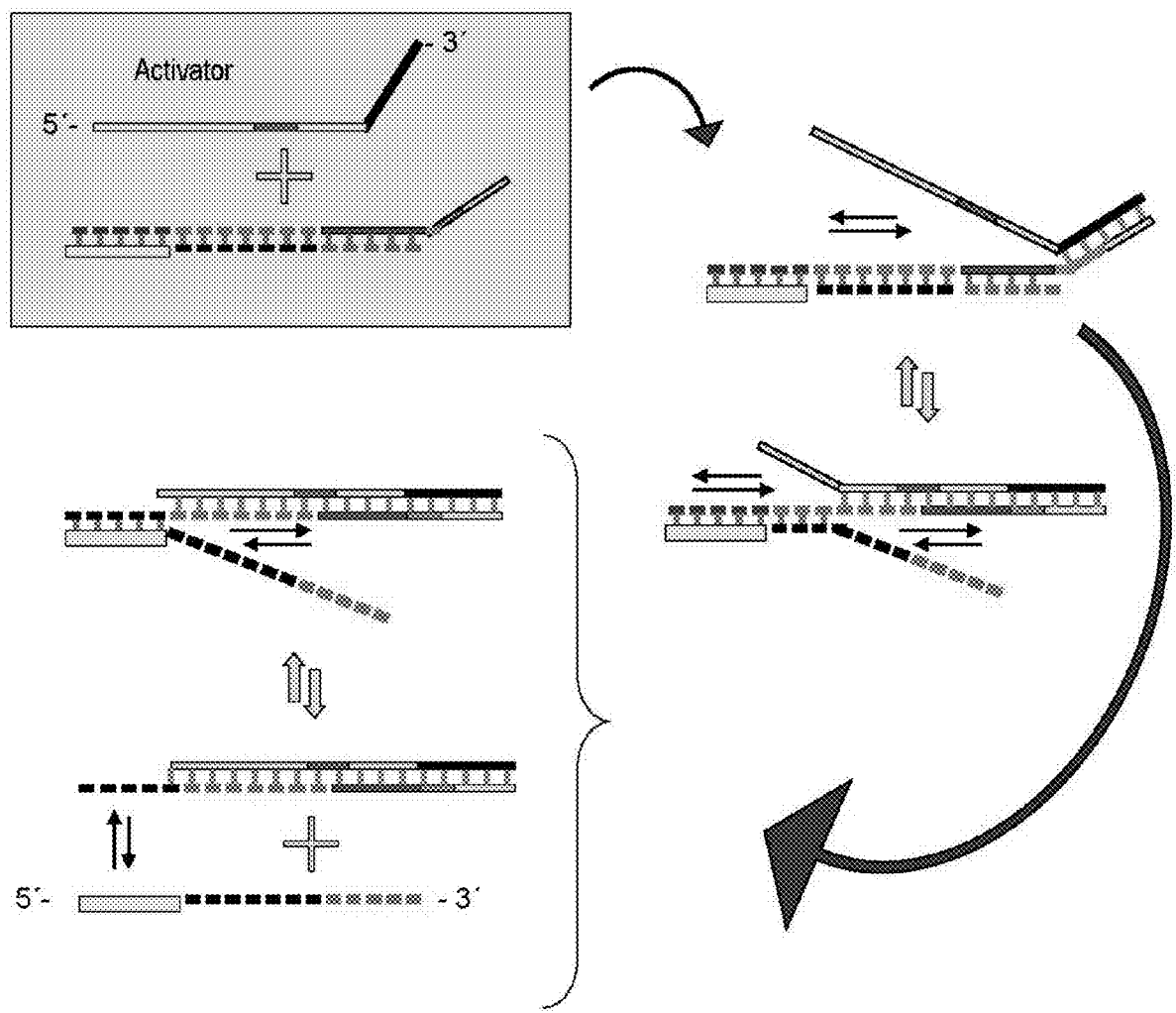
Figure 5:
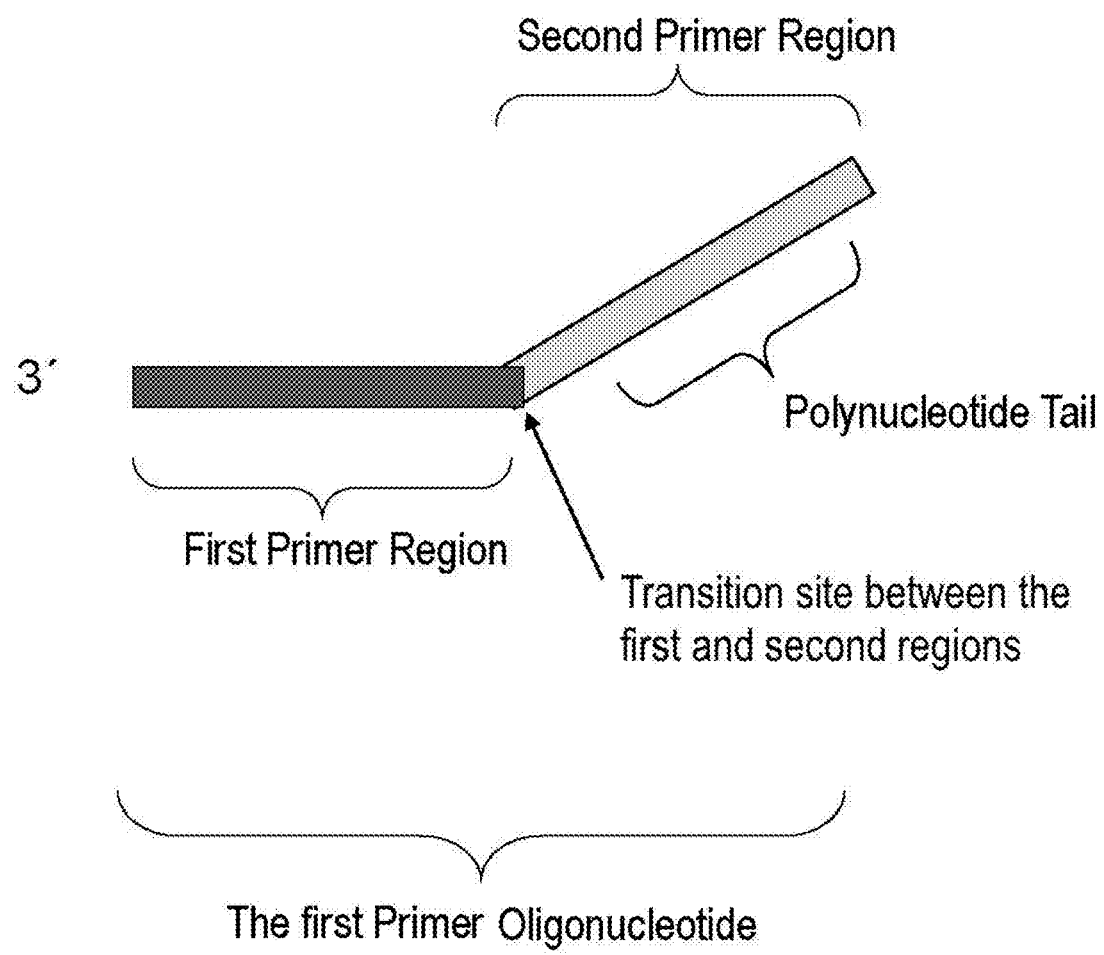
Figure 6:
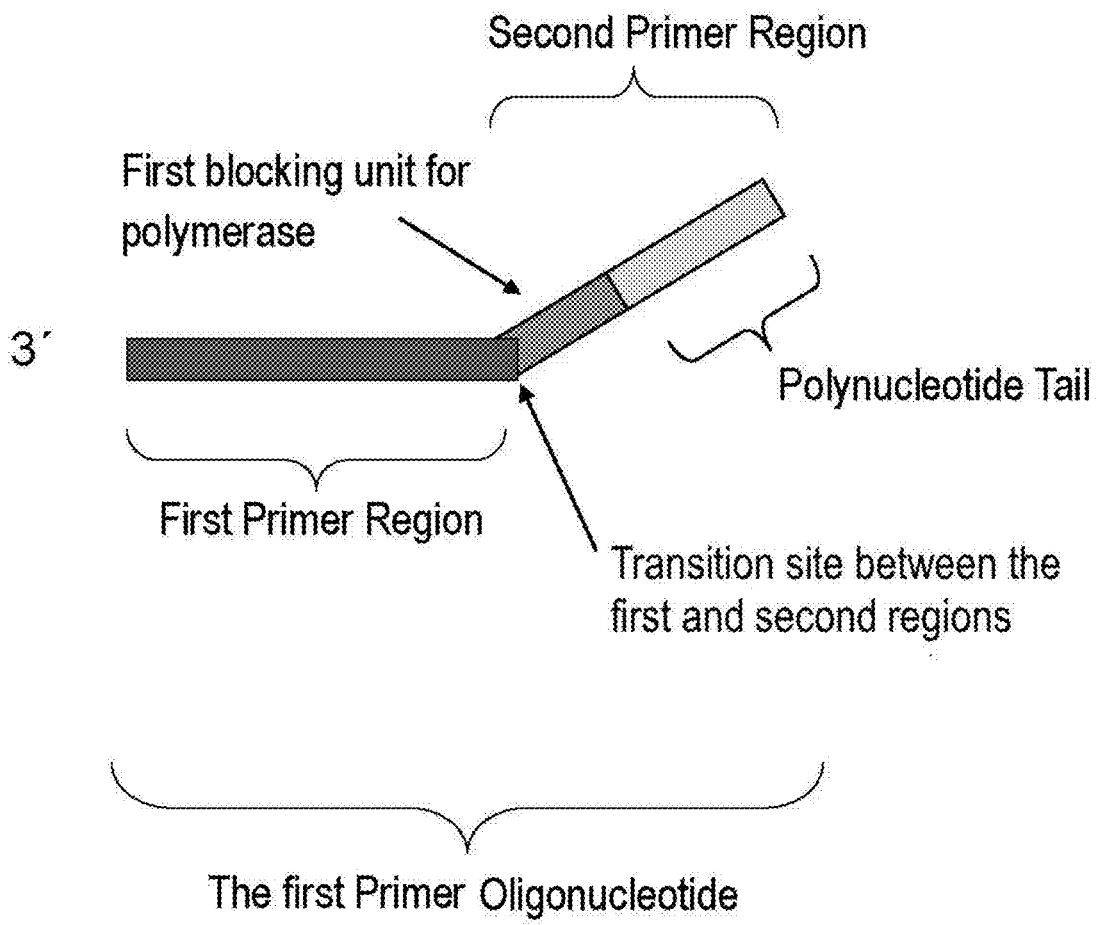
Figure 7:
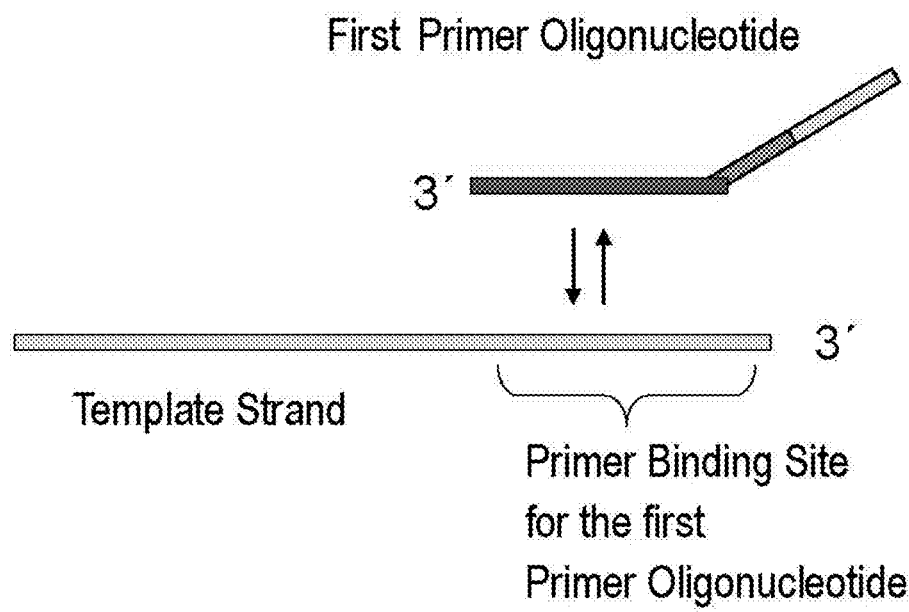
Figure 9:
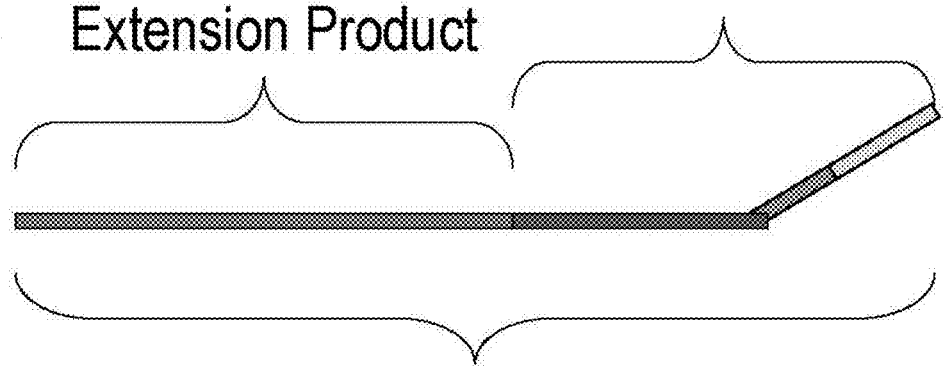
Figure 11:
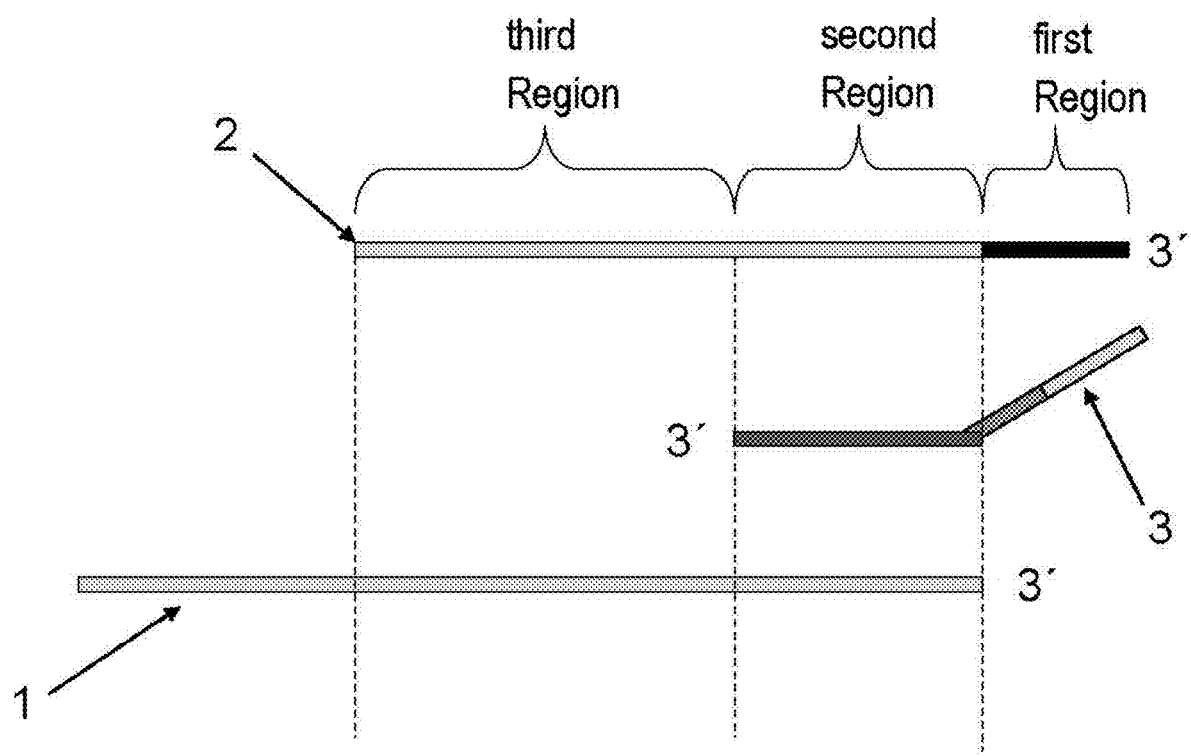
Figure 12:
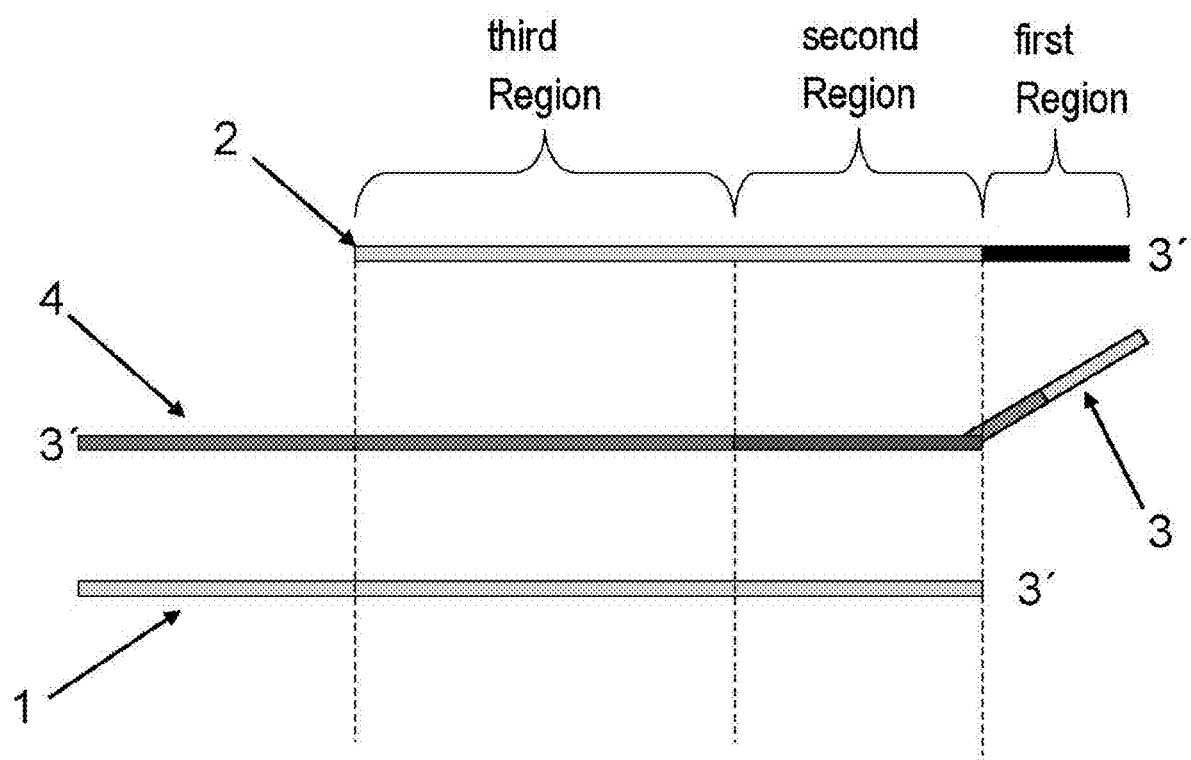

The first primer oligonucleotide (primer 1) is a nucleic acid chain that includes at least the following regions (FIGS. 5 and 6):

a first primer region in the 3' segment of the first primer oligonucleotide that can substantially sequence-specifically bind to a strand of a nucleic acid chain to be amplified a second region directly or via a linker linked to the 5' end of the first primer region of the first primer oligonucleotide that comprises a polynucleotide tail suitable to bind an activator oligonucleotide and support the strand displacement (step c) by the activator oligonucleotide, wherein the polynucleotide tail substantially remains single-stranded under the reaction conditions, i.e. does not form a stable hairpin structure or ds structures, and preferably is not copied by polymerase.

The total length of the first primer oligonucleotide is between 10 and 80, preferably between 15 and 50, better between 20 and 30 nucleotides or equivalents thereof (e.g., nucleotide modifications). The structure of the first primer oligonucleotide is adapted such that it is able to reversibly bind to the activator oligonucleotide under the selected reaction conditions. Moreover, the structure of the first primer oligonucleotide is adapted to its primer function. Moreover, the structure is adapted such that a strand displacement by means of the activator oligonucleotide can be performed. Altogether, structures of the first and second regions are adapted such that an exponential amplification can be performed.

In an advantageous embodiment of the invention the first and second regions of the primer are coupled in a conventional 5'-3' arrangement. In a further embodiment of the invention coupling of both sections is done via a 5'-5' bond, so that the second region has an opposite direction to the first region.

Coupling regions between each other/among each other is done preferably covalently. In one embodiment, coupling between the first and second regions is a 5'-3' phosphodiester coupling that is conventional for DNA. In a further embodiment it is a 5'-5' phosphodiester coupling. In a further embodiment, it is a 5'-3' phosphodiester coupling, wherein between adjacent terminal nucleotides or nucleotide modifications of both regions at least one linker (e.g., a C3, C6, C12, or a HEG linker or an abasic modification) is positioned.

Individual regions can include different nucleotide modifications. Here, individual elements of nucleotides can be modified: nucleobase and backbone (sugar content and/or phosphate content). Moreover, there can be used modifications that lack at least one component of the standard nucleotide building blocks or are modified, e.g., PNA.

In a further embodiment, a second region of the first primer oligonucleotide comprises further sequences that do not bind to the activator oligonucleotide. These sequences can be used for other purposes, e.g., for binding to the solid phase. These sequences are preferably localized at the 5' end of the polynucleotide tail.

In a further embodiment, a first primer oligonucleotide can comprise a characteristic label. Examples of such a label are dyes (e.g., FAM, TAMRA, Cy3, Alexa 488 etc.) or biotin or other groups that can specifically be bound, e.g., digoxigenin.

The First Primer Region of the First Primer Oligonucleotide

The sequence length is between ca. 3-30 nucleotides, preferably between 5 and 20 nucleotides, wherein the sequence is mainly complementary to the 3' segment of a strand of the nucleic acid chain to be amplified. In detail, said primer region has to be able to specifically bind to the complementary 3' segment of a second primer extension product. Said first region is to be copyable in backward synthesis and also functions as a template for a 2nd strand. Preferably, the nucleotide building blocks are linked among each other via common 5'-3' phosphodiester binding or phosphothioester binding.

The first primer region preferably includes nucleotide monomers that do not or only marginally affect the function of the polymerase, these are for example:

natural nucleotides (dA, dT, dC, dG etc.) or modifications thereof without altered base pairing modified nucleotides, 2-amino-dA, 2-thio-dT or other nucleotide modifications with diverging base pairing.

In a preferred embodiment, the 3'-OH end of said region is preferably free from modifications and has a functional 3'—OH group that can be recognized by polymerase. The first primer region functions as an initiator of the synthesis of the first primer extension product in the amplification. In a further preferred embodiment, the first region comprises at least one phosphorothioate compound, so that no degradation of the 3' end of the primers by 3' exonuclease activity of polymerases can take place.

The sequence of the first region of the first primer oligonucleotide and the sequence of the second region of the activator oligonucleotide are preferably complementary to each other.

In one embodiment, the first primer region or its 3' segment can bind to sequence segments of a target sequence.

The Second Region of the First Primer Oligonucleotide

The second region of the first primer oligonucleotide is preferably a nucleic acid sequence that comprises at least one polynucleotide tail that remains preferably uncopied by polymerase during the synthesis reaction and that can bind to the first region of the activator oligonucleotide. The segment of the second region that mainly binds to the activator oligonucleotide can be referred to as polynucleotide tail.

Further, the second region of the first primer oligonucleotide not only has to specifically bind the activator oligonucleotide under reaction conditions, but also has to participate in the process of strand displacement by means of the activator oligonucleotide. Accordingly, the structure of the second region must be suitable for causing a spatial proximity between the activator oligonucleotide and the corresponding double strand end (in detail, the 3' end of the second primer extension product).

Configuration of the structure of the second region of the first primer oligonucleotide is illustrated in detail in several embodiments. Here, the arrangement of the oligonucleotide segments and modifications used are taken into account that lead to a stop in the polymerase-catalyzed synthesis.

The length of the second region is between 3 and 60, preferably between 5 and 40, preferably between 6 and 15 nucleotides or equivalents thereof.

The sequence of the second region may be chosen arbitrarily. Preferably, it is non-complementary to the nucleic acid to be amplified and/or to the second primer oligonucleotide and/or to the first region of the first primer oligonucleotide. Moreover, it preferably does not contain any self-complementary segments such as hairpins or stem loops.

The sequence of the second region is preferably adapted to a sequence of the first region of the activator oligonucleotide, so that both sequences can bind under reaction conditions. In a preferred embodiment, said binding is reversible under reaction conditions: thus, there is an equilibrium between components bound to each other and unbound components.

The sequence of the second region of the first primer oligonucleotide is preferably selected such that the number of complementary bases that can bind to the first region of the activator oligonucleotide is between 1 and 40, better between 3 and 20, preferably between 6 and 15.

The function of the second region among others is to bind the activator oligonucleotide. In one embodiment, said binding preferably is specific, so that a second region of a first primer oligonucleotide can bind a specific activator oligonucleotide. In another embodiment, a second region can bind more than only one activator oligonucleotide under reaction conditions.

In general, there is no need for a perfect match in the sequence between the second region of the first primer oligonucleotide and the first region of the activator oligonucleotide. The degree of the complementarity between the second region of the first primer oligonucleotide and the first region of the activator oligonucleotide can be between 20% and 100%, better between 50% and 100%, preferably between 80% and 100%. The respectively complementary regions can be positioned directly adjacent to each other or also comprise non-complementary sequence segments therebetween.

In one embodiment, the second region of the first primer oligonucleotide can include at least one Tm-modifying modification. By incorporating such modifications the stability of the bond between the second region of the first primer oligonucleotide and the first region of the activator oligonucleotide can be modified. For example, Tm-rising modifications (nucleotide modifications or non-nucleotide modifications) can be used such as LNA nucleotides, 2-amino adenosines or MGB modifications. On the other hand, also Tm-decreasing modifications can be used such as for example inosine nucleotide. In the structure of the second region also linkers (e.g., C3, C6, HEG linkers) can be integrated.

For strand displacement the activator oligonucleotide has to be brought in spatial proximity of the double strand end of the nucleic acid to be amplified. Said double strand end consists of segments of the first primer region of the first primer extension product and a correspondingly complementary 3' segment of the second primer extension product.

The polynucleotide tail mainly complementary binds the activator oligonucleotide under reaction conditions and thus, causes a transient approximation of the second region of the activator oligonucleotide and of the first region of an extended primer extension product, so that the complementary bond between said elements can be initiated during a strand displacement process.

In one embodiment, binding of the activator oligonucleotide to the polynucleotide tail of the first primer oligonucleotide directly leads to such a contact. This means that the polynucleotide tail and the first primer region of the first primer oligonucleotide have to be directly coupled to each other. Owing to such an arrangement there may be a direct contact between complementary bases of the second region of the activator oligonucleotide and corresponding bases of the first primer region after an activator oligonucleotide has bound in its first region, so that a strand displacement can be initiated.

In a further embodiment, there are other structures of the second region of the first primer oligonucleotide between structures of the polynucleotide tail and the first primer region. Thus, after an activator oligonucleotide has bound to the polynucleotide tail this is not directly positioned to the first primer region, but in a certain distance thereto. The structures between the non-copyable polynucleotide tail and the copyable first primer region of the primer oligonucleotide can generate such a distance. Said distance has a value that is between 0.1 and 20 nm, preferably between 0.1 and 5 nm, better between 0.1 and 1 nm.

Such structures for example represent linkers (e.g., C3 or C6 or HEG linkers) or segments that are not complementary to the activator oligonucleotide (e.g., in the form of non-complementary, non-copyable nucleotide modifications). The length of these structures can generally be measured in chain atoms. Said length is between 1 and 200 atoms, preferably between 1 and 50 chain atoms, preferably between 1 and 10 chain atoms.

In order to keep the polynucleotide tail of polymerase uncopyable under amplification conditions the second region of the first primer oligonucleotide generally comprises sequence-alignments or structures, respectively that lead to a stop of the polymerase in the synthesis of the second primer extension product after the polymerase has successfully copied the first primer region. Said structures are to prevent the polynucleotide tail of the second region from being copied. Thus, the polynucleotide tail preferably remains uncopied by the polymerase.

In one embodiment, such structures are between the first primer region and the polynucleotide tail.

In a further embodiment, the sequence of the polynucleotide tail can include nucleotide modifications that lead to a stop of the polymerase. In this way, a sequence segment of the second region of the first primer oligonucleotide can comprise both functions: it is both a polynucleotide tail and a sequence of nucleotide modifications leading to a stop of the polymerase.

Modifications in the second region of the first primer oligonucleotide that lead to a synthesis stop and thus, leave the polynucleotide tail uncopied in this application are combined under the term "first blocking unit or a stop region".

In the Following, Further Embodiments of Structures are Given that can Lead to the Stop in the Synthesis of the Second Strand.

Several building blocks in the oligonucleotide synthesis are known that hinder polymerase from reading the template and lead to termination of the polymerase synthesis. For example, non-copyable nucleotide modifications or non-nucleotide modifications are known. There are also synthesis types/alignments of nucleotide monomers within an oligonucleotide that lead to the stop of the polymerase (e.g., 5'-5 alignment or 3'-3' alignment). Primer oligonucleotides having a non-copyable polynucleotide tail are also known in the prior art (e.g., Scorpion primer structures or primers for binding to the solid phase). Both primer variants describe primer oligonucleotide structures that are able to initiate the synthesis of a strand, so that a primer extension reaction can take place. The result is a first strand that also integrates the primer structure with tail in the primer extension product. In the synthesis of a complementary strand to the first primer extension product, e.g., during a PCR reaction, the second strand is extended to the "blocking unit/stop structure" of the primer structure. Both described primer structures are designed such that the 5' portion of the primer oligonucleotide remains single-stranded and is not copied by the polymerase.

In a further embodiment, the second region of the primer oligonucleotide comprises a polynucleotide tail that has a conventional alignment from 5' to 3' in its entire length and includes non-copyable nucleotide modifications. Such non-copyable nucleotide modifications are for example 2'-O-alkyl RNA modifications, PNA, morpholino. Said modifications can be differently distributed in the second primer region.

Non-copyable nucleotide modifications in the polynucleotide tail can share between 20% and 100%, preferably more than 50% of the nucleotide building blocks. Preferably, these nucleotide modifications are in the 3' segment of the second region and thus, border on the first region of the first primer oligonucleotide.

In one embodiment, the sequence of the non-copyable nucleotide modifications is at least partially complementary to the sequence in the template strand, so that the primer binding to the template is done by including at last part of said nucleotide modifications. In a further embodiment, the sequence of the non-copyable nucleotide modifications is non-complementary to the sequence in the template strand.

The non-copyable nucleotide modifications are preferably covalently coupled to each other and thus, represent a sequence segment in the second region. The length of this segment comprises between 1 and 40, preferably between 1 and 20 nucleotide modifications, more preferably between 3 and 10 nucleotide modifications.

In a further embodiment, the second region of the first primer oligonucleotide comprises a polynucleotide tail that has a conventional alignment from 5'-3' in its entire length and includes non-copyable nucleotide modifications (e.g., 2'-O-alkyl modifications) and at least one non-nucleotide linker (e.g., C3, C6, HEG linker). The function of a non-nucleotide linker is to covalently connect adjacent nucleotides or nucleotide modifications and at the same time to site-specifically interrupt the synthesis function of the polymerase.

Such a non-nucleotide linker is not to space the structures of the polynucleotide tail and of the first primer region too far from each other. Rather, the polynucleotide tail is to be in a spatial proximity to the first primer region. A non-nucleotide linker are modifications that are not longer than 200 chain atoms in their length, even more advantageous not longer than 50 chain atoms, particularly preferred not longer than 10 chain atom. The minimum length of such a linker can be one atom. An example of such non-nucleotide linkers are straight or branched alkyl linkers having an alkyl chain that includes at least one carbon atom, advantageously at least 2 to 30, more preferably 4 to 18. Such linkers are sufficiently known in the oligonucleotide chemistry (e.g., C3, C6 or C12 linkers) and can be incorporated during solid phase synthesis of oligonucleotides between the sequence of the polynucleotide tail and the sequence of the first region of the first primer oligonucleotide. Another example of such non-nucleotide linkers are linear or branched polyethylene glycol derivatives. A known example in the oligonucleotide chemistry is hexaethylene glycol (HEG). A further example of such non-nucleotide linkers are abasic modifications (e.g., THF modification, as an analogue of dRibose).

If one or more of such modifications are integrated in a second region they can effectively interfere with the copy function of a polymerase during its synthesis of the second primer extension product, so that downstream segments remain uncopied after such a modification. The number of such modifications in the second region can be between 1 and 100, preferably between 1 and 10, preferably between 1 and 3.

The position of such non-nucleotide linker can be at the 3' end of the second region and thus, represent the transition to the first region and the second region of the primer oligonucleotide.

Also, the position of the non-nucleotide linker in the central segment of the second region can be used. Thus, a polynucleotide tail is divided into at least two segments. In this embodiment, the 3' segment of the polynucleotide tail includes at least one, better more, e.g., between 2 and 20, preferably between 2 and 10 non-copyable nucleotide modifications. These non-copyable nucleotide modifications preferably are on the transition between the first and second regions of the primer oligonucleotide.

In a further embodiment, the second region of the primer oligonucleotide comprises a polynucleotide tail that has an alignment from 5' to 3' in its total length and includes at least one nucleotide monomer in an "reverse" alignment from 3' to 5' and that are positioned at the transition between the first and second regions of the first primer oligonucleotide.

In a further embodiment, the second region of the primer oligonucleotide comprises a polynucleotide tail, wherein such a polynucleotide tail completely consists of nucleotides that directly border on the first region of the first primer oligonucleotide in a reversed alignment, so that the coupling of the first and second regions is by the 5'-5' position. An advantage of such an alignment is that the polymerase after having copied the first region encounters a "reverse" alignment of nucleotides, which typically leads to the termination of the synthesis at this site.

In a "reverse" alignment of nucleotides in the total length of the polynucleotide tail preferably the 3'-terminal nucleotide of the polynucleotide tail is to be blocked at its 3'-OH end in order to prevent side reactions. Alternatively, also a terminal nucleotide can be used that has no 3'—OH groups at all, e.g., a didesoxynucleotide.

In such an embodiment, of course also the corresponding nucleotide alignment in the activator oligonucleotide is to be adapted. In such a case, the first and second regions of the activator oligonucleotide have to be linked in a 3'-3' alignment.

In a further embodiment, the second region of the primer oligonucleotide comprises a polynucleotide tail that has a conventional alignment from 5' to 3' in its total length and includes at least one nucleotide modification that does not represent a complementary nucleobase to the polymerase if the synthesis is performed exclusively with natural dNTPs (dATP, dCTP, dGTP, dTTP, or dUTP).

For example, Iso-dG or Iso-dC nucleotide modifications can be integrated in the second region of the first primer oligonucleotide as single, but preferably several (at least 2 to 20) nucleotide modifications. Further examples of nucleobase modifications are various modifications of the extended genetic alphabet. Such nucleotide modifications preferably do not support a complementary base pairing with natural nucleotides, so that a polymerase (at least theoretically) does not insert a nucleotide from the series (dATP, dCTP, dGTP, dTTP, or dUTP). In reality, however there may be a rudimentary insertion, especially at higher concentrations of dNTP substrates and prolonged incubation times (e.g., 60 min or longer). Hence, preferably several of such nucleotide modifications positioned at adjacent sites are to be employed. The stop of the polymerase synthesis is effected by lacking appropriate complementary substrates for these modifications. Oligonucleotides having Iso-dC or Iso-dG can be synthesized with standard methods and are available from several commercial suppliers (e.g., Trilink-Technologies, Eurogentec, Biomers GmbH). Alternatively, also the sequence of the first region of the activator oligonucleotide can be adapted to the sequence of such a second primer region. Here, complementary nucleobases of the extended genetic alphabet can accordingly be integrated in the first region of the activator oligonucleotide during the chemical synthesis. For example, Iso-dG can be integrated in the second region of the first primer nucleotide, its complementary nucleotide (Iso-dC-5-Me) can be placed at the appropriate site in the first region of the activator oligonucleotide.

In summary, the termination of the synthesis of polymerase in the second region may be achieved in different manners. However, this blockage preferably only takes place when the polymerase has copied the first region of the first primer oligonucleotide. In this way it is ensured that a second primer extension product has an appropriate primer binding site in its 3' segment. This primer binding site is exposed during the strand displacement and thus, is available for a new binding of a further first primer oligonucleotide.

In the synthesis of the complementary strand to the first primer extension product the primer extension reaction stops before the polynucleotide tail. Since in this way this polynucleotide tail remains single-stranded for interaction with the activator oligonucleotide and thus, is available for binding it supports the initiation of the strand displacement reaction by the activator oligonucleotide by bringing the corresponding complementary segments of the activator oligonucleotide in close proximity to the appropriate duplex end. In this way, the distance between the complementary part of the activator oligonucleotide (second region) and the complementary part of the extended primer oligonucleotide (first region) is reduced to a minimum. Such a spatial proximity facilitates the initiation of the strand displacement.

In the context of a schematic illustration of a nucleic acid-mediated strand displacement reaction now a complementary sequence of an activator oligonucleotide is in close proximity of the appropriate duplex end. This results in competition for the binding to the first region of the first primer oligonucleotide between the strand of the activator oligonucleotide and the template strand complementary to the primer. By repetitively closing and forming base pairing between the primer region and the complementary segment of the activator oligonucleotide (second region of the activator nucleotide) or the complementary segment of the template strand, respectively initiation of the nucleic acid-mediated strand displacement process occurs.

Generally, the yield of the initiation of the strand displacement is the higher the closer the corresponding complementary sequence part of the activator oligonucleotide is to the complementary segment of the primer region. However, when this distance is increased the yield of the initiation of the strand displacement decreases.

In the context of the present invention it is not mandatory that the initiation of the strand displacement works at the maximum yield. Thus, distances between the 5' segment of the first primer region of the first primer oligonucleotide, that binds to a complementary strand of the template and forms a complementary duplex, and a corresponding complementary sequence part in the activator oligonucleotide when bound to the polynucleotide tail of the second region of the first primer oligonucleotide may be in the following ranges: between 0.1 and 20 nm, better between 0.1 and 5 nm, even better between 0.1 and 1 nm. In the preferred case, said distance is less than 1 nm. Expressed in other units said distance corresponds to a track of less than 200 atoms, even better less than 50 atoms, even better less than 10 atoms. In the preferred case, said distance is one atom. The distance information is for orientation only and to illustrate that shorter distances between these structures are preferred. In many cases, said distance can only be measured by analyzing the exact structures of oligonucleotides and evaluating the measurement of sequence distances or linker lengths.

The first primer may also comprise further sequence parts that are not needed for an interaction with the activator oligonucleotide or the template strand. Such sequence parts for example can bind further oligonucleotides that are used as detection probes or immobilization partners in the binding to the solid phase.

Primer Function of the First Primer Oligonucleotide

The first primer oligonucleotide may be used in several individual steps. First of all, it exerts a primer function in the amplification. Thereby, a primer extension reaction is performed using the second primer extension product as a template. In a further embodiment, the first primer oligonucleotide at the beginning of the amplification reaction can use the start nucleic acid chain as template. In a further embodiment, the first primer oligonucleotide can be used in designing/providing a start nucleic acid chain.

During the amplification the first primer functions as an initiator of the synthesis of the first primer extension product using the second primer extension product as a template. The 3' segment of the first primer comprises a sequence that can mainly complementary bind to the second primer extension product. The enzymatic extension of the first primer oligonucleotide using the second primer extension product as a template results in the formation of the first primer extension product. Such a first primer extension product comprises the target sequence or sequence portions thereof. In the course of the synthesis of the second primer extension product the sequence of the copyable portion of the first primer oligonucleotide is recognized by polymerase as a template and a corresponding complementary sequence is synthesized, so that a respective primer binding site results for the first primer oligonucleotide. Synthesis of the first primer extension product is up to and including the 5' segment of the second primer oligonucleotide. Immediately following synthesis of the first primer extension product said product is bound to the second primer extension product and forms a double-stranded complex. The second primer extension product is sequence-specifically displaced from said complex by the activator oligonucleotide. Thereby, the activator oligonucleotide binds to the first primer extension product. Following a successful strand displacement by the activator oligonucleotide the second primer extension product in turn itself can function as a template for the synthesis of the first primer extension product. The now free 3' segment of the first primer extension product can bind a further second primer oligonucleotide, so that a new synthesis of the second primer extension product can be initiated.

Moreover, the first primer oligonucleotide can function as an initiator of the synthesis of the first primer extension product starting from the start nucleic acid chain at the beginning of the amplification. In one embodiment, the sequence of the first primer is completely complementary to the corresponding sequence segment of a start nucleic acid chain. In a further embodiment, the sequence of the first primer oligonucleotide is only partially complementary to the corresponding sequence segment of a start nucleic acid chain. However, said diverging complementarity is not to prevent the first primer oligonucleotide from starting a mainly sequence-specific primer extension reaction. The respective differences in complementarity of the first primer oligonucleotide to the respective position in the start nucleic acid chain are preferably in the 5' segment of the first region of the first primer oligonucleotide, so that in the 3' segment mainly complementary base pairing and initiation of the synthesis is possible. For the initiation of the synthesis for example especially the first 4-10 positions in the 3' segment are to be completely complementary to the template (start nucleic acid chain). The remaining nucleotide positions may diverge from a perfect complementarity. Thus, the degree of a perfect complementarity in the remaining 5' segment of the first region of the first primer oligonucleotide can comprise ranges between 50% to 100%, better between 80% and 100% of the base composition. According to the length of the first region of the first primer oligonucleotide the sequence divergences are 1 to at most 15 positions, better 1 to at most 5 positions. Thus, the first primer oligonucleotide can initiate a synthesis of a start nucleic acid chain. In a subsequent synthesis of the second primer extension product copyable sequence parts of the first primer oligonucleotide are copied by polymerase, so that in turn in subsequent synthesis cycles a completely complementary primer binding site is formed within the second primer extension product for the binding of the first primer oligonucleotide and is available in subsequent synthesis cycles.

In a further embodiment, the first primer oligonucleotide can be used in the preparation of a start nucleic acid chain. Thereby, such a first primer oligonucleotide can mainly/preferably sequence-specifically bind to a nucleic acid (e.g., a single-stranded genomic DNA or RNA or equivalents thereof comprising a target sequence) and initiate a template-dependent primer extension reaction in the presence of a polymerase. The binding position is selected such that the primer extension product comprises a desired target sequence. Extension of the first primer oligonucleotide results in a nucleic acid strand that has a sequence complementary to a template. Such a strand can be detached from the template (e.g., by heat or alkali) and thus, converted to a single-stranded form. Such a single-stranded nucleic acid chain can function as a start nucleic acid chain at the beginning of the amplification. Such a start nucleic acid chain in its 5' segment comprises the sequence portions of the first primer oligonucleotide, further it comprises a target sequence or equivalents thereof and a primer binding site for the second primer oligonucleotide. Further steps are explained in section "start nucleic acid chain".

The synthesis of the first primer extension product is a primer extension reaction and forms an individual step in the amplification. The reaction conditions during this step are accordingly adapted. Reaction temperature and reaction time are selected such that the reaction can successively take place. The preferred temperature in this step depends on the polymerase used and the binding strength of the respective first primer oligonucleotide to its primer binding site and comprises for example ranges of 15° C. to 75° C., better of 20 to 65° C., preferably of 25° C. to 65° C. The concentration of the first primer oligonucleotide comprises ranges of 0.01 μmol/l to 50 μmol/l, better of 0.1 μmol/l to 20 μmol/l, preferably of 0.1 μmol/l to 10 μmol/l.

In one embodiment, all steps of the amplification proceed under stringent conditions that prevent or delay the formation of non-specific products/by-products. Such conditions are for example higher temperatures, for example above 50° C.

If more than one specific nucleic acid chain is to be amplified in one batch, in one embodiment, preferably sequence-specific primer oligonucleotides are used for amplification of the corresponding target sequences.

Preferably, sequences of the first, the second primer oligonucleotides and of the activator oligonucleotide are adapted to each other such that side reactions, e.g., primer dimer formation, are minimized. For that, for example the sequences of the first and second primer oligonucleotides are adapted to each other such that both primer oligonucleotides are not able to start or support, respectively an amplification reaction in the absence of an appropriate template and/or a target sequence and/or a start nucleic acid chain. This can be achieved for example in that the second primer oligonucleotide does not comprise a primer binding site for the first primer oligonucleotide and the first primer oligonucleotide does not comprise a primer binding site for the second primer oligonucleotide. Moreover, it is to be avoided that the primer sequences comprise extended self-complementary structures (self-complement).

In one embodiment, the synthesis of the first and second primer extension products proceeds at the same temperature. In a further embodiment, the synthesis of the first and second primer extension products proceeds at different temperatures. In a further embodiment, synthesis of the first primer extension product and strand displacement by the activator oligonucleotide proceed at the same temperature. In a further embodiment, synthesis of the first primer extension product and strand displacement by the activator oligonucleotide proceed at different temperatures.

Preferred Embodiments of the Activator Oligonucleotide

An activator oligonucleotide (FIG. 10) comprises:
a first single-stranded region that can bind to the polynucleotide tail of the second region of the first primer oligonucleotide,
a second single-stranded region that can substantially complementary bind to the first region of the first primer oligonucleotide,
a third single-stranded region that is substantially complementary at least to one segment of the extension product of the first primer extension product,
and the activator oligonucleotide does not function as a template for primer extension of the first or second primer oligonucleotides.

In general, the sequence of the third region of the activator oligonucleotide is adapted to the sequence of the nucleic acid to be amplified, since this is relevant as a template for the order of the nucleotides in the extension product of a first primer. The sequence of the second region of the activator oligonucleotide is adapted to the sequence of the first primer region. The structure of the first region of the activator oligonucleotide is adapted to the sequence of the second region of the first primer oligonucleotide, especially to the nature of the polynucleotide tail.

An activator oligonucleotide can also include further sequence segments that do not belong to the first, second or third regions. These sequences can be attached for example as flanking sequences to the 3' and 5' end. Preferably, these sequence segments do not interfere with the function of the activator oligonucleotide.

The structure of the activator oligonucleotide preferably has the following properties:

The individual regions are covalently bound among each other. Binding for example can be via conventional 5'-3' binding. For example, a phosphodiester binding or nuclease-resistant phosphothioester binding may be used.

An activator oligonucleotide can bind to the polynucleotide tail of the first primer oligonucleotide by means of its first region, wherein binding is mainly mediated by hybridizing complementary bases. The length of said first region is 3-80 nucleotides, preferably 4-40 nucleotides, particularly preferred 6-20 nucleotides. The degree of sequence matching between the sequence of the first region of the activator oligonucleotide and the sequence of the second region of the first primer oligonucleotide can be between 20% and 100%, preferably between 50% and 100%, particularly preferred between 80% and 100%. Binding of the first region of the activator oligonucleotide preferably is to be specific to the second region of the first primer oligonucleotide under reaction conditions.

The sequence of the first region of the activator oligonucleotide is preferably selected such that the number of complementary bases that can complementary bind to the second region of the first primer oligonucleotide is between 1 and 40, better between 3 and 20, preferably between 6 and 15.

Since the activator oligonucleotide does not represent a template for polymerase it can include nucleotide modifications that do not support the polymerase function that can be both base modifications and/or sugar phosphate backbone modifications. The activator oligonucleotide in its first region can for example include nucleotide and/or nucleotide modifications that are selected from the following list: DNA, RNA, LNA ("locked nucleic acids" analogues with 2'-4' bridge-type binding in the sugar residue), UNA ("unlocked nucleic acids" without a binding between 2'-3' atoms of the sugar residue), PNA ("peptide nucleic acids" analogues), PTO (phosphorothioate), morpholino analogues, 2'-O-alkyl RNA modifications (such as 2'-OMe, 2'-O propargyl, 2'-O-(2-methoxyethyl), 2'-O-propyl-amine), 2'-halo RNA, 2'-amino RNA etc. These nucleotides or nucleotide modifications are linked to each other for example by a conventional 5'-3' binding or 5'-2' binding. For example, a phosphodiester binding or nuclease-resistant phosphothioester binding can be used.

The activator oligonucleotide in its first region can include nucleotides and/or nucleotide modifications, wherein the nucleobases are selected from the following list: adenine and analogues thereof, guanine and analogues thereof, cytosine and analogues thereof, uracil and analogues thereof, thymine and analogues thereof, inosine or other universal bases (e.g., nitroindol), 2-amino-adenine and analogues thereof, iso-cytosine and analogues thereof, iso-guanine and analogues thereof.

The activator oligonucleotide in its first region can include non-nucleotide compounds that are selected from the following list: intercalating substances that can affect the binding strength between the activator oligonucleotide and the first primer oligonucleotide, e.g., MGB, naphthalene etc. The same elements can also be used in the second region of the first primer.

The activator oligonucleotide in its first region can include non-nucleotide compounds, e.g., linkers such as C3, C6, HEG linkers that can link individual segments of the first region to each other.

The activator oligonucleotide can bind to the first primer region of the first primer oligonucleotide by means of its second region, wherein binding is substantially mediated by the hybridization of complementary bases.

The length of the second region of the activator oligonucleotide is adapted to the length of the first region of the first primer oligonucleotide and preferably corresponds to it. It is between ca. 3-30 nucleotides, preferably between 5 and 20 nucleotides. The sequence of the second region of the activator oligonucleotide is preferably complementary to the first region of the first primer oligonucleotide. The degree of matching in complementarity is between 80% and 100%, preferably between 95% and 100%, preferably 100%. The second region of the activator oligonucleotide preferably includes nucleotide modifications that prevent polymerase in the extension of the first primer oligonucleotide, but do not block or substantially prevent formation of complementary double strands, for example 2'-O-alkyl RNA analogues (e.g., 2'-O-Me, 2'-O-(2-methoxyethyl), 2'-O-propyl, 2'-O-propargyl nucleotide modifications), LNA, PNA or morpholino nucleotide modifications. Individual nucleotide monomers are preferably linked via a 5'-3' binding, but alternatively also a 5'-2' binding between nucleotide monomers can be used.

The sequence length and its nature of the first and second regions of the activator oligonucleotide are preferably selected such that binding of said regions to the first primer oligonucleotide under reaction conditions at least in one reaction step of the method is reversible. That is, that the activator oligonucleotide and the first primer oligonucleotide certainly can specifically bind to each other, but this binding is not to result in the formation of a complex of both elements that is permanently stable under reaction conditions. Rather, an equilibrium between a bound complex form of activator oligonucleotide and first primer oligonucleotide and a free form of individual components is to be intended or enabled under reaction conditions at least in one reaction step. In this way it is ensured that at least part of the first primer oligonucleotides under reaction conditions is present in a free form and can interact with the template to initiate a primer extension reaction. On the other hand, in this way it is ensured that the respective sequence regions of the activator oligonucleotides are available for binding with an extended primer oligonucleotide.

By selecting the temperature during the reaction the portion of free, single-stranded and thus, reactive components can be affected: by decreasing the temperature first primer oligonucleotides bind to the activator oligonucleotides, so that both participants bind a complementary double-stranded complex. In this way, the concentration of single-stranded forms of individual components can be reduced. An increase of the temperature can result in the dissociation of both components in a single-stranded form. In the range of the melting temperature of the complex (activator oligonucleotide/first primer oligonucleotide) ca. 50% of the components are present in the single-stranded form and ca. 50% as a double-stranded complex. Thus, by using appropriate temperatures the concentration of single-stranded forms in the reaction mixture can be affected.

In embodiments of the amplification method that include a change in temperature between individual reaction steps the desired reaction conditions can be effected during the respective reaction steps. For example, by using temperature ranges of about the melting temperatures of complexes of activator oligonucleotide/first primer oligonucleotide portions of free forms of individual components can be affected. Here, the temperature used results in destabilization of complexes comprising activator oligonucleotide/first primer oligonucleotide, so that during this reaction step individual complex components at least transiently become single-stranded and thus, are enabled to interact with other reaction partners. For example, the first sequence region of the activator oligonucleotide can be released from the double-stranded complex with a non-extended first primer and thus, interact with the second sequence region of an extended first primer oligonucleotide and thus, initiate a strand displacement. On the other hand, the release of a first, non-extended primer oligonucleotide from a complex comprising activator oligonucleotide/first primer oligonucleotide results in that the first primer region becomes single-stranded and thus, can interact with the template, so that a primer extension by a polymerase can be initiated. Here, the temperature used must exactly correspond to the melting temperature of the complex of activator oligonucleotide/first primer oligonucleotide. It is sufficient if the temperature in one reaction step is used about in the range of the melting temperature. For example, the temperature in one of the reaction steps comprises ranges of Tm±10° C., better Tm±5° C., preferably Tm±3° C. of the complex of activator oligonucleotide/first primer oligonucleotide.

Such a temperature can be adjusted for example during the reaction step that comprises a sequence-specific strand displacement by the activator oligonucleotide.

In embodiments of the amplification method that do not comprise a change in temperature between individual reaction steps and where amplification proceeds under isothermal conditions reaction conditions are maintained for the entire duration of the amplification reaction under which an equilibrium between a complex form of activator oligonucleotide and the first primer oligonucleotide and a free form of individual components is possible.

The ratio between a complex form of activator oligonucleotide and the first primer oligonucleotide and free forms of individual components can be affected both by reaction conditions (e.g., temperature and Mg2+ concentration) and by the structures and concentrations of the individual components.

The sequence length and its nature of the first and second region of the activator oligonucleotide in one embodiment are selected such that under given reaction conditions (e.g., in the reaction step of a strand displacement by the activator oligonucleotide) the ratio between a portion of a free activator oligonucleotide and a portion of an activator oligonucleotide in a complex with a first primer oligonucleotide comprises the following ranges: of 1:100 to 100:1, preferably of 1:30 to 30:1, particularly preferred of 1:10 to 10:1. The ratio between a portion of a free first primer oligonucleotide and a portion of a first primer oligonucleotide in a complex with an activator oligonucleotide comprises ranges of 1:100 to 100:1, preferably of 1:30 to 30:1, particularly preferred of 1:10 to 10:1.

In one embodiment, the concentration of the first primer oligonucleotide is higher than the concentration of the activator oligonucleotide. In this way, there is an excess of the first primer in the reaction and the activator oligonucleotide, for its effect, has to be released from the binding with the first primer by selecting appropriate reaction temperatures. In general, this is done by raising the temperature until sufficient concentrations of free forms of the activator oligonucleotide are present.

In a further embodiment, the concentration of the first primer oligonucleotide is lower than the concentration of the activator oligonucleotide. In this way, there is an excess of the activator oligonucleotide and the first primer oligonucleotide, for its effect, has to be detached from the binding with the activator oligonucleotide by selecting appropriate reaction temperatures. In general, this is done by raising the temperature until sufficient concentrations of free forms of the first primer oligonucleotide are present.

With isothermal conditions there is an equilibrium: certain portions of the first primer oligonucleotide and activator oligonucleotide are bound to each other, whereas others are present as a single-stranded form in the reaction.

The activator oligonucleotide can bind to at least one segment of the specifically synthesized extension product of the first primer oligonucleotide by means of its third region (FIGS. 11 to 21). Binding is preferably done by the hybridization of complementary bases between the activator oligonucleotide and the extension product synthesized by polymerase.

In order to support the strand displacement reaction the sequence of the third region preferably is to have a high complementarity to the extension product. In one embodiment, 100% of the sequence of the third region is complementary to the extension product.

Preferably, the third region binds to the segment of the extension product that immediately follows the first region of the first primer oligonucleotide. Thus, the segment of the extension product preferably is in the 5' segment of the total extension product of the first primer oligonucleotide.

Preferably, the third region of the activator oligonucleotide is not bound over the entire length of the extension product of the first primer oligonucleotide. Preferably, one segment at the 3' end of the extension product remains unbound. Said 3'-terminal segment is needed for the binding of the second primer oligonucleotide.

The length of the third region is accordingly adapted such that the third region binds to the 5'-standing segment of the extension product, but does not bind the 3'-standing segment of the extension product.

The total length of the third region of the activator oligonucleotide is 2 to 100, preferably 6 to 60, particularly preferred 10 to 40 nucleotides or equivalents thereof. The activator oligonucleotide can complementary bind to the segment of the extension product over this length and thus, displace this 5'-standing segment of the extension product from the binding with its complementary template strand.

The length of the 3'-standing segment of the extension product that is not bound by the activator oligonucleotide comprises for example ranges between 5 and 60 nucleotides, preferably between 10 and 40, preferably between 15 and 30 nucleotides.

Said 3'-standing segment of the extension product is not displaced by the activator oligonucleotide from the binding with the template strand. Also in case of a completely bound third region of the activator oligonucleotide to its complementary segment of the extension product the first primer extension product can remain bound with the template strand via its 3'-standing segment. The binding strength of said complex is preferably selected such that it can for example spontaneously dissociate under reaction conditions (step e)). This can be achieved for example in that the melting temperature of said complex of the 3'-standing segment of the extension product of the first primer oligonucleotide and its template strand is about in the range of the reaction temperature or below the reaction temperature in a respective reaction step (reaction step e). In case of a low stability of said complex in the 3' segment of the extension product a complete binding of the third region of the activator oligonucleotide to the 5'-standing segment of the extension product results in a rapid dissociation of the first primer extension product from its template strand.

Altogether, the activator oligonucleotide has an appropriate structure to exert its function: under the respective reaction conditions it is able to sequence-specifically displace the extended first primer oligonucleotide from the binding with the template strand, whereby the template strand is converted to the single-stranded form and thus, is available for further bindings with a new first primer oligonucleotide and its target sequence-specific extension by polymerase.

In order to fulfill the function of the strand displacement the regions one, two and three of the activator oligonucleotide are mainly to be present in the single-stranded form under reaction conditions. Hence, double-stranded self-complementary structures (e.g., hairpins) in these regions are to be avoided, if possible, since they can lower the functionality of the activator oligonucleotide.

In the method according to the invention the activator oligonucleotide is not to be present as a template, hence the first primer oligonucleotide, when attached to the activator oligonucleotide under reaction conditions, is not to be extended by polymerase.

This is preferably achieved by the use of nucleotide modifications that prevent polymerase from copying the strand. Preferably, the 3' end of the first primer oligonucleotide remains unextended if the first primer oligonucleotide binds to the activator oligonucleotide under reaction conditions.

The extent of blockage/hindrance/deceleration/complication of the reaction can be between a full expression of this property (e.g., 100% blockage under given reaction conditions) and a partial expression of this property (e.g., 30-90% blockage under given reaction conditions). Preferred are nucleotide modifications that alone or coupled in series (e.g., as a sequence fragment consisting of modified nucleotides) can prevent the extension of a first primer more than 70%, preferably more than 90%, more preferably more than 95%, and particularly preferred 100%.

The nucleotide modifications can comprise base modifications and/or sugar phosphate residue modifications. Sugar phosphate modifications are preferred, since by a combination with conventional nucleobases an arbitrary complementary sequence of an activator oligonucleotide can be arranged. The nucleotide with modifications in the sugar phosphate residue that can result in the hindrance or blockage of the synthesis of the polymerase, for example includes: 2'-O-alkyl modifications (e.g., 2'-O-methyl, 2'-O-(2-methoxyethyl), 2'-O-propyl, 2'-O-propargyl nucleotide modifications), 2'-amino-2'-deoxy-nucleotide modifications, 2'-amino-alkyl-2'-deoxy-nucleotide modifications, PNA, morpholino modifications etc.

Blockage can be both by a single nucleotide modification or only by coupling several nucleotide modifications in series (e.g., as a sequence fragment consisting of modified nucleotides). For example, at least 2, preferably at least 5, particularly preferred at least 10 of such nucleotide modifications can be coupled next to each other in the activator oligonucleotide.

An activator oligonucleotide can have a uniform type of nucleotide modifications or comprise at least two different types of nucleotide modification.

The position of such nucleotide modifications in the activator oligonucleotide preferably is to prevent the polymerase from extending the 3' end of a first primer oligonucleotide bound to the activator oligonucleotide.

In one embodiment, such nucleotide modifications are located in the second region of the activator oligonucleotide. In a further embodiment, such nucleotide modifications are located in the third region of the activator oligonucleotide. In a further embodiment, such nucleotide modifications are located in the second and in the third regions of the activator oligonucleotide.

For example, at least 20%, preferably at least 50% of the positions of the second region of the activator oligonucleotide consist of such nucleotide modifications.

For example, at least 20%, preferably at least 50% of the positions of the third region of the activator oligonucleotide consist of such nucleotide modifications.

The sequence of the nucleobases of these nucleotide modifications is adapted to the demands on the sequence in the respective region.

The rest are for example natural nucleotide or nucleotide modifications that do not hinder polymerase function at all or only marginally, e.g., DNA nucleotides, PTO nucleotides, LNA nucleotides, RNA nucleotides. Here, further modifications, for example base modifications such as 2-amino-adenosine, 2-aminopurines, 5-methyl-cytosines, inosines, 5-nitroindoles, 7-deaza-adenosine, 7-deaza-guanosine, 5-propyl-cytosine, 5-propyl-uridine or non-nucleotide modifications such as dyes, or MGB modifications etc. can be used e.g., to adjust binding strength of individual regions of the activator oligonucleotide. The individual nucleotide monomers can be coupled to each other via a conventional 5'-3' binding or also else via a 5'-2' binding.

A segment of the activator oligonucleotide with nucleotide modifications that prevent an extension of the 3' end of a first primer oligonucleotide bound to an activator oligonucleotide by polymerase is referred to as "second blocking unit". The length of said segment can include between 1 to 50 nucleotide modifications, preferably between 4 and 30. Said segment can be located in the activator oligonucleotide for example such that the 3' end of the bound first primer oligonucleotide is in this segment. Thus, this segment can span regions two and three.

In one embodiment, preferably no linker structures or spacer structures such as C3, C6, HEG linkers are used to prevent extension of the 3' end of a first primer oligonucleotide bound to the activator oligonucleotide.

The activator oligonucleotide in addition to regions one, two and three can also comprise further sequence segments that flank the above-mentioned regions for example in the 5' segment or 3' segment of the activator oligonucleotide. Such sequence elements can be used for example for further functions such as for example interaction with probes, binding to solid phase etc. Such regions preferably do not interfere with the function of regions one to three. The length of these flanking sequences may be for example between 1 to 50 nucleotides. Moreover, an activator oligonucleotide can comprise at least one element for immobilization to a solid phase, e.g., a biotin residue. Moreover, an activator oligonucleotide can comprise at least one element for detection, e.g., a fluorescent dye.

Effect of the Activator Oligonucleotide on Double Strand Separation by Sequence-Dependent Strand Displacement (Schematic Explanation)

In the following, the mechanism of action of the activator oligonucleotide is to be schematically illustrated.

Re-synthesized strands that comprise primer binding sites are bound to their templates immediately after they have been synthesized and thus, are substantially not accessible for direct binding of further primers. Only after separation or opening of the double strand or its sequence parts with a primer binding site, e.g., during or as a result of a strand displacement reaction or as a result of a double strand dissociation such a sequence part with a primer binding site can bind to a new primer oligonucleotide and thus, is available for another round of the synthesis reaction.

Thus, conversion of re-synthesized sequence parts with primer binding sites to a single-stranded stage represents an essential prerequisite for the repetition of synthesis-processes and thus, also for an amplification. Factors that can have influence on said process can affect the amplification.

Strand displacement of the second primer extension product according to the invention is done with cooperation/by binding of the activator oligonucleotide to the first primer extension product.

Binding of the activator oligonucleotide to the first primer extension product goes beyond the sequence of the first primer. Here, the re-synthesized strand segment of the first primer extension product is bound by the activator oligonucleotide and can be displaced from the binding with its template strand, for example represented by the second primer extension product.

This strand displacement leads to an opening of the double strand consisting of the first and second primer extension products. Said double strand opening can be locally (e.g., only in sequence segments that are directly displaced by the activator oligonucleotide) or go beyond segments, for example if the remaining double strand is destabilized by a further influencing factor, which can result in a complete separation of both primer extension products (complete detachment of the second primer extension product). Such factors can be for example temperature effect on the stability of the double strand under given reaction conditions. Further factors are for example enzymes that can destabilize or open a double strand (e.g., helicases or recombinases) or further oligonucleotides that can open a double strand by strand displacement.

As a result of the strand displacement both primer binding sites are converted from their double-stranded stage to a single-stranded stage. Thus, their ability to bind further primers is restored.

Factors that have influence on this process and affect amplification are for example a complete separation of both primer extension products.

Complete dissociation/detachment of the second primer extension product from the first primer extension product (complete strand dissociation) can have a positive effect on the kinetics of individual steps. This is especially the case, if minor concentrations of both primer extension products are present in the reaction mixture. Re-association of both primer extension products to a double strand under these circumstances is decelerated and primer binding sites remain in their single-stranded stage for a longer period of time.

Equilibrium/Reversibility of the Displacement by the Activator Oligonucleotide

Binding of the activator oligonucleotide to the first primer extension product is conditional upon formation of complementary base pairs between both strands and thus, reversible under reaction conditions.

Binding of the activator oligonucleotide to the first primer extension product can be undone by several factors. These are, for example:
- polymerase-dependent strand displacement during the synthesis of the second primer extension product up to the terminator in the first primer,
- strand displacement by the second primer extension product to form complementary strands between the first and second primer extension products,
- partial strand displacement by the 3' segment of the second primer and its binding to the first primer extension product with displacement by the 5' segment of the activator oligonucleotide.

Figure 22:
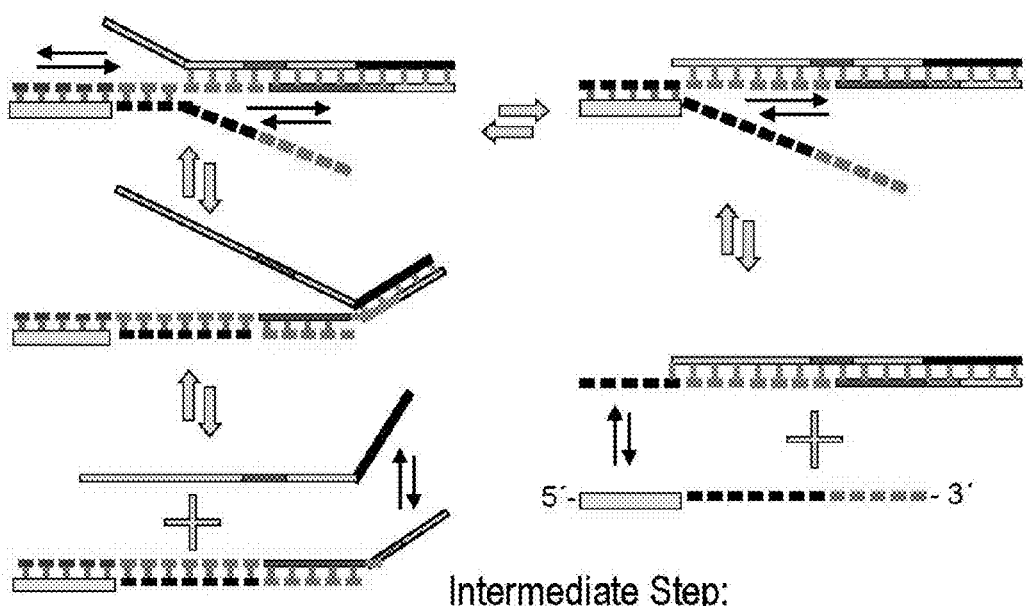

The second primer extension product can bind to the first primer extension product to form complementary base pairings and thereby displace the activator oligonucleotide. Thus, there is a competition between the activator oligonucleotide and the second primer extension product for the binding to the first primer extension product. As long as all three strands form a three-strand complex (here, the complex comprises the first primer extension product that is bound to the second primer extension product and the activator oligonucleotide via its complementary sequence parts) the strand displacement reaction can be in both directions: both the activator oligonucleotide can displace the second primer extension product and vice versa, the second primer extension product can displace the activator oligonucleotide. These strand displacement processes are in equilibrium. Here, strand displacement taking placing in the context of this complex can lead up to sequence positions that result in a complete dissociation/detachment of a strand from the three-strand complex under given reaction conditions (FIG. 22).

This is especially the case if reaction conditions participate in duplex destabilization (e.g., by the use of an appropriate reaction temperature, Mg2+ concentration and Tm-changing substances) and the construction of sequence parts favors such a detachment/dissociation, e.g., by adjusting the stabilities of the respective sequence parts. In this context, stabilities of complexes of sequence parts are important that comprise a complex of the first section of the activator oligonucleotide and the second section of the first primer and a complex of the 3' segment of the first primer extension product with its primer binding site for the second primer oligonucleotide and accordingly the second primer oligonucleotide or the second primer extension product. Stability of both complexes can have influence on the equilibrium in the three-strand complex: a higher stability in the complex of the activator oligonucleotide and the first primer generally favors the strand displacement of the second primer extension product. In turn, a higher stability between the 3' segment of the first primer extension product and the second primer oligonucleotide generally favors the displacement of the activator oligonucleotide.

Stability of respective sequence parts can be affected for example in that the respective sequence parts are reduced or increased in their lengths. In general, extension of the first region of the activator oligonucleotide and of the corresponding second region of the first primer oligonucleotide results in an enhanced displacement of the synthesized second primer extension product. In turn, extension of the 3' segment of the first primer extension product and accordingly of the second primer extension product results in an enhancement of the displacement of the activator oligonucleotide.

During strand displacement processes within a three-strand complex intermediate stages can be achieved in which detachment/dissociation of one of the participants is particularly favored under given reaction conditions.

In one case, the second primer extension product is completely detached from the binding with the first primer extension product, in another case the activator oligonucleotide can completely be detached from the binding with the first primer extension product.

As long as all three strands are bound in context of a three-strand complex there is a certain equilibrium in the progress of the strand displacement in both directions.

This equilibrium can be affected by several factors.

These are for example strand detachment, degree of complementarity between individual structures or the presence of sequence divergences (e.g., mutations), use of nucleotide modifications or non-nucleotide modifications that have a stabilizing or destabilizing effect on a complementary binding of nucleic acid strands.

Of particular importance for the described equilibrium is the degree of complementarity between the activator oligonucleotide and a double strand synthesized by polymerase: a sequence difference of only one nucleotide can result in a delay of the amplification and a difference of three nucleotides can cause stop of the amplification.

In general, sequence differences between the activator oligonucleotide and the first primer extension product have a negative effect on the ability of the activator oligonucleotide to form a double strand with such a first primer extension product.

In contrast, a second primer extension product is synthesized by polymerase generally as a perfect-match product using the first primer extension product. In general, in this way formation of a double strand is favored.

If there is a sequence divergence between the activator oligonucleotide and the first primer extension product a shift in the equilibrium of the strand displacement can occur in the context of the three-strand complex.

As a result of the competition for the binding to the first primer extension product formation of a perfect-match double strand between the first and second primer extension products is favored over the formation of a mismatch double strand. The result is deceleration or even prevention of the strand displacement of the second primer extension product. This can lead to the deceleration or reduction of yields or even to the prevention of the amplification.

Shifting the equilibrium in strand displacement as a result of such a sequence-dependency (perfect-match vs. mismatch situation between the first primer extension product and the activator oligonucleotide) can influence the reaction. For example, rate of the reaction can be affected such that a perfect-match situation between the first primer extension product and the activator oligonucleotide is favored and mismatches can be excluded from amplification.

Said influence of the sequences is illustrated in examples 1, 3, and 4.

By changes in said equilibrium dissociation processes of both primer extension products can be accelerated, decelerated, or even cancelled. Thus, amplification becomes faster, slower, or possibly will even not take place at all.

Thus, by the design of the sequence of the complementary portions in the activator oligonucleotide (during oligonucleotide design and chemical synthesis) nucleic acid chains can be amplified with predetermined sequences. Other nucleic acid chains that have a diverging sequence can be excluded from amplification or their amplification is kinetically disadvantaged, respectively.

It was especially surprising that this sequence effect of the activator oligonucleotide was very distinct in its third region. The third region of the activator oligonucleotide according to the invention is to bind to the sequence part of the first primer extension product that is synthesized by polymerase. Thus, said sequence part of the first primer extension product is in the central segment of the nucleic acid chain to be amplified. For example, it can comprise the target sequence.

Thus, amplification is subject to a constant control of the sequence contents in this sequence segment: strand displacement of the second primer extension product and thus, its conversion to the single-stranded form depends on the match in complementarity of the activator oligonucleotide and the first primer extension product.

Thus, an activator oligonucleotide can exert a sequence control after each primer extension process.

As a result of this control several states can be achieved:
In case of a perfect match in the matching of the synthesized strands with the activator oligonucleotide successful strand displacement occurs that can proceed up to dissociation of the second primer extension product. Thereby, the corresponding sequence parts with primer binding sites are converted to the single-stranded state and conditions are created in that a further synthesis round can take place.

In case of mismatches in the matching of the synthesized strands with the activator oligonucleotide (e.g., in sequences that do not correspond to a given alignment of the nucleotides in the third region of the activator oligonucleotide) strand displacement can be negatively affected: The equilibrium is on the side of the double strand formation between the first primer extension product and a respective template. The strand displacement process becomes slower or only partially takes place, what leads to a reduction of the availability of sequence parts with free primer binding sites. Altogether, thus mismatches can lead to the deceleration of the amplification or to the disruption of amplification.

In this way, a control loop can be established after each synthesis repetition:

After binding and extension of the primers double strands are formed that are sufficiently stable in the absence of the activator oligonucleotide under given reaction conditions, so that no spontaneous dissociation occurs. The sequence parts with primer binding sites in the context of double strands formed are prevented from an interaction with new primers. The system has reached a state in which no further synthesis can take place.

In the presence of an activator oligonucleotide re-synthesized sequences are examined in view of their sequence contents by interaction with the activator oligonucleotide.

In case of a correct matching with given sequence contents of the activator oligonucleotide strand displacement occurs, wherein the template strands are replaced by re-synthesized strands. Thereby, primer binding sites are converted to a single-stranded state and are available for a new interaction with primers and thus, for a further synthesis. Thus, the system of both primer extension products is put into an active state. Thus, the activator oligonucleotide has an activating effect on the system.

In case of a lacking matching with given sequence contents of the activator oligonucleotide strand displacement of the template strands of re-synthesized strands is affected. Strand displacement and/or detachment either is quantitatively decelerated or completely cancelled. Thus, primer binding sites are not converted to the single-stranded state at all or less often. Thus, no primer binding sites at all or quantitatively less are available for a new interaction with primers. Thus, the system of both primer extension products is less often put into an active state or an active state is not achieved at all.

Efficacy of the double strand opening of the re-synthesized primer extension products after each single synthesis step has an effect on the potentially obtainable yields in subsequent cycles: the less free/single-stranded primer binding sites are provided to a nucleic acid chain to be amplified at the beginning of a synthesis step, the smaller is the number of re-synthesized strands of the nucleic acid chain to be amplified in this step. In other words:

The yield of a synthesis cycle is proportional to the amount of primer binding sites that are available for the interaction with the corresponding complementary primers. Altogether, in this way a control loop can be realized.

Said control loop corresponds to a real-time/on-line control of synthesized fragments: sequence control is performed in the reaction mixture while the amplification takes place. Said sequence control is performed in accordance with a given pattern and the oligonucleotide system (by a strand-opening effect of the activator oligonucleotide) is able to distinguish between "correct" and "incorrect" states without external interventions. In the correct state the synthesis of sequences is continued, in the incorrect state synthesis is either decelerated or completely prevented. The resulting differences in the yields of "correct" and "incorrect" sequences after each step have an effect on the whole amplification that comprises a number of such steps.

In an exponential amplification said dependency is exponential, so that even minor divergences in efficacy in one single synthesis cycle due to sequence divergences can mean a significant delay in time of the whole amplification or cause a complete absence of a detectable amplification in a given time frame.

This effect of the real-time control of the re-synthesized nucleic acid chains is associated with the employment of the activator oligonucleotide and thus, the influence of the activator oligonucleotide during an amplification significantly goes beyond the length of primer oligonucleotides.

Further Influencing Factors

In general, factors that can have effect on strand displacement reaction, e.g., influence the extent, equilibrium, and/or rate of said process, can also have effect on the exponential amplification.

Such factors are for example reaction conditions (e.g., temperature, Mg2+ concentration, DMSO, betaines, TPAC, buffer components), presence of secondary structures within the activator oligonucleotide (e.g., hairpin structures or G quadruplexes), use of nucleotide modifications in the activator oligonucleotide (that stabilize, e.g., 2-amino-dA or 5-propargyl-dC, LNA-nucleotides, or destabilize, e.g., inosine, the double strand) or non-nucleotide modifications that stabilize, e.g., MGB, or destabilize, e.g., sterically "bulky groups" that affect the geometry of the A form or B form of the nucleic acid strands (e.g., dyes or ligands coupled to nucleotide) the double strand, or intercalating substances, e.g., SYBR green, Eva green dyes.

In individual cases such factors can be used to positively or negatively affect the equilibrium of the strand displacement and thus, favor or decelerate or prevent amplification of certain sequences. The extent of the influence can be determined experimentally.

Reaction Conditions at Strand Displacement Reaction

The displacement of the second primer extension product from the binding with the first primer extension product by means of a sequence-dependent strand displacement by the activator oligonucleotide forms an individual step in the amplification. The reaction conditions during said step are accordingly adapted. Reaction temperature and reaction time are selected such that the reaction can successfully take place.

In a preferred embodiment strand displacement by the activator oligonucleotide is up to detachment/dissociation of the second primer extension product from the binding with the first primer extension product. Such a dissociation of the 3' segment of the first primer extension product of complementary portions of the second primer extension product can be spontaneous during a temperature-dependent/temperature-related separation of both primer extension products. Such a dissociation has a favorable effect on the kinetics of the amplification reaction and can be affected by the choice of the reaction conditions, e.g., by means of temperature conditions. Therefore, temperature conditions are selected such that a successful strand displacement by complementary binding of the activator oligonucleotide favors a dissociation of the second primer extension product from the 3' segment of the first primer extension product.

The temperature in this step comprises for example ranges of 15° C. to 75° C., better of 30° C. to 70° C., preferably of 50° C. to 70° C.

With a given length of the first region of the activator oligonucleotide and the second region of the first primer oligonucleotide (comprising for example ranges of 3 to 25 nucleotide monomers, better of 5 to 15 nucleotide monomers) a strand displacement reaction generally can successfully be initiated. In case of a complete complementarity of the activator oligonucleotide to the respective portions of the first primer extension product the activator oligonucleotide can bind to the first primer extension product except for the 3' segment of the first primer extension product and displace the second primer extension product. Thus, the second primer extension product remains connected to the 3' segment of the first primer extension product. The strength of said connection can be affected depending on temperature. When reaching a critical temperature this connection can disintegrate and both primer extension products can dissociate. The shorter the sequence of the 3' segment, the more instable the connection and the lower the temperature that causes a spontaneous dissociation.

A spontaneous dissociation can for example be achieved in the temperature range that is about the melting temperature. In one embodiment, the temperature of the steps of strand displacement by the activator oligonucleotide is about at the melting temperature (Tm±3° C.) of the complex comprising the 3' segment of the first primer extension product that is not bound by the activator oligonucleotide and the second primer oligonucleotide or the second primer extension product, respectively.

In one embodiment, the temperature of the steps of strand displacement by the activator oligonucleotide is at about the melting temperature (Tm±5° C.) of the complex comprising the 3' segment of the first primer extension product that is not bound by the activator oligonucleotide and the second primer oligonucleotide or the second primer extension product, respectively.

In one embodiment, the temperature of the steps of strand displacement by the activator oligonucleotide is above the melting temperature of the complex comprising the 3' segment of the first primer extension product that is not bound by the activator oligonucleotide and the second primer oligonucleotide or the second primer extension product, respectively. Such a temperature comprises temperature ranges of about Tm+5° C. to Tm+20° C., better of Tm+5° C. to Tm+10° C. By using a higher temperature the equilibrium in said reaction step can be shifted toward dissociation. Thereby, the kinetics of the reaction can favorably be influenced. Using too low temperatures in the step of strand displacement by means of the activator oligonucleotide can lead to a significant deceleration of the amplification.

The temperature of the strand displacement steps by the activator oligonucleotide can also be estimated approximately and adapted to the dissociation temperature.

In a further embodiment, a first primer extension product comprises a 3' segment that is not bound by the activator oligonucleotide and that comprises sequence lengths of 4 to about 8 nucleotides. In this embodiment, a spontaneous dissociation in general can already be achieved with temperature ranges between 15° C. and 50° C. Also higher temperatures lead to dissociation.

In one embodiment, a first primer extension product comprises a 3' segment that is not bound by the activator oligonucleotide and that comprises sequence lengths of 9 to about 18 nucleotides. In this embodiment, a spontaneous dissociation in general can already be achieved with temperature ranges between 40° C. and 65° C. Also higher temperatures lead to dissociation.

In one embodiment, a first primer extension product comprises a 3' segment that is not bound by the activator oligonucleotide and that comprises sequence lengths of 15 to about 25 nucleotides. In this embodiment, a spontaneous dissociation in general can already be achieved with temperature ranges between 50° C. and 70° C. Also higher temperatures lead to dissociation.

In one embodiment, a first primer extension product comprises a 3' segment that is not bound by the activator oligonucleotide and that comprises sequence lengths of 20 to about 40 nucleotides. In this embodiment, a spontaneous dissociation in general can already be achieved with temperature ranges between 50° C. and 75° C. Also higher temperatures lead to dissociation.

The composition of the 3' segment of the first primer extension product and optionally adding melting temperature-affecting oligonucleotide modifications (e.g., MGB) or reaction conditions (e.g., TPAC, betaines) can have effect on the choice of the temperature. A corresponding adjustment can therefore be made.

In one embodiment, all steps of the amplification proceed under stringent conditions that prevent or decelerate the formation of non-specific products/by-products. Such conditions are for example higher temperatures, for example above 50° C.

In one embodiment, the individual steps of strand displacement by the activator oligonucleotides proceed at the same temperature such as the synthesis of the first and second primer extension products. In a further embodiment, the individual steps of strand displacement by the activator oligonucleotides proceed at a temperature that differs from the temperature of the respective synthesis of the first and second primer extension products. In a further embodiment, the synthesis of the first primer extension product and strand displacement by the activator oligonucleotide proceed at the same temperature. In a further embodiment, synthesis of the second primer extension product and strand displacement by the activator oligonucleotide proceed at the same temperature.

The concentration of the activator oligonucleotide comprises ranges of 0.01 µmol/l to 50 µmol/l, better of 0.1 µmol/l to 20 µmol/l, preferably of 0.1 µmol/l to 10 µmol/l.

Figure 13:
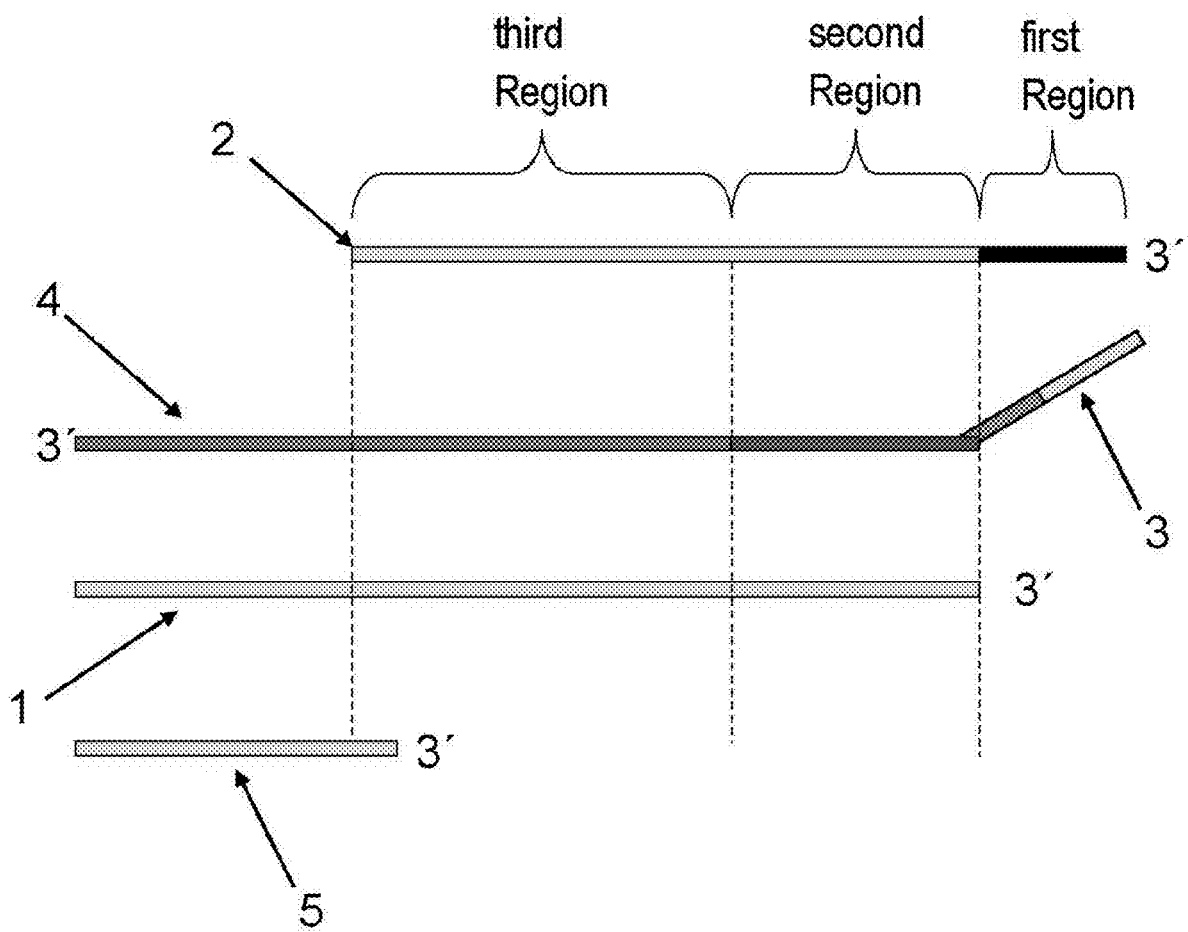
Figure 14:
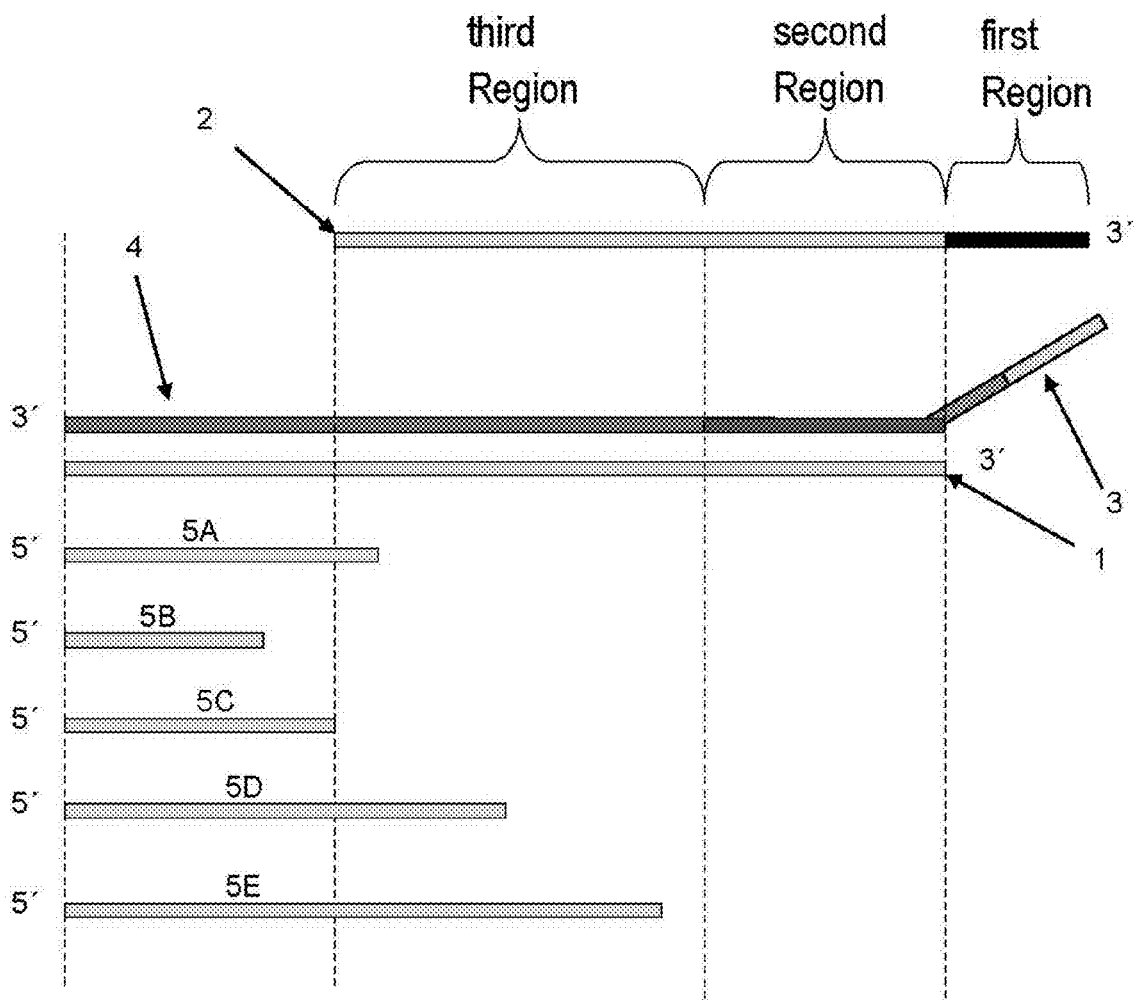
Figure 15:
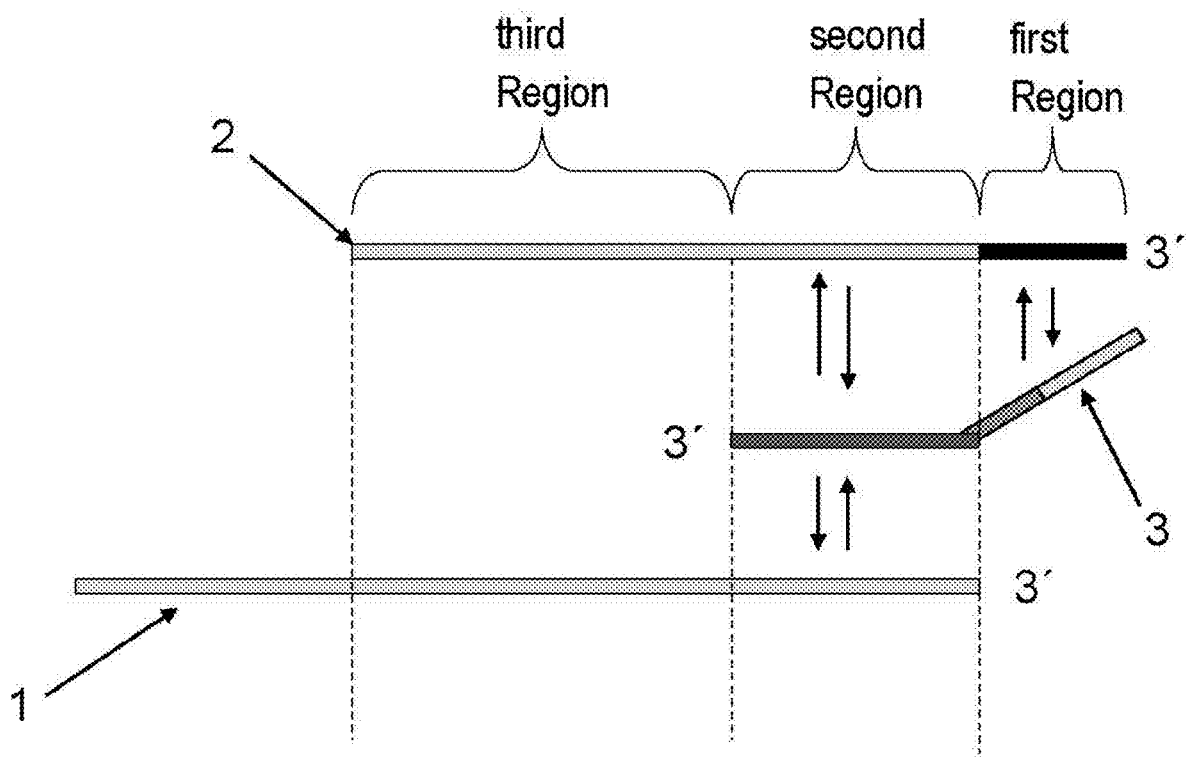
Figure 16:
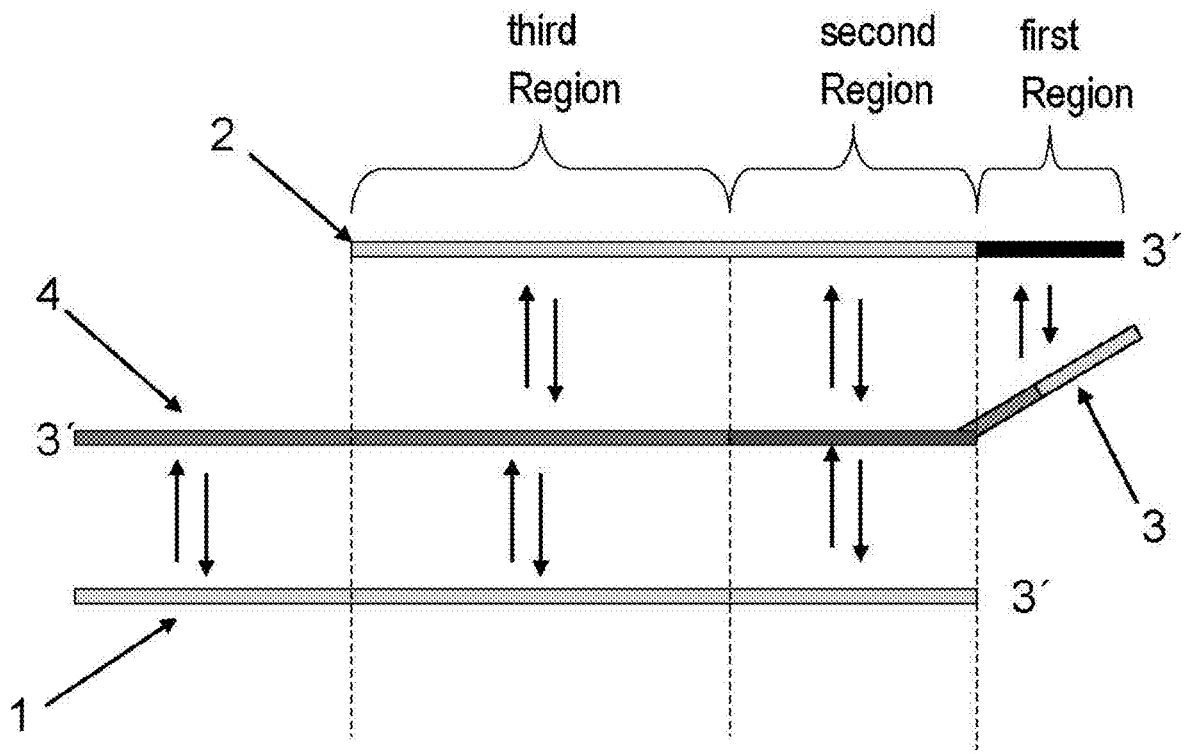
Figure 19:
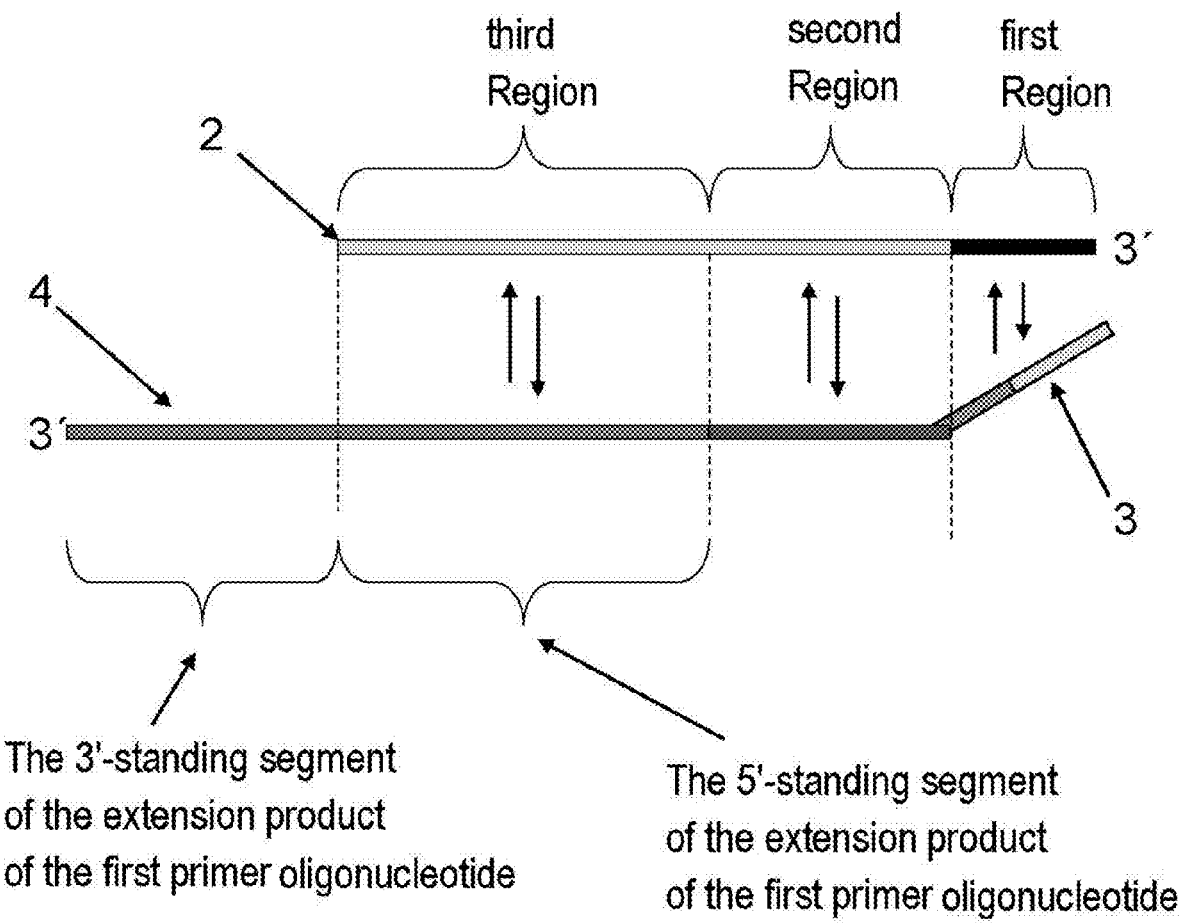
Figure 20:
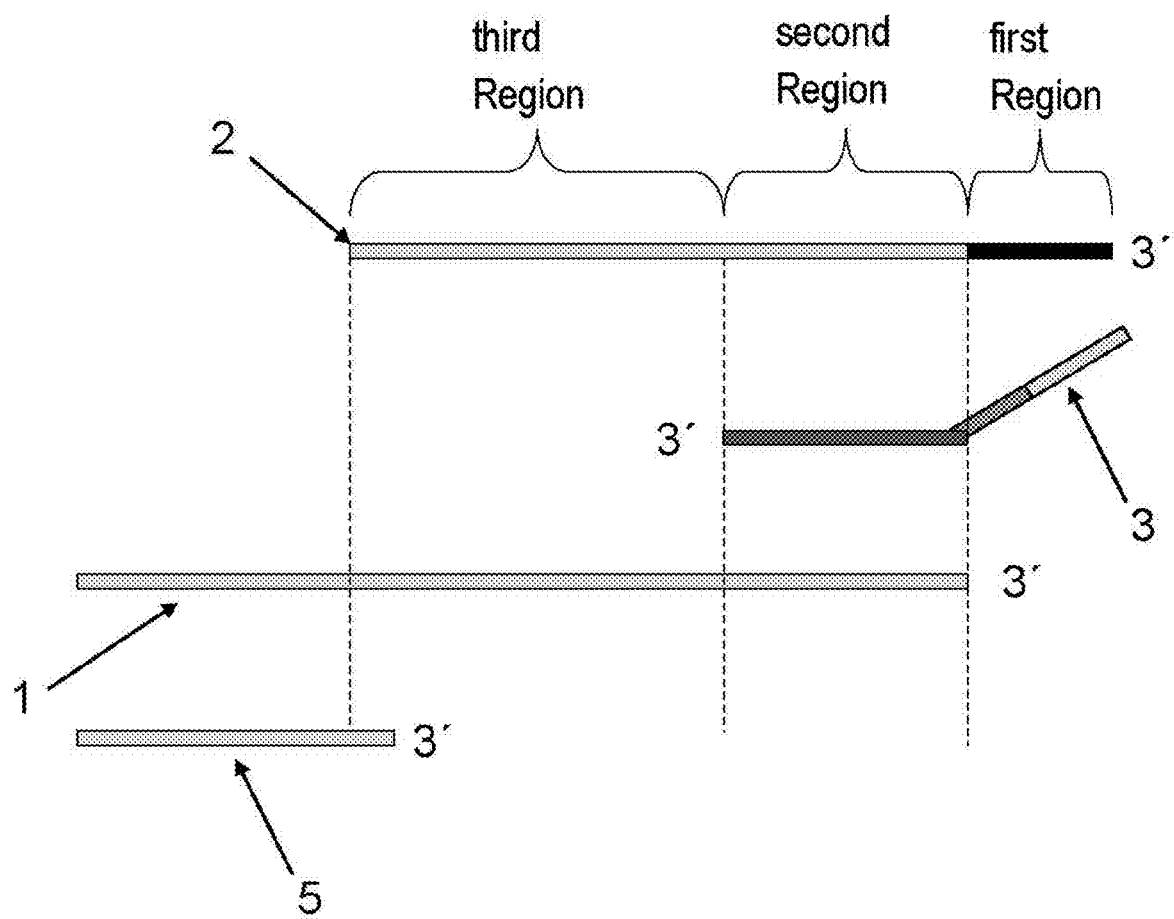
Figure 21:
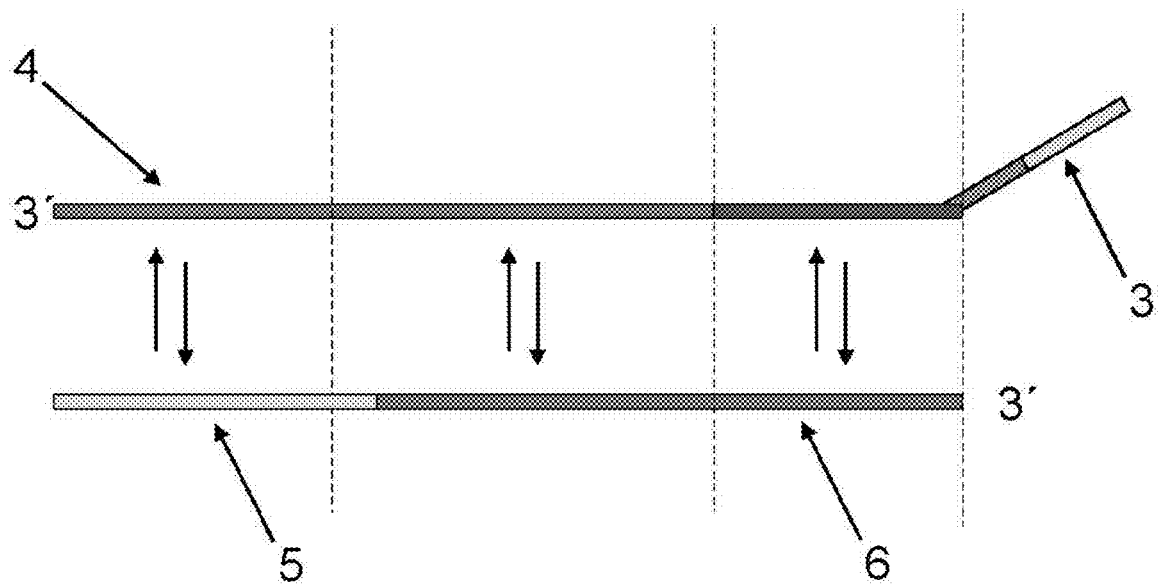

Preferred Embodiments of the Second Primer Oligonucleotide (Primer 2):

An oligonucleotide that with its 3' segment is able to bind to a substantially complementary sequence within the nucleic acid to be amplified or equivalents thereof and to initiate a specific second primer extension reaction (FIG. 13). This second primer oligonucleotide thus is able to bind to the 3' segment of a first specific primer extension product of the first primer oligonucleotide and to initiate a polymerase-dependent synthesis of a second primer extension product. In one embodiment, each second primer oligonucleotide is specific for one nucleic acid to be amplified each.

The second primer oligonucleotide is to be copyable upon backward synthesis and also functions as a template itself during the synthesis of the first primer extension product.

The length of the second primer oligonucleotide can be between 15 and 100 nucleotides, preferably between 20 and 60 nucleotides, particularly preferred between 30 and 50 nucleotides. The nucleotide building blocks are preferably linked to each other via common 5'-3' phosphodiester binding or phosphothioester binding. Such a primer oligonucleotide can be chemically synthesized in the desired manner.

In one embodiment, the second primer oligonucleotide can include nucleotide monomers that do not or only insignificantly influence the function of polymerase, these are for example:

natural nucleotides (dA, dT, dC, dG etc.) or their modifications without changed base pairing modified nucleotides, 2-amino-dA, 2-thio-dT or other nucleotide modifications with diverging base pairing (e.g., universal base pairs such as for example inosine 5-nitroindole).

In a preferred embodiment, the 3'-OH end of this region is preferably free from modifications and has a functional 3'—OH group that is recognized by polymerase and can be extended dependent on a template. In a further preferred embodiment, the 3' segment of the second primer comprises at least one phosphorothioate compound, so that the 3' end of the primer cannot be degraded by the 3' exonuclease activity of polymerases.

The second primer oligonucleotide can be used in several individual steps. First, it exerts a primer function in the amplification. Thereby, a primer extension reaction using the first primer extension product as a template is performed. In a further embodiment, the second primer oligonucleotide can use the start nucleic acid chain as a template at the beginning of the amplification reaction. In a further embodiment, the second primer oligonucleotide can be used in designing/providing a start nucleic acid chain.

During the amplification the second primer functions as an initiator of the synthesis of the second primer extension product using the first primer extension product as a template. The 3' segment of the second primer comprises a sequence that can mainly complementary bind to the first primer extension product. The enzymatic extension of the second primer oligonucleotide using the first primer extension product as a template leads to the formation of the second primer extension product. Such a synthesis typically takes place in parallel to the displacement of the activator oligonucleotide from its binding with the first primer extension product. Said displacement mainly is by polymerase and can partially be done by the second primer oligonucleotide. Such a second extension product comprises the target sequence or segments thereof. In the course of the synthesis of the second primer extension product the sequence of the copyable portion of the first primer oligonucleotide is recognized by polymerase as template and a respective complementary sequence is synthesized. Said sequence is in the 3' segment of the second primer extension product and comprises a primer binding site for the first primer oligonucleotide. The synthesis of the second primer extension product is up to the stop position in the first primer oligonucleotide. Immediately after the synthesis of the second primer extension product this product is bound to the first primer extension product and forms a double-stranded complex. The second primer extension product is sequence-specifically displaced from said complex by the activator oligonucleotide. After a successful strand displacement by the activator oligonucleotide the second primer extension product itself in turn can function as a template for the synthesis of the first primer extension product.

Moreover, the second primer oligonucleotide can function as an initiator of the synthesis of the second primer extension product starting from the start nucleic acid chain at the beginning of the amplification. In one embodiment, the sequence of the second primer is completely complementary to the corresponding sequence segment of a start nucleic acid chain. In a further embodiment, the sequence of the second primer oligonucleotide is only partially complementary to the corresponding sequence segment of a start nucleic acid chain. However, said diverging complementarity is not to prevent the second primer oligonucleotide from starting a mainly sequence-specific primer extension reaction. The respective divergences in complementarity of the second primer oligonucleotide to the respective position in the start nucleic acid chain are preferably in the 5' segment of the second primer oligonucleotide, so that in the 3' segment mainly complementary base pairing and initiation of the synthesis are possible. For the initiation of the synthesis for example particularly the first 4-10 positions in the 3' segment are to be fully complementary to the template (start nucleic acid chain). The remaining nucleotide positions can diverge from perfect complementarity. Thus, the degree of a perfect complementarity in the 5' segment can comprise ranges of 10% to 100%, better between 30% and 100% of the base composition. Depending on the length of the second primer oligonucleotide these divergences from a full complementarity in the 5' segment comprise from 1 to 40, better 1 to 20 nucleotide positions. In a further embodiment, the second primer oligonucleotide binds to the start nucleic acid chain only with its 3' segment, but not with its 5' segment. The length of such a 3' segment of the second primer oligonucleotide that is completely complementary to the start nucleic acid chain comprises ranges between 6 and 40 nucleotides, better between 6 and 30 nucleotides, preferably between 6 and 20. The length of a corresponding 5' segment of the second primer oligonucleotide that is non-complementary to the start nucleic acid chain comprises ranges between 5 and 60, better between 10 and 40 nucleotides. Thus, the second primer oligonucleotide is able to initiate the synthesis of a start nucleic acid chain. In a subsequent synthesis of the first primer extension product sequence parts of the second primer oligonucleotide are copied by polymerase, so that in turn in subsequent synthesis cycles a completely complementary primer binding site is formed within the first primer extension product for binding of the second primer oligonucleotide and is available in subsequent synthesis cycles.

In a further embodiment, the second primer oligonucleotide can be used during the preparation of a start nucleic acid chain. Here, such a second primer oligonucleotide can mainly/preferably sequence-specifically bind to a nucleic acid (e.g., a single-stranded genomic DNA or RNA or equivalents thereof comprising a target sequence) and initiate a template-depending primer extension reaction in the presence of a polymerase. The binding position is selected such that the primer extension product comprises a desired target sequence. Extending the second primer oligonucleotide results in a strand that has a sequence complementary to the template. Such a strand can be detached by the template (e.g., by heat or alkali) and so converted into a single-stranded form. Such a single-stranded nucleic acid chain can function as a start nucleic acid chain at the beginning of the amplification. Such a start nucleic acid chain comprises in its 5' segment the sequence portions of the second primer oligonucleotide, moreover it comprises a target sequence or equivalents thereof and a primer binding site for the first primer oligonucleotide. Further steps are explained in section "start nucleic acid chain".

In a preferred embodiment, the second primer oligonucleotide at least in its 3' segment comprises sequence portions that can complementary and sequence-specifically bind to a sequence segment of a target sequence and initiate/support a successful primer extension reaction by polymerase. The length of such a sequence segment comprises ranges of 6 and 40 nucleotides, better of 8 to 30 nucleotides, preferably of 10 to 25 nucleotides.

In one embodiment, the second primer oligonucleotide in its 3' and 5' segment comprises copyable sequence parts that are copied by polymerase in the synthesis of the first primer extension product. Thus, all sequence parts of the second primer are copied by polymerase. This leads to the formation of a primer binding site in the 3' segment of the first primer extension product.

In a further embodiment, the second primer oligonucleotide flanking its 5' segment with copyable sequence parts can comprise a further sequence segment that comprises non-copyable portions. Such a primer can be used for example as a "scorpion primer" in the detection. In such an embodiment, the second primer oligonucleotide comprises modifications that upset polymerase in copying said flanking sequence segment. Such modifications comprise for example C3 linkers or HEG linkers or other modifications that lead to the stop of polymerase. Further examples of such modifications are described in section "embodiments of the first primer oligonucleotide", see there.

In one embodiment, the second primer oligonucleotide with its copyable portions in their length corresponds to the 3' segment of the first primer extension product that is not bound by the activator oligonucleotide (FIG. 14B, Primer 5C). In the complex comprising the second primer oligonucleotide and the first primer extension product the 3' end of such a second primer oligonucleotide borders on the activator oligonucleotide that is bound to the first primer extension product. Extension of such a primer is done by using the first primer extension product as a template. In the extension of such a primer displacement of the activator oligonucleotide from the binding with the first primer extension product takes place by means of polymerase-dependent strand displacement. The corresponding second primer extension product is shown in FIG. 14C (primer extension product 6C).

In a further embodiment, the second primer oligonucleotide with its copyable sequence portions is shorter than the 3' segment of the first primer extension product that is not bound by the activator oligonucleotide (FIG. 14B, primer 5B). In the complex comprising the second primer oligonucleotide and the first primer extension product thus between the 3' end of such a primer and the activator oligonucleotide bound to the first primer extension product there is a single-stranded section of the first primer extension product. Extension of such a primer is done by using the first primer extension product as a template. In the extension of such a primer displacement of the activator oligonucleotide from the binding with the first primer extension product takes place by means of polymerase-dependent strand displacement. The corresponding second primer extension product is shown in FIG. 14C (primer extension product 6B).

In a further embodiment, the second primer oligonucleotide with its copyable portions is longer than the 3' segment of the first primer extension product that is not bound by the activator oligonucleotide (FIG. 14B, primers 5A, 5D, 5E). In the complex of the second primer oligonucleotide and the first primer extension product the 3' segment of the second primer and the 5' segment of the activator oligonucleotide compete for the binding to the first primer extension product. Binding of the 3' segment of the second primer to the first primer extension product that is required for an initiation of the synthesis is with the simultaneous partial displacement of the 5' segment of the activator oligonucleotide.

After initiation of the synthesis by polymerase there is the displacement of such a primer by using the first primer extension product as a template. In the extension of such a primer the displacement of the activator oligonucleotide from the binding with the first primer extension product is done by means of polymerase-dependent strand displacement. The corresponding second primer extension product is shown in FIG. 14C (primer extension product 6A, 6D, 6E). The sequence length of the 3' segment of the second primer oligonucleotide that displaces the 5' segment of the activator oligonucleotide can comprise the following regions: 1 to 50 nucleotides, better 3 to 30 nucleotides, preferably 5 to 20 nucleotides. Using second primer oligonucleotides of a greater length that exceeds the length of the 3' segment of the first primer extension product is for example advantageous in some embodiments. Such embodiments comprise for example a first primer extension product with its 3' segment that is not bound by the activator oligonucleotide being of a length of 5 to 40 nucleotides, better of 10 to 30 nucleotides. Especially with shorter 3' segments a longer second primer oligonucleotide offers an improved sequence specificity in the initiation of synthesis.

The binding strength of the second primer oligonucleotide to its primer binding site depends on the length of the primer. Generally, longer second primer oligonucleotides can be employed with higher reaction temperatures.

Preferably, sequences of the first and second primer oligonucleotides and of the activator oligonucleotide are adapted to each other such that side reactions, e.g., primer dimer formation, are minimized. For that, for example the sequence of the first and second primer oligonucleotides are adapted to each other such that both primer oligonucleotides are not able to start an amplification reaction in the absence of an appropriate template and/or a target sequence and/or a start nucleic acid chain. This can be achieved for example in that the second primer oligonucleotide does not comprise a primer binding site for the first primer oligonucleotide and the first primer oligonucleotide does not comprise a primer binding site for the second primer oligonucleotide. Moreover, it is to be avoided that the primer sequences comprise extended self-complementary structures (self-complement).

The synthesis of the second primer extension product is a primer extension reaction and forms an individual step in the amplification. The reaction conditions during this step are accordingly adapted. Reaction temperature and reaction time are selected such that the reaction can successfully take place. The preferred temperature in this step depends on the polymerase used and the binding strength of the respective second primer oligonucleotide to its primer binding site and comprises for example ranges of 15° C. to 75° C., better of 20 to 65° C., preferably of 25° C. to 65° C. The concentration of the second primer oligonucleotide comprises ranges of 0.01 µmol/l to 50 µmol/l, better of 0.1 µmol/l to 20 µmol/l, preferably of 0.1 µmol/l to 10 µmol/l.

In one embodiment, all steps of the amplification proceed under stringent conditions that prevent or decelerate the formation of non-specific products/by-products. Such conditions are for example higher temperatures, for example above 50° C.

If more than one specific nucleic acid chain has to be amplified in one batch, so in one embodiment preferably sequence-specific primer oligonucleotides are used for the amplification of the respective target sequences.

In one embodiment, the synthesis of the first and second primer extension products proceeds at the same temperature. In a further embodiment, the synthesis of the first and second primer extension products proceeds at different temperatures. In a further embodiment, synthesis of the second primer extension product and strand displacement by the activator oligonucleotide proceed at the same temperature. In a further embodiment, synthesis of the second primer extension product and strand displacement by the activator oligonucleotide proceed at different temperatures.

Exponential Vs. Linear Amplification

If both complementary strands (the first primer extension product and the second primer extension product, wherein both primer extension products can be templates for the syntheses of the complementary strands) are synthesized substantially in parallel to each other in the same batch an exponential propagation of both primer extension products can occur during such a reaction.

The primer extension products re-synthesized during a synthesis process close the respective complementary sequence parts to primers used, so that new primer binding sites are generated. In this way, re-synthesized strands themselves can function as templates in the subsequent synthesis processes.

If substantially only one primer extension product is synthesized as a result of cyclically repeated synthesis processes, so a linear amplification of said primer extension product occurs.

The rate of an exponential amplification generally can be higher than the rate of a linear amplification, especially at the beginning of an amplification, if the initial amounts of start nucleic acid chains are very low and the influence of reaction products on the reaction kinetics is still negligibly low. In general, the rate of the reaction decreases with an increase in the amount of synthesis products, so that a deceleration of the amplification has to be expected. In detail, efficiency and rate of individual process steps have an effect on the total rate of the method according to the invention. By changing/adapting the efficiency of individual steps the method of amplification according to the invention can be influenced in its rate and efficiency.

In the following, a preferred embodiment of the method is explained in detail as an example, namely an exponential amplification of a nucleic acid chain to be amplified.

An exponential synthesis reaction (amplification) results in an accumulation of both re-synthesized primer extension products that are regarded as the nucleic acid chain to be amplified. It is conditional upon a cyclic repetition of synthesis processes of both primer extension products and strand displacement processes (with the result of an opening of the respective primer binding site) that are at least partially conditional upon the sequence-specific strand displacement of the second primer extension product via the activator oligonucleotide.

Thereby, strand displacement of a second primer extension product mediated by the complementary binding of the activator oligonucleotide to the first primer extension product can lead to a permanent or transient separation of the first and second primer extension products. Said separation can be done completely or partially with the sequence-specific cooperation of the activator oligonucleotide.

If the activator oligonucleotide has successfully bound to the first primer extension product the number of complementary base pairings between the first and the second primer extension products is reduced. At the given reaction conditions thereby preferably the stability of the binding between the first and second primer extension products is reduced to such an extent that both primer extension products can be detached (e.g., the reaction temperature in this step is close to the melting temperature of the remaining complex of the first and second primer extension products). This results in a complete dissociation of a first primer extension product and a second primer extension product.

Due to low concentrations of synthesized primer extension products at the beginning of the reaction the re-association kinetics of said strands is significantly decelerated. The concentration of the synthesis products may for example range from sub-femtomolar up to nanomolar concentration ranges. It is known that in these concentration ranges re-association of complementary strands is slow. In this way, a complete detachment of the second primer extension product from the first primer extension product can have a positive effect on the reaction kinetics. By the molar excess of the first and second primers these bind to respective primer binding sites that have become free and thus, in a new synthesis can play an initiating role.

In a preferred embodiment, strand displacement of the second primer extension product by the activator oligonucleotide up to its separation from the first primer extension product is performed at reaction conditions that advantageously support a temperature-dependent strand detachment in the region of the 3' segment of the first primer extension product.

However, such reaction conditions are selected such that there is no complete strand dissociation between the first and second primer extension products, if the activator oligonucleotide does not or only incomplete bind to the first primer extension product.

By the complete detachment of the two primer extension products now this strand is present in the single-stranded form in the reaction solution, so that new first primer has substantially unhindered access to its respective primer binding site in this strand. In general, this has a positive effect on the reaction kinetics of the initiation of the synthesis reaction of the first primer extension product.

That is, in some cases, there results a advantageous combination of reaction conditions during the step of the strand displacement process by the activator oligonucleotide and the progress/extent of strand displacement of the second primer extension product up to the positions in its sequence at which the remaining double strand of the 3' segment of the first primer extension product and the second primer extension product increasingly becomes instable and very likely degrades under such reaction conditions, so that a complete detachment from the first primer extension product occurs.

Due to low concentrations of synthesis products at the beginning of the reaction and the associated almost negligible re-association of both synthesized strands a positive effect is exerted on the rate of the synthesis of such strands.

With increasing concentrations of re-synthesized strands generally reaction rate decreases. This effect is at least partially attributed to the accelerated re-association of both primer extension products, which results in a reduced exposition of primer binding sites.

By changing reaction conditions that suppress such a re-association the rate of the reaction can be favored. For example, the concentration of the second primer can be increased, which can lead to a competitive occupation of the second primer binding site. On the other hand, the temperature of the method can be increased with an increasing progress of the reaction.

In an advantageous embodiment of the method both primers are employed substantially in equally high concentrations or in concentration ranges that are approximately equally high.

In a further advantageous embodiment of the method at least one of both primers is employed in a higher concentration than its partner primer. Here, the differences in concentrations may be in ranges that are between 1:2 to 1:50, advantageously between 1:2 to 1:10.

This can result in an asymmetric amplification reaction in which the concentration of a primer extension product is accordingly higher than that of the other strand.

The examples cited below are to be stated only to demonstrate the method and are not to be interpreted as being limiting.

The structures, sequences, and reaction conditions given in the examples are only to represent and illustrate the mode of function of the method and do not function as a limitation.

EXAMPLES

Material and Methods:
Reagents were commercially purchased from the following suppliers:
  unmodified and modified oligonucleotides (Eurofins MWG, Eurogentec, Biomers, Trilink Technologies, IBA Solutions for Life Sciences)
  polymerases NEB (New England Biolabs)
  dNTPs: Jena Bioscience
  intercalating Eva green dye: Jena Bioscience
  buffer substances and other chemicals: Sigma-Aldrich
  plastic goods: Sarstedt
  Solution 1 (buffer solution 1):
  potassium glutamate, 50 mmol/l, pH 8.0
  magnesium acetate, 10 mmol/l
  Triton X-100, 0.1% (v/v)
  EDTA, 0.1 mmol/l
  TPAC (tetrapropylammonium chloride), 50 mmol/l, pH 8.0
  Eva green dye (the dye was employed in accordance with the manufacturer's instructions in dilution of 1:50).
  Solution 2 (amplification reaction solution 2) (standard reaction):
  potassium glutamate, 50 mmol/l, pH 8.0
  magnesium acetate, 10 mmol/l
  dNTP (dATP, dCTP, dTTP, dGTP), 200 µmol/leach
  polymerase (Bst 2.0 WarmStart, 120,000 U/ml NEB), 12 units/10 µl
  Triton X-100, 0.1% (v/v)
  EDTA, 0.1 mmol/l
  TPAC (tetrapropylammonium chloride), 50 mmol/l, pH 8.0
  Eva green dye (the dye was employed in accordance with the manufacturer's instructions in dilution of 1:50)
  primer 1: 10 µmol/l
  primer 2: 10 µmol/l
  activator oligonucleotide: 10 µmol/l
  template strand—variable concentrations such as indicated in the examples.

All concentrations are indications of the final concentrations in the reaction. Deviations from the standard reaction are indicated accordingly.

The melting temperature (Tm) of the participating components was determined upon concentration of 1 µmol/l of the respective components in solution 1. Deviating parameters are indicated respectively.

General Information on Reactions

Primer extension reactions and amplification were performed at a reaction temperature of 65° C. in a standard manner. Deviations are indicated.

The reaction was started by heating the reaction solutions to the reaction temperature since Bst 2.0 polymerase Warmstart at lower temperatures is mainly inhibited in its function by a temperature-sensitive oligonucleotide (according to the manufacturer's specifications). The polymerase becomes increasingly more active from a temperature of ca. 45° C., at a temperature of 65° C. no differences between polymerase Bst 2.0 and Bst 2.0 Warmstart could be observed. In order to prevent the extensive formation of by-products (e.g., primer dimer) during the preparation phase of a reaction polymerase Bst 2.0 Warmstart was used. Deviations are specifically indicated.

The reaction was stopped by heating the reaction solution to above 80° C., e.g., 10 min at 95° C. At this temperature polymerase Bst 2.0 is irreversibly denaturized and the result of synthesis reaction cannot be changed later.

The reactions were carried out in a thermostat having a fluorimeter. For that, a commercial Real-Time PCR apparatus was used, StepOne Plus (Applied Biosystems, Thermofischer). The reaction volume by default was 10 µl. Deviations are indicated.

Both end-point detection and kinetic observations have been made. In end-point detections the signal was recorded for example by a nucleic acid-bound dye, e.g., by TMR (tetramethyl rhodamine, also referred to as TAMRA) or by FAM (fluorescein). The wavelengths for exciting and measuring the fluorescence signals of FAM and TMR are stored as the factory settings in the StepOne Plus Real-Time PCR apparatus. Also, an intercalating dye (Eva green) was used in end-point measurements, e.g., in measuring the melting curve). Eva green is an intercalating dye and an analogue of the frequently employed SYBR green dye, however, with a slightly less inhibition of polymerases. The wavelengths for exciting and measuring the fluorescence signals of SYBR green and Eva green are identical and stored as the factory settings in the StepOne Plus Real-Time PCR apparatus. Fluorescence can continuously be detected by means of built-in detectors, i.e. "online" or "real-time". Since the polymerase during its synthesis synthesizes a double strand this technique could be used for kinetic measurements (real-time monitoring) of the reaction. Due to a certain cross-talk between color channels in the StepOne Plus apparatus a partially increased basal signal intensity was observed in measurements in which e.g., TMR-labeled primers were used in concentrations of more than 1 µmol/l (e.g., 10 µmol/l). It was observed that the TMR signal in the SYBR green channel leads to increased basic values. These increased basic values were taken into account in calculations.

The kinetic observations of courses of reactions were routinely recorded by means of fluorescence signals of fluorescein (FAM-TAMRA Fret pair) or intercalating dyes (Eva green). Time-dependence of the signal course was detected (real-time signal detection in the StepOne plus PCR apparatus. An increase of the signal during a reaction compared to a control reaction was interpreted depending on the structure of the batch. For example, an increase in the signal using EVA green dye was interpreted as an indication of an increase in the amount of double-stranded nucleic acid chains during the reaction, and thus, judged to be the result of a synthesis by DNA polymerase.

In some reactions a melting curve determination was performed following the reaction. Such measurements allow to draw conclusions about the presence of double strands that for example can absorb intercalating dyes and this way significantly enhance signal intensity of dyes. With the rising temperature the proportion of double strands decreases and also the signal intensity decreases. The signal depends on the length of the nucleic acid chains and on the sequence composition. Said technique is well known to the skilled person.

When using melting curve analysis in context with reactions that contained significant proportions of modified nucleic acid chains (e.g., activator oligonucleotides or primers) it was found that the signal of the Eva green dye can behave different for example between the B form of the DNA and the A form of modified nucleic acid chains. For example, in the B form of the double-stranded nucleic acid chains (usually taken on for classical DNA sections) a higher signal intensity was observed than with double-stranded nucleic acid chains having the same sequence of nucleobases that can take on an A-form-like conformation (e.g., by several 2'-O-Me modifications of nucleotides). This observation was taken into account when intercalating dyes were employed.

As needed, the reaction was analyzed by means of capillary electrophoresis and the length of fragments formed was compared to a standard. In preparation for the capillary electrophoresis the reaction mixture was diluted in a buffer (Tris-HCl, 20 mmol/l, pH 8.0, and EDTA, 20 mmol/l, pH 8.0) such that the concentration of labeled nucleic acids was ca. 20 nmol/l. Capillary electrophoresis was performed at GATC-Biotech (Konstanz, Germany) as contractual service. In accordance with the specifications of the supplier the capillary electrophoresis was performed on an ABI 3730 Cappilary Sequencer under standard conditions for Sanger sequencing using a POP7 gel matrix at ca. 50° C. and a constant voltage (ca. 10 kV). The conditions used resulted in the denaturation of double strands, so that in the capillary electrophoresis the single-stranded form of nucleic acid chains was separated. Electrophoresis is a standard technique in the genetic analysis. The automated capillary electrophoresis is employed routinely in Sanger sequencing to this day. The fluorescence signal is continuously recorded during the capillary electrophoresis (usually using virtual filters), so that an electrophoretogram is generated in which the signal intensity correlates to the duration of the electrophoresis. With shorter fragments, e.g., unused primers, there is observed an early signal peak, with extended fragments there is a temporal shift of the signals proportional to the length of the extended regions. Thanks to controls with known lengths the length of extended fragments can be measured. Said technique is known to a skilled person and is also employed by default in fragment length polymorphism.

Example 1

Nucleic Acid-Dependent Strand Displacement Under Isothermal Conditions

The example demonstrates the basic ability of single-stranded complementary nucleic acid chains of a nucleic acid-dependent, mainly sequence-specific strand displacement in the absence of strand-separating proteins or enzymes (e.g., helicases or recombinases) and without consuming chemically stored energy in the form of ATP. It is demonstrated that a double strand (formed of strands here referred to as A1 and B1, so that a A1:B1 double strand results) that is stable under reaction conditions can be opened by single-stranded nucleic acid chain (here referred to as C1 oligonucleotide) that is substantially complementary to certain segments of strand A1. As a result of this double strand opening strand B1 is converted to the single-stranded form, at the same time a new A1:C1 double strand is formed. The sequence of the C1 nucleic acid chains used in this example was constructed such that a nucleic acid chain-mediated sequence-specific strand displacement reaction can take place on a double-stranded DNA fragment under isothermal conditions. In this example no polymerase was added to the reaction, thus, no new nucleic acid strands were synthesized and no amplification of nucleic acid chains took place.

To detect strand displacement and separation of a pre-formed double strand both strands to be separated were labeled with fluorophores, so that a FRET pair (consisting of fluorescein and TAMRA) was formed. The fluorophores were positioned at an end of the A1:B1 double strand, i.e. at complementary ends of both strands. The nucleic acid strands used here were chemically synthesized, the fluorophores were chemically coupled to the corresponding strand ends during the chemical synthesis. The distance between fluorophores, when both strands are complementary to each other, were selected such that an effective quenching of the fluorescein fluorescence by a TAMRA dye can take place. If the strands are separated by any effect, e.g., by temperature or strand displacement, the distance between individual fluorophores is increased, so that the intensity of the fluorescence signal of the fluorescein marker is increased. The maximum intensity of the fluorescein marker is achieved if both strands (A1 and B1) are completely separated. By observing the intensity of the fluorescence and its dependence on the action of various parameters (e.g., temperature, addition of complementary or non-complementary sequences for strand displacement etc.) it is possible to draw conclusions as to the amount of the labeled strands still bound to each other.

In example 1 the principle of the nucleic acid-dependent sequence-specific strand displacement reaction is illustrated. Both kinetics of the strand displacement reaction and temperature-dependence of the opening of the pre-formed double strand (A1:B1) were observed by recording the fluorescence signal during the course of the reaction. Both isothermal reaction conditions and conditions with a temperature gradient were tested.

Preparation of the Starting Material:

For the individual sequences also the laboratory's internal designations were indicated in addition to the sequence and SEQ ID NO.

Double Strand (A1:B1)

The sequences for double strand A1:B1 are artificial sequences that were randomly selected, wherein attention was paid to the absence of extensive hairpins and long G segments or C segments, respectively. Both strands are able to form a complementary double strand. A double strand has a Tm of ca. 75° C. (a further double strand has a Tm of ca. 77° C. s.b.) that is higher than the reaction temperature of 65° C. Thus, such a double strand is stable under reaction conditions. Strand A1 is longer than the respective strand B1, so that a 5' overhang is generated. Said 5' overhang on the A1 strand was designed in analogy to the polynucleotide tail of a first primer extension product. However, to facilitate the synthesis said 5' overhang did not contain modifications that block polymerase activity. Since in the present example no polymerase was present in the reaction absence/presence of such modifications played a subordinate role. Said 5' overhang is complementary to the first region of the single-stranded nucleic acid chain (C1), so that a specific binding of the C1 nucleic acid chain to said overhang can take place under reaction conditions. Thanks to said binding a sufficient spatial proximity between one end of the A1:B1 double strand and corresponding complementary segments of the single-stranded C1 nucleic acid chains is caused, so that a strand displacement reaction can take place. As the result of this reaction a new double strand A1:C1 can be generated and the B1 strand can be converted to its single-stranded form.

```
A1 strand
ES-10-3504
                                          SEQ ID NO: 1
5' CCGAAGCTCGCAGGAACTCAGAGTGTGGAGAGGACGATAGCTAGTCAG

ATGATGAAGTT 3'TMR
```

The sequence consists of DNA. A 3'-terminal TAMRA modification (terminal TMR modification) was already attached during the synthesis.

```
B1 strand
T-A6P-10-3506
                                          SEQ ID NO: 2
5'FAM 5' CATCATCTGACTAGCTATCGTCCTCTCCACACTCTGAGTTC

CTGCGAG 3'

B1 strand
T-A6P-10-3507
                                          SEQ ID NO: 3
5'FAM 5' CATCATCTGACTAGCTATCGTCCTCTCCACACTCTGAGTTC

CTGC 3'
```

Both strands consist of DNA. A 5'-terminal fluorescein dye modification (terminal FAM modification) was selected as the reporter and was already attached to the respective strand during the synthesis with conventional methods of the oligonucleotide chemistry.

Two variants of the double strand were generated. Variant 1 contains a double strand with a shorter overhang in the 5' segment of the A1 strand (6 nucleotides), said double strand consists of SEQ ID NO: 1 and SEQ ID NO: 2), variant 2 contains a double strand with a longer overhang in the 5' segment of the A1 strand (9 nucleotides), said double strand consists of SEQ ID NO: 1 and SEQ ID NO: 3), the respective complementary segments are underlined. Overhangs on the 3' segment of the A1 strand were designed for synthetic reasons and in this example play a subordinate role.

```
A1:B1 double strand (variant 1)
                                          SEQ ID NO: 1
TMR 3' ttGAAGTAGTAGACTGATCGATAGCAGGAGAGGTGTGAGACTCA AGGACGCTCGAAGCC
                                          SEQ ID NO: 2
FAM 5' CATCATCTGACTAGCTATCGTCCTCTCCACACTCTGAGTTCCTG

CGAG

A1:B1 double strand (variant 2)
                                          SEQ ID NO: 1
TMR 3' ttGAAGTAGTAGACTGATCGATAGCAGGAGAGGTGTGAGACTCA AGGACGCTCGAAGCC
                                          SEQ ID NO: 3
FAM 5' CATCATCTGACTAGCTATCGTCCTCTCCACACTCTGAGTTCCTG

C
```

Single-Stranded Nucleic Acid Chains (C1 Oligonucleotides):

A single-stranded nucleic acid chain (in this example referred to as C1 oligonucleotide) under certain conditions can lead to a strand displacement reaction on strand A1:B1 with the simultaneous formation of a new double strand with A1 (A1:C1 double strand). Here, strand B1 is at least partially converted to its single-stranded form. In extreme cases, a strand displacement can lead to a complete dissociation of A1:B1, so that the B1 strand is completely separated from the A1 strand.

C1 oligonucleotides and the activator oligonucleotides have a similar function: they mediate nucleic acid-dependent strand displacement on the respective double strand. The designation C1 oligonucleotide is used in the present example. Because of the absence of the polymerase in said example certainly also C1 oligonucleotides can comprise polymerase-blocking nucleotide modifications, however, presence of said modifications is not a prerequisite to demonstrate strand displacement (s.b.). The designation activator oligonucleotide is used in examples in which the reaction mixture comprises a polymerase and which demonstrate an exponential amplification. Unlike C1 oligonucleotides activator oligonucleotides have to include polymerase-blocking nucleotide modifications.

Due to the similar function of C1 oligonucleotides and the activator oligonucleotides the sequence composition of C1 oligonucleotides is designed similar to the structure of activator oligonucleotides. The C1 oligonucleotides have to comprise the segments complementary to the A1 strand in order that strand displacement can run. C1 oligonucleotides have a single-stranded first, second, and third region (see, structure of activator oligonucleotides). With the first region C1 oligonucleotides can bind to the single-stranded 5' overhang of the A1 strand, regions two and three bind the inner segments of the A1 strand, like with the binding of an activator oligonucleotide and a first primer extension product.

In this example also the ability of activator oligonucleotide structures for an effective strand displacement is to be demonstrated. For this reason some C1 nucleic acid chains have been designed identically to activator oligonucleotides (e.g., SEQ ID NO: 4, 5, 6, and 7). Other C1 nucleic acid chains (SEQ ID NO: 8, 9, and 10) have only been used in this example for demonstration purposes of the strand displacement, they consist of DNA and do not contain internal modifications that can block polymerase activity. Since in the present example no polymerase was present in the reaction absence/presence of such modifications in this example played a subordinate role. The structures of the respective single-stranded nucleic acid chains (C1 oligonucleotides) are summarized below:

C1 Oligonucleotides (Group 1, Oligonucleotides Having the Structure of Activator Oligonucleotides):

The following four C1 oligonucleotides can optionally be present as activator oligonucleotides.

A6 8504-001
SEQ ID NO: 4
5'-[CGUCCUCUCCACACUCUGAGUUCCUG]CGAGCTTCGGTACAAG-3'

A6 8504-002
SEQ ID NO: 5
5'-[AAAACAAACUAGCUAUCGUCCUCUCCACACUCUGAGUUCCUG]CGAG

CTTCGGTACAAG-3'

A6 8507
SEQ ID NO: 6
5'-CTAGCTATCGTCCTCTCCACA[CUCUGAGUUCCUG]CGAGCTTCGGTA

CAAG-3'

A26-1000-103 (negative control)
SEQ ID NO: 7
5'- [AUUCAAAUGUGUUCUCAACGUCCUCUACUCAUGUUCCUG]CGAGCT

TCGGTACAAAA-3'

Numbering from 5' to 3'

The sequence with SEQ ID NO 4, 5, 6, and 7 have been constructed as activator oligonucleotides. They comprise 2'-O-Me nucleotide modifications (indicated in [ ] brackets) and DNA nucleotide (in the 3' segment and optionally in the 5' segment), the 3'—OH group of the 3'-terminal nucleotide was blocked by a phosphate residue. Oligonucleotides were chemically synthesized by a commercial supplier. The underlined segment of the sequence can complementary bind to the A1 strand. The nucleic acids with SEQ ID NO 4, 5, and 6 in their regions one, two, and three are complementary to the sequence of strand A1 (complementary sequences of the second region merge into the complementary sequences of the third region). Such a continuous alignment of complementary nucleobases is to support a strand displacement.

The nucleic acid with SEQ ID NO 7 is complementary in regions one and two (from positions 33 to 49), but it contains a sequence that is non-complementary to A1 (positions 1-18 and 27-32). Part of this non-complementary sequence is directly placed on the 5' segment of the second region in order to prevent progress of the strand displacement beyond this region. The nucleic acid chain functions as a negative control.

C1-Oligonucleotides (Group 2, No Activator Oligonucleotides):

The following three oligonucleotides were also employed in the strand displacement reaction.

A6 8510
SEQ ID NO: 8
5'-TTTTTCTAGCTATCGTCCTCTCCACACTCTGAGTTCCTGCGAGCTTCG

GTACAAG 3'

A6 8512
SEQ ID NO: 9
5' TTTTTCTAGCTATCGTCATCTCCACACTCTGAGTTACTGCGAGCTTCG

GTACAAG 3'

A6 8514-1
SEQ ID NO: 10
5' TTTTTCTAGCTATCGTCCTCTCCACA CTGAGTTCCTGCGAGCTTCGG

TACAAG 3'

Numbering from 5' to 3'

The sequence with SEQ ID NO 8-10 has been construed in its nucleobase composition similar to the above-mentioned activator oligonucleotides. However, no groups leading to polymerase blockage have been inserted at the respective sites in the inner segment of the oligonucleotides: there are no modifications of the sugar phosphate backbone (polymerase-blocking modifications) in the inner region of the sequence as well as a 3'-blocking group. Said C1 oligonucleotides completely consist of DNA nucleotides. Oligonucleotides were chemically synthesized by a commercial supplier. The underlined segment of the sequence can complementary bind to the A1 strand. Here, SEQ ID NO 8 contains a throughout complementary segment. This segment corresponds to a first, second, and third region in an activator oligonucleotide. The nucleic acids with SEQ ID NO 9 and 10 each comprise two sequence divergences of throughout complementary sequences to A1 strand. SEQ ID NO 9 in positions 18 and 36 each contains an A nucleotide instead of its C nucleotide. Nucleotides in these positions do not represent a complementary nucleobase to the respective positions in strand A1. Nucleic acid chain with SEQ ID NO 10 has a divergence in complementarity in the form of a deletion: between positions 26 and 27 2 nucleotides are lacking (CT). This divergence leads to a disruption of a complementary row with the formation of an A1:C1 double strand.

First Primer Oligonucleotide (Primer 1).

The first primer oligonucleotide was employed in the reaction to initiate a temperature-dependent start of the strand displacement.

```
A6P-10-1001
                                    SEQ ID NO: 11
5'-GTA[CCGAAGC]T*[CG]CAGGAAC-3'

Numbering from 5' to 3'
```

The first primer oligonucleotide comprises 2'-O-Me nucleotide modifications (indicated in [ ] brackets) and DNA nucleotide (in the 3' segment and optionally in the 5' segment), the 3'—OH group of the 3'-terminal nucleotide is free. The oligonucleotide in its position 11 has a dT nucleotide modified with a TAMRA dye (shown as T* in the sequence). The oligonucleotide was chemically synthesized by a commercial supplier. The primer with its sequence can complementary bind to C1 oligonucleotides. Thanks to this binding between primer 1 and the C1 oligonucleotide certain sequence segments of the respective C1 oligonucleotide are double-stranded during the assembling of the reaction mixture (performed under room temperature) and cannot interact with the single-stranded overhang of the A1 strand.

Preparation of a Complementary Double Strand (A1 and B1)

Both complementary strands of nucleic acids (A1 and B1) were combined in concentrations of 1 µmol/l each in the buffer solution 1 (without Eva green dye), short-term heated and left at room temperature for cooling, so that a double strand (A1:B1) can be formed over the complementary region. This results in two variants of double strands:

Variant 1 contains sequences with SEQ ID NO: 1 and SEQ ID NO: 2

Variant 2 contains sequences with SEQ ID NO: 1 and SEQ ID NO: 3

Preparation of Single-Stranded Nucleic Acid Chain (C1), (without Primer 1 Complex)

The respective single-stranded nucleic acid chain (C1) was presented in buffer solution 1 (without Eva green dye) in a concentration of 10 µmol/l.

Preparation of C1:Primer 1 Complexes of Single-Stranded Nucleic Acid Chain (C1) and Primer 1

In order to reversibly block the first and second regions of the single-stranded nucleic acid chain (C1) primer 1 was added to the respective C1 oligonucleotide in equimolar concentration, so that a partially double-stranded C1:primer 1 complex could be formed. Primer 1 specifically binds to the first and second regions of the C1 oligonucleotide and thus, blocks a sequence segment that can interact with the overhang of the A1 strand during the preparation phase of the reaction mixture (under room temperature). Said complex is stable at room temperature and can only dissociate to its component parts under reaction conditions, so that the first and second regions of the C1 oligonucleotide become single-stranded and thus, can interact with corresponding structures of the double strand (A1:B1). The complexes of C1 oligonucleotide and primer 1 were also presented in buffer solution 1 (without Eva green dye) in a concentration of 10 µmol/l.

Preparation of the Reaction Mixture, Start of the Reaction and Reaction Conditions The reaction mixture was prepared by combining equal volumes (5 µl each) of a solution with a double strand (A1:B1) and a solution with a C1 oligonucleotide or C1 primer 1 complex to be tested at room temperature. In the resulting reaction mixture the individual strands are present in the following concentrations:

double strand A1:B1 in a concentration of 0.5 µmol/l single strand (C1) or complex C1-primer 1 in a concentration of 5 µmol/l single strand B1 (as FAM signal control) in a concentration of 0.5 µmol/l.

Observation of the Course of the Strand Displacement Under Isothermal Conditions of 65° C.

The thus prepared reaction mixture was transferred to an appropriate reaction vessel (microwell plate) in a thermostat with a fluorescence detection function. As the thermostat a real-time PCR apparatus ("StepOne Plus", StepOne Software v2.1 ABI, Themorfischer) was used. The reaction mixture was pre-heated to a temperature of first 50° C. for ca. 50 sec (cycles 1 to 5) and subsequently heated to 65° C. This temperature was maintained for ca. 10 min (cycles 6 to 30 were recorded), so that a strand displacement reaction could proceed under isothermal conditions and be observed. The fluorescence signal of FAM was recorded depending on time (real-time function of the apparatus). Thanks to the use of the real-time PCR apparatus a software program with the appropriate FAM filter adjustments supplied by the manufacturer could be used. The minimum time interval between two measurements intended by the manufacturer was 10 sec (minimum adjustable time interval), which in total resulted in an apparatus-related measuring cycle of ca. 15 to 18 sec. The course of the FAM signal was recorded with this maximum recording rate.

Observation of the Separation of A1 and B1 During a Thermal Gradient (50° C.-95° C.) in the Presence/Absence of C1 Oligonucleotides.

In a further experiment, the reaction mixture was continuously heated from 50° C. to 95° C. (temperature gradient). During this heating phase also the FAM signal was detected, wherein a FAM signal measurement was made every 0.5° C. of rise in temperature. This resulted in a thermo profile of the reaction mixture in which the signal intensity of the FAM report was recorded depending on the temperature. Also this experiment was performed by means of the real-time PCR apparatus (StepOne Plus), wherein the program was used for the melting curve determination (pre-installed by the supplier, software version StepOne v2.1).

Both experiments were evaluated for the respective reaction mixture and the results are represented in the following. The composition of individual reactions is indicated in the appropriate places.

Figure 24:
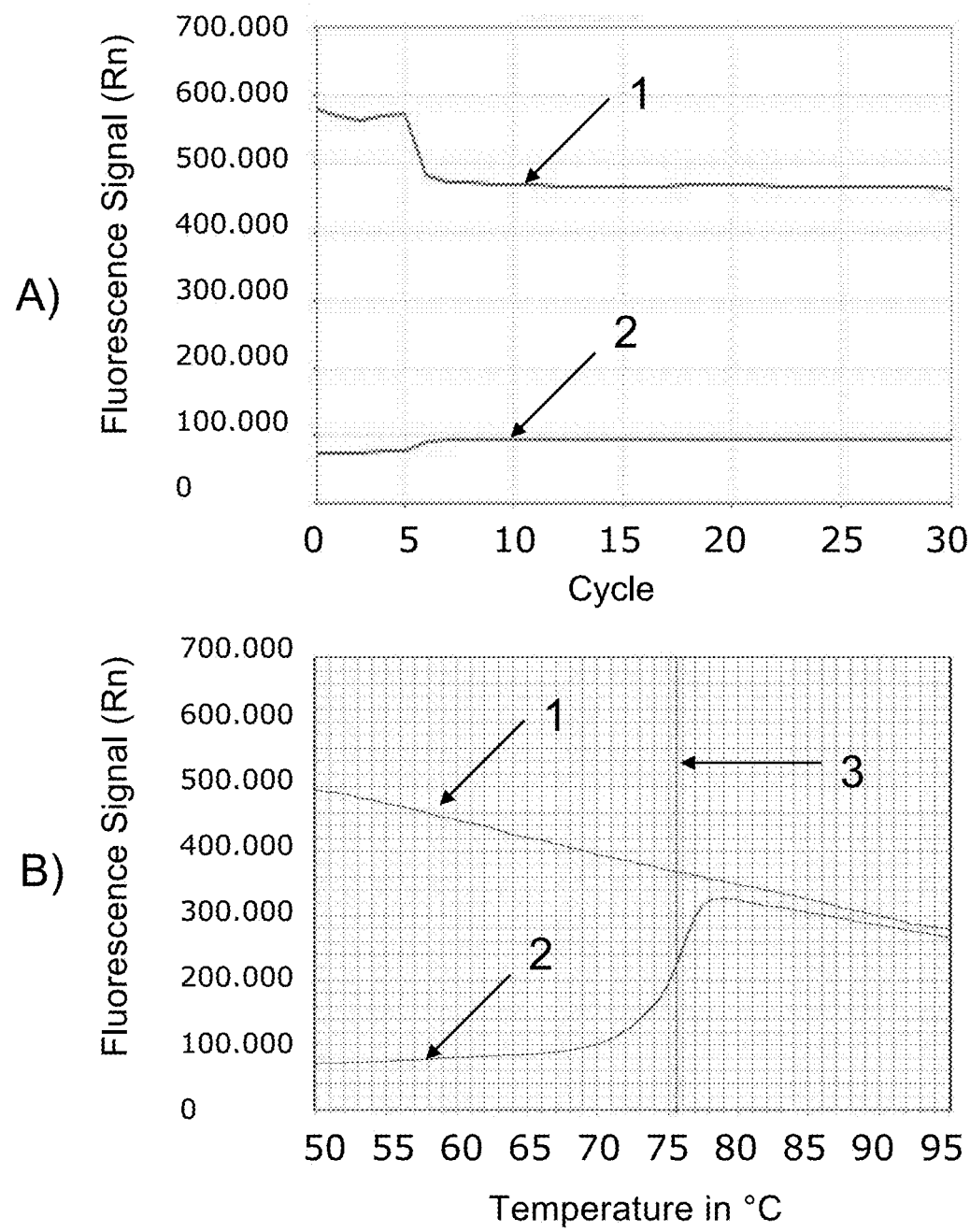
Figure 25:
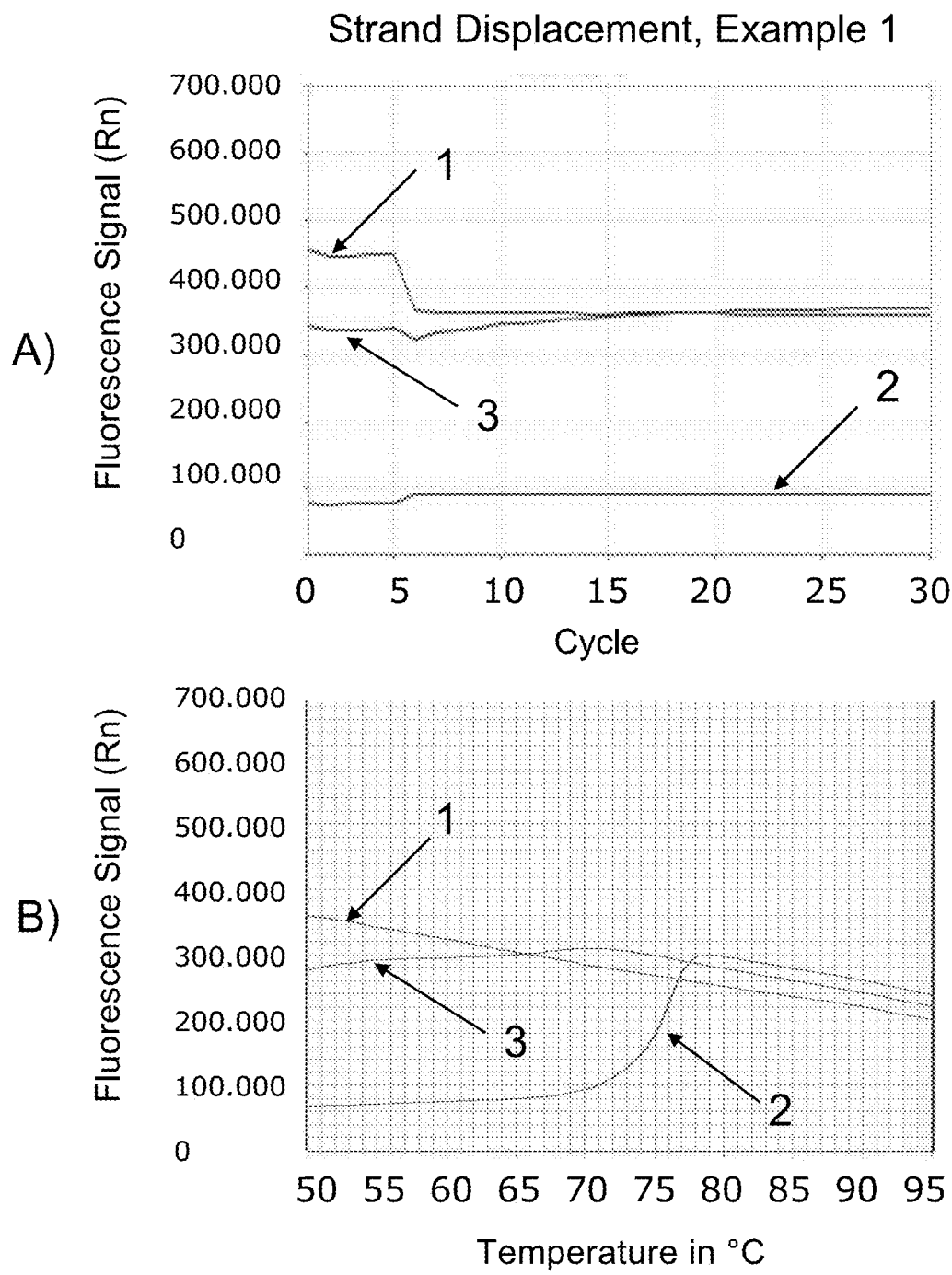

Result:

1. Test of the Detection System:

The functionality of the FRET pair of FAM and TAMRA was examined in two control batches. The first control batch contained only a B1 strand labeled with a FAM dye (FIG. 24 arrow 1), the second control batch contained both a A1 strand labeled with TAMRA and a B1 strand labeled with FAM (A1:B1 double strand) (FIG. 24 arrow 2). Both the temporal course of the signals under isothermal conditions (FIG. 24 A) and the behavior of the signal in the temperature gradient were recorded (FIG. 24 B). There is seen a stable signal line at isothermal conditions (65° C.) for both control batches (FIG. 24 A). In recording the temperature gradient (FIG. 24 B) of the double strand (arrow 2) it is seen a rise in the fluorescence of the FAM reporter from ca. 70° C. The signal reaches its maximum at ca. 80° C. and subsequently behaves like a single strand (see arrow 1). The calculated melting temperature of this strand (variant 2 of the double strand A1:B1 with 9 nucleotides in the 5' overhang of the A1 strand) is at ca. 75° C. (arrow 3). At this temperature by definition half of the double strand is molten, so that half of strands A1 and B1 each are single-stranded. The control batches for variant 1 of double strand A1:B1 with 6 nucleotides in the 5' overhang of the A1 strand behave similar, the Tm of this variant 1 is at ca. 77° C.

Arrows 1 and 2 also in the following FIGS. 24 to 29 show the respective control batches with a single-stranded FAM-labeled B1 strand (arrow 1) and a labeled double strand A1:B1 (arrow 2).

2. Strand Displacement by a Simile-Stranded Complementary Oligonucleotide

In case of a throughout complementary composition of the sequences of the C1 oligonucleotides and A1 strands (e.g., reaction between A1:B1 variant 2 and C1 oligonucleotide SEQ ID NO 5 A6 8504) strand displacement of the B1 strand sometimes was so fast that a significant part of the B1 strands was present in the single-stranded form already during the preparation of the reaction mixture or even before the start of the recording. This can be seen from the increased signal intensity in FIG. 25 (arrow 3). Already the first measurement (cycle 1) has a significantly higher signal level than the control reaction with an A1:B1 double strand without C1 oligonucleotide. Thus, the B1 strand already prior to the first measurement is present in the single-stranded form. Reactions with the A1:B1 double strand variant 1 also show a similar behavior.

Replacement of the C1 oligonucleotide by another throughout complementary C1 oligonucleotide (e.g., SEQ ID NO 4, 6, or 8) basically shows a similar behavior. The high intensity of the fluorescence signal of the FAM reporter already at the beginning of the measurement indicates the presence of the B1 strand in the single-stranded form even before the first measurement. This behavior of the respective C1 oligonucleotides shows that the optionally present differences in the composition of the sugar phosphate backbone (DNA vs. 2'-O-methyl modifications) in the present example caused only insignificant differences as a result of the strand displacement by single C1 oligonucleotides. Both oligonucleotides with longer 2'-O-Me segments and oligonucleotides that completely consist of DNA lead to the same result. The continuous order of complementary bases especially in regions two and three of the C1 oligonucleotides provides for a strand displacement with high yields.

Figure 26:
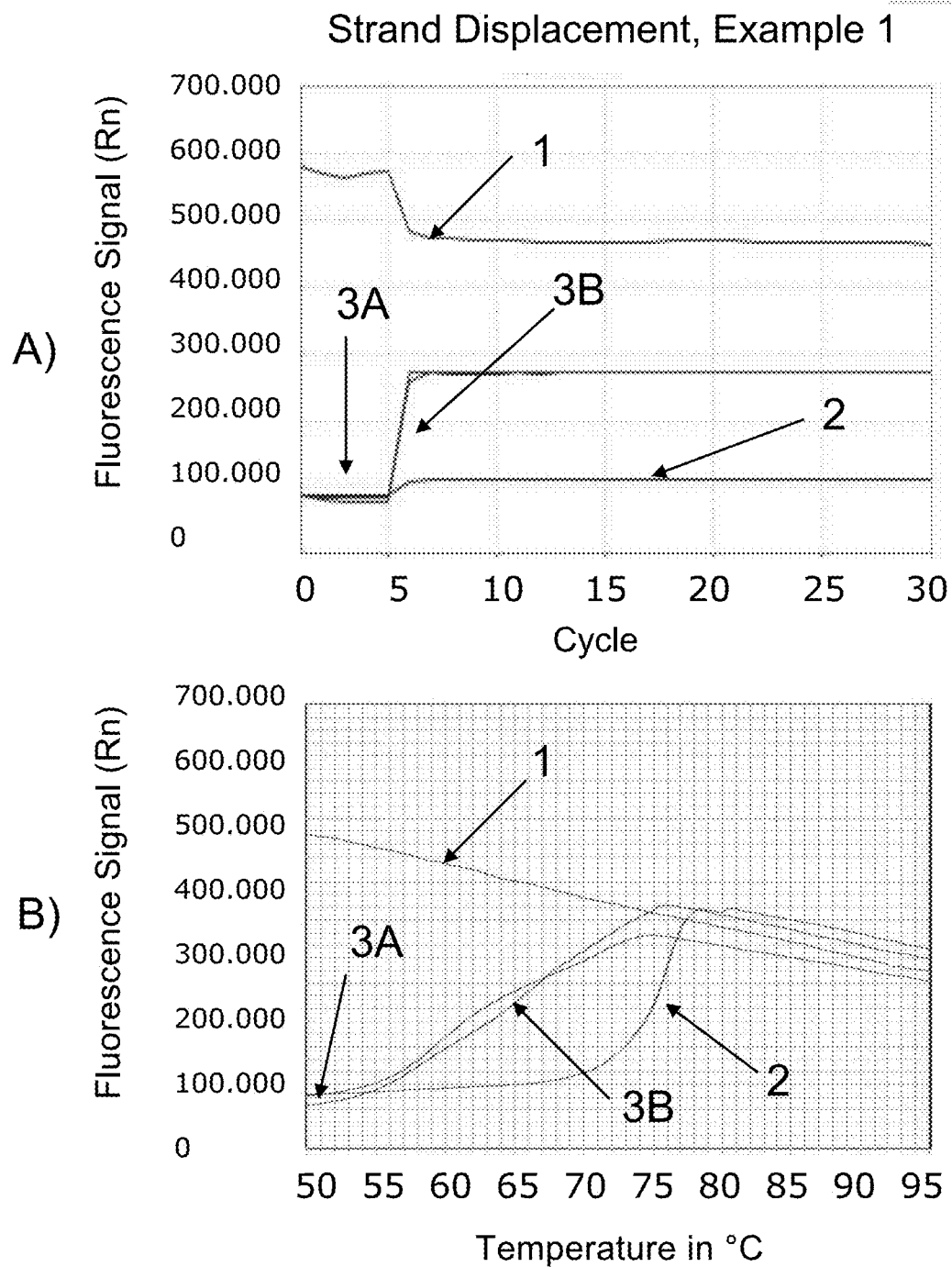

The use of the C1 strand with SEQ ID NO: 4 (8504 short) with a continuous complementary composition of individual regions, however with a shorter complementary third region, led to the result illustrated in FIG. 26. Batches with C1 and A1:B1 double strand variant 1 as well as C1 and A1:B1 double strand variant 2 behave similar (arrow 3): only after increasing the temperature to 65° C. strand displacement occurs.

Shortening the C1 sequence at its 5' end (corresponds to the third region of an activator oligonucleotide) (SEQ ID NO: 4) resulted in the fact that a longer sequence part in the 3' segment of the A1 strand is not complementary bound by the C1 oligonucleotide, so that this 3'-standing segment of the A1 strand can remain in contact with the 5' segment of the B1 strand (positions 1 to 18 of the 5' segment of the B1 strand). This double-stranded fragment is sufficiently stable at 50° C., so that the A1:B1 double strand on its labeled end sufficiently keeps contact also at 50° C. and the signal of FAM at this temperature is sufficiently quenched (arrow 3, cycles 1 to 5, FIG. 26). When raising the temperature to 65° C. (arrow 3B FIG. 26) presence of the C1 oligonucleotide resulted in the fact that ca. half of the population of A1:B1 double strands dissociated into single strands. An equilibrium is generated between an A1:B1 double strand form and a single strand form of the B1 strand β-strand complex). The fluorescence intensity of the FAM reporter in the batch corresponds to ca. 50% of the intensity of a free strand. This behavior is attributed to the fact that with an assumed fully developed strand displacement by the C1 oligonucleotide (i.e. complete binding between complementary regions of the A1 strand and the C1 oligonucleotide) the remaining contact between the 3' segment of the A1 strand and the 5' segment of the B1 strand at this temperature is no longer sufficiently stable, so that there is a spontaneous, temperature-induced separation of the A1 and B1 strands in this segment. Under reaction conditions a single-stranded B1 strand in turn can bind to the 3' segment of the A1 strand again and lead to the strand displacement of the C1 oligonucleotide. Thus, the system is in equilibrium between the A1:B1 double strand, the C1:A1 double strand and their intermediate forms β-strand complex).

3. Strand Displacement by a Single-Stranded Oligonucleotide with Divergences in the Sequence Composition Testing the influence of sequence divergences was performed with C1 oligonucleotides that in their composition of the nucleobases comprised two or more non-complementary bases that were in the second or third region of the C1 oligonucleotide. This diverging base composition of C1 resulted in the fact that no continuous complementary order of base pairings would be generated in a double strand, to be expected, of A1 and C1.

Figure 27:
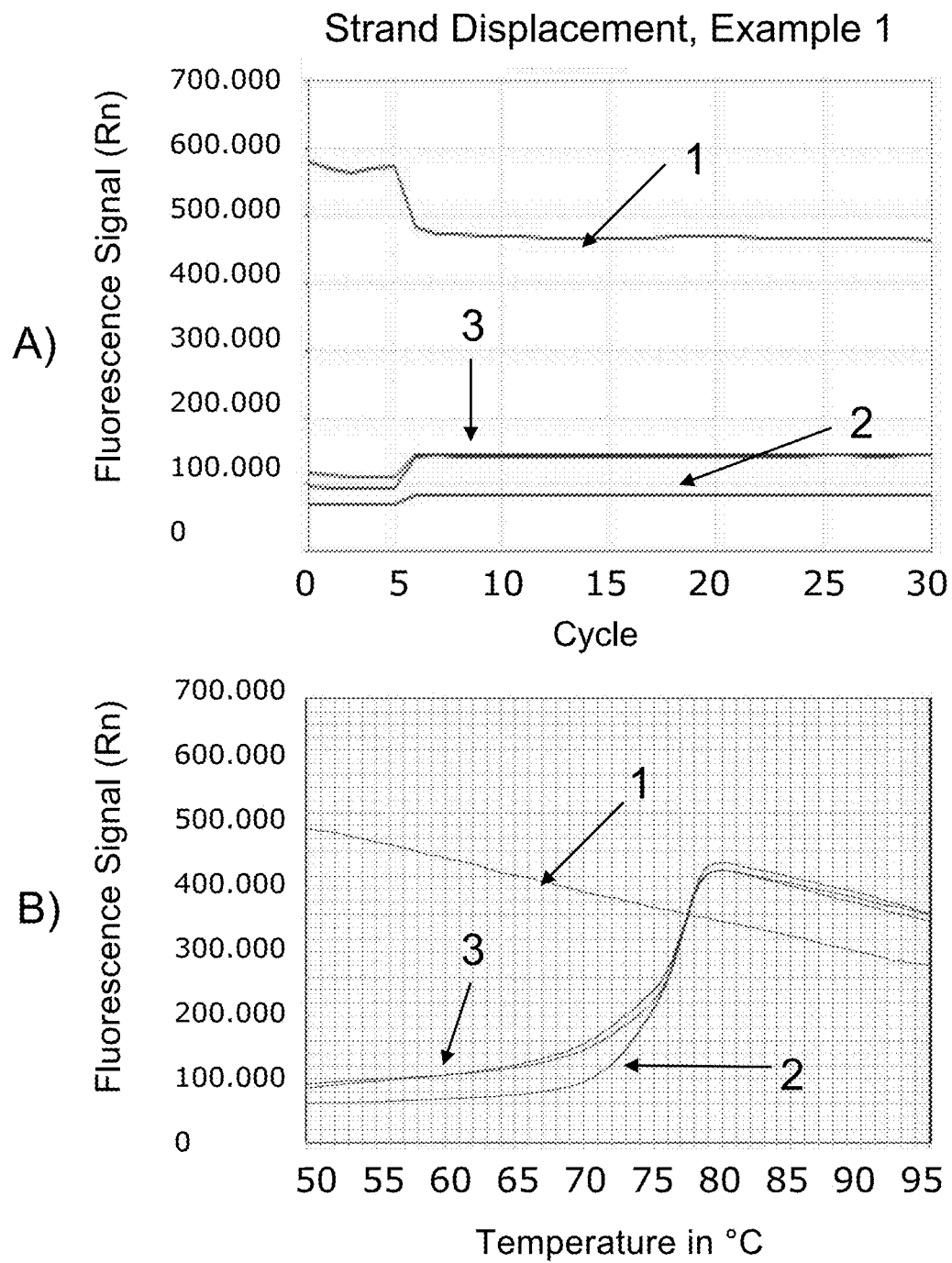

In FIG. 27 the result of the interaction between the C1 oligonucleotide SEQ ID NO 5 and the A1:B1 double strand variant 1 is shown. The divergences from the continuously complementary sequence are seen in positions 18 and 36 (SEQ ID NO 9) and the deletion between positions 26 and 27 (SEQ ID NO 10). Both C1 oligonucleotides lead to a slight change in the fluorescence of the FAM reporter (FIG. 27, arrow 3). Such a low signal intensity of the FAM reporter is associated with a mainly bound form of the B1 strand to the A1 strand. In other words, a C1 oligonucleotide with divergences in the nucleobase composition in the second and third regions resulted in a reduction of yields in strand displacement: the A1:B1 double strand was hardly opened and only a small proportion of B1 strands was converted to the single-stranded form. The equilibrium of the reaction was mainly on the side of the A1:B1 double strand.

A further increase in the number of deviations in the nucleobase composition resulted in a complete cancelation of the strand displacement. The C1 oligonucleotide with SEQ ID NO: 7 comprises a continuously complementary nucleobase sequence in the first and second region, however has significant divergences in the third region of its sequence. These sequence divergences are partially in the 3' segment of the third region of the C1 oligonucleotide (positions 26-32) and thus, are directly located on the second region. The addition of such a C1 oligonucleotide to the presented A1:B1 double strand did not result in a measurable change in the fluorescence of the FAM reporter below 65° C.; the signal has remained on the level of the intact A1:B1 double strand. That is, that even though the C1 oligonucleotide was able to complementary bind to the A1 strand with its first and second regions (these regions comprise complementary sequences between the C1 and A1 strands) the divergence of the sequence composition in the third region resulted in a complete cancelation of a successful strand displacement under given reaction conditions, the A1:B1 double strand has mainly remained intact. This is seen in context with the stability of the remaining A1:B1 double strand. In case of a complementary binding of the first and second regions of the C1 oligonucleotide to the A1 strand the A1 strand and the B1 strand remain complementary bound to each other via a significantly long segment. Under given conditions this stability of this remaining, not displaced double-stranded segment (A1:B1) is sufficiently high to hold both strands together and to prevent a measurable separation of the B1 from A1. The equilibrium of the reaction in this case is completely on the side of the A1:B1 double strand, no measurable separation of these strands occurs.

4. Kinetics of the Strand Displacement

For the measurement of the kinetics of the strand displacement C1:primer 1 complexes and prepared A1:B1 double strands were used. The advantage with the use of C1-primer 1 complexes is that primer 1 could already bound to complementary regions of the C1 oligonucleotide in advance, which resulted in a double strand that is stable at room temperature. Thanks to this reaction arrangement a strand displacement could not be started until primer 1 has been separated from C1 strands under reaction conditions, e.g., when raising the reaction temperature to 65° C. (corresponds about the Tm of primer 1 (Tm plus/minus 5° C.). By releasing the complementary regions in the C1 oligonucleotide this could now interact with the A1:B1 double strand under reaction conditions and optionally result in strand displacement.

In order to demonstrate the kinetics of the sequence-dependent strand displacement variant 1 of the A1:B1 strand was contacted with the C1-primer 1 complex (consisting of SEQ ID NO 5 and 11) and first heated to 50° C. (cycles 1-5) and then to 65° C. (cycle 6 and further), as illustrated above. The course of the signal from the FAM reporter is seen in FIG. 28. It is seen an almost constant line between cycles 1 and 5 (50° C.) and afterwards a sharp increase in the fluorescence of the FAM reporter from the $6^{th}$ measuring cycle (65° C.). In the subsequent 10 cycles (6 to 16) signal intensity of the FAM reporter reaches ca. 90% of the maximum possible fluorescence. The increase in the signal intensity suggests the separation of strands A1 and B1. The half-life of the separation of the A1:B1 double strand calculated therefrom was ca. 40-50 sec. In contrast, the increase in fluorescence of the FAM reporter using variant 2 of the A1:B1 strand with the same C1:primer 1 complex (consisting of SEQ ID NO 5 and 11) was significantly faster (FIG. 29, arrow 3). The calculated half-life of the separation of the A1:B1 double strand in this batch was less than 10 sec at given reaction conditions.

The difference between variants 1 and 2 of the A1:B1 double strand first of all is in the length of the 5' overhang of the A1 strand with which the A1 strand comes in initial contact with the C1 oligonucleotide. The B1 strand of variant 1 is longer than in variant 2, the thus resulting difference results in a 5' overhang in variant 1 of 6 nucleotides in length and a 5' overhang in variant 2 of 9 nucleotides in length. By the complementary compositions of respective segments in the C1 oligonucleotide it is to be assumed that the binding to the 9-nucleotide overhang is somewhat more stable than the binding to a 6-nucleotide overhang.

A comparison of the kinetics of the increase in fluorescence between variant 1 and variant 2 of the A1:B1 double strand resulted in the conclusion that the length of the 5' overhang on the A1 strand and thus, also stability of an intermediate complex, that is formed during the reaction and consists of an A1 overhang and a C1 oligonucleotide, may be relevant: the more stable this complex of an A1 overhang and a C1 oligonucleotide, the more effective or faster strand displacement can take place with otherwise the same parameters. This intermediate complex of an A1 overhang and the first region of the C1 oligonucleotide brings the C1 oligonucleotide in sufficient spatial proximity to the corresponding duplex end of the A1:B1 oligonucleotide, so that a strand displacement can take place. In the present batch a complex binding between the C1 oligonucleotide and the 5' overhang of the A1 strand results in an approximately identical spatial proximity of the complexed C1 oligonucleotide to the duplex end of the A1:B1 double strand both with variant 1 and variant 2. However, the differences in the kinetics of the strand displacement show that a higher stability of the binding of the intermediate complex with the same spatial proximity can lead to an increase in efficacy of the process of strand displacement. The equilibrium can be shifted faster.

In the following examples individual embodiments of an exponential amplification are illustrated. These examples are for illustration of the function of individual elements of the exponential amplification and are not to be understood as a limitation. The method is demonstrated using isothermal conditions.

During an exponential amplification a polymerase-dependent nucleic acid synthesis simultaneously proceeds with the nucleic acid-dependent strand displacement. The reaction batches comprise polymerases and dNTPs as substrates. Instead of a C1 oligonucleotide activator oligonucleotides are used that comprise nucleotide modifications in their strands that lead to a local blockage of the polymerase activity, so that activator oligonucleotides do not act as a template during amplification. Two primers each are employed in one amplification: the first primer oligonucleotide and the second primer oligonucleotide. The first primer oligonucleotide comprises a polynucleotide tail that can specifically bind activator oligonucleotides and so bring about spatial proximity to the duplex end of a nucleic acid to be amplified, so that a strand displacement of the second primer extension product can take place. The second primer oligonucleotide can bind to the 3' segment of the first primer extension product and thus, initiates the synthesis of the second primer extension product.

Example 2

This example demonstrates an exponentially proceeding amplification of an artificial DNA fragment under isothermal conditions. Here, the re-synthesized strands function as templates for the later synthesis of the complementary partner strands. The synthesis takes place depending on the presence of a specific template. Multiplication of nucleic acids to be amplified is by approx. factor $10^9$ based on the initial amount of the template employed.

Starting Material:

Template:

As part of a nucleic acid to be amplified a single-stranded DNA template was used. The sequence of template 001 (SEQ ID NO 12) was randomly selected and examined in view of avoiding too large elongation (more than 6 bases) that leads to a double strand formation within the same strand in order to prevent formation of so-called hairpins. This DNA sequence was artificially synthesized by a commercial supplier. The DNA sequence does not bear any nucleotide modifications. The 3' end of the template strand is open and not blocked. This template is to function as an example of a single-stranded nucleic acid to be amplified.

```
Template 001:
T35-4401-601
                                          (SEQ ID NO 12)
5'-ATACTACAATGTCACTTACGTCCTCTCCACACTCTGAGTTCCTGCGA
G-3'

(order of numbering: 1-48)
```

The measured melting temperature of a DNA double strand that includes template 001 as a strand is 77° C. (Tm measured in solution 1).

Primer 1 (First Primer Oligonucleotide)

```
           Primer 001-01:
           A6P-10-1001
                                          SEQ ID NO: 13
           5'-GTA[CCGAAGC]T*[CG]CAGGAAC-3' numbering from 5' to 3'
```

The first primer oligonucleotide comprises 2'-O-Me nucleotide modifications (indicated in [ ] brackets) and DNA nucleotides (in the 3' segment and optionally in the 5' segment), the 3'—OH group of the 3'-terminal nucleotide is free. The oligonucleotide in its position 11 has a dT nucleotide modified with TAMRA dye (shown as T* in the sequence).

Primer 2 (Second Primer Oligonucleotide)

```
           Primer 001-02:
           PA6-35-4401-608
                                          (SEQ ID NO 14)
           5'-AAAAAAAC ATACTACAATGTCACTTAC-3'

(order of numbering: 1-27)
```

This primer is needed to initiate the synthesis of the $2^{nd}$ strand. The nucleotides in positions 9-27 are identical to template 001.

Activator Oligonucleotide 001-01

```
Activator oligonucleotide 001-01:
A6 8505
                                          (SEQ ID NO 15)
5'-[CUAGCUAUCGUCCUCUCCACACUCUGA GUUCC]TGCGAGCTTCGGT
ACAAG X-3'

(order of numbering: 1-50)
```

The activator oligonucleotide comprises 2'-O-Me nucleotide modifications (indicated in [ ] brackets) and DNA nucleotides (in the 3' segment). The 3'—OH group of the 3'-terminal nucleotide was blocked by a phosphate residue (here designated with X). The oligonucleotide was chemically synthesized by a commercial supplier. The underlined segment of the sequence can complementary bind to the first primer extension product. This continuous alignment of complementary nucleobases is to support a strand displacement. The nucleotides and nucleotide modifications are linked to each other with phosphodiester binding.

The activator oligonucleotide includes three regions:
first region=positions 35-50
second region=positions 28-34
third region=positions 1-27

These components were used as follows in the reaction mixture:
template 001 2 fmol/l
activator oligonucleotide 001-01: 10 μmol/l
primer 001-01: 10 μmol/l
primer 001-02: 10 μmol/l Further components of the reaction were used as amplification reaction solution 2:
potassium glutamate, 50 mmol/l, pH 8.0
magnesium acetate, 10 mmol/l
dNTP (dATP, dCTP, dTTP, dGTP), 200 μmol/l each
polymerase (Bst 2.0 WarmStart, 120,000 U/ml NEB), 12 units/10 μl
Triton X-100, 0.1% (v/v)
EDTA, 0.1 mmol/l
TPAC (tetrapropylammonium chloride), 50 mmol/l, pH 8.0
Eva green dye (the dye was employed in accordance with the specifications of the manufacturer in dilution 1:50).

Start of the Reaction and Reaction Conditions

The preparation of the reaction mixture took place at room temperature. The template was added to the reaction batch as the last component. A control batch contained no template.

The thus prepared reaction mixtures were transferred in one suitable reaction vessel each (microwell plate) in a thermostat having a fluorescence detection function. As the thermostat a real-time PCR apparatus ("StepOne Plus", StepOne Software v2.1 ABI, Themorfisher) was used. The reaction was started by heating the reaction mixture to 65° C.

The reaction temperature was held constant throughout the amplification (40 min) at 65° C. (isothermal amplification). Subsequently, the reaction was heated to 95° C. for 10 min. During the reaction the intensity of the fluorescence signal of Eva green dye was recorded. The measuring intervals between adjacent measurements were one minute each.

Evaluation:

The Primer Extension Products to be Expected:

The first primer extension product 001-01 to be expected after the first primer extension on template 001: (SEQ ID NO 16)

```
5'-GTACCGAAGCTCGCAGGAACTCAGAGTGTGGAGAGGACGTAAGTGAC

ATTGTAGTAT-3'

(order of numbering: 1-57)
```

Underlined regions are illustrated by 2'-O-Me modifications of the first primer oligonucleotide. Not underlined regions are 2'-deoxynucleotides (DNA).

This first primer extension product can complementary bind the second primer oligonucleotide in the 3' region and thus, itself function as a template for the synthesis of the second primer product.

The synthesis of the second primer extension product is up to the modified region of the first primer oligonucleotide. Here, polymerase can be stopped either immediately before the modified region or only after some nucleotide modifications have been copied. The second primer extension product 001-02 (SEQ ID NO 17) to be expected using the first primer extension product as a template:

```
5'-AAAAAAACATACTACAATGTCACTTACGTCCTCTCCACACTCTGAGT

TCCTGCGAG-3'

(order of numbering: 1-56)
```

Here, the four underlined 3'-standing nucleotides are indicated as an assumed maximum extension of the second primer extension product on the sequence of the first primer extension product. These nucleotides form complementary positions to some 2'-O-Me modified nucleotides of the first primer oligonucleotide. Polymerase can also synthesize shorter strands under reaction conditions, so that a mixture of primer extension products can result, since polymerase synthesis can be stopped already before the modified region of the first primer oligonucleotide or only after some modifications have been copied. Such primer extension products are accordingly shorter (they include for example positions 1 to 52 or 1 to 53 or 1 to 54 or 1 to 55). The exact position of the termination of the synthesis of the second primer extension product and thus, the exact length of the second primer extension product at its 3' end at this point is of minor interest as long as all amplifiable second primer extension products are able to bind the first primer oligonucleotide and themselves appear as template for the synthesis of the first primer extension product. The polymerase-dependent copy of the second primer extension product leads to the generation of a further first primer extension product that also includes a complementary sequence to the 5' segment of the second primer oligonucleotide.

As a result of an exponential amplification two primer extension products are generated that can form a complementary double strand.

The structure to be expected of the double strand that consists of both maximum extended primer extension products is illustrated in the following:

(SEQ ID NO 18)
5'-GTA<u>CCGAAGCTCG</u>CAGGAACTCAGAGTGTGGAGAGGACGTAAGTGAC

ATTGTAGTATGTTTTTTT-3'

(SEQ ID NO 19)
3'-GAGCGTCCTTGAGTCTCACACCTCTCCTGCATTCACTGTAACATCAT

ACAAAAAAA-5'

In the course of the exponential amplification there is an accumulation of these primer extension products that represent the main product of the exponential amplification. The thus amplified strands represent the nucleic acid to be amplified. They include the sequence of the template employed in the reaction. Underlined regions are illustrated by 2'-O-Me modifications. Not underlined regions are 2'-deoxynucleotides (DNA).

The double strand generated during the reaction can bind Eva green dye, so that the signal intensity of the dye can increase with progressing reaction.

The result of the course of the signal intensity is seen in FIG. 30. Arrow 1 shows the course of the signals in a reaction with a template. Arrow 2 shows the course of the reaction without a template. After an initial plateau phase a signal increase of the fluorescence signal was observed from ca. 30 min in the reaction that contained template 001. The control reaction without template 001 showed no change in the signal intensity over the entire recorded period of 40 min. The continuously high level of the basic fluorescence is related to the fact that primer 001-01 contains a fluorescence marker (dT-TMR in position 11).

To verify the identity of the signal an aliquot of both reactions was analyzed by means of CE. Since the first primer oligonucleotide includes a fluorescence marker (dT-TMR in position 11) the signal could be recorded during CE. The result of the CE is seen in FIG. 31.

In FIG. 31 (A) the CE course of the control reaction is seen. There is seen a peak that was assigned to the unreacted primer 001-01. In FIG. 31 (B) the CE course of the reaction with a template is seen. There is seen a peak (1) that corresponds to the unreacted primer 001-01 as well as a further peak (2) that is shifted by ca. 460 CE units to the right (which corresponds to a longer molecule). It was found in parallel control experiments that under given CE conditions 10.2 to ca. 10.3 CE units of length correspond to a sequence difference of one nucleotide. Thus, the distance between peak (1) and peak (2) measured in CE corresponds in length ca. 44-45 nucleotides between both separated labeled sequences. This sequence difference corresponds to the length of the extension product of the first primer extension product (SEQ ID NO 20) to be expected in an exponential amplification, it is 45 nucleotides.

(SEQ ID NO 20)
5'-GTACCGAAGCTCGCAGGAAC

<u>TCAGAGTGTGGAGAGGACGTAAGTGACATTGTAGTATGTTTTTTT</u>-3'

(the first extension product of the first primer oligonucleotide to be expected is underlined)

The intensity of the signal in peak (2) shows that less than 50% of the initially employed primer 001-01 were extended in the reaction. The concentration of the generated product was estimated at about 1 µmol/l to 2 µmol/l, starting from the signal intensity of the consumed primer. Thus, the yield was ca. 10-20% as measured after primer 001-01 consumption.

Thus, in the exponential amplification a template-induced multiplication of the sequence to be amplified occurs, wherein the initial concentration of template 001 corresponded to 2 fmol/l and the concentration of the product of the amplification reaction was estimated at ca. 1 to 2 µmol/l. Thus, the multiplication factor calculated therefrom is ca. $5 \times 10^8$ to $10^9$. The exponential amplification proceeded under isothermal conditions.

The result of the exponential reaction depends on the presence of the template and activator oligonucleotide as well as primer 1, primer 2, polymerase, dNTPs and appropriate buffer conditions. Further, the reaction depends on the sequence composition of individual participating nucleic acid components: activator oligonucleotide and primer 1 and primer 2. In the following it is dealt with the structure-effect principle of these components.

Explanations on the Design of Sequences
Template:

The sequence of the nucleic acid to be amplified serves as the starting point for the design of the sequences of primer 1, primer 2, and activator oligonucleotide. This nucleic acid to be amplified comprises a target sequence that has to be specifically amplified.

The sequence length of the extension product of the first primer oligonucleotide to be expected is 45 nucleotides. The total length of the first primer extension product is 65 nucleotides. The length of the extension product to be expected is between 25 and 29 nucleotides. The total length of the second primer extension product is between 52 and 56 nucleotides (according to the position of the terminator of the polymerase during the synthesis of the second primer extension product). The length of the complementary double strand of the nucleic acid to be amplified consists of the first primer extension product and the second primer extension product, thus is between 52 and 56 nucleotides. The first primer extension product in its 5' segment has a single-stranded region that corresponds to the polynucleotide tail of the first primer oligonucleotide.

The sequence length of the nucleic acid to be amplified in the present example is sufficiently large, so that the melting temperature of the specific double strand formed during the reaction of the first and second primer extension products is ca. 78° C. and thus, is above the reaction temperature of 65° C. It is assumed that the double strand formed during the reaction is substantially stable and does not spontaneously dissociate to its single strands.

Primer 1

The first primer oligonucleotide includes a first primer region and a second region with a polynucleotide tail that is not copied by polymerase and is able to bind an activator oligonucleotide.

First Primer Region:

Positions 14-20 form the first primer region of the first primer oligonucleotide.

These 3'-standing nucleotides of primer 001-01 (positions 14-20) are to specifically bind to the template and permit a primer extension reaction. Therefore, the sequence of these positions is adapted to template 001 (positions 38-44). These seven 3'-terminal nucleotides are DNA nucleotides and are linked by means of phosphodiester compounds. This segment initiates the primer extension by a polymerase in the synthesis of the first strand and functions as a template in the synthesis of the second strand by the polymerase, so that a strand complementary to this segment can be formed.

Second Primer Region:

The second region on the 5' side is attached to the first primer region (positions 1-13). The structures in the second region inter alia are to hinder polymerase in the synthesis of the second strand from copying the polynucleotide tail. Moreover, these structures are to be able to bind activator oligonucleotide and support it in the strand displacement. For this reason mainly 2'-O-methyl nucleotide modifications were used (positions 4 to 10 and 12 to 13) that are linked to each other via a 5'-3' phosphodiester binding. These 2'-O-methyl nucleotide modifications are examples of modifications that are able to hinder polymerase from copying the polynucleotide tail.

The sequence of 5'-standing nucleotides of primer 001-01 (positions 1-9) is randomly selected, wherein care has been taken that this sequence has no extensive self-complementary segments, further no complementary binding sites in the template to be amplified as well as no multiple G nucleotides that stand in adjacent positions and thus, can form G quadruplexes. Positions 10 to 13 are complementary to template 001 and inter alia are to support binding of the first region to the template.

The sequence (positions 1-9) functions as the polynucleotide tail and during the reaction is to be able to bind the activator oligonucleotide and thereby cause spatial proximity to the duplex end, so that strand displacement can take place. Positions 1 to 3 are illustrated by DNA nucleotides, positions 4 to 9 are 2'-O-Me nucleotide modifications. All nucleotides and nucleotide modifications are linked to each other via phosphodiester binding.

The transition between the first primer region and the second region with the polynucleotide tail in this example is smooth: the second region is directly coupled to the first region via phosphodiester binding. This creates favorable requirements for the initiation of a strand displacement to a duplex end by an activator oligonucleotide. Both regions are aligned in the same direction: from 5' to 3'. The second region with the polynucleotide tail is in the 5' segment, the first primer region is in the 3' segment.

In the synthesis of the second complementary strand the polymerase from position 13 of the first primer oligonucleotide is confronted with 2'-O-methyl nucleotide modifications that block or complicate further synthesis. Certainly, a single 2'-O-Me nucleotide modification (if inserted into the template strand) does not necessarily lead to the complete blockage of the polymerase synthesis, so the further synthesis is complicated or decelerated, respectively.

Thanks to the sequential coupling of several nucleotide modifications polymerase is successfully inhibited in its synthesizability and is not able to copy the remaining polynucleotide tail. It is of secondary importance whether the complete inhibition of the polymerase in the region of the second region of the primer oligonucleotide already appears after a single 2'-O-methyl nucleotide modification has been copied or only after several 2'-O-methyl nucleotide modifications have been copied as long as sufficient uncopied nucleotides or nucleotide modifications remain in the second region (polynucleotide tail) and can bind to the activator oligonucleotide under reaction conditions to initiate a successful strand displacement.

For reasons of illustration and not as a limitation it is hereby noted that the polymerase can copy up to and including position 10 of the first primer oligonucleotide. That is, that the segment of the second region adjoining the first primer region is partially copied by the polymerase. Hence, in the diagram four nucleotide positions of the second region are considered to be copied by the polymerase. The residual nucleotide positions of the second region remain uncopied and permit a specific binding of the activator oligonucleotide.

Primer 2:

Primer 2 is necessary for the initiation of the synthesis of the second strand. The nucleotides in positions 9-27 are identical to template 001. Said positions are to complementary bind to the 3' segment of the first primer extension product at the beginning of the amplification and thus, initiate the synthesis of the second strand. Primer 2 consists of DNA nucleotides that are linked to each other via conventional 5'-3'-phosphodiester bindings. The 5' segment of the second primer in this example first forms an overhang (position 1 to 8), which however can be copied by polymerase. In the course of the reaction the nucleic acid chain to be amplified is extended by the 5' overhang of the second primer.

Primer 2 uses the first primer extension product as a template, so that copyable portions of the first primer extension product are copied by the polymerase. Thereby, the second primer is extended and a double strand is formed in the copyable segment of the first primer extension product. However, the polynucleotide tail of the second region of the first primer remains uncopied. The primer extension product in its 3' segment includes a sequence that is able to complementary bind the first primer oligonucleotide.

Activator Oligonucleotide:

First Region:

The first region (positions 35-50) includes a sequence (positions 35-47) complementary to the second region of the first primer oligonucleotide (positions 1-13). The three 3'-terminal nucleotides form a 3' overhang and in the present example do not have functional meaning. The first region in this example consists of 2'-deoxynucleotides that are coupled via a conventional 5'-3'-phosphodiester binding. The terminal 3'—OH group is blocked by a phosphate residue and thus, cannot be extended by the polymerase.

Second Region:

The second region of the activator oligonucleotide includes a sequence (positions 28-34) complementary to the first region of the first primer oligonucleotide (positions 14-20). The second region of the activator oligonucleotide in its 5' segment includes 2'-O-methyl nucleotide modifications (positions 28-32). Positions 34 and 35 are formed by 2'-deoxynucleotides. The individual nucleotides and nucleotide modifications are coupled to each other via a conventional 5'-3'-phosphodiester binding. The first and second regions of the activator oligonucleotide are smoothly coupled to each other via a conventional 5'-3'-phosphodiester binding.

Sequence length and nature of the first and second regions of the activator oligonucleotide are adapted to complementary regions of the first primer oligonucleotide, so that the first primer oligonucleotide can reversibly bind to the activator oligonucleotide under reaction conditions. Thus, there is equilibrium between the free, single-stranded and the bound, double-stranded form between these two components.

Third Region:

The third region of the activator oligonucleotide includes a sequence (positions 9-27) complementary to a segment of the first primer extension product (positions 21-39) to be expected that is to be synthesized by polymerase during the amplification. The third region along its entire length consists of 2'-O-methyl nucleotide modifications (positions 1-27). The individual nucleotide modifications are coupled to each other via a conventional 5'-3'-phosphodiester binding. The second and third regions of the activator oligonucleotide are smoothly coupled to each other via a conventional 5'-3'-phosphodiester binding. The eight 5'-terminal nucleotide modifications form a 5' overhang that is non-complementary to the first primer extension product.

The sequence of the activator oligonucleotide is made up such that it is able to form a complementary double strand with its positions 9-47 with part of the first primer extension product (positions 1 to 39). Positions 1 to 9 and positions 48-50 do not participate in the formation of a double strand with the first primer extension product. At the same time the sequence of the activator oligonucleotide is made up such that it can form a complementary double strand with its nucleotide positions 28-47 with the first primer oligonucleotide. Thereby, the 3' end of the first primer can complementary bind to the activator oligonucleotide. In order to prevent the extension of the 3' end of the first primer oligonucleotide by a polymerase the activator oligonucleotide includes nucleotide modifications that prevent the synthetic effect of the polymerase. In this example these are 2'-O-methyl nucleotide modifications. In this example the activator oligonucleotide in positions 1-32 consists of 2'-O-methyl nucleotide modifications. In this way the 3' end of the first primer in case of a correct hybridization binds in the sequence segment that comprises nucleotide modifications. Such an arrangement of the interaction between the activator oligonucleotide and the first primer oligonucleotide is to prevent an undesired extension of the first primer oligonucleotide once it has complementary bound to the activator oligonucleotide. Thanks to modifications in the third region of the activator oligonucleotide also preventively the possibility of a non-specific extension by polymerase is generally reduced. In order to promote strand displacement sequences have been used in the respective segments of the activator oligonucleotide that are complementary to their binding partners in the first primer extension product. Since both sequence mismatches and chain disruptions by modifications without nucleobases (e.g., C3 linkers or C18 linkers) can reduce efficacy of a strand displacement and/or its rate such structure variants have been avoided in this example.

The activator oligonucleotide is to contact the double strand of the nucleic acid to be amplified under reaction conditions via binding to the polynucleotide tail of the first primer extension product. In this example, preferably the binding is reversible under reaction conditions. Thereby, the double strand at the beginning of the reaction consists of the first primer extension product and template 001 and later in the reaction of the first and second primer extension products.

Nature and length of the activator oligonucleotide are to be sufficient to perform a strand displacement that leads to a separation of the primer extension products in sufficient yields.

The sufficient separation of both primer extension products is to ensure that sequence segments of both primer extension products with the respective sequence parts having primer binding sites become accessible for binding of the respective complementary primer oligonucleotides. In the present example, the length of the activator oligonucleotide is 50 nucleotides (deoxynucleotides plus nucleotide modifications), wherein 39 of them can complementary bind to the first primer extension product. Therefore, the activator oligonucleotide was able to first at least partially displace template 001 and later in the reaction also the second primer extension product from the binding with the first primer extension product under reaction conditions by means of strand displacement.

Thereby, template 001 and the second primer extension product, respectively became completely or partially single-stranded, so that a new first primer oligonucleotide could bind to the accordingly complementary sequence segment and could be extended by means of the polymerase. In the present example, the third region only binds a 5'-standing segment of the first primer extension product. In the present example, the length of this complementary segment is 19 nucleotides.

The 3'-standing sequence portions of the first primer extension product were not bound by the activator oligonucleotide. This 3'-standing segment of the first primer extension product in its single-stranded form is to be able to bind the second primer oligonucleotide to permit a primer extension reaction. In order that during the reaction a further second primer oligonucleotide can bind to the first primer extension fragment the 3'-standing segment of the first primer extension product has to be converted to the single-stranded form and separated from the binding with the template or with a second primer extension product. In the present example, this is achieved by separating both synthesized strands under reaction conditions during an isothermal reaction. During the strand displacement by the activator oligonucleotide an intermediate product of the strand displacement reaction is formed that consists of a first primer extension product, the activator oligonucleotide, and a second primer extension product. The second primer extension product in this intermediate product is complementary bound to the 3'-standing segment of the first primer extension product. However, the stability of this resulting double strand is significantly reduced compared to a completely bound second primer extension product. Under reaction conditions a spontaneous separation of this double strand (dissociation of the first and second primer extension products) occurs, so that the second primer extension product is completely detached from the first primer extension product. The 3' segment of the first primer extension product is single-stranded immediately after the separation from the second primer extension product.

The single-stranded 3'-terminal segment of the first primer extension product both can contact the template or the second primer extension product, respectively and bind to the second primer oligonucleotide. Due to a molar excess of the second primer oligonucleotide used the possibility of contact with the second primer oligonucleotide is much higher. Especially, this is the case at the beginning of the reaction: in the present example the template is employed in a concentration of 1 fmol/l. During the first replication cycles of the exponential amplification the concentration of synthesized second primer extension products remains significantly below the value of 1 μmol/l for a longer period of time. In contrast, the second primer oligonucleotide is used in a concentration of 10 μmol/l. Thus, it results an excess of $10^{10}$ of second primer oligonucleotides over the template and over the synthesized second primer extension products, especially during the initial phases of the exponential amplification. In later phases of the amplification now the second primer extension product present in higher concentrations competes for the binding to the 3' segment of the first primer extension product, so that the reaction can be decelerated.

Example 3

Verification of the Specificity of the Amplification Reaction

In this example, influence of a change in sequence in the template on the amplification has been investigated. Three nucleotides from the central region of the template were removed. The peripheral regions that are crucial for binding primers were identically designed as in example 2. When the first primer oligonucleotide is extended a complementary strand is formed that has a sequence complementary to the template and thus comprises these divergences in the sequence. In this way it was to be verified which effect such a mismatch between a first primer extension product generated thereby and an activator oligonucleotide has on the amplification. Designing the sequences took place like in example 2.

The following templates have been used:
template (SEQ ID NO 21) with a sequence composition that leads to a first primer extension product with a perfect-match in matching with activator oligonucleotide:

```
T-A6P-15-4401
5' GTAGTTCTCACTTACGTCCTCTCCACACTCTGAGTTCCTGCGAG 3'
```

The binding sequence for the first primer oligonucleotide is underlined.
template (SEQ ID NO 22) with a sequence composition that leads to a first primer extension product with a mismatch with the activator oligonucleotide:

```
T-A6P-15-4401-5
5' GTAGTTCTCACTTACGTCCTCTCCCTCTGAGTTCCTGCGAG 3'
```

The binding sequence for the first primer oligonucleotide is underlined.

In both templates respective primer binding sites are identical, so that it is expected that with primer oligonucleotides a successful first primer extension reaction can be initiated.

Both templates differ only in one point:

```
T-A6P-15-4401
                                         (SEQ ID NO 21)
5' GTAGTTCTCACTTACGTCCTCTCCACACTCTGAGTTCCTGCGAG
3'

T-A6P-15-4401-5
                                         (SEQ ID NO 22)
5' GTAGTTCTCACTTACGTCCTCTCC_CTCTGAGTTCCTGCGAG 3'
```

The Point of Difference is Underlined

Thus, also differences in respective primer extension products of the first and second primer oligonucleotides have to be expected. The point of difference is in the 5' segment of the extension product of the first primer oligonucleotide.

The following primers have been used:
the first primer oligonucleotide (SEQ ID NO 23):

```
        A6P-10-1002TMR7
        5' 7765567876 CAGGAAC 3'
```

A=2'-deoxy-adenosine
C=2'-deoxy-cytosine
G=2'-deoxy-guanosine
T=2'-deoxy-thymidine (thymidine)
Modifications:
5=2'-O-Me A (2'-O-methyl-adenosine)
6=2'-O-Me G (2'-O-methyl-guanosine)
7=2'-O-Me C (2'-O-methyl-cytosine)
8=dT-TMR
the second primer oligonucleotide (SEQ ID NO 24):

```
        PA6-15-4401-10
        5' CACGAGTAGTTCTCACTTAC 3'
```

The following activator oligonucleotide 002-01 (SEQ ID NO 25) has been used:

```
A6 8504
5'-CTAGCTAT CGTCCTCT CCACACT CTGA GTTCCTGCGAG

CTTC GGTAC AAG X 3'

68576858 67866868 6656568 6875 788668 7CGAG CTTC

GGTAC AAG
```

A=2'-deoxy-adenosine
C=2'-deoxy-cytosine
G=2'-deoxy-guanosine
T=2'-deoxy-thymidine (thymidine)
5=2'-O-Me A (2'-O-Methyl-adenosine)
6=2'-O-Me C (2'-O-Methyl-cytosine)
7=2'-O-Me G (2'-O-Methyl-guanosine)
8=2'-O-Me U (2'-O-Methyl-uridine)
X=3'-phosphate group for blocking a possible extension by polymerase.

The nucleotides and nucleotide modifications are linked to each other with a phosphodiester binding. The 3' end is blocked with a phosphate group to prevent a possible extension by the polymerase.

The template of perfect match sequence composition was employed in concentrations of 1 nmol/l, 1 μmol/l, and 1 fmol/l.

The template of mismatch sequence composition was used in a concentration of 1 nmol/l.

In the control reaction no template was employed. Other reaction conditions were as in example 2. FIG. 32 shows the result of the reaction.

When using a perfect match template (SEQ ID NO 21) a complementary strand of a primer extension product is synthesized. This extension product both is complementary to the perfect-match template and to the activator oligonucleotide used. This constellation was illustrated in detail in example 2. It serves as a basis for a successful amplification.

In contrast, when using a mismatch sequence (SEQ ID NO 22) in the synthesis of the first primer extension product a complementary strand of the extension product is generated that certainly is completely complementary to the mismatch template, but in this way deviates from being complementary to the third region of the activator oligonucleotide. This deviation takes place in the 5'-standing segment of the extension product that is to react with the activator oligonucleotide so that the strand displacement process can progress. As shown in the present example the absence of three nucleotides in respective positions interferes with a strand displacement by the activator oligonucleotide.

FIG. 32 shows this influence of the sequence divergences between activator oligonucleotide and the extension product of the first primer oligonucleotide. Divergences in 3 positions in the sequence of the activator oligonucleotide from the sequence of the primer extension product synthesized on the mismatch template show the dependence of the amplification on the matching in the order of the complementary bases in the activator oligonucleotide and the template or the first primer extension product, respectively. Only removing 3 bases from the region of the extension product already led to a suppression of the amplification to a level, which in the present example is even below the negative control.

The control reactions with a perfect match template (arrows 1-3) showed a concentration dependency of the amplification. With decreasing concentration the reaction took longer time to synthesize a sufficient amount of the nucleic acid to be amplified so that the signal increases above the level of the baseline.

The negative control reaction without a template also showed an increase in the signal, but in a significantly later time interval with respect to reactions with a perfect-match template.

The arrows in FIG. 32 show:
perfect match template (SEQ ID NO 21) 1 nmol/l concentration (arrow 1)
perfect match template (SEQ ID NO 21) 1 µmol/l concentration (arrow 2)
perfect match template (SEQ ID NO 21) 1 fmol/l concentration (arrow 3)
negative control: no template in the reaction (arrow 4) (2 control reactions are indicated, both without template)
mismatch template (SEQ ID NO 22) 1 nmol/l concentration (arrow 5)

This result illustrates the meaning of the base composition in the activator oligonucleotide: Deviations from the complementarity between the activator oligonucleotide and the primer extension product can lead to a deceleration or even disruption of the amplification.

It was shown in this example that both sequence ends of the perfect match template and the mismatch template completely match and thus, the potential for binding both primer oligonucleotides was equal, both reactions proceeded completely different: in case of a complete complementarity between the activator oligonucleotide and the 5' segment of the extension product of the first primer oligonucleotide the amplification proceeded as planned. Disruption of the strand displacement by a sequence divergence (in this case three nucleotides were absent in the 5' segment of the extension product of the first primer) resulted in the strong suppression of the amplification.

Example 4

Use of Another Template Sequence with Another Suitable Activator Oligonucleotide First, an artificial sequence of 49 nucleotides was synthetically generated (Eurofins) that includes a sequence of the MIP gene of *Legionella pneumophila* between primer 1 and primer 2 (SEQ ID NO 26), template 003-01. As a control template 003-02 (SEQ ID NO 27) of a sequence composition was synthetically generated (Eurofins) that results in a first primer extension product with a mismatch with the activator oligonucleotide (5 nucleotides). For the amplification of such a new template 003 two primers (primer 1, first primer oligonucleotide (identical to SEQ ID NO 13 in example 2) and primer 2, second primer oligonucleotide (SEQ ID NO 28) as well as an activator oligonucleotide (SEQ ID NO 29) that is suitable for template 003-01 have been generated. Designing the sequences was as described in example 2.

The following templates have been used:
template 003-01 (SEQ ID NO 26) of a sequence composition that leads to a first primer extension product with a perfect match in matching with the activator oligonucleotide:

LP-T1-1000-103
5' CTACAATGTCACTTAC<u>ACGTTCTTAACAAGTTTCAG</u>CCGTTCCTGC

GAG 3'

The sequence segment of the MIP gene of *L. pneumonia* is underlined.
The template consists of DNA nucleotides.
template (SEQ ID NO 27) of a sequence composition that leads to a first primer extension product with a mismatch with the activator oligonucleotide:

LP-T1-1001-118
5' CTACAATGTCACTTAC<u>ACGTTCTTAACAAGTTT</u>GTTCCTGCGAG 3'

The sequence segment of the MIP gene of *L. pneumonia* is underlined (this segment is shorter than in SEQ ID NO 26 by 5 nucleotides).
The template consists of DNA nucleotides.
In both templates the respective primer binding sites are identical, so that it can be expected that a successful first primer extension reaction by primer oligonucleotides each can be initiated.

LP-T1-1000-103
(SEQ ID NO 26)
5' CTACAATGTCACTTACACGTTCTTAACAAGTTTCAG<u>CCGTTCCTGCGAG</u> 3'

LP-T1-1001-118
(SEQ ID NO 27)
5' CTACAATGTCACTTACACGTTCTTAACAAGTTT <u>GTTCCTGCGAG</u> 3'

Binding Site for Primer 1 Underlined

Both templates only differ in one position:

```
LP-T1-1000-103
                                        (SEQ ID NO 26)
5' CTACAATGTCACTTACACGTTCTTAACAAGTTTCAGCCGTTCCTGC

GAG 3'

LP-T1-1001-118
                                        (SEQ ID NO 27)
5' CTACAATGTCACTTACACGTTCTTAACAAGTTT GTTCCTGCGAG

3'
```

The Point of Difference Between the Templates is Underlined

This position is in the region that is synthesized by polymerase in the synthesis of the first primer extension product. The point of difference is in the 5' segment of the extension product of the first primer oligonucleotide. Thus, also differences in the respective primer extension products of the first and second primer oligonucleotides are to be expected.

The following primers have been used:
The first primer oligonucleotide (SEQ ID NO 13) is identical to primer 1 in example 2:
Primer 1
Primer 001-01 (20 nucleotides):
The sequence of the first primer oligonucleotide:

```
    A6P-10-1001
                                        (SEQ ID NO 13)
    5' GTACCGAAGCTCGCAGGAAC 3'

(order of numbering: 1-20)
```

Underlined regions are illustrated by 2'-O-Me modifications. Non-underlined regions are 2'-deoxynucleotides (DNA).

the second primer oligonucleotide (SEQ ID NO 28):

```
    LP-P2-1000-211
    (SEQ ID NO 17):
    5' CTACAATGTCACTTAC ACGTTCTTAACAAGTTT 3'
```

The first and the second primer oligonucleotides can bind both templates (SEQ ID NO 26 and 27) to respective primer binding sites.

The following activator oligonucleotide 003 (SEQ ID NO 29) has been used:

```
LP-A1-1000-104
5'-A*A*A*A*C*A*A*A[AACCGAACAACAAAUGAAAGACGUUCUUA

ACAAGUUUCAGCCGUUCCUG]CGAGCTTCGGTACAAG X 3'
```

The sequence at the 3'-standing segment consists of DNA nucleotides
A=2'-deoxy-adenosine
C=2'-deoxy-cytosine
G=2'-deoxy-guanosine
T=2'-deoxy-thymidine (thymidine)
The sequence in square brackets [ ], positions 9-58, consists of 2'-O-Me nucleotide modifications that are linked via phosphodiester binding: 2'-O-Me A (2'-O-methyl-adenosine), 2'-O-Me C (2'-O-methyl-cytosine), 2'-O-Me G (2'-O-methyl-guanosine), 2'-O-Me U (2'-O-methyl-uridine).

Connections between 5'-standing nucleotides (positions 1-8) are linked via phosphorothioate connections (PTO); the respective positions are designated with (*).

X=3'-phosphate group for blocking a possible extension by polymerase.

The 3' end is blocked with a phosphate group to prevent a possible extension by the polymerase.

The concentration of templates at the beginning of the reaction was 10 µmol/l (for perfect match and mismatch). In a further control reaction no template was employed. The reaction was carried out for 60 min at 65° C. Other reaction conditions were kept as in example 1.

Results

Figure 33:
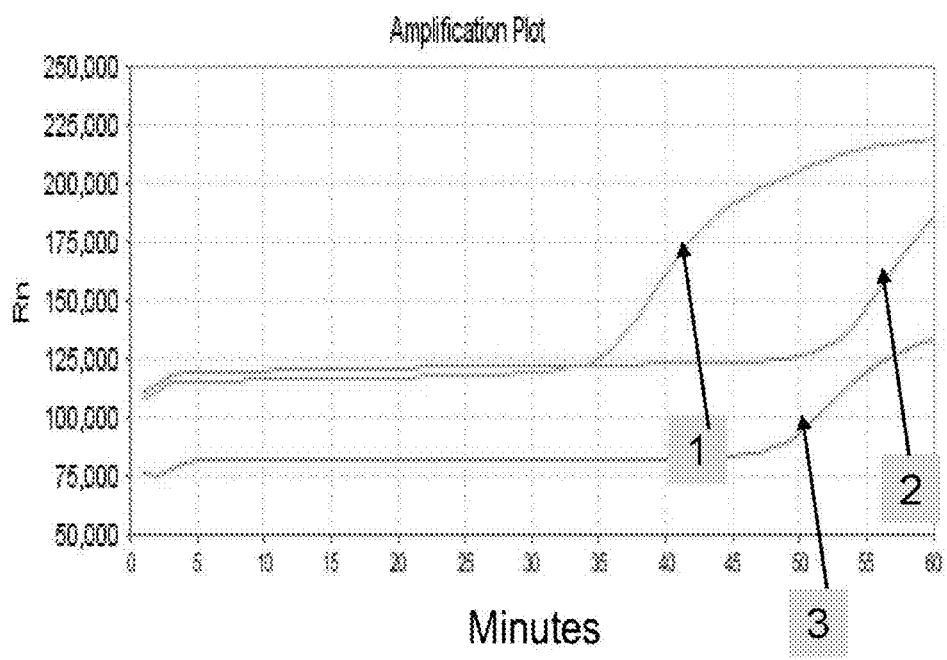
FIG. 33 shows the trend of the signal intensity during an amplification according to the invention, as described in example 4.

The course of the reaction is shown in FIG. 33. It is seen that the reaction, that contained a perfect match template, after 35 min results in an increase of the fluorescence signal (arrow 1). Certainly, reactions with mismatch and negative control also result in a signal, but that comes significantly later (ca. 45 min or 50 min, respectively).

Evaluation:

The increase in the signal in FIG. 33 correlates with the presence of a perfect match template 003-01. A very similar sequence having the same primer binding sites and a significantly similar section between the primers, however with a deletion of 5 nucleotides, differs in the course of the amplification and is in the region of the negative control.

This difference is attributed to the following situations:

When using a perfect match template (SEQ ID NO 26) a complementary strand of a primer extension product is synthesized. This extension product both is complementary to the perfect match template and to the corresponding positions of the activator oligonucleotide (SEQ ID NO 29) used. This constellation was illustrated in detail in example 1. It serves as a basis for a successful amplification.

In the following, sequences are compared and respective segments labeled that form a complementary double strand with appropriate reaction partners under the reaction:

Templates

```
LP-T1-1000-103
                                        (SEQ ID NO 26)
5' CTACAATGTCACTTACACGTTCTTAACAAGTTTCAGCCGTTCCTGC

GAG 3'

LP-T1-1001-118
                                        (SEQ ID NO 27)
5' CTACAATGTCACTTACACGTTCTTAACAAGTTT GTTCCTGCGAG

3'
```

Binding Site for Primer 1 Underlined

Primer 1 and Primer 2:

```
    primer 1: A6P-10-1001
                                       (SEQ ID NO: 13)
    5' GTACCGAAGCTCGCAGGAAC 3'
```

Binding Site to Template Underlined primer 2: LP-P2-1000-211
(SEQ ID NO 28):
5' <u>CTACAATGTCACTTAC</u> ACGTT

CTTAACAAGTTT 3'

(It is underlined the 5' segment of the second primer oligonucleotide that can complementary bind to the 3' segment of the first primer extension product, wherein said 3' segment of the first primer extension product is non-complementary to the third region of the activator oligonucleotide.)

Activator Oligonucleotide

LP-A1-1000-104
(SEQ ID NO 29)
5'-A*A*A*A*C*A*A*A[AACCGAACAACAAAUGAAAG<u>ACGUUCUUAAC</u>

<u>AAGUUUCAGCC</u>GUUCCUG]CGAGCTTCGGTACAAG X 3'

(Positions of the third region of the activator oligonucleotide that perfectly match the extension product of the first primer oligonucleotide on the template 003-01 (SEQ ID NO 14) are underlined.)

LP-A1-1000-104
(SEQ ID NO 29)
5'-A*A*A*A*C*A*A*A[AACCGAACAACAAAUGAAAG<u>ACGUUCUUAA</u>

<u>CAAGUUUCAGCCGUUCCUG</u>]CGAGCTTCGGTACAAG X 3'

(Positions of the activator oligonucleotide that perfectly match the primer extension product of the first primer oligonucleotide on template 003-01 (SEQ ID NO 14) are underlined.) This fragment is longer than the fragment that interacts with the extension product of the first primer oligonucleotide, since the whole primer extension product consists of the first primer oligonucleotide and the extension product.

It is seen that there is no smooth transition in the complementarity between the first primer extension product (that was synthesized to the perfect match template 003-01) and the segments of the second region and the third region of the activator oligonucleotide. This constellation supports the formation of the new double strand between the activator oligonucleotide and the first primer extension product, so that a sufficient strand displacement of the template strand or a second primer extension product can take place. Altogether, this leads to a positive amplification result.

In contrast, when using a mismatch sequence (SEQ ID NO 15) in the synthesis of the first primer extension product a complementary strand of the extension product is generated that however is completely complementary to the mismatch template, but that way deviates from being complementary to the third region of the activator oligonucleotide. This deviation takes place in the 5'-standing segment of the extension product that is to react with the activator oligonucleotide so that a strand displacement process can progress. As shown in the present example, absence of fife nucleotides in the respective positions interferes with a strand displacement by the activator oligonucleotide, which leads to a disturbance of the amplification.

LP-A1-1000-104
(SEQ ID NO 29)
5'-A*A*A*A*C*A*A*A[AACCGAACAACAAAUGAAAG<u>ACGUUCUUAA</u>

<u>CAAGUUU</u>CAGCCGUUCCUG]CGAGCTTCGGTACAAG X 3'

(Positions of the third region of the activator oligonucleotide that perfectly match the extension product of the first primer oligonucleotide on template 003-02 (SEQ ID NO 26) are underlined.)

LP-A1-1000-104
(SEQ ID NO 29)
5'-A*A*A*A*C*A*A*A[AACCGAACAACAAAUGAAAG<u>ACGUUCUUAA</u>

<u>CAAGUUUCAGCCGUUCCUG</u>]CGAGCTTCGGTACAAG X 3'

(Positions of the activator oligonucleotide that perfectly match the extension product of the first primer oligonucleotide on template 003-01 (SEQ ID NO 27) are underlined.)

It is seen an expected interruption of the binding of a complementary double strand between the activator oligonucleotide 003 and the first primer extension product that was formed on the mismatch template. This interruption corresponds to the portion of the primer extension product of template 003-02 (SEQ ID NO 27) that corresponds to the omitted segment of template 003-02. This position is between the second and third regions of the activator oligonucleotide.

Such a difference in the complementarity of the double strand potentially to be expected between the activator oligonucleotide 003 (SEQ ID NO 29) and the first primer extension product of a perfect match template 003-01 or the first primer extension product of a mismatch template 003-02 can lead to differences in the strand displacement reaction that result in a hindrance of the amplification.

This result demonstrated the meaning of the base composition in the activator oligonucleotide: deviations from complementarity between the activator oligonucleotide and the primer extension product can lead to interruption of the amplification.

In this example it was shown that even though sequence ends of the perfect match template and the mismatch template completely match and thus, the potential for binding both primer oligonucleotides was equal, both reactions proceeded completely different: in case of a complete complementarity between the activator oligonucleotide and the 5' segment of the extension product of the first primer oligonucleotide amplification proceeded as planned. Such an interruption of the strand displacement by a sequence divergence (in this case, fife nucleotides were absent in the 5' segment of the extension product of the first primer) resulted in the suppression of the amplification.

Example 5

It is shown in this example that further structure variants of the first primer oligonucleotide are able to support an exponential amplification of a nucleic acid chain to be amplified. These structure variants differ in the group used to stop the polymerase in the synthesis of the second primer extension product. One modification each was used as a group leading to the stop of the polymerase: C3 linker, C18 linker (also known as HEG linker, hexaethylene glycol linker), or Iso-dC-S-Me.

Moreover, it is shown in this example that a primer 2 with its 3' segment complementary to the first primer extension product is able to partially displace the activator oligonucleotide from the binding to the first primer extension product and can support a successful amplification.

For testing purposes the same nucleic acid to be amplified was used as described in example 2.

Template 001-01: T35-4401-601
(SEQ ID NO 12)
5'-ATACTACAATGTCACTTACGTCCTCTCCACACTCTGAGTTCCTGC

GAG-3'

(order of numbering: 1-48)

Activator Oligonucleotide:

The same activator oligonucleotide 001-01 was used as described in example 2:

Activator oligonucleotide 001-01: A6 8505
(SEQ ID NO: 15)
5'-[CUAGCUAUCGUCCUCUCCACACUCUGA GUUCC]TGCGAGCTT

CGGTACAAG X-3'

(order of numbering: 1-50)

The activator oligonucleotide comprises 2'-O-Me nucleotide modifications (indicated in [ ] brackets) and DNA nucleotides (in the 3' segment). The 3'—OH group of the 3'-terminal nucleotide was blocked by a phosphate residue (here designated with X).

The following variants of the first primer oligonucleotides have been used:

P-1001-100 TMR C3 (SEQ ID NO 30)

5'-6T57765568 CTCGCAGGAAC-3'

8=C3 linker

P-1001-103 TMR C18 (SEQ ID NO 31)

5'-6T577655687T76CAGGAAC-3'

8=C18 linker (HEG linker, hexaethylene glycol)

P-10-1002-IsoC4 (SEQ ID NO 32)

5'-7765568TCGCAGGAAC-3'

8=Iso-dC-5-Me (modification)

Further positions have been occupied as follows:

A=2'-deoxy-adenosine

C=2'-deoxy-cytosine

G=2'-deoxy-guanosine

T=2'-deoxy-thymidine (thymidine)

Modifications:

5=2'-O-Me A (2'-O-methyl-adenosine)

6=2'-O-Me G (2'-O-methyl-guanosine)

7=2'-O-Me C (2'-O-methyl-cytosine)

5' of first primer oligonucleotides has been modified with TAMRA dye. (TMR-modification).

The respective second region of each first primer oligonucleotide is underlined.

Conventional 5'-3' links between adjacent nucleotides and nucleotide modifications have been selected. Also modifications have been attached in a 5'-3' alignment. All sequences have been synthesized by commercial suppliers with standard synthesis chemistry (phosphoroamidite chemistry).

The following second primer oligonucleotide has been used:

Primer 001-02: PA6-35-4401-604
(SEQ ID NO: NN 33)
5'-GCTCATACTACAATGTCACTTACGTCCTCT-3'

(order of numbering in 5'-3': 1-30)

The second primer consists of DNA.

The composition of the reaction mixture and the start of the reaction were carried out as described example 2.

These components have been employed in the reaction mixture as follows:

template 001-01: 10 µmol/l
activator oligonucleotide 001-01: 10 µmol/l
the respective primer 1: 10 µmol/l
primer 001-02: 10 µmol/l Further components of the reaction have been employed as amplification reaction solution 2:

potassium glutamate, 50 mmol/l, pH 8.0
magnesium acetate, 10 mmol/l
dNTP (dATP, dCTP, dTTP, dGTP), 200 µmol/leach
polymerase (Bst 2.0 WarmStart, 120,000 U/ml NEB), 12 units/10 µl
Triton X-100, 0.1% (v/v)
EDTA, 0.1 mmol/l
TPAC (tetrapropylammonium chloride), 50 mmol/l, pH 8.0
Eva green dye (dye was employed in accordance with the specification of the manufacturer in dilution 1:50).

The reaction was carried out in the amplification reaction solution 2 under isothermal reaction conditions at 65° C. for the period (as indicated). The fluorescence signal of Eva green was recorded during the reaction as described in example 2. The result of the recordings of the signal intensity during the reaction is illustrated in FIG. 34.

Evaluation:

By using the listed first primer oligonucleotides generation of the following first primer extension products is to be expected:

(SEQ ID NO: NN 34)
5'-XXXXXXX TCAGAGTGTGGAGAGGACGTAAGTGACATTGTAGTAT

GAGC-3'

The respective sequence of the corresponding first primer oligonucleotide is marked with "XXXXXXX". Directly afterwards the sequence of the first extension product to be expected is given (41 NT). The extension product is underlined.

Different primer 1 structures were tested for their ability to support an exponential amplification under isothermal conditions. Thereby, different groups leading to the stop of the polymerase have been integrated in the second region of the first primer oligonucleotide: C3 linker, C18 linker (also known as HEG linker, hexaethylene glycol linker), or Iso-dC-5-Me. In the synthesis of the second primer extension product the synthesis of the second primer extension product is position-specifically interrupted, so that the polynucleotide tail of the second region remains uncopied.

The respective signal profile of the reaction is shown in FIG. 34.

Reaction with primer 1 (C3 linker) with SEQ ID NO: 30 is shown in FIG. 34 (A).

Reaction with primer 1 (C18 linker) with SEQ ID NO: 31 is shown in FIG. 34 (B).

Reaction with primer 1 (Iso-dC-5-Me) with SEQ ID NO: 32 is shown in FIG. 34 (C).

All listed structure variants of the first primer oligonucleotide resulted in a successful exponential amplification. In designing the first primer oligonucleotides the following aspects were taken into account:

First primer region of the first primer oligonucleotide has to be able to specifically bind to the nucleic acid to be amplified and initiate a detectable primer extension reaction by the polymerase used.

First primer region of the first primer oligonucleotide has to complementary bind to the second region of the activator oligonucleotide so that a strand displacement reaction can effectively take place.

Second region of the first primer oligonucleotide comprises a polynucleotide tail that is to specifically bind the first region of the activator oligonucleotide.

Between the first region and the polynucleotide tail of the second region of the first primer oligonucleotide first blocking unit leading to the blockage of the polymerase-dependent synthesis or termination or to the stop of the polymerase-dependent synthesis is integrated that hinders polymerase from copying the polynucleotide tail.

Binding between the first primer oligonucleotide and the activator oligonucleotide is to be reversible under the isothermal conditions used. Altogether, there is to be equilibrium between a single-stranded form of the first primer oligonucleotide and a form of the first primer oligonucleotide that is complementary bound to the activator oligonucleotide under the selected reaction conditions.

In selecting the sequence length and sequence composition of the second primer oligonucleotide the following aspects were taken into account:

Primer length comprises 30 nucleotides. Positions 5-30 of the sequence of the second primer oligonucleotide are complementary to the sequence-specific first primer extension product that is already generated after the first primer extension reaction. Thus, primer 2 can initiate a primer extension reaction for the second primer extension product.

The 3' segment (positions 23-30) of the second primer oligonucleotide in the present example competes for the binding to the first sequence-specific primer extension product with the activator oligonucleotide. Said 3' segment can lead to a nucleic acid-dependent strand displacement of the corresponding segment of the activator oligonucleotide. In such a strand displacement the 3'-terminal nucleotide of the second primer oligonucleotide contacts the first sequence-specific primer extension product, so that the polymerase can initiate an effective sequence-specific second primer extension reaction that leads to the synthesis of the second sequence-specific strand. This synthesis takes place with simultaneous strand displacement of the activator oligonucleotide by the polymerase. The length of said 3' segment in this example was selected such that no overlapping of complementary sequence parts with the first primer oligonucleotide can take place.

In the present example, the 5' segment (22 nucleotides, positions 1 to 22) of the second primer oligonucleotide can complementary bind to the 3' segment of the sequence-specific first primer extension product. Said 5' segment does not compete with the activator oligonucleotide for the binding to the first primer extension product and thus, does not lead to a strand displacement of the activator oligonucleotide from the binding to the first primer extension product. The Tm of said 5' segment of the second primer oligonucleotide is selected such that a temperature-induced spontaneous strand separation between a first sequence-specific primer extension product and a second sequence-specific primer extension product is favored in case of a complete binding of the activator oligonucleotide to the first sequence-specific primer extension product. Separation of both strands results in a single-stranded form of the 3' segment of the first primer extension product.

Example 6

Influence of Individual Nucleotide Changes in the Template on the Rate of the Amplification Reaction In this example the influence of a change in sequence in the template on the amplification was investigated, wherein individual nucleotide monomers were replaced by other nucleotide monomers. The peripheral regions that are relevant for the binding of primers have been designed identically. In this way it was to be verified which effect such mismatch positions between a first primer extension product generated thereby and a given activator oligonucleotide has on the amplification. Designing the sequences was in the same manner like in examples 2 and 3.

The following templates have been used:

template (SEQ ID NO 21) with a sequence composition that leads to a first primer extension product with a perfect match in matching with the activator oligonucleotide:

T-A6P-15-4401
(SEQ ID NO: 21)
5' GTAGTTCTCACTTACGTCCTCTCCACACTCTGA GTTCCTGCG

AG 3'

The binding sequence for the first primer oligonucleotide is underlined.

Moreover, further templates (SEQ ID NO 36-38) with a sequence composition that leads to a first primer extension product with a mismatch with the activator oligonucleotide have been used:

T-A6P-15-4401-1
(SEQ ID NO: 35)
5' GTAGTTCTCACTTACGTCCTCTCCACACTATGA GTTCCTGCGAG 3'

T-A6P-15-4401-2
(SEQ ID NO: 36)
5' GTAGTTCTCACTTACGTCCTCTCCAAACTCTGA GTTCCTGC

GAG 3'

T-A6P-15-4401-3
(SEQ ID NO: 37)
5' GTAGTTCTCACTTACGTCCTATCCACACTCTGA GTTCCTGCGAG 3'

T-A6P-15-4401-4
(SEQ ID NO: 38)
5' GTAGTTCTCACTTACGTACTCTCCACACTCTGA GTTCCTGC

GAG 3'

The binding sequence for the first primer oligonucleotide is underlined.

Diverging bases (to SEQ ID NO 21) are marked BOLD IN ITALICS.

In all templates (with a perfect match in matching and integrated mismatches) the respective primer binding sites are identical, so that a successful first primer extension reaction by the primer oligonucleotides each could be initiated.

By the amplification with the polymerase there are differences in the amplified sequences over the unchanged templates (SEQ ID NO:21). The corresponding points of differences are in the 5' segment of the extension product of the first primer oligonucleotide.

The following primers have been used:
the first primer oligonucleotide (SEQ ID NO 23):

```
(A6P-10-1002 TMR7)  5' 7765567876 CAGGAAC 3'
``` having the meaning of:
A=2'-deoxy-adenosine
C=2'-deoxy-cytosine
G=2'-deoxy-guanosine
T=2'-deoxy-thymidine (thymidine) and the modifications:
5=2'-O-Me A (2'-O-methyl-adenosine)
6=2'-O-Me G (2'-O-methyl-guanosine)
7=2'-O-Me C (2'-O-methyl-cytosine)
8=dT-TMR
the second primer oligonucleotide (SEQ ID NO 24):

```
(PA6-15-4401-10)  5' CACGAGTAGTTCTCACTTAC 3'
```

The following activator oligonucleotide 002-01 (SEQ ID NO 25) has been used:

```
A6 8504
5'-CTAGCTAT CGTCCTCT CCACACT CTGA GTTCCTGCGAG
CTTC GGTAC AAG X 3'  68576858 67866868 6656568 6875
788668 7CGAG CTTC GGTAC AAG
``` having the following meaning:
A=2'-deoxy-adenosine
C=2'-deoxy-cytosine
G=2'-deoxy-guanosine
T=2'-deoxy-thymidine (thymidine)
5=2'-O-Me A (2'-O-methyl-adenosine)
6=2'-O-Me C (2'-O-methyl-cytosine)
7=2'-O-Me G (2'-O-methyl-guanosine)
8=2'-O-Me U (2'-O-methyl-uridine)
X=3'-phosphate group for blocking a possible extension by polymerase.

The nucleotides and nucleotide modifications are linked to each other by a phosphodiester binding. The 3' end is blocked with a phosphate group to prevent a possible extension by the polymerase.

The template with a perfect match sequence composition was employed in concentrations of 1 nmol/l, 1 µmol/l, and 1 fmol/l. The template with a mismatch sequence composition was used in a concentration of 1 nmol/l.

In the control reaction no template was used. The other reaction conditions were kept as in example 2. FIG. 35 shows the result of the reaction.

When using a perfect match template (SEQ ID NO 21) a complementary strand of a primer extension product is synthesized. Said extension product is complementary both to the perfect match template and to the activator oligonucleotide used. This constellation has been explained in detail in example 2. It serves as a basis for a successful amplification.

In contrast, when using mismatch sequences (SEQ ID NO 35-38) in the synthesis of the first primer extension product a complementary strand of the extension product is generated that certainly is completely complementary to the mismatch template, but in this way deviates from being completely complementary to the third region of the activator oligonucleotide. This deviation in complementarity are in the 5'-standing segment of the extension product of the first primer extension product that is to react with the activator oligonucleotide so that the strand displacement process can progress. As is shown in the present example, mismatches between corresponding sites can interfere with the strand displacement by the activator oligonucleotide. The amplification therefore proceeds slower overall.

FIG. 35 shows this influence of the sequence differences between the activator oligonucleotide and the extension product of the first primer oligonucleotide. Divergences in only one position in the sequence of the activator oligonucleotide from the sequence of the primer extension product synthesized on the mismatch template show the dependency of the amplification in the matching in the order of the complementary bases in the activator oligonucleotide and the template or the first primer extension product. The respective mutations cause a deceleration of the amplification reaction.

The control reactions with a perfect match template (arrows 1-3, FIG. 35 A) showed a concentration dependency of the amplification. With decreasing concentration the reaction took longer time to synthesize a sufficient amount of the nucleic acid to be amplified so that the signal increases above the level of the baseline.

The negative control reaction without a template also showed an increase in the signal, but in a significantly later time interval with respect to reactions with a perfect-match template.

The arrows in FIG. 35 A show:
perfect match template (SEQ ID NO 21) 1 nmol/l concentration (arrow 1)
perfect match template (SEQ ID NO 21) 1 µmol/l concentration (arrow 2)
perfect match template (SEQ ID NO 21) 1 fmol/l concentration (arrow 3)
negative control: no template in the reaction (arrow 4)
The arrows in FIG. 35 B show:
perfect match template (SEQ ID NO 21) 1 nmol/l concentration (arrow 1)
negative control: no template in the reaction (arrow 4)
mismatch template (SEQ ID NO 35) 1 nmol/l concentration (arrow 5) T-A6P-15-4401-1
mismatch template (SEQ ID NO 36) 1 nmol/l concentration (arrow 6) T-A6P-15-4401-2
mismatch template (SEQ ID NO 37) 1 nmol/l concentration (arrow 7) T-A6P-15-4401-3
mismatch template (SEQ ID NO 38) 1 nmol/l concentration (arrow 8) T-A6P-15-4401-4

This result illustrates the meaning of the base composition in the activator oligonucleotide: Divergences from the complementarity between the activator oligonucleotide and the primer extension product by only one complementary base in some cases can lead to a significant delay in the exponential amplification.

It was shown in this example that, even though terminal sequence segments of a perfect match template and a mismatch template completely match and thus, the potential for binding both primer oligonucleotides during the exponential amplification was equal, both reactions proceeded different: in case of a complete complementarity between the activator oligonucleotide and the 5' segment of the extension product of the first primer oligonucleotide the amplification proceeded as planned. The presence of individual mismatches between the activator oligonucleotide and a primer extension product can lead to a deceleration of an exponential amplification reaction.

The invention claimed is:

1. A method for amplification of a nucleic acid comprising the following steps:
   a) hybridizing a first primer oligonucleotide to the 3' segment of a strand of a nucleic acid chain to be amplified, wherein the nucleic acid chain to be amplified comprises a target sequence, wherein the first primer oligonucleotide comprises:
   a first primer region in the 3' segment of the first primer oligonucleotide that can sequence-specifically bind to a strand of a nucleic acid chain to be amplified,
   a second region that is directly or via a linker linked to the 5' end of the first primer region of the first primer oligonucleotide and that comprises a polynucleotide tail which is suitable for binding an activator oligonucleotide and supporting strand displacement by the activator oligonucleotide, wherein the polynucleotide tail remains substantially uncopied by polymerase,
   b) extending the first primer oligonucleotide by means of a polymerase to form a first primer extension product comprising a sequence that is complementary to the target sequence of the nucleic acid chain to be amplified,
   c) binding the activator oligonucleotide to the polynucleotide tail of the second region of the first extended primer oligonucleotide, wherein the activator oligonucleotide comprises:
   a first single-stranded region that can bind to the polynucleotide tail of the second region of the first primer oligonucleotide,
   a second single-stranded region that is substantially complementary and can bind to the first region of the first primer oligonucleotide,
   a third single-stranded region that is substantially complementary to at least a segment of the extension product, which has been synthesized by polymerase, of the first primer extension product, which immediately follows the first primer region,
   wherein the activator oligonucleotide does not serve as template for a primer extension of the first primer oligonucleotide,
   d) binding the activator oligonucleotide to the first primer region of the first extended primer oligonucleotide by displacing the strand of the nucleic acid chain to be amplified that is complementary to said first primer region,
   e) binding the activator oligonucleotide to the complementary segment of the extension product of the first extended primer oligonucleotide by displacing the strand of the nucleic acid chain to be amplified that is complementary to said extension product, wherein the 3' segment of the first primer extension product becomes single-stranded,
   f) hybridizing a second oligonucleotide primer to the first primer extension product, wherein the 3' segment of the second oligonucleotide primer comprises a sequence that can hybridize to the first primer extension product; and
   g) extending the second oligonucleotide primer with polymerase to form a second primer extension product, wherein the extension takes place up to and including the first primer region of the first primer oligonucleotide and said first primer region is copied by the polymerase, wherein the polynucleotide tail of the second region remains uncopied,
   h) repeating steps a)-g) until the desired degree of amplification has been achieved.

2. The method according to claim 1, wherein the method is carried out substantially isothermal.

3. The method according to claim 1, wherein step (e) of the method is modified in that it comprises the binding of the activator oligonucleotide to the complementary segment of the extension product of the first extended primer oligonucleotide by displacing the strand of the nucleic acid chain to be amplified that is complementary to said extension product until said complementary strand of the nucleic acid to be amplified is detached from the first primer extension product, wherein the 3' segment of the first primer extension product becomes single-stranded.

4. The method according to claim 1, wherein step (f) of the method is modified in that it comprises the hybridization of a second oligonucleotide primer to the first primer extension product, wherein at the same time there is at least a partial displacement of the activator oligonucleotide from the binding with the first extension product by strand displacement.

5. The method according to claim 1, wherein step (g) of the method is modified such that it comprises a displacement of the activator oligonucleotide from the binding with the first primer extension product with the participation of the polymerase.

6. The method according to claim 1, wherein step (h) of the method is modified in that it comprises the binding of the activator oligonucleotide to the uncopied polynucleotide tail of the first extended primer oligonucleotide and a displacement of the second primer extension product from the binding to the first primer extension product with the simultaneous formation of a complementary double strand with a segment of the first specific extension product of the first primer oligonucleotide.

7. The method according to claim 1, wherein it comprises the simultaneous amplification of the first and second primer extension products in an exponential reaction by using the first and second primer oligonucleotides and the activator oligonucleotide, wherein the formed primer extension products function as a template for the mutual synthesis.

8. The method according to claim 2, wherein it comprises the simultaneous amplification of the first and second primer extension products in an exponential reaction by using the first and second primer oligonucleotides and the activator oligonucleotide, wherein the formed primer extension products function as a template for the mutual synthesis.

9. The method according to claim 3, wherein it comprises the simultaneous amplification of the first and second primer extension products in an exponential reaction by using the first and second primer oligonucleotides and the activator oligonucleotide, wherein the formed primer extension products function as a template for the mutual synthesis.

* * * * *

```
                        SEQUENCE LISTING

<160> NUMBER OF SEQ ID NOS: 38

<210> SEQ ID NO 1
<211> LENGTH: 59
<212> TYPE: DNA
<213> ORGANISM: artificial sequence
<220> FEATURE:
<223> OTHER INFORMATION: target

<400> SEQUENCE: 1
ccgaagctcg caggaactca gagtgtggag aggacgatag ctagtcagat gatgaagtt        59

<210> SEQ ID NO 2
<211> LENGTH: 48
<212> TYPE: DNA
<213> ORGANISM: artificial sequence
<220> FEATURE:
<223> OTHER INFORMATION: complementary

<400> SEQUENCE: 2
catcatctga ctagctatcg tcctctccac actctgagtt cctgcgag                    48

<210> SEQ ID NO 3
<211> LENGTH: 45
<212> TYPE: DNA
<213> ORGANISM: artificial sequence
<220> FEATURE:
<223> OTHER INFORMATION: variant

<400> SEQUENCE: 3
catcatctga ctagctatcg tcctctccac actctgagtt cctgc                       45

<210> SEQ ID NO 4
<211> LENGTH: 42
<212> TYPE: DNA
<213> ORGANISM: artificial sequence
<220> FEATURE:
<223> OTHER INFORMATION: activator oligonucleotide

<400> SEQUENCE: 4
cguccucucc acacucugag uuccugcgag cttcggtaca ag                          42

<210> SEQ ID NO 5
<211> LENGTH: 58
<212> TYPE: DNA
<213> ORGANISM: artificial sequence
<220> FEATURE:
<223> OTHER INFORMATION: activator oligonucleotide

<400> SEQUENCE: 5
aaaacaaacu agcuaucguc cucuccacac ucugaguucc ugcgagcttc ggtacaag         58

<210> SEQ ID NO 6
<211> LENGTH: 50
<212> TYPE: DNA
<213> ORGANISM: artificial sequence
<220> FEATURE:
<223> OTHER INFORMATION: activator oligonucleotide

<400> SEQUENCE: 6
```
ctagctatcg tcctctccac acucugaguu ccugcgagct tcggtacaag            50

<210> SEQ ID NO 7
<211> LENGTH: 56
<212> TYPE: DNA
<213> ORGANISM: artificial sequence
<220> FEATURE:
<223> OTHER INFORMATION: negative control

<400> SEQUENCE: 7
auucaaaugu guucucaacg uccucuacuc auguuccugc gagcuucggu acaaaa      56

<210> SEQ ID NO 8
<211> LENGTH: 55
<212> TYPE: DNA
<213> ORGANISM: artificial sequence
<220> FEATURE:
<223> OTHER INFORMATION: A6 8510

<400> SEQUENCE: 8
tttttctagc tatcgtcctc tccacactct gagttcctgc gagcttcggt acaag       55

<210> SEQ ID NO 9
<211> LENGTH: 55
<212> TYPE: DNA
<213> ORGANISM: artificial sequence
<220> FEATURE:
<223> OTHER INFORMATION: A6 8512

<400> SEQUENCE: 9
tttttctagc tatcgtcatc tccacactct gagttactgc gagcttcggt acaag       55

<210> SEQ ID NO 10
<211> LENGTH: 53
<212> TYPE: DNA
<213> ORGANISM: artificial sequence
<220> FEATURE:
<223> OTHER INFORMATION: A6-8514-1

<400> SEQUENCE: 10
tttttctagc tatcgtcctc tccacactga gttcctgcga gcttcggtac aag         53

<210> SEQ ID NO 11
<211> LENGTH: 20
<212> TYPE: DNA
<213> ORGANISM: artificial sequence
<220> FEATURE:
<223> OTHER INFORMATION: primer

<400> SEQUENCE: 11
gtaccgaagc tcgcaggaac                                              20

<210> SEQ ID NO 12
<211> LENGTH: 48
<212> TYPE: DNA
<213> ORGANISM: artificial sequence
<220> FEATURE:
<223> OTHER INFORMATION: target

<400> SEQUENCE: 12
atactacaat gtcacttacg tcctctccac actctgagtt cctgcgag               48

<210> SEQ ID NO 13
<211> LENGTH: 20
<212> TYPE: DNA
<213> ORGANISM: artificial sequence

```
<220> FEATURE:
<223> OTHER INFORMATION: primer

<400> SEQUENCE: 13
gtaccgaagc tcgcaggaac                                             20

<210> SEQ ID NO 14
<211> LENGTH: 27
<212> TYPE: DNA
<213> ORGANISM: artificial sequence
<220> FEATURE:
<223> OTHER INFORMATION: second primer

<400> SEQUENCE: 14
aaaaaaacat actacaatgt cacttac                                     27

<210> SEQ ID NO 15
<211> LENGTH: 50
<212> TYPE: DNA
<213> ORGANISM: artificial sequence
<220> FEATURE:
<223> OTHER INFORMATION: activator oligonucleotide

<400> SEQUENCE: 15
cuagcuaucg uccucuccac acucugaguu cctgcgagct tcggtacaag             50

<210> SEQ ID NO 16
<211> LENGTH: 57
<212> TYPE: DNA
<213> ORGANISM: artificial sequence
<220> FEATURE:
<223> OTHER INFORMATION: elongation product

<400> SEQUENCE: 16
gtaccgaagc tcgcaggaac tcagagtgtg gagaggacgt aagtgacatt gtagtat    57

<210> SEQ ID NO 17
<211> LENGTH: 56
<212> TYPE: DNA
<213> ORGANISM: artificial sequence
<220> FEATURE:
<223> OTHER INFORMATION: second primer elongation product

<400> SEQUENCE: 17
aaaaaaacat actacaatgt cacttacgtc ctctccacac tctgagttcc tgcgag     56

<210> SEQ ID NO 18
<211> LENGTH: 65
<212> TYPE: DNA
<213> ORGANISM: artificial sequence
<220> FEATURE:
<223> OTHER INFORMATION: amplification product

<400> SEQUENCE: 18
gtaccgaagc tcgcaggaac tcagagtgtg gagaggacgt aagtgacatt gtagtatgtt 60
ttttt                                                             65

<210> SEQ ID NO 19
<211> LENGTH: 56
<212> TYPE: DNA
<213> ORGANISM: artificial sequence
<220> FEATURE:
<223> OTHER INFORMATION: amplification product

<400> SEQUENCE: 19
```

```
gagcgtcctt gagtctcaca cctctcctgc attcactgta acatcataca aaaaaa      56
```

<210> SEQ ID NO 20
<211> LENGTH: 65
<212> TYPE: DNA
<213> ORGANISM: artificial sequence
<220> FEATURE:
<223> OTHER INFORMATION: amplification product

<400> SEQUENCE: 20

```
gtaccgaagc tcgcaggaac tcagagtgtg gagaggacgt aagtgacatt gtagtatgtt   60
ttttt                                                               65
```

<210> SEQ ID NO 21
<211> LENGTH: 44
<212> TYPE: DNA
<213> ORGANISM: artificial product
<220> FEATURE:
<223> OTHER INFORMATION: target

<400> SEQUENCE: 21

```
gtagttctca cttacgtcct ctccacactc tgagttcctg cgag                    44
```

<210> SEQ ID NO 22
<211> LENGTH: 41
<212> TYPE: DNA
<213> ORGANISM: artificial product
<220> FEATURE:
<223> OTHER INFORMATION: target with one mismatch

<400> SEQUENCE: 22

```
gtagttctca cttacgtcct ctccctctga gttcctgcga g                       41
```

<210> SEQ ID NO 23
<211> LENGTH: 7
<212> TYPE: DNA
<213> ORGANISM: artificial sequence
<220> FEATURE:
<223> OTHER INFORMATION: first primer

<400> SEQUENCE: 23

```
caggaac                                                              7
```

<210> SEQ ID NO 24
<211> LENGTH: 20
<212> TYPE: DNA
<213> ORGANISM: artificial sequence
<220> FEATURE:
<223> OTHER INFORMATION: second primer

<400> SEQUENCE: 24

```
cacgagtagt tctcacttac                                               20
```

<210> SEQ ID NO 25
<211> LENGTH: 66
<212> TYPE: DNA
<213> ORGANISM: artificial sequence
<220> FEATURE:
<223> OTHER INFORMATION: activator oligonucleotide

<400> SEQUENCE: 25

```
ctagctatcg tcctctccac actctgagtt cctgcgagct tcggtacaag cgagcttcgg   60
tacaag                                                              66
```

```
<210> SEQ ID NO 26
<211> LENGTH: 49
<212> TYPE: DNA
<213> ORGANISM: artificial sequence
<220> FEATURE:
<223> OTHER INFORMATION: MIP Gene

<400> SEQUENCE: 26
ctacaatgtc acttacacgt tcttaacaag tttcagccgt tcctgcgag          49

<210> SEQ ID NO 27
<211> LENGTH: 44
<212> TYPE: DNA
<213> ORGANISM: artificial sequence
<220> FEATURE:
<223> OTHER INFORMATION: target with one mismatch

<400> SEQUENCE: 27
ctacaatgtc acttacacgt tcttaacaag tttgttcctg cgag               44

<210> SEQ ID NO 28
<211> LENGTH: 33
<212> TYPE: DNA
<213> ORGANISM: artificial sequence
<220> FEATURE:
<223> OTHER INFORMATION: second primer oligonucleotide

<400> SEQUENCE: 28
ctacaatgtc acttacacgt tcttaacaag ttt                           33

<210> SEQ ID NO 29
<211> LENGTH: 73
<212> TYPE: DNA
<213> ORGANISM: artificial sequence
<220> FEATURE:
<223> OTHER INFORMATION: activator oligonucleotide

<400> SEQUENCE: 29
aaaacaaaaa ccgaacaaca aaugaaagac guucuuaaca aguuucagcc guccugcga    60 gcuucgguac aag                                                     73

<210> SEQ ID NO 30
<211> LENGTH: 11
<212> TYPE: DNA
<213> ORGANISM: artificial sequence
<220> FEATURE:
<223> OTHER INFORMATION: first primer

<400> SEQUENCE: 30
ctcgcaggaa c                                                   11

<210> SEQ ID NO 31
<211> LENGTH: 7
<212> TYPE: DNA
<213> ORGANISM: artificial sequence
<220> FEATURE:
<223> OTHER INFORMATION: first primer variant

<400> SEQUENCE: 31 caggaac                                                        7

<210> SEQ ID NO 32
<211> LENGTH: 10
<212> TYPE: DNA
<213> ORGANISM: artificial sequence
<220> FEATURE:
```

<223> OTHER INFORMATION: first primer variant

<400> SEQUENCE: 32
tcgcaggaac                                                          10

<210> SEQ ID NO 33
<211> LENGTH: 30
<212> TYPE: DNA
<213> ORGANISM: artificial sequence
<220> FEATURE:
<223> OTHER INFORMATION: second primer

<400> SEQUENCE: 33
gctcatacta caatgtcact tacgtcctct                                    30

<210> SEQ ID NO 34
<211> LENGTH: 41
<212> TYPE: DNA
<213> ORGANISM: artificial sequence
<220> FEATURE:
<223> OTHER INFORMATION: elongation product

<400> SEQUENCE: 34
tcagagtgtg gagaggacgt aagtgacatt gtagtatgag c                       41

<210> SEQ ID NO 35
<211> LENGTH: 44
<212> TYPE: DNA
<213> ORGANISM: artificial sequence
<220> FEATURE:
<223> OTHER INFORMATION: template with one mismatch

<400> SEQUENCE: 35
gtagttctca cttacgtcct ctccacacta tgagttcctg cgag                    44

<210> SEQ ID NO 36
<211> LENGTH: 44
<212> TYPE: DNA
<213> ORGANISM: artificial sequence
<220> FEATURE:
<223> OTHER INFORMATION: template with one mismatch

<400> SEQUENCE: 36
gtagttctca cttacgtcct ctccaaactc tgagttcctg cgag                    44

<210> SEQ ID NO 37
<211> LENGTH: 44
<212> TYPE: DNA
<213> ORGANISM: artificial sequence
<220> FEATURE:
<223> OTHER INFORMATION: template with one mismatch

<400> SEQUENCE: 37
gtagttctca cttacgtcct atccacactc tgagttcctg cgag                    44

<210> SEQ ID NO 38
<211> LENGTH: 44
<212> TYPE: DNA
<213> ORGANISM: artificial sequence
<220> FEATURE:
<223> OTHER INFORMATION: template with one mismatch

<400> SEQUENCE: 38
gtagttctca cttacgtact ctccacactc tgagttcctg cgag                    44